(12) United States Patent
Cho et al.

(10) Patent No.: US 7,632,924 B2
(45) Date of Patent: Dec. 15, 2009

(54) ANTIGEN-BINDING POLYPEPTIDES AND THEIR USES

(75) Inventors: Ho Sung Cho, San Diego, CA (US);
Thomas O. Daniel, La Jolla, CA (US);
Troy E. Wilson, San Marino, CA (US);
Thomas P. Cujec, San Diego, CA (US);
Feng Tian, San Diego, CA (US);
Anna-Maria Hays, La Jolla, CA (US);
Bruce E. Kimmel, San Diego, CA (US);
Lillian Ho, San Diego, CA (US)

(73) Assignee: Ambrx, Inc., La Jolla, CA (US)

( * ) Notice: Subject to any disclaimer, the term of this patent is extended or adjusted under 35 U.S.C. 154(b) by 272 days.

(21) Appl. No.: 11/155,909

(22) Filed: Jun. 17, 2005

(65) Prior Publication Data

US 2006/0153860 A1    Jul. 13, 2006

Related U.S. Application Data

(60) Provisional application No. 60/581,334, filed on Jun. 18, 2004, provisional application No. 60/648,222, filed on Jan. 28, 2005, provisional application No. 60/654,018, filed on Feb. 17, 2005.

(51) Int. Cl.
*C12P 21/08* (2006.01)

(52) U.S. Cl. ............... 530/387.3; 530/387.1; 530/387.7; 530/350

(58) Field of Classification Search ................. 530/350, 530/387.1, 387.3, 387.7
See application file for complete search history.

(56) References Cited

U.S. PATENT DOCUMENTS

| | | | |
|---|---|---|---|
| 3,773,919 A | 11/1973 | Boswell et al. | |
| 4,289,872 A | 9/1981 | Denkewalter et al. | |
| 4,412,989 A | 11/1983 | Iwashita et al. | |
| 4,414,148 A | 11/1983 | Jansen et al. | |
| 4,485,045 A | 11/1984 | Regen | |
| 4,511,502 A | 4/1985 | Builder et al. | |
| 4,511,503 A | 4/1985 | Olson et al. | |
| 4,512,922 A | 4/1985 | Jones et al. | |
| 4,544,545 A | 10/1985 | Ryan et al. | |
| 4,551,433 A | 11/1985 | DeBoer | |
| 4,569,789 A | 2/1986 | Blattler et al. | |
| 4,619,794 A | 10/1986 | Hauser | |
| 4,659,839 A | 4/1987 | Nicolotti et al. | |
| 4,670,417 A | 6/1987 | Iwasaki et al. | |
| 4,671,958 A | 6/1987 | Rodwell et al. | |
| 4,680,338 A | 7/1987 | Sundoro | |
| 4,689,406 A | 8/1987 | Banks et al. | |
| 4,699,784 A | 10/1987 | Shih et al. | |
| 4,738,921 A | 4/1988 | Belagaje et al. | |
| 4,755,465 A | 7/1988 | Gray et al. | |
| 4,837,148 A | 6/1989 | Cregg | |
| 4,859,600 A | 8/1989 | Gray et al. | |
| 4,876,197 A | 10/1989 | Burke et al. | |
| 4,880,734 A | 11/1989 | Burke et al. | |
| 4,902,502 A | 2/1990 | Nitecki et al. | |
| 4,904,584 A | 2/1990 | Shaw | |
| 4,929,555 A | 5/1990 | Cregg et al. | |
| 5,021,234 A | 6/1991 | Ehrenfeld | |
| 5,089,398 A | 2/1992 | Rosenberg et al. | |
| 5,122,614 A | 6/1992 | Zalipsky | |
| 5,162,601 A | 11/1992 | Slightom | |
| 5,219,564 A | 6/1993 | Zalipsky et al. | |
| 5,229,490 A | 7/1993 | Tam | |
| 5,231,178 A | 7/1993 | Holtz et al. | |
| 5,252,714 A | 10/1993 | Harris et al. | |
| 5,281,698 A | 1/1994 | Nitecki | |
| 5,290,686 A | 3/1994 | Kendal et al. | |
| 5,324,639 A | 6/1994 | Brierley et al. | |
| 5,324,844 A | 6/1994 | Zalipsky | |
| 5,382,657 A | 1/1995 | Karasiewicz et al. | |
| 5,446,090 A | 8/1995 | Harris | |
| 5,468,478 A | 11/1995 | Saifer et al. | |
| 5,473,034 A | 12/1995 | Yasui et al. | |
| 5,476,653 A | 12/1995 | Pitt et al. | |
| 5,516,657 A | 5/1996 | Murphy et al. | |
| 5,516,673 A | 5/1996 | Margel et al. | |
| 5,532,142 A | 7/1996 | Johnston et al. | |
| 5,559,213 A | 9/1996 | Hakimi et al. | |
| 5,571,709 A | 11/1996 | Devauchelle et al. | |
| 5,580,723 A | 12/1996 | Wells et al. | |

(Continued)

FOREIGN PATENT DOCUMENTS

DE    3218121    11/1983

(Continued)

OTHER PUBLICATIONS

Paul (Fundamental Immunology, 3rd Edition, 1993, pp. 292-295).*

(Continued)

*Primary Examiner*—Stephen L Rawlings
*Assistant Examiner*—Brad Duffy
(74) *Attorney, Agent, or Firm*—John W. Wallen, III; Kristin S. Eaton

(57) ABSTRACT

Novel antigen-binding polypeptides (ABP) and uses thereof are provided.

8 Claims, 21 Drawing Sheets

U.S. PATENT DOCUMENTS

| | | |
|---|---|---|
| 5,583,023 A | 12/1996 | Cerutti et al. |
| 5,602,034 A | 2/1997 | Tekamp-Olson |
| 5,605,827 A | 2/1997 | Jackwood et al. |
| 5,612,460 A | 3/1997 | Zalipsky |
| 5,629,203 A | 5/1997 | Shuster |
| 5,629,384 A | 5/1997 | Veronese et al. |
| 5,643,575 A | 7/1997 | Martinez et al. |
| 5,650,234 A | 7/1997 | Dolence et al. |
| 5,672,662 A | 9/1997 | Harris et al. |
| 5,674,706 A | 10/1997 | Shuster |
| RE35,749 E | 3/1998 | Rosenberg et al. |
| 5,736,625 A | 4/1998 | Callstrom et al. |
| 5,739,208 A | 4/1998 | Harris |
| 5,747,646 A | 5/1998 | Hakimi et al. |
| 5,750,373 A | 5/1998 | Garrard et al. |
| 5,753,220 A | 5/1998 | Suzuki et al. |
| 5,762,939 A | 6/1998 | Smith et al. |
| 5,766,885 A | 6/1998 | Carrington et al. |
| 5,808,096 A | 9/1998 | Zalipsky |
| 5,824,778 A | 10/1998 | Ishikawa et al. |
| 5,824,784 A | 10/1998 | Kinstler et al. |
| 5,834,250 A | 11/1998 | Wells et al. |
| 5,834,594 A | 11/1998 | Hakimi et al. |
| 5,843,733 A | 12/1998 | Estes |
| 5,849,860 A | 12/1998 | Hakimi et al. |
| 5,858,368 A | 1/1999 | Smith et al. |
| 5,861,279 A | 1/1999 | Zhang et al. |
| 5,871,986 A | 2/1999 | Boyce |
| 5,891,676 A | 4/1999 | Estes |
| 5,900,461 A | 5/1999 | Harris |
| 5,932,462 A | 8/1999 | Harris et al. |
| 5,939,285 A | 8/1999 | Devauchelle et al. |
| 5,965,393 A | 10/1999 | Hasnain et al. |
| 5,980,948 A | 11/1999 | Goedemoed et al. |
| 5,989,868 A | 11/1999 | Harrison et al. |
| 5,990,237 A | 11/1999 | Bentley et al. |
| 6,004,573 A | 12/1999 | Rathi et al. |
| 6,013,433 A | 1/2000 | Pellett et al. |
| 6,013,478 A | 1/2000 | Wells et al. |
| 6,017,731 A | 1/2000 | Tekamp-Olson et al. |
| 6,083,723 A | 7/2000 | Tekamp-Olson |
| 6,096,304 A | 8/2000 | McCutchen |
| 6,126,944 A | 10/2000 | Pellett et al. |
| 6,129,912 A | 10/2000 | Hortin et al. |
| 6,168,932 B1 | 1/2001 | Uckun et al. |
| 6,183,985 B1 | 2/2001 | Shuster |
| 6,183,987 B1 | 2/2001 | van de Wiel et al. |
| 6,201,072 B1 | 3/2001 | Rathi et al. |
| 6,214,966 B1 | 4/2001 | Harris |
| 6,225,060 B1 | 5/2001 | Clark et al. |
| 6,245,528 B1 | 6/2001 | Chao |
| 6,261,805 B1 | 7/2001 | Wood |
| RE37,343 E | 8/2001 | Tekamp-Olson |
| 6,281,211 B1 | 8/2001 | Cai et al. |
| 6,306,821 B1 | 10/2001 | Mikos et al. |
| 6,312,923 B1 | 11/2001 | Tekamp-Olson |
| 6,337,191 B1 | 1/2002 | Swartz et al. |
| 6,338,846 B1 | 1/2002 | Kang et al. |
| 6,342,216 B1 | 1/2002 | Fidler et al. |
| 6,361,969 B1 | 3/2002 | Galeotti |
| 6,368,825 B1 | 4/2002 | Chao |
| 6,420,339 B1 | 7/2002 | Gegg et al. |
| 6,423,685 B1 | 7/2002 | Drummond et al. |
| 6,428,954 B1 | 8/2002 | Wells et al. |
| 6,436,386 B1 | 8/2002 | Roberts et al. |
| 6,451,346 B1 | 9/2002 | Shah et al. |
| 6,451,561 B1 | 9/2002 | Wells et al. |
| 6,461,603 B2 | 10/2002 | Bentley et al. |
| 6,515,100 B2 | 2/2003 | Harris |
| 6,521,427 B1 | 2/2003 | Evans |
| 6,552,167 B1 | 4/2003 | Rose |
| 6,586,207 B2 | 7/2003 | Tirrell et al. |
| 6,602,498 B2 | 8/2003 | Shen |
| 6,608,183 B1 | 8/2003 | Cox |
| 6,610,281 B2 | 8/2003 | Harris |
| 6,646,110 B2 | 11/2003 | Nissen et al. |
| 6,927,042 B2 | 8/2005 | Schultz et al. |
| 7,045,337 B2 | 5/2006 | Schultz et al. |
| 7,052,872 B1 | 5/2006 | Hansen et al. |
| 7,083,970 B2 | 8/2006 | Schultz et al. |
| 2001/0021763 A1 | 9/2001 | Harris |
| 2001/0044526 A1 | 11/2001 | Shen |
| 2001/0056171 A1 | 12/2001 | Kozlowski |
| 2002/0002250 A1 | 1/2002 | Bentley et al. |
| 2002/0037949 A1 | 3/2002 | Harris et al. |
| 2002/0040076 A1 | 4/2002 | Harris et al. |
| 2002/0042097 A1 | 4/2002 | Tirrell et Kiick |
| 2002/0052009 A1 | 5/2002 | Hornauer et al. |
| 2002/0052430 A1 | 5/2002 | Harris et Kozlowski |
| 2002/0055169 A1 | 5/2002 | Tekamp-Olson |
| 2002/0072573 A1 | 6/2002 | Bentley et al. |
| 2002/0081660 A1 | 6/2002 | Swartz et al. |
| 2002/0082345 A1 | 6/2002 | Kozlowski et al. |
| 2002/0086939 A1 | 7/2002 | Kozlowski |
| 2002/0099133 A1 | 7/2002 | Kozlowski |
| 2002/0103345 A1* | 8/2002 | Zhu ..................... 530/388.15 |
| 2002/0156047 A1 | 10/2002 | Zhao |
| 2003/0023023 A1 | 1/2003 | Harris et al. |
| 2003/0082575 A1* | 5/2003 | Schultz et al. ................. 435/6 |
| 2003/0105224 A1 | 6/2003 | Roberts et al. |
| 2003/0105275 A1 | 6/2003 | Bentley et al. |
| 2003/0108885 A1 | 6/2003 | Schultz et al. |
| 2003/0114647 A1 | 6/2003 | Harris et al. |
| 2003/0143596 A1 | 7/2003 | Bentley et al. |
| 2003/0158333 A1 | 8/2003 | Roberts et Frang |
| 2003/0162949 A1 | 8/2003 | Cox |
| 2003/0220447 A1 | 11/2003 | Harris |
| 2003/0228274 A1 | 12/2003 | Rose |
| 2004/0001838 A1 | 1/2004 | Zhao et al. |
| 2004/0013637 A1 | 1/2004 | Bentley et Zhao |
| 2004/0198637 A1 | 10/2004 | Schultz et al. |
| 2004/0265952 A1* | 12/2004 | Deiters et al. .............. 435/68.1 |
| 2005/0009049 A1 | 1/2005 | Chin et al. |
| 2005/0085619 A1 | 4/2005 | Wilson et al. |
| 2005/0170404 A1 | 8/2005 | Cho et al. |
| 2005/0220762 A1 | 10/2005 | Cho et al. |

FOREIGN PATENT DOCUMENTS

| | | |
|---|---|---|
| EP | 036 676 | 9/1981 |
| EP | 036 776 | 9/1981 |
| EP | 052 322 | 5/1982 |
| EP | 058 481 | 8/1982 |
| EP | 073 657 | 3/1983 |
| EP | 102 324 | 3/1984 |
| EP | 121 775 | 10/1984 |
| EP | 127 839 | 12/1984 |
| EP | 133 988 | 3/1985 |
| EP | 143 949 | 6/1985 |
| EP | 154 316 | 9/1985 |
| EP | 155 476 | 9/1985 |
| EP | 164 556 | 12/1985 |
| EP | 183 503 | 6/1986 |
| EP | 188 256 | 7/1986 |
| EP | 229 108 | 7/1987 |
| EP | 244 234 | 11/1987 |
| EP | 267 851 | 5/1988 |
| EP | 284 044 | 9/1988 |
| EP | 324 274 | 7/1989 |
| EP | 329 203 | 8/1989 |
| EP | 340 986 | 11/1989 |
| EP | 400 472 | 12/1990 |
| EP | 402 378 | 12/1990 |
| EP | 439 508 | 8/1991 |

| | | |
|---|---|---|
| EP | 480 480 | 4/1992 |
| EP | 510 356 | 10/1992 |
| EP | 605 963 | 7/1994 |
| EP | 732 403 | 9/1996 |
| EP | 809 996 | 12/1997 |
| EP | 921 131 | 6/1999 |
| EP | 946 736 | 10/1999 |
| JP | 83-118008 | 1/1985 |
| WO | WO 88/07082 | 9/1988 |
| WO | WO 89/01037 | 2/1989 |
| WO | WO 89/01038 | 2/1989 |
| WO | WO 90/01556 | 2/1990 |
| WO | WO 90/02186 | 3/1990 |
| WO | WO 90/02566 | 3/1990 |
| WO | WO 90/05785 | 5/1990 |
| WO | WO 90/10078 | 9/1990 |
| WO | WO 90/10277 | 9/1990 |
| WO | WO 90/13540 | 11/1990 |
| WO | WO 90/14428 | 11/1990 |
| WO | WO 91/00357 | 1/1991 |
| WO | WO 92/01801 | 2/1992 |
| WO | WO 92/02628 | 2/1992 |
| WO | WO 92/16555 | 10/1992 |
| WO | WO 92/16619 | 10/1992 |
| WO | WO 93/03173 | 2/1993 |
| WO | WO 93/15189 | 8/1993 |
| WO | WO 93/21259 | 10/1993 |
| WO | WO 94/04193 | 3/1994 |
| WO | WO 94/09027 | 4/1994 |
| WO | WO 94/14758 | 7/1994 |
| WO | WO 94/15625 | 7/1994 |
| WO | WO 94/17039 | 8/1994 |
| WO | WO 94/18247 | 8/1994 |
| WO | WO 94/28024 | 12/1994 |
| WO | WO 95/00162 | 1/1995 |
| WO | WO 95/06058 | 3/1995 |
| WO | WO 95/11924 | 5/1995 |
| WO | WO 95/13090 | 5/1995 |
| WO | WO 95/13312 | 5/1995 |
| WO | WO 95/20672 | 8/1995 |
| WO | WO 95/33490 | 12/1995 |
| WO | WO 96/00080 | 1/1996 |
| WO | WO 96/06161 | 2/1996 |
| WO | WO 96/07670 | 3/1996 |
| WO | WO 96/21469 | 7/1996 |
| WO | WO 96/25496 | 8/1996 |
| WO | WO 96/29400 | 9/1996 |
| WO | WO 96/40791 | 12/1996 |
| WO | WO 96/41813 | 12/1996 |
| WO | WO 97/03106 | 1/1997 |
| WO | WO 97/18832 | 5/1997 |
| WO | WO 97/26332 | 7/1997 |
| WO | WO 97/32607 | 9/1997 |
| WO | WO 98/05363 | 2/1998 |
| WO | WO 98/26080 | 6/1998 |
| WO | WO 98/32466 | 7/1998 |
| WO | WO 98/37208 | 8/1998 |
| WO | WO 98/41562 | 9/1998 |
| WO | WO 98/48837 | 11/1998 |
| WO | WO 99/03887 | 1/1999 |
| WO | WO 99/05297 | 2/1999 |
| WO | WO 99/07862 | 2/1999 |
| WO | WO 99/09193 | 2/1999 |
| WO | WO 99/10515 | 3/1999 |
| WO | WO 99/31257 | 6/1999 |
| WO | WO 99/32134 | 7/1999 |
| WO | WO 99/32139 | 7/1999 |
| WO | WO 99/32140 | 7/1999 |
| WO | WO 99/45130 | 9/1999 |
| WO | WO 99/51721 | 10/1999 |
| WO | WO 99/66951 A2 | 12/1999 |
| WO | WO 99/67291 | 12/1999 |
| WO | WO 00/20032 | 4/2000 |
| WO | WO 00/26354 | 5/2000 |
| WO | WO 00/55345 | 9/2000 |
| WO | WO 00/55353 | 9/2000 |
| WO | WO 01/05956 | 1/2001 |
| WO | WO 01/27301 | 4/2001 |
| WO | WO 01/90390 | 11/2001 |
| WO | WO 02/06305 | 1/2002 |
| WO | WO 02/085923 | 10/2002 |
| WO | WO 02/085923 A | 10/2002 |
| WO | WO 02/086075 | 10/2002 |
| WO | WO 03/101972 | 12/2003 |
| WO | WO 2004/035605 | 4/2004 |
| WO | WO 2004/035743 | 4/2004 |
| WO | WO 2004/058946 | 7/2004 |
| WO | WO 2004/094593 | 11/2004 |
| WO | WO 2005/007624 | 1/2005 |
| WO | WO 2005/007870 | 1/2005 |
| WO | WO 2005/019415 | 3/2005 |
| WO | WO 2005/035727 | 4/2005 |
| WO | WO 2005/074524 | 8/2005 |
| WO | WO 2005/074546 | 8/2005 |
| WO | WO 2005/074650 | 8/2005 |

OTHER PUBLICATIONS

Rudikoff et al (Proc. Natl. Acad. Sci. USA, 79:1979-1983, Mar. 1982).*
Colman (Research in Immunology, 145:33-36, 1994).*
Bendig M. M. (Methods: A Companion to Methods in Enzymology, 1995; 8:83-93).*
MacCallum et al (J. Mol. Biol., 262, 732-745, 1996).*
Casset et al (Biochemical and Biophysical Research Communications, 307:198-205, 2003).*
Abuchowski, A. et al. "Cancer therapy with chemically modified enzymes. I. Antitumor properties of polyethylene glycol-asparaginase conjugates," Cancer Biochem Biophys. Jun. 1984;7(2):175-86.
Altschul, SF et al. "Gapped BLAST and PSI-BLAST: a new generation of protein database search programs," Nucleic Acids Res. Sep. 1, 1997;25(17):3389-402.
Altschul, SF et al. "Basic local alignment search tool," J Mol Biol. Oct. 5, 1990;215(3):403-10.
Amann, E et al., "Vectors bearing a hybrid trp-lac promoter useful for regulated expression of cloned genes in Escherichia coli," Gene. Nov. 1983;25(2-3):167-78.
Anderson, JC et al., "Exploring the limits of codon and anticodon size," Chem Biol. Feb. 2002;9(2):237-44.
Andresz, H et al. Abstract of "Chemische Synthese verzweigter Polysaccharide, 5; Kopplung von Oligosacchariden und Amylose an verschiedene Träger durch Hydrazonbindung," Makromol. Chem. 1978;179:301 Abstract.
Arnold, FH. "Protein engineering for unusual environments," Curr Opin Biotechnol. Aug. 1993;4(4):450-5.
Azoulay, M., et al. "Glutamine analogues as Potential Antimalarials," Eur. J. Med. Chem. (1991); 26(2):201-5.
Bain, JD, et al. "Biosynthetic site-specific incorporation of a non-natural amino acid into a polypeptide," J. Am Chem Soc 1989;111(20):8013-8014.
Ballance, DJ et al., "Transformation of Aspergillus nidulans by the orotidine-5'-phosphate decarboxylase gene of Neurospora crassa," Biochem Biophys Res Commun. Apr. 15, 1983;112(1):284-9.
Barany, F. et al., "Genetic disease detection and DNA amplification using cloned thermostable ligase," Proc Natl Acad Sci U S A. Jan. 1, 1991;88(1):189-93.
Barton, DHR et al., "Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives," Tetrahedron (1987) 43:4297-4308.
Bass, S et al., "Mutant Trp repressors with new DNA-binding specificities," Science (1988) 242:240-245.
Batzer, MA et al., "Enhanced evolutionary PCR using oligonucleotides with inosine at the 3'-terminus," Nucleic Acids Res. Sep. 25, 1991;19(18):5081.

Beach, D et al., "Functionally homologous cell cycle control genes in budding and fission yeast," Nature Dec. 1982; 300:706-709.

Beauchamp, CO et al., "A new procedure for the synthesis of polyethylene glycol-protein adducts; effects on function, receptor recognition, and clearance of superoxide dismutase, lactoferrin, and alpha 2-macroglobulin," Anal Biochem. May 1983;131(1):25-33.

Bernstein, FC, et al. "The protein data bank: a computer-based archival file for macromolecular structures," J. Mol. Biol. 1977;112:535-542.

Boissel, JP et al., "Erythropoietin structure-function relationships. Mutant proteins that test a model of tertiary structure," J Biol Chem. Jul. 25, 1993;268(21):15983-93.

Boles, JO et al. "Bio-incorporation of telluromethionine into buried residues of dihydrofolate reductase," Nat Struct Biol. May 1994;1(5):283-4.

Botstein, D et D Shortle, "Strategies and applications of in vitro mutagenesis," Science. Sep. 20, 1985;229(4719):1193-201.

Brunner, J. "New photolabeling and crosslinking methods," Annu Rev Biochem. 1993;62:483-514.

Buchner, J. et al., "A method for increasing the yield of properly folded recombinant fusion proteins: Single-chain immunotoxins from renaturation of bacterial inclusion bodies," Anal. Biochem. 1992;205(2): 263-270.

Bückmann et al. "Functionalization of Poly(ethylene glycol) and Monomethoxy-Poly(ethylene glycol)," Makromol. Chem. 1981;182:1379-84.

Budisa, N et al. "High-level biosynthetic substitution of methionine in proteins by its analogs 2-aminohexanoic acid, selenomethionine, telluromethionine and ethionine in *Escherichia coli*," Eur J Biochem. Jun. 1, 1995;230(2):788-96.

Budisa, N et al., "Bioincorporation of telluromethionine into proteins: a promising new approach for X-ray structure analysis of proteins," J Mol Biol. Jul. 15, 1997;270(4):616-23.

Budisa, N et al., "Toward the experimental codon reassignment in vivo: protein building with an expanded amino acid repertoire," FASEB J. Jan. 1999;13(1):41-51.

Cai, X-Y et al., "Expression, Purification, and Characterization of an Activated Cytokine-Suppressive Anti-inflammatory Drug-Binding Protein 2 (CSBP2) Kinase from Baculovirus-Infected Insect Cells," Protein Expression and Purification 1997; 10(2):263-74.

Carbonell, LF et al., "Baculovirus-mediated expression of bacterial genes in dipteran and mammalian cells," J Virol. Oct. 1985;56(1):153-60.

Carrasco, M. and R. Brown, "A Versatile Set of Aminooxy Amino Acids for the Synthesis of Neoglycopeptides," J. Org. Chem. (2003); 68(23): 8853-8858.

Carter, P. "Site-directed mutagenesis," Biochem J. Jul. 1, 1986; 237(1):1-7.

Carter, P et al., "Improved oligonucleotide site-directed mutagenesis using M13 vectors" Nucleic Acids Res. Jul. 25, 1985;13(12):4431-43.

Carter, P. "Improved oligonucleotide-directed mutagenesis using M13 vectors" Methods Enzymol. 1987;154:382-403.

Chaiken, IM. "Semisynthetic peptides and proteins," CRC Crit Rev Biochem. 1981;11(3):255-301.

Chin, JW et al., "Addition of p-azido-L-phenylalanine to the genetic code of *E. coli*," J Am Chem Soc. Aug. 7, 2002;124(31):9026-7.

Chin, JW et al., "Addition of a photocrosslinking amino acid to the genetic code of *Escherichia coli*," Proc Natl Acad Sci U S A. Aug. 20, 2002;99(17):11020-4. Epub Aug. 1, 2002.

Chin, JW et al., "An expanded eukaryotic genetic code," Science. Aug. 15, 2003;301(5635):964-7.

Chin, JW & P. G. Schultz, "In vivo photocrosslinking with unnatural amino acid mutagenesis," Chembiochem. Nov. 4, 2002; 3(11):1135-7.

Christie, B.D. & Rapoport, H. "Synthesis of Optically Pure Pipecolates from L-Asparagine. Application to the Total Synthesis of (+)-Apovincamine through Amino Acid Decarbonylation and Iminium Ion Cyclization," J. Org. Chem. 1985;50(8):1239-1246.

Clark, R et al., "Long-acting growth hormones produced by conjugation with polyethylene glycol," J Biol Chem. Sep. 6, 1996;271(36):21969-77.

Corey, D.R., Schultz, P.G. "Generation of a hybrid sequence-specific single-stranded deoxyribonuclease," Science 1987;238(4832):1401-1403.

Cornish, VW, et al., "Site-Specific Protein Modification Using a Ketone Handle," J. Am. Chem. Soc. 1996; 118(34):8150-8151.

Cornish, VW et al., "Probing Protein Structure and Function with an Expanded Genetic Code," Angew Chem Int Ed Engl,1995;34(6):621-33.

Craig, J.C. et al. "Absolute Configuration of the Enantiomers of 7-Chloro-4 ([4-(diethylamino)-1-methylbutyl]amino)quinoline (Chloroquine)," J. Org. Chem. 1988; 53(6):1167-1170.

Cregg, JM et al., "*Pichia pastoris* as a host system for transformations," Mol Cell Biol. Dec. 1985;5(12):3376-85.

Crick, FHC, et al. "General nature of the genetic code for proteins," Nature. Dec. 30, 1961;192:1227-32.

Dale et al., Oligonucleotide-directed random mutagenesis using the phosphorothioate method, Methods Mol. Biol.1996;57:369-374.

Das, S et al., "Transformation of *Kluyveromyces fragilis*," J Bacteriol. Jun. 1984;158(3):1165-7.

Dawson, P. E. and S. B. H. Kent, "Synthesis of native proteins by chemical ligation," Annu. Rev. Biochem. 2000; 69:923-60.

De Boer, HA et al., "The tac promoter: a functional hybrid derived from the trp and lac promoters," Proc Natl Acad Sci U S A. Jan. 1983;80(1):21-5.

De Louvencourt, L et al., "Transformation of *Kluyveromyces lactis* by killer plasmid DNA," J Bacteriol. May 1983;154(2):737-42.

Debinski, W et al. "A wide range of human cancers express interleukin 4 (IL4) receptors that can be targeted with chimeric toxin composed of IL4 and Pseudomonas exotoxin," J Biol Chem. Jul. 5, 1993;268(19):14065-70.

Deiters, A., et al., "Adding Amino Acids with Novel Reactivity to the Genetic Code of *Saccharomyces Cerevisiae*," J. Am. Chem. Soc. 2003; 125(39):11782-11783.

Delgado, C et al., "The uses and properties of PEG-linked proteins," Crit Rev Ther Drug Carrier Syst. 1992;9(3-4):249-304.

Dennis, MS et al., "Albumin binding as a general strategy for improving the pharmacokinetics of proteins," J Biol Chem. Sep. 20, 2002;277(38):35035-43. Epub Jul. 15, 2002.

Dolphin, CT et al., "Missense mutation in flavin-containing monooxygenase 3 gene, FMO3, underlies fish-odour syndrome," Nat Genet. Dec. 1997;17(4):491-4.

Doring, V et al., "Enlarging the amino acid set of *Escherichia coli* by infiltration of the valine coding pathway," Science. Apr. 20, 2001;292(5516):501-4.

Dougherty, DA. "Unnatural amino acids as probes of protein structure and function," Curr Opin Chem Biol. Dec. 2000;4(6):645-52.

Duewel, H et al., "Incorporation of trifluoromethionine into a phage lysozyme: implications and a new marker for use in protein 19F NMR," Biochemistry. Mar. 18, 1997;36(11):3404-16.

Eghtedarzadeh MK & S Henikoff "Use of oligonucleotides to generate large deletions" Nucleic Acids Res. Jun. 25, 1986;14(12):5115.

Elling L et MR Kula., "Immunoaffinity partitioning: synthesis and use of polyethylene glycol-oxirane for coupling to bovine serum albumin and monoclonal antibodies," Biotechnol Appl Biochem. Jun. 1991;13(3):354-62.

Elliott, S et al., "Yeast-derived recombinant human insulin-like growth factor I: production, purification, and structural characterization," J Protein Chem. Feb. 1990;9(1):95-104.

Ellman, J.A., Mendel, D., Anthony-Cahill, S., Noren, C.J., Schultz, P.G. "Biosynthetic method for introducing unnatural amino acids site-specifically into proteins," Methods in Enz., 1992;202:301-336.

Ellman, JA, et al. "Site-specific incorporation of novel backbone structures into proteins," Science. Jan. 10, 1992;255(5041):197-200.

England, P. M., et al., "Backbone mutations in transmembrane domains of a ligand-gated ion channel: implications for the mechanism of gating," Cell. Jan. 8, 1999;96(1):89-98.

Eppstein et al., "Biological Activity of Liposome-Encapsulated Murine Interferon is Mediated by a Cell Membrane Receptor," Proc. Natl. Acad. Sci. U.S.A.(1985); 82: 3688-3692.

Fieschko, JC et al., "Controlled expression and purification of human immune interferon from high-cell-density fermentations of *Saccharomyces cerevisiae*," Biotech. Bioeng. (1987) 29(9):1113-21.

Forster, AC et al., "Programming peptidomimetic syntheses by translating genetic codes designed de novo," Proc Natl Acad Sci U S A. May 27, 2003;100(11):6353-7. Epub May 16, 2003.

Frankel, A et al., "Encodamers: unnatural peptide oligomers encoded in RNA," Chem Biol. Nov. 2003;10(11):1043-50.

Fraser, MJ et al., "Expression of eucaryotic genes in insect cell cultures," In Vitro Cell. Dev. Biol. 1989; 25:225-235.

Friedman, O.M. & R. Chatterrji. "Synthesis of Derivatives of Glutamine as Model Substrates for Anti-Tumor Agents," J. Am. Chem. Soc. 1959; 81(14):3750-3752.

Fritz HJ et al., "Oligonucleotide-directed construction of mutations: a gapped duplex DNA procedure without enzymatic reactions in vitro," Nucleic Acids Res. Jul. 25, 1988;16(14B):6987-99.

Fromm, M. et al., "Expression of Genes Transferred into Monocot and Dicot Plant Cells by Electroporation," Proc. Natl. Acad. Sci. USA (1985) 82:5824-8.

Furter, R. "Expansion of the genetic code: site-directed p-fluorophenylalanine incorporation in *Escherichia coli*," Protein Sci. Feb. 1998;7(2):419-26.

Gaertner, HF et al., "Construction of protein analogues by site-specific condensation of unprotected fragments," Bioconjug Chem. May-Jun. 1992;3(3):262-8.

Gaertner, HF et al., "Chemo-enzymic backbone engineering of proteins. Site-specific incorporation of synthetic peptides that mimic the 64-74 disulfide loop of granulocyte colony-stimulating factor," J Biol Chem. Mar. 11, 1994;269(10):7224-30.

Gallivan, JP et al., "Site-specific incorporation of biotinylated amino acids to identify surface-exposed residues in integral membrane proteins," Chem Biol. Oct. 1997;4(10):739-49.

Gellissen, G et al., "Heterologous protein production in yeast," Antonie Van Leeuwenhoek. Aug. 1992;62(1-2):79-93.

Geoghegan, KF and JG Stroh, "Site-directed conjugation of nonpeptide groups to peptides and proteins via periodate oxidation of a 2-amino alcohol. Application to modification at N-terminal serine," Bioconjug Chem. Mar.-Apr. 1992;3(2):138-46.

Gillam, S. & M Smith, "Site-specific mutagenesis using synthetic oligodeoxyribonucleotide primers: I. Optimum conditions and minimum oligodeoxyribonucleotide length," Gene 1979; 8(1):81-97.

Gleeson, MA et al., "Transformation of the methylotrophic yeast hansenula polymorphica," J. Gen. Microbiol. (1986) 132:3459-3465.

Goeddel, DV, "Systems for heterologous gene expression," Methods Enzymol. 1990;185:3-7.

Goeddel, DV et al., "Synthesis of human fibroblast interferon by *E. coli*," Nucleic Acids Res. Sep. 25, 1980;8(18):4057-74.

Goodson RJ et NV Katre. "Site-directed pegylation of recombinant interleukin-2 at its glycosylation site," Biotechnology (N Y). Apr. 1990;8(4):343-6.

Graves, SW et al., "Expression, purification, and initial kinetic characterization of the large subunit of the human mitochondrial DNA polymerase," Biochemistry. Apr. 28, 1998;37(17):6050-8.

Griffin, BA et al., "Specific Covalent Labeling of Recombinant Protein Molecules Inside Live Cells," Science (1998) 281:269-272.

Grundström T et al., "Oligonucleotide-directed mutagenesis by microscale 'shot-gun' gene synthesis," Nucleic Acids Res. May 10, 1985;13(9):3305-16.

Guckian, KM and ET Kool, "Highly Precise Shape Mimicry by a Difluorotoluene Deoxynucleoside, a Replication-Competent Substitute for Thymidine," Angew. Chem. Int. Ed. Engl (1998) 36(24):2825-8.

Hamano-Takaku, F et al., "A mutant *Escherichia coli* tyrosyl-tRNA synthetase utilizes the unnatural amino acid azatyrosine more efficiently than tyrosine," J Biol Chem. Dec. 22, 2000;275(51):40324-8.

Hang, HC and CR Bertozzi, "Chemoselective approaches to glycoprotein assembly," Acc Chem Res. Sep. 2001;34(9):727-36.

Harris, JM et al. "Synthesis and Characterization of Poly(ethylene Glycol) Derivatives," J. Polym. Sci. Chem. Ed. 1984; 22:341-352.

Harris, JM. "Laboratory Synthesis of Polyethylene Glycol Derivatives," JMS-Rev. Macromol. Chem. Phys. 1985;C25(3): 325-373.

Hendrickson, WA et al., "Selenomethionyl proteins produced for analysis by multiwavelength anomalous diffraction (MAD): a vehicle for direct determination of three-dimensional structure," EMBO J. May 1990;9(5):1665-72.

Henikoff, S and JG Henikoff "Amino Acid Substitution Matrices from Protein Blocks," Proc. Natl. Acad. Sci. USA 1992; 89:10915-9.

Hess, B. et al., "Cooperation of glycolytic enzymes," J. Adv. Enzyme Reg. (1969) 7:149-67.

Hinnen, A et al., "Transformation of yeast," Proc Natl Acad Sci U S A. Apr. 1978;75(4):1929-33.

Hirao, I et al., "An unnatural base pair for incorporating amino acid analogues into proteins," Nat Biotechnol. Feb. 2002;20(2):177-82.

Hitzeman, RA et al., "Isolation and characterization of the yeast 3-phosphoglycerokinase gene (PGK) .by an immunological screening technique," J. Biol Chem. Dec. 25, 1980;255(24):12073-80.

Hofmann, K., et H. Bohn. "Studies on polypeptides. XXXVI. The effect of pyrazole-imidazole replacements on the S-protein activating potency of an S-peptide fragment," J. Am Chem, (1966);88(24) :5914-5919.

Hohsaka, T et al., "Efficient Incorporation of Nonnatural Amino Acids with Large Aromatic Groups into Streptavidin in In Vitro Protein Synthesizing Systems," J. Am. Chem. Soc. 1999; 121(1); 34-40.

Hohsaka, T et al., "Incorporation of Two Different Nonnatural Amino Acids Independently into a Single Protein through Extension of the Genetic code," J. Am. Chem. Soc. 1999; 121(51):12194-12195.

Holland, MJ et JP Holland., "Isolation and identification of yeast messenger ribonucleic acids coding for enolase, glyceraldehyde-3-phosphate dehydrogenase, and phosphoglycerate kinase," Biochemistry. Nov. 14, 1978;17(23):4900-7.

Holland, MJ et al., "The primary structures of two yeast enolase genes. Homology between the 5' noncoding flanking regions of yeast enolase and glyceraldehyde-3-phosphate dehydrogenase genes," J Biol Chem. Feb. 10, 1981;256(3):1385-95.

Hsiao, CL et J Carbon, "High-frequency transformation of yeast by plasmids containing the cloned yeast ARG4 gene," Proc Natl Acad Sci U S A. Aug. 1979;76(8):3829-33.

Huisgen, R. in 1, 3-Dipolar Cycloaddition Chemistry, vol. 1, 1984; Ed. Padwa A.; John Wiley and Sons, New York, p. 1-176.

Hwang, KJ et al., "Hepatic uptake and degradation of unilamellar sphingomyelin/cholesterol liposomes: a kinetic study," Proc Natl Acad Sci U S A. Jul. 1980;77(7):4030-4.

Ibba, M et al., "Substrate specificity is determined by amino acid binding pocket size in *Escherichia coli* phenylalanyl-tRNA synthetase," Biochemistry. Jun. 14, 1994;33(23):7107-12.

Ibba, M and H Hennecke, "Relaxing the substrate specificity of an aminoacyl-tRNA synthetase allows in vitro and in vivo synthesis of proteins containing unnatural amino acids," FEBS Lett. May 15, 1995;364(3):272-5.

Ito, H. et al., "Transformation of intact yeast cells treated with alkali cations," J. Bacteriol. 1983; 153(1):163-8.

Jackson, DY et al. "A designed peptide ligase for total synthesis of ribonuclease A with unnatural catalytic residues," Science. Oct. 14, 1994;266(5183):243-7.

Jakobsson, PJ et al., "Identification and characterization of a novel human microsomal glutathione S-transferase with leukotriene C4 synthase activity and significant sequence identity to 5-lipoxygenase-activating protein and leukotriene C4 synthase," J Biol Chem. Sep. 6, 1996;271(36):22203-10.

Jencks, W.P., "Studies on the Mechanism of Oxime and Semicarbazone Formation," J. Am. Chem. Soc.; 1959; 81(2):475-481.

Joppich, M. et al. "Peptides Flanked by Two Polymer Chains, 1; Synthesis of Glycyl-L-tryptophylglycine Substituted by Poly(ethylene oxide) at both the Carboxy and the Amino End Groups," Makromol. Chem. 1979;180:1381-4.

Kaiser, ET. "Synthetic approaches to biologically active peptides and proteins including enzymes," Acc Chem Res, (1989); 22(2) :47-54.

Kaiser, ET et al. "The chemical modification of enzymatic specificity," Annu Rev Biochem. 1985;54:565-95.

Kaiser, ET and DS Lawrence. "Chemical mutation of enzyme active sites," Science. Nov. 2, 1984;226(4674):505-11.

Karlin, S and SF Altschul "Applications and statistics for multiple high-scoring segments in molecular sequences," Proc Natl Acad Sci U S A. Jun. 15, 1993;90(12):5873-7.

Kayser, B., et al., "Alkyne bridged alpha- amino acids by palladium mediated coupling of alkynes with N-t-Boc-4-iodo-phenylalanine methyl ester," Tetrahedron (1997); 53(7): 2475-2484.

Kelly, JM and MJ Hynes, "Transformation of *Aspergillus niger* by the amdS gene of *Aspergillus nidulans*," EMBO J. 1985; 4(2):475-479.

Kiick, K. L. And D. A. Tirrell, "Protein Engineering by In Vivo Incorporation of Non-Natural Amino Acids: Control of Incorporation of Methionine Analogues by Methionyl-tRNA Synthetase," Tetrahedron (2000), 56:9487-9493.

Kiick, KL et al., "Incorporation of azides into recombinant proteins for chemoselective modification by the Staudinger ligation," Proc Natl Acad Sci U S A. Jan. 8, 2002;99(1):19-24. Epub Dec. 18, 2001.

Kim, DM and JR Swartz, "Regeneration of adenosine triphosphate from glycolytic intermediates for cell-free protein synthesis," Biotechnol Bioeng. Aug. 20, 2001;74(4):309-16.

Kim, DM and JR Swartz, "Oxalate improves protein synthesis by enhancing ATP supply in a cell-free system derived from *Escherichia coli*," Biotechnology Letters, 2000; 22:1537-1542.

Kim, DM, and JR Swartz, "Prolonging cell-free protein synthesis by selective reagent additions," Biotechnol Prog. May-Jun. 2000;16(3):385-90.

Kim, DM, and JR Swartz, "Prolonging cell-free protein synthesis with a novel ATP regeneration system," Biotechnol Bioeng. 1999;66(3):180-8.

King, F.E. & Kidd, D.A.A. "A New Synthesis of Glutamine and of γ-Dipeptides of Glutamic Acid from Phthylated Intermediates," J. Chem. Soc. 1949; 3315-3319.

Kingsman, AJ et al., "Replication in *Saccharomyces cerevisiae* of plasmid pBR313 carrying DNA from the yeast trpl region," Gene. Oct. 1979;7(2):141-52.

Kitts, PA et al. "Linearization of baculovirus DNA enhances the recovery of recombinant virus expression vectors," Nucleic Acids Res. Oct. 11, 1990;18(19):5667-72.

Klein, TM et al., "High-velocity microprojectiles for delivering nucleic acids into living cells," Nature 1987; 327(6117):70-73.

Kobayashi, T. et al., "Structural basis for orthogonal tRNA specificities of tyrosyl-tRNA synthetases for genetic code expansion," Nature Structural Biology (2003); 10(6):425-432.

Kogan, TP. "The synthesis of substituted methoxy-poly(ethyleneglycol) derivatives suitable for selective protein modification," Synthetic Comm. 1992; 22(16):2417-24.

Kool, ET. "Synthetically modified DNAs as substrates for polymerases," Curr Opin Chem Biol. Dec. 2000;4(6):602-8.

Koskinen, A.M.P. & Rapoport, H. "Synthesis of 4-Substituted Prolines as Conformationally Constrained Amino Acid Analogues," J. Org. Chem. (1989) 54(8):1859-1866.

Kost, TA et al., "Production of a urokinase plasminogen activator-IgG fusion protein (uPA-IgG) in the baculovirus expression system," Gene. Apr. 29, 1997;190(1):139-44.

Kramer, W et al., "The gapped duplex DNA approach to oligonucleotide-directed mutation construction," Nucleic Acids Res. Dec. 21, 1984;12(24):9441-56.

Kramer, W & Fritz HJ. "Oligonucleotide-directed construction of mutations via gapped duplex DNA" Methods Enzymol. 1987;154:350-67.

Kramer, W. et al., "Improved enzymatic in vitro reactions in the gapped duplex DNA approach to oligonucleotide-directed construction of mutations," Nucleic Acids Res. Jul. 25, 1988;16(14B):7207.

Kramer, B. et al., "Different base/base mismatches are corrected with different efficiencies by the methyl-directed DNA mismatch-repair system of *E. coli*," Cell. Oct. 1984;38(3):879-87.

Kreitman, RJ and I. Pastan "Purification and characterization of IL6-PE4E, a recombinant fusion of interleukin 6 with Pseudomonas exotoxin," Bioconjug Chem. Nov.-Dec. 1993;4(6):581-5.

Krieg, UC, et al. "Photocrosslinking of the signal sequence of nascent preprolactin to the 54-kilodalton polypeptide of the signal recognition particle," Proc Natl Acad Sci U S A. Nov. 1986;83(22):8604-8.

Kunitani, M. et al., "Reversed-phase chromatography of interleukin-2 muteins," J Chromatogr. May 30, 1986;359:391-402.

Kunkel, "The efficiency of oligonucleotide directed mutagenesis," in Nucleic Acids & Molecular Biology 1987; Eckstein, F. and Lilley, D.M.J. eds.; Springer Verlag, Berlin; 124-135.

Kunkel, TA "Rapid and efficient site-specific mutagenesis without phenotypic selection," Proc Natl Acad Sci U S A. Jan. 1985;82(2):488-92.

Kunkel, TA et al., "Rapid and efficient site-specific mutagenesis without phenotypic selection," Methods Enzymol. 1987;154:367-82.

Kunze, G et al., "Transformation of the industrially important yeasts *Candida maltosa* and *Pichia guilliermondii*," J. Basic Microbiol. 1985; 25:141-4.

Kurtz et al., "Integrative transformation of *Candida albicans*, using a cloned *Candida* ADE2 gene," Mol Cell Biol. Jan. 1986;6(1):142-9.

Kurtzhals, P et al., "Albumin binding of insulins acylated with fatty acids: characterization of the ligand-protein interaction and correlation between binding affinity and timing of the insulin effect in vivo," Biochem J. Dec. 15, 1995;312 ( Pt 3):725-31.

Langer, R et al., "Biocompatibility of polymeric delivery systems for macromolecules," J Biomed Mater Res. Mar. 1981;15(2):267-77.

Langer, R. "Controlled release of macromolecules, " Chem. Tech. 1982; 12: 98-105.

Liebman, JM et al., "When less is more: enhanced baculovirus production of recombinant proteins at very low multiplicities of infection," Biotechniques. Jan. 1999;26(1):36-8, 40, 42.

Ling, MM et BH Robinson, "Approaches to DNA mutagenesis: an overview" Anal Biochem. Dec. 15, 1997;254(2):157-78.

Liu, H. et al. "A Method for the Generation of Glycoprotein Mimetics," J. Am. Chem. Soc. 2003 125(7): 1702-1703.

Liu, D.R. & Schultz, P.G. "Progress toward the evolution of an organism with an expanded genetic code," Proc Natl Acad Sci U S A. Apr. 27, 1999;96(9):4780-5.

Lorimer, I. A. et I. Pastan, "Random recombination of antibody single chain Fv sequences after fragmentation with DNaseI in the presence of Mn2+," Nucleic Acids Res. Aug. 11, 1995;23(15):3067-8.

Lu, T. et al. "Probing ion permeation and gating in a K +channel with backbone mutations in the selectivity filter," Nature Neurosci. Mar. 2001;4(3):239-246.

Luckow, VA and MD Summers, "High level expression of nonfused foreign genes with Autographa californica nuclear polyhedrosis virus expression vectors," Virology. May 1989;170(1):31-9.

Ma, C et al., "In vitro protein engineering using synthetic tRNA(Ala) with different anticodons," Biochemistry. Aug. 10, 1993;32(31):7939-45.

Magliery, TJ et al. "Expanding the Genetic Code: Selection of Efficient Suppressors of Four-base Codons and Identification of "Shifty" Four-base Codons with a Library Approach in *Escherichia coli*," J Mol Biol. Mar. 30, 2001;307(3):755-69.

Mahal, L. K., et al., "Engineering chemical reactivity on cell surfaces through oligosaccharide biosynthesis," Science. May 16, 1997;276(5315):1125-8.

Makrides, SC et al., "Extended in vivo half-life of human soluble complement receptor type 1 fused to a serum albumin-binding receptor," J Pharmacol Exp Ther. Apr. 1996;277(1):534-42.

Mamot, C, et al., "Epidermal growth factor receptor (EGFR)—targeted immunoliposomes mediate specific and efficient drug delivery to EGFR- and EGFRvIII-overexpressing tumor cells," Cancer Res. Jun. 15, 2003;63(12):3154-61.

Mandecki, W. Oligonucleotide-directed double-strand break repair in plasmids of *Escherichia coli*: a method for site-specific mutagenesis, Proc Natl Acad Sci U S A. Oct. 1986;83(19):7177-81.

Mann, SG and LA King, "Efficient transfection of insect cells with baculovirus DNA using electroporation," J Gen Virol. Dec. 1989;70 (Pt 12):3501-5.

Matsoukas, JM et al., "Differences in backbone structure between angiotensin II agonists and type I antagonists," J Med Chem. Nov. 10, 1995;38(23):4660-9.

McMinn, DL et al., "Efforts toward Expansion of the Genetic Alphabet: DNA Polymerase Recognition of a Highly Stable, Self-Pairing Hydrophobic Base," J. Am. Chem. Soc. 1999; 121(49):11585-6.

Meggers, E et al., "A Novel Copper-Mediated DNA Base Pair," J. Am. Chem. Soc. 2000; 122(43):10714-10715.

Mehvar, R.,"Modulation of the pharmacokinetics and pharmacodynamics of proteins by polyethylene glycol conjugation" J Pharm Pharm Sci. Apr.-Jan. 2000;3(1):125-36.

Mendel, D, et al. "Site-directed mutagenesis with an expanded genetic code," Annu Rev Biophys Biomol Struct. 1995;24:435-62.

Miller, LK, "Baculoviruses as gene expression vectors," Ann. Rev. Microbiol. 1988; 42:177-99.

Miller, LK. "Insect baculoviruses: powerful gene expression vectors," Bioessays. Oct. 1989;11(4):91-5.

Miller, JC et al. "Flash decaging of tyrosine sidechains in an ion channel," Neuron. Apr. 1998;20(4):619-24.

Minks, C. et al., Noninvasive tracing of recombinant proteins with "fluorophenylalanine-fingers," Anal Biochem. Aug. 15, 2000;284(1):29-34.

Miyanohara, A et al., "Expression of hepatitis B surface antigen gene in yeast," Proc Natl Acad Sci U S A. Jan. 1983;80(1):1-5.

Moore, B. et al., "Quadruplet codons: implications for code expansion and the specification of translation step size," J. Mol. Biol. 2000; 298(2):195-209.

Mosbach, K. et al., "Formation of proinsulin by immobilized *Bacillus subtilis*," Nature Apr. 1983; 302:543-545.

Nakamaye, KL & Eckstein F, "Inhibition of restriction endonuclease Nci I cleavage by phosphorothioate groups and its application to oligonucleotide-directed mutagenesis" Nucleic Acids Res. Dec. 22, 1986;14(24):9679-98.

Nakatsuka, T., et al. "Peptide segment coupling catalyzed by the semisynthetic enzyme thiosubtilisin," J Am Chem Soc, 1987; 109(12): 3808-3810.

Nambiar, KP et al., "Total synthesis and cloning of a gene coding for the ribonuclease S protein," Science (1984) 223: 1299-1301.

Needleman, SB and Wunsch CD, "A general method applicable to the search for similarities in the amino acid sequence of two proteins," J Mol Biol. Mar. 1970;48(3):443-53.

Neet, KE et al. "Properties of thiol-subtilisin. The consequences of converting the active serine residue to cysteine in a serine protease," J Biol Chem. Dec. 25, 1968;243(24):6392-401.

Nielsen, UB, et al., "Therapeutic efficacy of anti-ErbB2 immunoliposomes targeted by a phage antibody selected for cellular endocytosis," Biochim Biophys Acta. Aug. 19, 2002;1591(1-3):109-118.

Nomura, T. et al., "Purification, cDNA Cloning, and Expression of UDP-Gal: Glucosylceramide -1,4-Galactosyltransferase from Rat Brain," J. Biol. Chem. 1998; 273(22):13570-7.

Noren, CJ et al. "A general method for site-specific incorporation of unnatural amino acids into proteins," Science. Apr. 14, 1989;244(4901):182-8.

Nowak, MW et al., "Nicotinic receptor binding site probed with unnatural amino acid incorporation in intact cells," Science. Apr. 21, 1995;268(5209):439-42.

Ogawa, AK et al., "Efforts toward the Expansion of the Genetic Alphabet: Information Storage and Replication with Unnatural Hydrophobic Base Pairs," J. Am. Chem. Soc. 2000; 122(14):3274-3287.

Ogawa, AK et al., "Rational Design of an Unnatural Base Pair with Increased Kinetic Selectivity," J. Am. Chem. Soc. 2000; 122(36);8803-8804.

Ohtsuka, E et al., "An alternative approach to deoxyoligonucleotides as hybridization probes by insertion of deoxyinosine at ambiguous codon positions," J Biol Chem. Mar. 10, 1985;260(5):2605-8.

Olson et al. "Preparation and Characterization of Poly(ethylene glycol)yated Human Growth Hormone Antagonist," in Poly(ethylene glycol) Chemistry & Biological Applications, 1997; Eds. JM Harris & S. Zalipsky; ACS, Washington, D.C., 170-181.

Padwa, A. "Intermolecular 1,3-Dipolar Cycloadditions," in Comprehensive Organic Synthesis, vol. 4, (1991) Ed. Trost, B. M.; Pergamon, Oxford, 1069-1109.

Palva, I et al., "Secretion of interferon by *Bacillus subtilis*," Gene. May-Jun. 1983;22(2-3):229-35.

Park, JW, et al., "Development of anti-p185HER2 immunoliposomes for cancer therapy," Proc Natl Acad Sci U S A. Feb. 28, 1995;92(5):1327-31.

Park, JW, et al., "Anti-HER2 immunoliposomes: enhanced efficacy attributable to targeted delivery," Clin Cancer Res. Apr. 2002;8(4):1172-81.

Patnaik, R. and JR Swartz, "*E. coli*-based in vitro transcription/translation: in vivo-specific synthesis rates and high yields in a batch system," Biotechniques. May 1998;24(5):862-8.

Pearson, WR and DJ Lipman, "Improved tools for biological sequence comparison," Proc Natl Acad Sci U S A. Apr. 1988;85(8):2444-8.

Pepinsky, RB., et al., "Improved pharmacokinetic properties of a polyethylene glycol-modified form of interferon-beta-1a with preserved in vitro bioactivity," J Pharmacol Exp Ther. Jun. 2001;297(3):1059-66.

Piccirilli, JA et al., "Enzymatic incorporation of a new base pair into DNA and RNA extends the genetic alphabet," Nature 1990; 343:33-37.

Pintar, A et al. "CX, an algorithm that identifies protruding atoms in proteins," Bioinformatics. Jul. 2002;18(7):980-4.

Pitha, J et al. "Detergents linked to polysaccharides: preparation and effects on membranes and cells," Eur J Biochem. Feb. 15, 1979;94(1):11-8.

Polgar, L. and ML Bender. "A new enzyme containing a synthetically formed active site. Thiol-subtilisin." J. Am Chem Soc., 1966; 88(13): 3153-3154.

Pollack, SJ et al. "Introduction of nucleophiles and spectroscopic probes into antibody combining sites," Science. Nov. 18, 1988;242(4881):1038-40.

Preneta, AZ. "Separation on the basis of size: gel permeation chromatography," in Protein Purification Methods, a practical approach, 1989; Eds. Harris & Angal; IRL Press, Oxford; 293-306.

Raibaud, O et M Schwartz. "Positive control of transcription initiation in bacteria," Annu Rev Genet. 1984;18:173-206.

Reverey, H. et al., "Differential Fatty Acid Selection during Biosynthetic S-Acylation of a Transmembrane Protein (HEF) and Other Proteins in Insect Cells (Sf9) and in Mammalian Cells (CV1)," J. Biol. Chem. 1996; 271(39):23607-10.

Rivier, J et R McClintock, "Reversed-phase high-performance liquid chromatography of insulins from different species," J Chromatogr. Sep. 23, 1983;268(1):112-9.

Roberts, et al., "Generation of an antibody with enhanced affinity and specificity for its antigen by protein engineering," Nature 1987;328:731-734.

Roberts, RW and JW Szostak, "RNA-peptide fusions for the in vitro selection of peptides and proteins," Proc Natl Acad Sci U S A. Nov. 11, 1997;94(23):12297-302.

Roggenkamp, R. et al., "Transformation of the methylotrophic yeast Hansenula polymorpha by autonomous replication and integration vectors," Mol. Genetics and Genomics 1986;202(2):302-8.

Romani et al. "Synthesis of unsymmetrical cystine peptides: directed disulfide pairing with the sulfenohydrazide method," in Chemistry of Peptides and Proteins 1984; eds. Voelter, W. et al.; Walter de Gruyter et al., Berlin; vol. 2:29-33.

Romanos, MA et al., "Foreign gene expression in yeast: a review," Yeast. Jun. 1992;8(6):423-88.

Rosenthal, GA. "L-canaline: a potent antimetabolite and anti-cancer agent from leguminous plants," Life Sci.1997;60(19):1635-41.

Rossolini, GM et al., "Use of deoxyinosine-containing primers vs degenerate primers for polymerase chain reaction based on ambiguous sequence information," Mol. Cell. Probes 1994; 8:91-98.

Rostovtsev, VV et al., "A stepwise huisgen cycloaddition process: copper(I)-catalyzed regioselective "ligation" of azides and terminal alkynes," Angew Chem Int Ed Engl Jul. 15, 2002;41(14):2596-9.

Rowles, J et al., "Cloning and characterization of PDK4 on 7q21.3 encoding a fourth pyruvate dehydrogenase kinase isoenzyme in human," J Biol Chem. Sep. 13, 1996;271(37):22376-82.

Sakmar, TP and Khorana HG, "Total synthesis and expression of a gene for the alpha-subunit of bovine rod outer segment guanine nucleotide-binding protein (transducin)" Nucleic Acids Res. Jul. 25, 1988;16(14A):6361-72.

Sandler and Karo, "Polyoxyalkylation of hydroxyl compounds," in Polymer Synthesis, vol. 3, 1980; Academic Press, New York, 138-161.

Sartore, L et al., "Enzyme modification by MPEG with an amino acid or peptide as spacer arms," Appl Biochem Biotechnol. Jan. 1991;27(1):45-54.

Sawhney, AS et al., "Bioerodible Hydrogels Based on Photopolymerized Poly(ethylene glycol)-co-poly(alpha-hydroxy acid) Diacrylate Macromers," Macromolecules 1993; 26(4):581-7.

Saxon, E and C. Bertozzi, "Cell Surface Engineering by a Modified Staudinger Reaction," Science (2000); 287(5460):2007-2010.

Sayers, JR et al., "Strand specific cleavage of phosphorothioate-containing DNA by reaction with restriction endonucleases in the presence of ethidium bromide" Nucleic Acids Res. Feb. 11, 1988;16(3):803-14.

Sayers, JR, et al. "5'-3' exonucleases in phosphorothioate-based oligonucleotide-directed mutagenesis," Nucleic Acids Res. Feb. 11, 1988;16(3):791-802.

Schanbacher, FL et al. "Galactosyltransferase Acceptor Specificity of the Lactose Synthetase A Protein," J. Biol. Chem. 1970;245(19):5057-5061.

Schmidt, M et al., "Baculovirus-mediated large-scale expression and purification of a polyhistidine-tagged rubella virus capsid protein," Protein Expr Purif. Apr. 1998;12(3):323-30.

Schneider, E., et al., "Functional Purification of a Bacterial ATP-Binding Cassette Transporter Protein (MalK) from the Cytoplasmic Fraction of an Overproducing Strain," Protein Expr. Purif. 1995; 6(1):10-14.

Schnolzer, M. and SBH Kent. "Constructing proteins by dovetailing unprotected synthetic peptides: backbone-engineered HIV protease," Science. Apr. 10, 1992;256(5054):221-5.

Scouten, WH. "A survey of enzyme coupling techniques," Methods Enzymol. 1987;135:30-65.

Shao, J and JP Tam, "Unprotected Peptides as Building Blocks for the Synthesis of Peptide Dendrimers with Oxime, Hydrazone, and Thiazolidine Linkages," J. Am. Chem. Soc. 1995; 117(14):3893-3899.

Sharma, N. et al., "Efficient introduction of aryl bromide functionality into proteins in vivo," FEBS Lett. Feb. 4, 2000;467(1):37-40.

Shimatake, H et M Rosenberg, "Purified λ regulatory protein cII positively activates promoters for lysogenic development," Nature Jul. 1981; 292:128-132.

Shine, J and L Dalgarno, "Determinant of cistron specificity in bacterial ribosomes," Nature. Mar. 6, 1975;254(5495):34-8.

Sidman, KR et al., "Controlled release of macromolecules and pharmaceuticals from synthetic polypeptides based on glutamic acid," Biopolymers. Jan. 1983;22(1):547-56.

Sieber, V. et al., "Libraries of hybrid proteins from distantly related sequences," Nature Biotechnology, May 2001;19:456-460.

Siffert, W et al., "Association of a human G-protein beta3 subunit variant with hypertension," Nat Genet. Jan. 1998;18(1):45-8.

Sikorski, RS et al., "A System of Shuttle Vectors and Yeast Host Strains Designed for Efficient Manipulation of DNA in *Saccharomyces cerevisiae*," Genetics (1989) 122:19-27.

Sisk, WP et al., "High-level expression and purification of secreted forms of herpes simplex virus type 1 glycoprotein gD synthesized by baculovirus-infected insect cells," J Virol. Feb. 1994;68(2):766-75.

Sjolander, A et al., "The serum albumin-binding region of streptococcal protein G: a bacterial fusion partner with carrier-related properties," J Immunol Methods. Feb. 14, 1997;201(1):115-23.

Smith, M. "In vitro mutagenesis" Ann. Rev. Genet. 1985; 19:423-462.

Smith, GE et al., "Production of human beta interferon in insect cells infected with a baculovirus expression vector," Mol Cell Biol. Dec. 1983;3(12):2156-65.

Stanley, SL et al., "The serine-rich Entamoeba histolytica protein is a phosphorylated membrane protein containing O-linked terminal N-acetylglucosamine residues," J Biol Chem. Feb. 24, 1995;270(8):4121-6.

Steitz, JA et al. "Genetic signals and nucleotide sequences in messenger RNA," in Biological Regulation and Development: Gene Expression 1979; ed. R. F. Goldberger; Plenum Press, New York; 349-399.

Stemmer, WPC, "Rapid evolution of a protein in vitro by DNA shuffling," Nature 1994;370(4):389-391.

Stemmer, WP "DNA shuffling by random fragmentation and reassembly: In vitro recombination for molecular evolution," Proc Natl Acad Sci U S A. Oct. 25, 1994;91(22):10747-51.

Studier, FW et BA Moffatt, "Use of bacteriophage T7 RNA polymerase to direct selective high-level expression of cloned genes," J. Mol Biol. May 5, 1986;189(1):113-30.

Subasinghe, N. et al., "Quisqualic acid analogues: synthesis of beta-heterocyclic 2-aminopropanoic acid derivatives and their activity at a novel quisqualate-sensitized site," J Med Chem. Nov. 27, 1992;35(24):4602-7.

Switzer, C et al., "Enzymatic incorporation of a new base pair into DNA and RNA," J. Am. Chem. Soc. 1989; 111(21):8322-8323.

Tabor, S et CC Richardson, "A bacteriophage T7 RNA polymerase/promoter system for controlled exclusive expression of specific genes," Proc Natl Acad Sci U S A. Feb. 1985;82(4):1074-8.

Tae, EL et al., "Efforts toward Expansion of the Genetic Alphabet: Replication of DNA with Three Base Pairs," J. Am. Chem. Soc. 2001; 123(30):7439-7440.

Tang, Y et al., "Fluorinated Coiled-Coil Proteins Prepared In Vivo Display Enhanced Thermal and Chemical Stability," Angew Chem Int Ed Engl. Apr. 17, 2001;40(8):1494-1496.

Taylor, JW et al., "The use of phosphorothioate-modified DNA in restriction enzyme reactions to prepare nicked DNA," Nucleic Acids Res. Dec. 20, 1985;13(24):8749-64.

Taylor, JW et al., "The rapid generation of oligonucleotide-directed mutations at high frequency using phosphorothioate-modified DNA," Nucleic Acids Res. Dec. 20, 1985;13(24):8765-85.

Tijssen, P. "Overview of principles of hybridization and the strategy of nucleic acid assays," in Laboratory Techniques in Biochemistry and Molecular Biology—Hybridization with Nucleic Probes, Part I, 1993; Elsevier Science Publishers, Amsterdam, 19-78.

Tilburn, J. et al., "Transformation by integration in Aspergillus nidulans," Gene. Dec. 1983;26(2-3):205-21.

Tondelli, L. et al. "Poly(ethylene Glycol) Imidazolyl Formates as Oligomeric Drug-Binding Matrices," J. Controlled Release 1985;1(4):251-7.

Tornoe, CW et al., "Peptidotriazoles on solid phase: [1,2,3]-triazoles by regiospecific copper(i)-catalyzed 1,3-dipolar cycloadditions of terminal alkynes to azides," J Org Chem. May 3, 2002;67(9):3057-64.

Trotter, KM and HA Wood, "Transfection techniques for producing recombinant baculoviruses," in Methods in Molecular Biology—Baculovirus Expression Protocols, vol. 39 (1995); Ed. C.D. Richardson, 97-107.

Tschumper, G. et al., "Sequence of a yeast DNA fragment containing a chromosomal replicator and the TRP1 gene," Gene 1980; 10(2):157-66.

Turcatti, G et al. "Probing the structure and function of the tachykinin neurokinin-2 receptor through biosynthetic incorporation of fluorescent amino acids at specific sites," J Biol Chem. Aug. 16, 1996;271(33):19991-8.

Van Den Berg, JA et al., "Kluyveromyces as a host for heterologous gene expression: expression and secretion of prochymosin," Biotechnology (N Y). Feb. 1990;8(2):135-9.

Van Hest, JC and DA Tirrell, "Efficient introduction of alkene functionality into proteins in vivo," FEBS Lett. May 22, 1998;428(1-2):68-70.

Van Hest, J. C. et al., "Efficient Incorporation of Unsaturated Methionine Analogues into Proteins in Vivo," J. Am. Chem. Soc.2000 ;122 (7); 1282-1288.

Van Solingen, P. et JB van der Plaat. "Fusion of yeast spheroplasts," J Bacteriol. May 1977;130(2):946-7.

Veronese, FM et al., "Surface modification of proteins. Activation of monomethoxy-polyethylene glycols by phenylchloroformates and modification of ribonuclease and superoxide dismutase," Appl Biochem Biotechnol. Apr. 1985;11(2):141-52.

Vlak, JM et al., "Functional studies on the p10 gene of Autographa californica nuclear polyhedrosis virus using a recombinant expressing a p10-beta-galactosidase fusion gene," J Gen Virol. Apr. 1988;69 (Pt 4):765-76.

Wang, Q., et al., "Bioconjugation by Copper(I)-Catalyzed Azide-Alkyne [3+2] Cycloaddition," J. Am. Chem. Soc. 2003; 125(11):3192-3193.

Wang, L. et al., "Addition of the keto functional group to the genetic code of *Escherichia coli*," Proc. Natl. Acad. Sci. (2003); 100(1):56-61.

Wang, L et al., "Expanding the genetic code of *Escherichia coli*," Science. Apr. 20, 2001;292(5516):498-500.

Wang, L & PG Schultz, "Expanding the genetic code," Chem Commun (Camb). Jan. 7, 2002;1:1-11.

Weissmann, C. "The cloning of interferon and other mistakes." in Interferon 3 1981; ed. I. Gresser; Academic Press, London, 101-134.

Wells, JA et al., "Importance of hydrogen-bond formation in stabilizing the transition state of subtilisin," Phil. Trans. R. Soc. Lond. A 1986; 317: 415-423.

Wells, JA et al., "Cassette mutagenesis: an efficient method for generation of multiple mutations at defined sites," Gene. 1985;34(2-3):315-23.

Woghiren, C et al. "Protected thiol-polyethylene glycol: a new activated polymer for reversible protein modification," Bioconjug Chem. Sep.-Oct. 1993;4(5):314-8.

Wong, SS et LJ Wong, "Chemical crosslinking and the stabilization of proteins and enzymes," Enzyme Microb Technol. Nov. 1992;14(11):866-74.

Wright, K. "Biotechnology: Insect virus as super-vector?," Nature (1986) 321(6072):718.

Yelton, MM et al., "Transformation of *Aspergillus nidulans* by using a trpC plasmid," Proc Natl Acad Sci U S A. Mar. 1984;81(5):1470-4.

Yelverton, E et al., "Bacterial synthesis of a novel human leukocyte interferon," Nucleic Acids Res. Feb. 11, 1981;9(3):731-41.

Zalipsky, S et al. "Attachment of drugs to polyethylene glycols," Eur. Polymer Journal. 1983 19(12):1177-83.

Zalipsky, S. "Functionalized poly(ethylene glycol) for preparation of biologically relevant conjugates," Bioconjug Chem. Mar.-Apr. 1995;6(2):150-65.

Zhang, Z., et al. "A new strategy for the site-specific modification of proteins in vivo," Biochemistry. Jun. 10, 2003;42(22):6735-46.

Zoller, MJ & M Smith, "Oligonucleotide-directed mutagenesis using M13-derived vectors: an efficient and general procedure for the production of point mutations in any fragment of DNA" Nucleic Acids Res. Oct. 25, 1982;10(20):6487-500.

Zoller, MJ & M. Smith, "Oligonucleotide-directed mutagenesis of DNA fragments cloned into M13 vectors" Methods Enzymol. 1983;100:468-500.

Zoller, MJ & Smith M, "Oligonucleotide-directed mutagenesis: a simple method using two oligonucleotide primers and a single-stranded DNA template," Methods Enzymol. 1987;154:329-50.

Caliceti, P. et FM Veronese. "Pharmacokinetic and biodistribution properties of poly(ethylene glycol)-protein conjugates," Adv Drug Deliv Rev. Sep. 26, 2003;55(10):1261-77.

Clark, EDB, "Refolding of recombinant proteins," Curr Opin Biotechnol Apr. 1, 1998;9(2):157-63.

Clark, EDB, "Protein refolding for industrial processes," Curr Opin Biotechnol Apr. 2001;12(2):202-7.

Davis, GD et al., "New fusion protein systems designed to give soluble expression in *Escherichia coli*," Biotechnol Bioeng Nov. 20, 1999;65(4):382-8.

Duncan, R. "The dawning era of polymer therapeutics," Nat Rev Drug Discov May 2003;2(5):347-60.

Gaertner, HF et RE Offord. "Site-specific attachment of functionalized poly(ethylene glycol) to the amino terminus of proteins," Bioconjug Chem Jan.-Feb. 1996;7(1):38-44.

Gu, Z et al. "Chromatographic methods for the isolation of, and refolding of proteins from, *Escherichia coli* inclusion bodies," Protein Expr Purif. Jun. 2002;25(1):174-9.

Hohsaka, T et M Sisido. "Incorporation of non-natural amino acids into proteins," Curr Opin Chem Biol. Dec. 2002;6(6):809-15.

Lilie, H et al. "Advances in refolding of proteins produced in *E. coli*," Curr Opin Biotechnol. Oct. 1998;9(5):497-501.

Tsumoto, K et al. "Practical considerations in refolding proteins from inclusion bodies," Protein Expr Purif. Mar. 2003;28(1):1-8.

Wang, W. "Instability, stabilization, and formulation of liquid protein pharmaceuticals," Int J Pharm. Aug. 20, 1999;185(2):129-88.

Dieters et al., "Adding Amino Acids with Novel Reactivity to the Genetic Code of Saccharomyces Cerevisiae", J. Am. Chem. Soc., Oct. 1, 2003, 125(39):11782-11783.

Levi et al., "A Retro-Inverso Miniantibody with Anti-HIV Activity", AIDS Research & Human Retroviruses, Jan. 1, 2000, 16(1):59-65.

* cited by examiner

D.

E.

F.

A.

Suppression: Western

B.

Purification: Coomassie

A.

A.

wt scFv108
IC50 =8.1 nM, r2=0.997

B.

scFv108 Ser136pAcF
IC50 =13.1 nM, r2=0.997

C.

scFv108 Ser136pAcF-5K PEG
IC50 =51 nM, r2=0.990

A.

B.

C.

D.

B.

ANTIGEN-BINDING POLYPEPTIDES AND THEIR USES

CROSS-REFERENCE TO RELATED APPLICATIONS

This application claims priority to U.S. provisional patent application Ser. No. 60/581,334, filed Jun. 18, 2004, U.S. provisional patent application Ser. No. 60/648,222, filed Jan. 28, 2005, and U.S. provisional patent application 60/654,018 filed Feb. 17, 2005, the specifications of which are incorporated herein in their entirety.

FIELD OF THE INVENTION

This invention relates to novel antigen-binding polypeptides comprising at least one non-naturally-encoded amino acid. The present invention relates generally to the field of the production and selection of antigen-binding polypeptides by the methods of molecular biology, using both chemistry and recombinant DNA.

BACKGROUND OF THE INVENTION

A naturally produced antibody (Ab) is a tetrameric structure consisting of two identical immunoglobulin (Ig) heavy chains and two identical light chains. The heavy and light chains of an Ab consist of different domains. Each light chain has one variable domain (VL) and one constant domain (CL), while each heavy chain has one variable domain (VH) and three or four constant domains (CH). Each domain, consisting of about 110 amino acid residues, is folded into a characteristic β-sandwich structure formed from two β-sheets packed against each other, the immunoglobulin fold. The VL domains each have three complementarity determining regions (CDR1-3) and the VH domains each have up to four complimentarity determining regions (CDR1-4), that are loops, or turns, connecting β-strands at one end of the domains. The variable regions of both the light and heavy chains generally contribute to antigen specificity, although the contribution of the individual chains to specificity is not necessarily equal. Antibody molecules have evolved to bind to a large number of molecules by using randomized CDR loops.

Functional substructures of Abs can be prepared by proteolysis and by recombinant methods. They include the Fab fragment, which comprises the VH-CH1 domains of the heavy chain and the VL-CL1 domains of the light chain joined by a single interchain disulfide bond, and the Fv fragment, which comprises only the VH and VL domains, and the Fc portion which comprises the non-antigen binding region of the molecule. In some cases, a single VH domain retains significant affinity for antigen (Ward et al., 1989, Nature 341, 554-546). It has also been shown that a certain monomeric K light chain will specifically bind to its antigen. (L. Masat et al., 1994, PNAS 91:893-896). Separated light or heavy chains have sometimes been found to retain some antigen-binding activity as well (Ward et al., 1989, Nature 341, 554-546).

Another functional substructure is a single chain Fv (scFv), comprised of the variable regions of the immunoglobulin heavy and light chain, covalently connected by a peptide linker (S-z Hu et al., 1996, Cancer Research, 56, 3055-3061). These small (Mr 25,000) proteins generally retain specificity and affinity for antigen in a single polypeptide and can provide a convenient building block for larger, antigen-specific molecules. The short half-life of scFvs in the circulation limits their therapeutic utility in many cases.

A small protein scaffold called a "minibody" was designed using a part of the Ig VH domain as the template (Pessi et al., 1993, Nature 362, 367-369). Minibodies with high affinity (dissociation constant ($K_d$) about $10^{-7}$ M) to interleukin-6 were identified by randomizing loops corresponding to CDR1 and CDR2 of VH and then selecting mutants using the phage display method (Martin et al., 1994, EMBO J. 13, 5303-5309).

Camels often lack variable light chain domains when IgG-like material from their serum is analyzed, suggesting that sufficient antibody specificity and affinity can be derived from VH domains (three or four CDR loops) alone. "Camelized" VH domains with high affinity have been made, and high specificity can be generated by randomizing only the CDR3.

An alternative to the "minibody" is the "diabody." Diabodies are small bivalent and bispecific antibody fragments, having two antigen-binding sites. The fragments comprise a heavy-chain variable domain ($V_H$) connected to a light-chain variable domain ($V_L$) on the same polypeptide chain ($V_H$-$V_L$). Diabodies are similar in size to the Fab fragment. By using a linker that is too short to allow pairing between the two domains on the same chain, the domains are forced to pair with the complementary domains of another chain and create two antigen-binding sites. These dimeric antibody fragments, or "diabodies," are bivalent and bispecific. See, P. Holliger et al., PNAS 90:6444-6448 (1993).

CDR peptides and organic CDR mimetics have been made (Dougall et al., 1994, Trends Biotechnol. 12, 372-379). CDR peptides are short, typically cyclic, peptides which correspond to the amino acid sequences of CDR loops of antibodies. CDR loops are responsible for antibody-antigen interactions. CDR peptides and organic CDR mimetics have been shown to retain some binding affinity (Smyth & von Itzstein, 1994, J. Am. Chem. Soc. 116, 2725-2733). Mouse CDRs have been grafted onto the human Ig framework without the loss of affinity (Jones et al., 1986, Nature 321, 522-525; Riechmann et al., 1988).

In the body, specific Abs are selected and amplified from a large library (affinity maturation). The processes can be reproduced in vitro using combinatorial library technologies. The successful display of Ab fragments on the surface of bacteriophage has made it possible to generate and screen a vast number of CDR mutations (McCafferty et al., 1990, Nature 348, 552-554; Barbas et al., 1991, Proc. Natl. Acad. Sci. USA 88,7978-7982; Winter et al., 1994, Annu. Rev. Immunol. 12, 433-455). An increasing number of Fabs and Fvs (and their derivatives) are produced by this technique. The combinatorial technique can be combined with Ab mimics.

A number of protein domains that could potentially serve as protein scaffolds have been expressed as fusions with phage capsid proteins. Review in Clackson & Wells, Trends Biotechnol. 12:173-184 (1994). Several of these protein domains have already been used as scaffolds for displaying random peptide sequences, including bovine pancreatic trypsin inhibitor (Roberts et al., PNAS 89:2429-2433 (1992)), human growth hormone (Lowman et al., Biochemistry 30:10832-10838 (1991)), Venturini et al., Protein Peptide Letters 1:70-75 (1994)), and the IgG binding domain of Streptococcus (O'Neil et al., Techniques in Protein Chemistry V (Crabb, L., ed.) pp. 517-524, Academic Press, San Diego (1994)). These scaffolds have displayed a single randomized loop or region. Tendamistat has been used as a presentation scaffold on the filamentous phage M13 (McConnell and Hoess, 1995, J. Mol. Biol. 250:460-470).

Receptor tyrosine kinases of the ErbB family play pivotal roles in cell growth and differentiation. Aberrant activation of these receptors is associated with human cancers. Dimerization (the pairing of receptors) is essential to the signaling activity of all ErbB receptors. Blocking the dimerization activity of ErbB2 has been shown to directly inhibit the ability of ErbB2 to dimerize with other ErbB receptor proteins. Inhibiting receptor dimerization prevents the activation of ErbB signaling pathways. An antagonistic molecule that down regulates ErbB signaling could function as an anti-tumor agent. The ErbB signaling network is currently a major target in the development of anti-tumor drugs. ErbB-1 is a specific receptor for EGF, while ErbB-2 has no known natural ligand. ErbB2 is able to form heterodimers with ErbB-1 upon addition of EGF. ErbB2 also functions as the preferred dimerization partner for the kinase-dead ErbB-3 and for ErbB-4, which are both receptors for the neuregulins. The ErbB signaling network can also be activated in an indirect manner during signaling by cytokines and ligands of G-coupled protein receptors, indicating that it plays a central role in the growth control of many different cell types.

The proto-oncogene c-erbB-1 encodes the epidermal growth factor receptor. Its name originates from the viral homolog v-erbB which was isolated from an avian erythroblastosis virus (AEV) where it was contained as a fragment of the chicken c-ErbB-1 gene lacking the amino-terminal ligand-binding domain. Over expression of erbB-1 genes occurs in a wide range of tumors, including squamous carcinomas of various sites and adenocarcinomas. The human c-erbB-1 gene is located in the chromosomal region 7p14 and 7p12.

The ErbB-2 proto-oncogene (also referred to as Neu, EGFR-2 or HER-2) is a member of the transmembrane receptor tyrosine kinase family, which also includes EGF receptor and EGFR-3 (HER-3 or ErbB-3). ErbB-2 encodes a transmembrane receptor-like glycoprotein of 185 kDa with intrinsic tyrosine kinase activity. Although, ErbB-2 does not have any known high-affinity ligands, its kinase activity can be activated without ligand by either over expression or hetero-association with other members of the ErbB family of receptors. Amplification of the ErbB-2 gene and over expression of its product has been detected in almost 40% of primary human breast tumors. ErbB-2 over expression is also observed in ovarian, gastric, salivary and non-small cell lung carcinomas. ErbB-2 is activated by the neuregulins in heterodimers with the neuregulin receptors ErbB-3 and ErbB-4. The humanized anti-ErbB-2 monoclonal antibody Herceptin (from monoclonal 4D5) has received FDA approval for treatment of cancers that over express ErbB-2. Another anti-ErbB2 antibody in development is Pertuzumab (from monoclonal 2C4). Specific inhibitors of the tyrosine kinase activity of ErbB-1 (EGF receptor) are also in clinical trials.

Anti-ErbB2 antibodies are known in the art, and include but are not limited to U.S. Pat. Nos. 4,753,894; 5,169,774; 5,677,171; 5,720,937; 5,720,954; 5,725,856; 5,770,195; 5,772,997; 5,783,186; 6,054,561; 6,165,464; 6,333,169; 6,015,567; 6,387,371; 6,399,063; 6,441,143; 6,458,356; 6,627,196, each of which is incorporated by reference herein.

Covalent attachment of the hydrophilic polymer poly(ethylene glycol), abbreviated PEG, is a method of increasing water solubility, bioavailability, increasing serum half-life, increasing therapeutic half-life, modulating immunogenicity, modulating biological activity, or extending the circulation time of many biologically active molecules, including proteins, peptides, and particularly hydrophobic molecules. PEG has been used extensively in pharmaceuticals, on artificial implants, and in other applications where biocompatibility, lack of toxicity, and lack of immunogenicity are of importance. In order to maximize the desired properties of PEG, the total molecular weight and hydration state of the PEG polymer or polymers attached to the biologically active molecule must be sufficiently high to impart the advantageous characteristics typically associated with PEG polymer attachment, such as increased water solubility and circulating half life, while not adversely impacting the bioactivity of the parent molecule.

PEG derivatives are frequently linked to biologically active molecules through reactive chemical functionalities, such as lysine, cysteine and histidine residues, the N-terminus and carbohydrate moieties. Proteins and other molecules often have a limited number of reactive sites available for polymer attachment. Often, the sites most suitable for modification via polymer attachment play a significant role in receptor binding, and are necessary for retention of the biological activity of the molecule. As a result, indiscriminate attachment of polymer chains to such reactive sites on a biologically active molecule often leads to a significant reduction or even total loss of biological activity of the polymer-modified molecule. R. Clark et al., (1996), *J. Biol. Chem.*, 271:21969-21977. To form conjugates having sufficient polymer molecular weight for imparting the desired advantages to a target molecule, prior art approaches have typically involved random attachment of numerous polymer arms to the molecule, thereby increasing the risk of a reduction or even total loss in bioactivity of the parent molecule.

Reactive sites that form the loci for attachment of PEG derivatives to proteins are dictated by the protein's structure. Proteins, including enzymes, are composed of various sequences of alpha-amino acids, which have the general structure $H_2N$—CHR—COOH. The alpha amino moiety ($H_2N$—) of one amino acid joins to the carboxyl moiety (—COOH) of an adjacent amino acid to form amide linkages, which can be represented as —(NH—CHR—CO)$_n$—, where the subscript "n" can equal hundreds or thousands. The fragment represented by R can contain reactive sites for protein biological activity and for attachment of PEG derivatives.

For example, in the case of the amino acid lysine, there exists an —$NH_2$ moiety in the epsilon position as well as in the alpha position. The epsilon —$NH_2$ is free for reaction under conditions of basic pH. Much of the art in the field of protein derivatization with PEG has been directed to developing PEG derivatives for attachment to the epsilon —$NH_2$ moiety of lysine residues present in proteins. "Polyethylene Glycol and Derivatives for Advanced PEGylation", Nektar Molecular Engineering Catalog, 2003, pp. 1-17. These PEG derivatives all have the common limitation, however, that they cannot be installed selectively among the often numerous lysine residues present on the surfaces of proteins. This can be a significant limitation in instances where a lysine residue is important to protein activity, existing in an enzyme active site for example, or in cases where a lysine residue plays a role in mediating the interaction of the protein with other biological molecules, as in the case of receptor binding sites.

A second and equally important complication of existing methods for protein PEGylation is that the PEG derivatives can undergo undesired side reactions with residues other than those desired. Histidine contains a reactive imino moiety, represented structurally as —N(H)—, but many chemically reactive species that react with epsilon —$NH_2$ can also react with —N(H)—. Similarly, the side chain of the amino acid cysteine bears a free sulfhydryl group, represented structurally as —SH. In some instances, the PEG derivatives directed at the epsilon —$NH_2$ group of lysine also react with cysteine, histidine or other residues. This can create complex, heterogeneous mixtures of PEG-derivatized bioactive molecules and risks destroying the activity of the bioactive molecule being targeted. It would be desirable to develop PEG derivatives that permit a chemical functional group to be introduced at a single site within the protein that would then enable the selective coupling of one or more PEG polymers to the bioactive molecule at specific sites on the protein surface that are both well-defined and predictable.

In addition to lysine residues, considerable effort in the art has been directed toward the development of activated PEG reagents that target other amino acid side chains, including cysteine, histidine and the N-terminus. See, e.g., U.S. Pat. No. 6,610,281 which is incorporated by reference herein, and "Polyethylene Glycol and Derivatives for Advanced PEGylation", Nektar Molecular Engineering Catalog, 2003, pp. 1-17. A cysteine residue can be introduced site-selectively into the structure of proteins using site-directed mutagenesis and other techniques known in the art, and the resulting free sulfhydryl moiety can be reacted with PEG derivatives that bear thiol-reactive functional groups. This approach is complicated, however, in that the introduction of a free sulfhydryl group can complicate the expression, folding and stability of the resulting protein. Thus, it would be desirable to have a means to introduce a chemical functional group into bioactive molecules that enables the selective coupling of one or more PEG polymers to the protein while simultaneously being compatible with (i.e., not engaging in undesired side reactions with) sulfhydryls and other chemical functional groups typically found in proteins.

As can be seen from a sampling of the art, many of these derivatives that have been developed for attachment to the side chains of proteins, in particular, the —$NH_2$ moiety on the lysine amino acid side chain and the —SH moiety on the cysteine side chain, have proven problematic in their synthesis and use. Some form unstable linkages with the protein that are subject to hydrolysis and therefore decompose, degrade, or are otherwise unstable in aqueous environments, such as in the bloodstream. Some form more stable linkages, but are subject to hydrolysis before the linkage is formed, which means that the reactive group on the PEG derivative may be inactivated before the protein can be attached. Some are somewhat toxic and are therefore less suitable for use in vivo. Some are too slow to react to be practically useful. Some result in a loss of protein activity by attaching to sites responsible for the protein's activity. Some are not specific in the sites to which they will attach, which can also result in a loss of desirable activity and in a lack of reproducibility of results. In order to overcome the challenges associated with modifying proteins with poly(ethylene glycol) moieties, PEG derivatives have been developed that are more stable (e.g., U.S. Pat. No. 6,602,498, which is incorporated by reference herein) or that react selectively with thiol moieties on molecules and surfaces (e.g., U.S. Pat. No. 6,610,281, which is incorporated by reference herein). There is clearly a need in the art for PEG derivatives that are chemically inert in physiological environments until called upon to react selectively to form stable chemical bonds.

Recently, an entirely new technology in the protein sciences has been reported, which promises to overcome many of the limitations associated with site-specific modifications of proteins. Specifically, new components have been added to the protein biosynthetic machinery of the prokaryote *Escherichia coli* (*E. coli*) (e.g., L. Wang, et al., (2001), *Science* 292:498-500) and the eukaryote *Sacchromyces cerevisiae* (*S. cerevisiae*) (e.g., J. Chin et al., *Science* 301:964-7 (2003)), which has enabled the incorporation of non-genetically encoded amino acids to proteins in vivo. A number of new amino acids with novel chemical, physical or biological properties, including photoaffinity labels and photoisomerizable amino acids, keto amino acids, and glycosylated amino acids have been incorporated efficiently and with high fidelity into proteins in *E. coli* and in yeast in response to the amber codon, TAG, using this methodology. See, e.g., J. W. Chin et al., (2002), *Journal of the American Chemical Society* 124:9026-9027; J. W. Chin, & P. G. Schultz, (2002), *ChemBioChem* 11:1135-1137; J. W. Chin, et al., (2002), *PNAS United States of America* 99:11020-11024; and, L. Wang, & P. G. Schultz, (2002), *Chem. Comm.*, 1-10. These studies have demonstrated that it is possible to selectively and routinely introduce chemical functional groups, such as ketone groups, alkyne groups and azide moieties, that are not found in proteins, that are chemically inert to all of the functional groups found in the 20 common, genetically-encoded amino acids and that may be used to react efficiently and selectively to form stable covalent linkages.

The ability to incorporate non-genetically encoded amino acids into proteins permits the introduction of chemical functional groups that could provide valuable alternatives to the naturally-occurring functional groups, such as the epsilon —$NH_2$ of lysine, the sulfhydryl —SH of cysteine, the imino group of histidine, etc. Certain chemical functional groups are known to be inert to the functional groups found in the 20 common, genetically-encoded amino acids but react cleanly and efficiently to form stable linkages. Azide and acetylene groups, for example, are known in the art to undergo a Huisgen [3+2] cycloaddition reaction in aqueous conditions in the presence of a catalytic amount of copper. See, e.g., Tornoe, et al., (2002) *Org. Chem.* 67:3057-3064; and, Rostovtsev, et al., (2002) *Angew. Chem. Int. Ed.* 41:2596-2599. By introducing an azide moiety into a protein structure, for example, one is able to incorporate a functional group that is chemically inert to amines, sulfhydryls, carboxylic acids, hydroxyl groups found in proteins, but that also reacts smoothly and efficiently with an acetylene moiety to form a cycloaddition product. Importantly, in the absence of the acetylene moiety, the azide remains chemically inert and unreactive in the presence of other protein side chains and under physiological conditions.

The present invention addresses, among other things, problems associated with the activity and production of antigen-binding polypeptides and fragments thereof, and also addresses the production of antigen-binding polypeptides with improved biological or pharmacological properties, such as improved therapeutic half-life.

BRIEF SUMMARY OF THE INVENTION

This invention provides antigen-binding polypeptides (ABP) comprising one or more non-naturally encoded amino acids. In some embodiments, the ABP comprises a complete antibody heavy chain. In some embodiments, the ABP comprises a complete antibody light chain. In some embodiments, the ABP comprises a variable region of an antibody light chain. In some embodiments, the ABP comprises a variable region of an antibody heavy chain. In some embodiments, the ABP comprises at least one CDR of an antibody light chain. In some embodiments, the ABP comprises at least one CDR of an antibody heavy chain. In some embodiments, the ABP comprises at least one CDR of a light chain and at least one CDR of a heavy chain. In some embodiments, the ABP comprises a Fab. In some embodiments, the ABP comprises two or more Fab's. In some embodiments, the ABP comprises a scFv. In some embodiments, the ABP comprises two or more scFv. In some embodiments, the ABP comprises a minibody.

In some embodiments, the ABP comprises two or more minibodies. In some embodiments, the ABP comprises a diabody. In some embodiments, the ABP comprises two or more diabodies. In some embodiments, the ABP comprises a variable region of a light chain and a variable region of a heavy chain. In some embodiments, the ABP comprises a complete light chain and a complete heavy chain. In some embodiments, the ABP comprises one or more Fc domain or portion thereof. In some embodiments, the ABP comprises a combination of any of the above embodiments. In some embodiments, the ABP comprises a homodimer, heterodimer, homomultimer or heteromultimer of any of the above embodiments. In some embodiments, the ABP comprises a polypeptide that binds to a binding partner wherein the binding partner comprises an antigen, a polypeptide, a nucleic acid molecule, a polymer, or other molecule or substance. In some embodiments, the ABP is associated with a non-antibody scaffold molecule or substance.

In some embodiments, the ABP comprises one or more post-translational modifications. In some embodiments, the ABP is linked to a linker, polymer, or biologically active molecule. In some embodiments, the ABP is linked to a bifunctional polymer, bifunctional linker, or at least one additional ABP. In some embodiments, the ABP is linked to a polypeptide that is not an ABP. In some embodiments, the antigen-binding polypeptide comprising a non-naturally encoded amino acid is linked to one or more additional antigen-binding polypeptides which may also comprise a non-naturally encoded amino acid.

In some embodiments, the non-naturally encoded amino acid is linked to a water soluble polymer. In some embodiments, the water soluble polymer comprises a poly(ethylene glycol) moiety. In some embodiments, the poly(ethylene glycol) molecule is a bifunctional polymer. In some embodiments, the bifunctional polymer is linked to a second polypeptide. In some embodiments, the second polypeptide is an antigen-binding polypeptide.

In some embodiments, the antigen-binding polypeptide comprises at least two amino acids linked to a water soluble polymer comprising a poly(ethylene glycol) moiety. In some embodiments, at least one amino acid is a non-naturally encoded amino acid.

In some embodiments, the antigen-binding polypeptide comprises a substitution, addition or deletion that modulates affinity of the antigen-binding polypeptide for an antigen when compared with the affinity of the corresponding antigen-binding polypeptide without the substitution, addition or deletion. In some embodiments, the antigen-binding polypeptide comprises a substitution, addition, or deletion that increases the stability of the antigen-binding polypeptide when compared with the stability of the corresponding antigen-binding polypeptide without the substitution, addition or deletion. In some embodiments, the antigen-binding polypeptide comprises a substitution, addition, or deletion that modulates the immunogenicity of the antigen-binding polypeptide when compared with the immunogenicity of the corresponding antigen-binding polypeptide without the substitution, addition or deletion. In some embodiments, the antigen-binding polypeptide comprises a substitution, addition, or deletion that modulates serum half-life or circulation time of the antigen-binding polypeptide when compared with the serum half-life or circulation time of the corresponding antigen-binding polypeptide without the substitution, addition or deletion.

In some embodiments, the antigen-binding polypeptide comprises a substitution, addition, or deletion that increases the aqueous solubility of the corresponding antigen-binding polypeptide when compared to the aqueous solubility of the corresponding antigen-binding polypeptide without the substitution, addition, or deletion. In some embodiments, the antigen-binding polypeptide comprises a substitution, addition, or deletion that increases the solubility of the antigen-binding polypeptide produced in a host cell when compared to the solubility of the corresponding antigen-binding polypeptide without the substitution, addition, or deletion. In some embodiments, the antigen-binding polypeptide comprises a substitution, addition, or deletion that increases the expression of the antigen-binding polypeptide in a host cell or synthesized in vitro when compared to the expression of the corresponding antigen-binding polypeptide without the substitution, addition, or deletion. In some embodiments, the antigen-binding polypeptide comprises a substitution, addition, or deletion that increases protease resistance of the antigen-binding polypeptide when compared to protease resistance of the corresponding antigen-binding polypeptide without the substitution, addition, or deletion.

In some embodiments the amino acid substitutions in the ABP may be with naturally occurring or non-naturally occurring amino acids, provided that at least one substitution is with a non-naturally encoded amino acid.

In some embodiments, the non-naturally encoded amino acid comprises a carbonyl group, an acetyl group, an aminooxy group, a hydrazine group, a hydrazide group, a semicarbazide group, an azide group, or an alkyne group.

In some embodiments, the non-naturally encoded amino acid comprises a carbonyl group. In some embodiments, the non-naturally encoded amino acid has the structure:

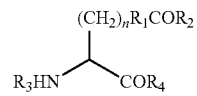

wherein n is 0-10; $R_1$ is an alkyl, aryl, substituted alkyl, or substituted aryl; $R_2$ is H, an alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group.

In some embodiments, the non-naturally encoded amino acid comprises an aminooxy group. In some embodiments, the non-naturally encoded amino acid comprises a hydrazide group. In some embodiments, the non-naturally encoded amino acid comprises a hydrazine group. In some embodiments, the non-naturally encoded amino acid residue comprises a semicarbazide group.

In some embodiments, the non-naturally encoded amino acid residue comprises an azide group. In some embodiments, the non-naturally encoded amino acid has the structure:

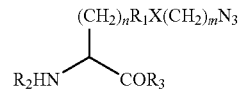

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group.

In some embodiments, the non-naturally encoded amino acid comprises an alkyne group. In some embodiments, the non-naturally encoded amino acid has the structure:

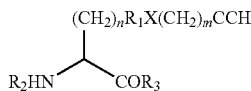

wherein n is 0-10; $R_1$ is an alkyl, aryl, substituted alkyl, or substituted aryl; X is O, N, S or not present; m is 0-10, $R_2$ is H, an amino acid, a polypeptide, or an amino terminus modification group, and $R_3$ is H, an amino acid, a polypeptide, or a carboxy terminus modification group.

In some embodiments, the polypeptide is an agonist, partial agonist, antagonist, partial antagonist, or inverse agonist of at least one activity of the antigen. In some embodiments, the agonist, partial agonist, antagonist, partial antagonist, or inverse agonist comprises a non-naturally encoded amino acid linked to a water soluble polymer. In some embodiments, the water soluble polymer comprises a poly(ethylene glycol) moiety. In some embodiments, the agonist, partial agonist, antagonist, partial antagonist, or inverse agonist comprises a non-naturally encoded amino acid and one or more post-translational modification, linker, polymer, or biologically active molecule.

The present invention also provides isolated nucleic acids comprising a polynucleotide that encodes an antigen-binding polypeptide wherein the polynucleotide comprises at least one selector codon including, but not limited to, SEQ ID NO: 18, 20, 22, 25, 27, 29. In some embodiments, the selector codon is selected from the group consisting of an amber codon, ochre codon, opal codon, a unique codon, a rare codon, and a four-base codon.

The present invention also provides methods of making an antigen-binding polypeptide linked to a water soluble polymer. In some embodiments, the method comprises contacting an isolated antigen-binding polypeptide comprising a non-naturally encoded amino acid with a water soluble polymer comprising a moiety that reacts with the non-naturally encoded amino acid. In some embodiments, the non-naturally encoded amino acid incorporated into the antigen-binding polypeptide is reactive toward a water soluble polymer that is otherwise unreactive toward any of the 20 common amino acids. In some embodiments, the non-naturally encoded amino acid incorporated into the antigen-binding polypeptide is reactive toward a linker, polymer, or biologically active molecule that is otherwise unreactive toward any of the 20 common amino acids.

In some embodiments, the antigen-binding polypeptide linked to the water soluble polymer is made by reacting an antigen-binding polypeptide comprising a carbonyl-containing amino acid with a poly(ethylene glycol) molecule comprising an aminooxy, hydrazine, hydrazide or semicarbazide group. In some embodiments, the aminooxy, hydrazine, hydrazide or semicarbazide group is linked to the poly(ethylene glycol) molecule through an amide linkage.

In some embodiments, the antigen-binding polypeptide linked to the water soluble polymer is made by reacting a poly(ethylene glycol) molecule comprising a carbonyl group with a polypeptide comprising a non-naturally encoded amino acid that comprises an aminooxy, hydrazine, hydrazide or semicarbazide group.

In some embodiments, the antigen-binding polypeptide linked to the water soluble polymer is made by reacting an antigen-binding polypeptide comprising an alkyne-containing amino acid with a poly(ethylene glycol) molecule comprising an azide moiety. In some embodiments, the azide or alkyne group is linked to the poly(ethylene glycol) molecule through an amide linkage.

In some embodiments, the antigen-binding polypeptide linked to the water soluble polymer is made by reacting an antigen-binding polypeptide comprising an azide-containing amino acid with a poly(ethylene glycol) molecule comprising an alkyne moiety. In some embodiments, the azide or alkyne group is linked to the poly(ethylene glycol) molecule through an amide linkage.

In some embodiments, the poly(ethylene glycol) molecule has a molecular weight of between about 0.1 kDa and about 100 kDa. In some embodiments, the poly(ethylene glycol) molecule has a molecular weight of between 0.1 kDa and 50 kDa.

In some embodiments, the poly(ethylene glycol) molecule is a branched polymer. In some embodiments, each branch of the poly(ethylene glycol) branched polymer has a molecular weight of between 1 kDa and 100 kDa, or between 1 kDa and 50 kDa.

In some embodiments, the water soluble polymer linked to the antigen-binding polypeptide comprises a polyalkylene glycol moiety. In some embodiments, the non-naturally encoded amino acid residue incorporated into the antigen-binding polypeptide comprises a carbonyl group, an aminooxy group, a hydrazide group, a hydrazine, a semicarbazide group, an azide group, or an alkyne group. In some embodiments, the non-naturally encoded amino acid residue incorporated into the ABP comprises a carbonyl moiety and the water soluble polymer comprises an aminooxy, hydrazide, hydrazine, or semicarbazide moiety. In some embodiments, the non-naturally encoded amino acid residue incorporated into the antigen-binding polypeptide comprises an alkyne moiety and the water soluble polymer comprises an azide moiety. In some embodiments, the non-naturally encoded amino acid residue incorporated into the antigen-binding polypeptide comprises an azide moiety and the water soluble polymer comprises an alkyne moiety.

The present invention also provides compositions comprising an antigen-binding polypeptide comprising a non-naturally-encoded amino acid and a pharmaceutically acceptable carrier. In some embodiments, the non-naturally encoded amino acid is linked to a water soluble polymer.

The present invention also provides cells comprising a polynucleotide encoding the antigen-binding polypeptide comprising a selector codon. In some embodiments, the cells comprise an orthogonal RNA synthetase and/or an orthogonal tRNA for substituting a non-naturally encoded amino acid into the antigen-binding polypeptide.

The present invention also provides methods of making an antigen-binding polypeptide comprising a non-naturally encoded amino acid. In some embodiments, the methods comprise culturing cells comprising a polynucleotide or polynucleotides encoding an antigen-binding polypeptide, an orthogonal RNA synthetase and/or an orthogonal tRNA under conditions to permit expression of the antigen-binding polypeptide; and purifying the antigen-binding polypeptide from the cells and/or culture medium.

The present invention also provides methods of increasing therapeutic half-life, serum half-life or circulation time of the antigen-binding polypeptides. The present invention also provides methods of modulating immunogenicity of the antigen-binding polypeptides. In some embodiments, the methods comprise substituting a non-naturally encoded amino acid for any one or more amino acids in naturally occurring antigen-binding polypeptides and/or linking the antigen-binding polypeptide to a linker, a polymer, a water soluble polymer, or a biologically active molecule.

The present invention also provides methods of treating a patient in need of such treatment with an effective amount of an antigen-binding polypeptide of the present invention. In some embodiments, the methods comprise administering to the patient a therapeutically-effective amount of a pharmaceutical composition comprising an antigen-binding polypeptide comprising a non-naturally-encoded amino acid and a pharmaceutically acceptable carrier. In some embodiments, the non-naturally encoded amino acid is linked to a water soluble polymer.

The present invention also provides antigen-binding polypeptides comprising a sequence shown in SEQ ID NO: 19, 21, 23, 24, 26, 28, 30, 31 and fragments thereof, or any other antigen-binding polypeptide sequence, except that at least one amino acid is substituted by a non-naturally encoded amino acid. In some embodiments, the non-naturally encoded amino acid is linked to a water soluble polymer. In some embodiments, the water soluble polymer comprises a poly(ethylene glycol) moiety. In some embodiments, the non-naturally encoded amino acid comprises a carbonyl group, an aminooxy group, a hydrazide group, a hydrazine group, a semicarbazide group, an azide group, or an alkyne group.

The present invention also provides pharmaceutical compositions comprising a pharmaceutically acceptable carrier and an antigen-binding polypeptide comprising the sequence shown in SEQ ID NO: 19, 21, 23, 24, 26, 28, 30, 31 and fragments thereof, or any other antigen-binding polypeptide sequence, wherein at least one amino acid is substituted by a non-naturally encoded amino acid. In some embodiments, the non-naturally encoded amino acid comprises a saccharide moiety. In some embodiments, the water soluble polymer is linked to the polypeptide via a saccharide moiety. In some embodiments, a linker, polymer, or biologically active molecule is linked to the antigen-binding polypeptide via a saccharide moiety.

The present invention also provides an antigen-binding polypeptide comprising a water soluble polymer linked by a covalent bond to the antigen-binding polypeptide at a single amino acid. In some embodiments, the water soluble polymer comprises a poly(ethylene glycol) moiety. In some embodiments, the amino acid covalently linked to the water soluble polymer is a non-naturally encoded amino acid present in the polypeptide.

The present invention provides an antigen-binding polypeptide comprising at least one linker, polymer, or biologically active molecule, wherein said linker, polymer, or biologically active molecule is attached to the polypeptide through a functional group of a non-naturally encoded amino acid ribosomally incorporated into the polypeptide. In some embodiments, the polypeptide is monoPEGylated. The present invention also provides a ABP polypeptide comprising a linker, polymer, or biologically active molecule that is attached to one or more non-naturally encoded amino acid wherein said non-naturally encoded amino acid is ribosomally incorporated into the polypeptide at pre-selected sites.

In another embodiment, conjugation of the antigen-binding polypeptide comprising one or more non-naturally occurring amino acids to another molecule, including but not limited to PEG, provides substantially purified antigen-binding polypeptide due to the unique chemical reaction utilized for conjugation to the non-natural amino acid. Conjugation of the antigen-binding polypeptide comprising one or more non-naturally encoded amino acids to another molecule, such as PEG, may be performed with other purification techniques performed prior to or following the conjugation step to provide substantially pure antigen-binding polypeptide.

BRIEF DESCRIPTION OF THE DRAWINGS

FIG. 5, Panel B shows PEGylation of pAcF-scFv-108 fragment-(S 136). FIG. 5, Panel C shows that no PEGylation of WT scFv fragments was observed.

FIG. 11, Panel B shows a Western blot of the samples shown in FIG. 11, Panel A with an anti-His antibody.

DEFINITIONS

Figure 1:
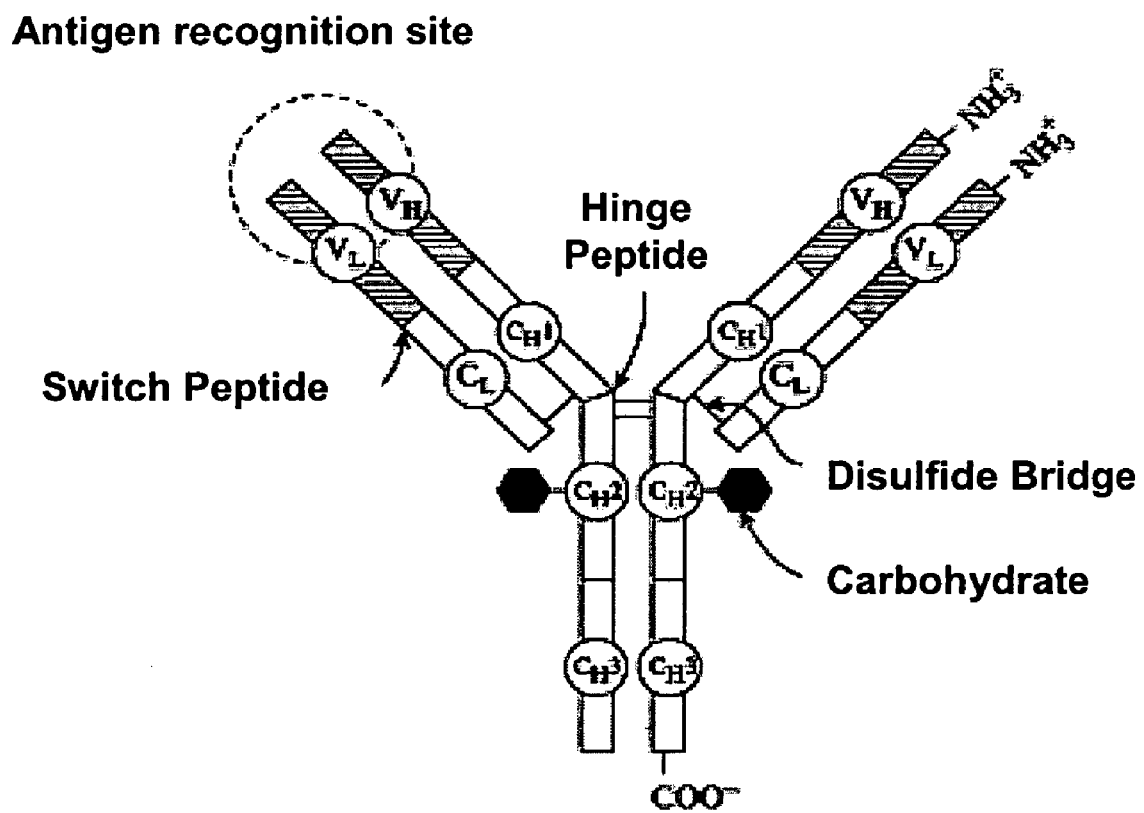
FIG. 1—A diagram of the general structure of an antibody molecule (IgG) and its antigen-binding portions is shown. The CDR's are contained within the antigen recognition site.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to an "antigen-binding polypeptide" or "ABP" is a reference to one or more such proteins and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

The term "substantially purified" refers to an ABP that may be substantially or essentially free of components that normally accompany or interact with the protein as found in its naturally occurring environment, i.e. a native cell, or host cell in the case of recombinantly produced ABP. ABP that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the ABP or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the ABP or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" ABP as produced by the methods of the present invention may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells or $E.\ coli,$ and cell contents. Thus, the term may encompass medium in which the host cell has been grown, e.g., medium into which the ABP has been secreted, including medium either before or after a proliferation step. The term also may encompass buffers or reagents that contain host cell lysates, such as in the case where the ABP is produced intracellularly and the host cells are lysed or disrupted to release the ABP.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, dithioerythritol, cysteine, cysteamine (2-aminoethanethiol), and reduced glutathione. It is readily apparent to those of ordinary skill in the art that a wide variety of reducing agents are suitable for use in the methods and compositions of the present invention.

"Oxidizing agent," as used hereinwith respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. It is readily apparent to those of ordinary skill in the art that a wide variety of oxidizing agents are suitable for use in the methods of the present invention.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Suitable denaturing agents or denaturants may be chaotropes, detergents, organic solvents, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N->2, 3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially $C_2$-$C_4$ alkanols such as ethanol or isopropanol), or lower alkandiols (especially $C_2$-$C_4$ alkandiols such as ethylene-glycol) may be used as denaturants. Phospholipids useful in the present invention may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two polypeptides which interact with each other and result in the transformation of unfolded or improperly folded polypeptides to native, properly folded polypeptides.

Antibodies are proteins, which exhibit binding specificity to a specific antigen. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in three segments called Complementarity Determining Regions (CDRs) both in the light chain and the heavy chain variable domains. The more highly conserved portions of the variable domains are called the framework regions (FR). The variable domains of native heavy and light chains each comprise four FR regions, largely adopting a β-sheet configuration, connected by three or four CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., Sequences of Proteins of Immunological Interest, 5th Ed. Public Health Service, National Institutes of Health, Bethesda, Md. (1991)).

The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. The heavy chain constant regions that correspond to the different classes of immunoglobulins are called α, δ, ε, γ and μ, respectively. Of the various human immunoglobulin classes, only human IgG1, IgG2, IgG3 and IgM are known to activate complement.

In vivo, affinity maturation of antibodies is driven by antigen selection of higher affinity antibody variants which are made primarily by somatic hypermutagenesis. A "repertoire shift" also often occurs in which the predominant germline genes of the secondary or tertiary response are seen to differ from those of the primary or secondary response.

The affinity maturation process of the immune system may be replicated by introducing mutations into antibody genes in vitro and using affinity selection to isolate mutants with improved affinity. Such mutant antibodies can be displayed on the surface of filamentous bacteriophage or microorganisms such as yeast, and antibodies can be selected by their affinity for antigen or by their kinetics of dissociation (off-rate) from antigen. Hawkins et al. J. Mol. Biol. 226:889-896 (1992). CDR walking mutagenesis has been employed to affinity mature human antibodies which bind the human envelope glycoprotein gp120 of human immunodeficiency virus type 1 (HIV-1) (Barbas III et al. PNAS (USA) 91: 3809-3813 (1994); and Yang et al. J. Mol. Biol. 254:392-403 (1995)); and an anti-c-erbB-2 single chain Fv fragment (Schier et al. J. Mol. Biol. 263:551567 (1996)). Antibody chain shuffling and CDR mutagenesis were used to affinity mature a high-affinity human antibody directed against the third hypervariable loop of HIV (Thompson et al. J. Mol. Biol. 256:77-88 (1996)). Balint and Larrick Gene 137:109-118 (1993) describe a computer-assisted oligodeoxyribonucleotide-directed scanning mutagenesis whereby all CDRs of a variable region gene are simultaneously and thoroughly searched for improved variants. An αvβ3-specific humanized antibody was affinity matured using an initial limited mutagenesis strategy in which every position of all six CDRs was mutated followed by the expression and screening of a combinatorial library including the highest affinity mutants (Wu et al. PNAS (USA) 95: 6037-6-42 (1998)). Phage displayed antibodies are reviewed in Chiswell and McCafferty TIBTECH 10:80-84 (1992); and Rader and Barbas III Current Opinion in Biotech. 8:503-508 (1997). In each case where mutant antibodies with improved affinity compared to a parent antibody are reported in the above references, the mutant antibody has amino acid substitutions in a CDR.

By "affinity maturation" herein is meant the process of enhancing the affinity of an antibody for its antigen. Methods for affinity maturation include but are not limited to computational screening methods and experimental methods.

By "antibody" herein is meant a protein consisting of one or more polypeptides substantially encoded by all or part of the antibody genes. The immunoglobulin genes include, but are not limited to, the kappa, lambda, alpha, gamma (IgG1, IgG2, IgG3, and IgG4), delta, epsilon and mu constant region genes, as well as the myriad immunoglobulin variable region genes. Antibody herein is meant to include full-length antibodies and antibody fragments, and include antibodies that exist naturally in any organism or are engineered (e.g. are variants).

By "antibody fragment" is meant any form of an antibody other than the full-length form. Antibody fragments herein include antibodies that are smaller components that exist within full-length antibodies, and antibodies that have been engineered. Antibody fragments include but are not limited to Fv, Fc, Fab, and (Fab')$_2$, single chain Fv (scFv), diabodies, triabodies, tetrabodies, bifunctional hybrid antibodies, CDR1, CDR2, CDR3, combinations of CDR's, variable regions, framework regions, constant regions, and the like (Maynard & Georgiou, 2000, Annu. Rev. Biomed. Eng. 2:339-76; Hudson, 1998, Curr. Opin. Biotechnol. 9:395-402).

By "computational screening method" herein is meant any method for designing one or more mutations in a protein, wherein said method utilizes a computer to evaluate the energies of the interactions of potential amino acid side chain substitutions with each other and/or with the rest of the protein.

By "Fc" herein is meant the portions of an antibody that are comprised of immunoglobulin domains Cγ2 and Cγ3 (Cγ2 and Cγ3). Fc may also include any residues which exist in the N-terminal hinge between Cγ2 and Cγ1 (Cγ1). Fc may refer to this region in isolation, or this region in the context of an antibody or antibody fragment. Fc also includes any modified forms of Fc, including but not limited to the native monomer, the native dimer (disulfide bond linked), modified dimers (disulfide and/or non-covalently linked), and modified monomers (i.e., derivatives).

By "full-length antibody" herein is meant the structure that constitutes the natural biological form of an antibody H and/or L chain. In most mammals, including humans and mice, this form is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, $C\gamma 1$, $C\gamma 2$, and $C\gamma 3$. In each pair, the light and heavy chain variable regions ($V_L$ and $V_H$) are together responsible for binding to an antigen, and the constant regions ($C_L$, $C\gamma 1$, $C\gamma 2$, and $C\gamma 3$, particularly $C\gamma 2$, and $C\gamma 3$) are responsible for antibody effector functions. In some mammals, for example in camels and llamas, full-length antibodies may consist of only two heavy chains, each heavy chain comprising immunoglobulin domains $V_H$, $C\gamma 2$, and $C\gamma 3$.

By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full-length antibodies, antibody fragments, and individual immunoglobulin domains including but not limited to $V_H$, $C\gamma 1$, $C\gamma 2$, $C\gamma 3$, $V_L$, and $C_L$.

By "immunoglobulin (Ig) domain" herein is meant a protein domain consisting of a polypeptide substantially encoded by an immunoglobulin gene. Ig domains include but are not limited to $V_H$, $C\gamma 1$, $C\gamma 2$, $C\gamma 3$, $V_L$, and $C_L$ as is shown in FIG. 1.

By "variant protein sequence" as used herein is meant a protein sequence that has one or more residues that differ in amino acid identity from another similar protein sequence. Said similar protein sequence may be the natural wild type protein sequence, or another variant of the wild type sequence. In general, a starting sequence is referred to as a "parent" sequence, and may either be a wild type or variant sequence. For example, preferred embodiments of the present invention may utilize humanized parent sequences upon which computational analyses are done to make variants.

By "variable region" of an antibody herein is meant a polypeptide or polypeptides composed of the $V_H$ immunoglobulin domain, the $V_L$ immunoglobulin domains, or the $V_H$ and $V_L$ immunoglobulin domains as is shown in FIG. 1 (including variants). Variable region may refer to this or these polypeptides in isolation, as an Fv fragment, as a scFv fragment, as this region in the context of a larger antibody fragment, or as this region in the context of a full-length antibody or an alternative, non-antibody scaffold molecule.

The present invention may be applied to antibodies obtained from a wide range of sources. The antibody may be substantially encoded by an antibody gene or antibody genes from any organism, including but not limited to humans, mice, rats, rabbits, camels, llamas, dromedaries, monkeys, particularly mammals and particularly human and particularly mice and rats. In one embodiment, the antibody may be fully human, obtained for example from a patient or subject, by using transgenic mice or other animals (Bruggemann & Taussig, 1997, Curr. Opin. Biotechnol. 8:455-458) or human antibody libraries coupled with selection methods (Griffiths & Duncan, 1998, Curr. Opin. Biotechnol. 9:102-108). The antibody may be from any source, including artificial or naturally occurring. For example the present invention may utilize an engineered antibody, including but not limited to chimeric antibodies and humanized antibodies (Clark, 2000, Immunol. Today 21:397-402) or derived from a combinatorial library. In addition, the antibody being optimized may be an engineered variant of an antibody that is substantially encoded by one or more natural antibody genes. For example, in one embodiment the antibody being optimized is an antibody that has been identified by affinity maturation.

With respect to ABP's of the invention, the term "antigenically specific" or "specifically binds" refers to ABP's that bind to one or more epitopes of an antigen or binding partner of interest, but which do not substantially recognize and bind other molecules in a sample containing a mixed population of antigens.

The term "bispecific ABP" or 'multispecific ABP" as used herein refers to an ABP comprising two or more antigen-binding sites or binding partner binding sites, a first binding site having affinity for a first antigen or epitope and a second binding site having binding affinity for a second antigen or epitope distinct from the first.

The term "epitope" as used herein refers to a site on an antigen or binding partner that is recognized by an ABP. An epitope may be a linear or conformationally formed sequence or shape of amino acids, if the antigen comprises a polypeptide. An epitope may also be any location on any type of antigen where an ABP binds to the antigen.

As used herein, "antigen-binding polypeptide" or "ABP" shall include those polypeptides and proteins that have at least the biological activity of specific binding to a particular binding partner such as antigen, as well as ABP analogs, ABP isoforms, ABP mimetics, ABP fragments, hybrid ABP proteins, fusion proteins, oligomers and multimers, homologues, glycosylation pattern variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), in vitro, in vivo, by microinjection of nucleic acid molecules, synthetic, transgenic, and gene activated methods. Specific examples of ABP include, but are not limited to, antibody molecules, heavy chain, light chain, variable region, CDR, Fab, scFv, alternative scaffold non-antibody molecules, ligands, receptors, peptides, or any amino acid sequence that binds to an antigen.

The term "ABP" or "antigen-binding polypeptide" refers to an ABP as described above, as well as a polypeptide that retains at least one biological activity of a naturally-occurring antibody, including but not limited to, activities other than antigen binding. Activities other than antigen binding include, but are not limited to, any one or more of the activities associated with the Fc.

Antigen-binding polypeptides include the pharmaceutically acceptable salts and prodrugs, and prodrugs of the salts, polymorphs, hydrates, solvates, biologically-active fragments, biologically-active variants and stereoisomers of the naturally-occurring human ABP as well as agonist, mimetic, and antagonist variants of the naturally-occurring human ABP and polypeptide fusions thereof. Fusions comprising additional amino acids at the amino terminus, carboxyl terminus, or both, are encompassed by the term "antigen-binding polypeptide." Exemplary fusions include, but are not limited to, e.g., methionyl ABP in which a methionine is linked to the N-terminus of ABP resulting from the recombinant expression, fusions for the purpose of purification (including but not limited to, to poly-histidine or affinity epitopes), fusions for the purpose of linking ABP's to other biologically active molecules, fusions with serum albumin binding peptides, and fusions with serum proteins such as serum albumin.

The term "antigen" or "binding partner" refers to a substance that is the target for the binding activity exhibited by the ABP. Virtually any substance may be an antigen or binding partner for an ABP. Examples of antigens or binding partners include, but are not limited to, Alpha-1 antitrypsin, Angiostatin, Antihemolytic factor, antibodies, Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-i alpha, Monocyte inflammatory protein-1 beta, RANTES, I309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GRO☐/MGSA, GRO, GRO, MIP-1, MIP-1, MCP-1), Epidermal Growth Factor (EGF), Erythropoietin ("EPO"), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-I, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase, Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase and many others.

Many of these proteins are commercially available (See, e.g., the Sigma BioSciences 2002 catalogue and price list), and the corresponding protein sequences and genes and, typically, many variants thereof, are well-known (see, e.g., Genbank).

Additional antigens or binding partners include, but are not limited to, transcriptional and expression activators. Example transcriptional and expression activators include genes and proteins that modulate cell growth, differentiation, regulation, or the like. Expression and transcriptional activators are found in prokaryotes, viruses, and eukaryotes, including fungi, plants, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA. Antigens or binding partners include, but are not limited to, expression activators such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Vaccine proteins may be antigens or binding partners including, but not limited to, proteins from infectious fungi, e.g., *Aspergillus, Candida* species; bacteria, particularly *E. coli*, which serves a model for pathogenic bacteria, as well as medically important bacteria such as *Staphylococci* (e.g., *aureus*), or *Streptococci* (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., vaccinia; Picomaviruses, e.g. polio; Togaviruses, e.g., rubella; Flaviviruses, e.g., HCV; and Coronaviruses), (-) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Antigens or binding partners may be enzymes including, but not limited to, amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase may also be antigens or binding partners.

For example, the antigen or binding partner may be a disease-associated molecule, such as tumor surface antigen such as B-cell idiotypes, CD20 on malignant B cells, CD33 on leukemic blasts, and HER2/neu on breast cancer. Alternatively, the antigen or binding partner may be a growth factor receptor. Examples of the growth factors include, but are not limited to, epidermal growth factors (EGFs), transferrin, insulin-like growth factor, transforming growth factors (TGFs), interleukin-1, and interleukin-2. For example, a high expression of EGF receptors has been found in a wide variety of human epithelial primary tumors. TGF-α has been found to mediate an autocrine stimulation pathway in cancer cells. Several murine monoclonal antibodies have been demonstrated to be able to bind EGF receptors, block the binding of ligand to EGF receptors, and inhibit proliferation of a variety of human cancer cell lines in culture and in xenograft medels. Mendelsohn and Baselga (1995) Antibodies to growth factors and receptors, in Biologic Therapy of Cancer, 2nd Ed., J B Lippincott, Philadelphia, pp 607-623. Thus, ABPs of the invention may be used to treat a variety of cancers.

The antigen or binding partner may also be cell surface protein or receptor associated with coronary artery disease such as platelet glycoprotein Iib/IIIa receptor, autoimmune diseases such as CD4, CAMPATH-1 and lipid A region of the gram-negative bacterial lipopolysaccharide. Humanized antibodies against CD4 have been tested in clinical trials in the treatment of patients with mycosis fungoides, generalized postular psoriasis, severe psorisis, and rheumatoid arthritis. Antibodies against lipid A region of the gram-negative bacterial lipopolysaccharide have been tested clinically in the treatment of septic shock. Antibodies against CAMPATH-1 have also been tested clinically in the treatment of against refractory rheumatoid arthritis. Thus, ABPs of the invention may be used to treat a variety of autoimmune diseases. Vaswani et al. (1998) "Humanized antibodies as potential therapeutic drugs" Annals of Allergy, Asthma and Immunology 81:105-115.

The antigen or binding partner may also be proteins or peptides associated with human allergic diseases, such as inflammatory mediator proteins, e.g. Interleukin-1 (IL-1), tumor necrosis factor (TNF), leukotriene receptor and 5-lipoxygenase, and adhesion molecules such as V-CAM/VLA-4. In addition, IgE may also serve as the antigen or binding partner because IgE plays pivotal role in type I immediate hypersensitive allergic reactions such as asthma. Studies have shown that the level of total serum IgE tends to correlate with severity of diseases, especially in asthma. Burrows et al. (1989) "Association of asthma with serum IgE levels and skin-test reactivity to allergens" New Engl. L. Med. 320:271-277. Thus, ABPs selected against IgE may be used to reduce the level of IgE or block the binding of IgE to mast cells and basophils in the treatment of allergic diseases without having substantial impact on normal immune functions.

The antigen or binding partner may also be a viral surface or core protein which may serve as an antigen to trigger immune response of the host. Examples of these viral proteins include, but are not limited to, glycoproteins (or surface antigens, e.g., GP120 and GP41) and capsid proteins (or structural proteins, e.g., P24 protein); surface antigens or core proteins of hepatitis A, B, C, D or E virus (e.g. small hepatitis B surface antigen (SHBsAg) of hepatitis B virus and the core proteins of hepatitis C virus, NS3, NS4 and NS5 antigens); glycoprotein (G-protein) or the fusion protein (F-protein) of respiratory syncytial virus (RSV); surface and core proteins of herpes simplex virus HSV-1 and HSV-2 (e.g., glycoprotein D from HSV-2).

The antigen or binding partner may also be a mutated tumor suppressor gene product that has lost its tumor-suppressing function and may render the cells more susceptible to cancer. Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth—cancer. Examples of the tumor suppressor genes include, but are not limited to, DPC-4, NF-1, NF-2, RB, p53, WT1, BRCA1 and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. p53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. Thus, ABPs may be used to block the interactions of the gene product with other proteins or biochemicals in the pathways of tumor onset and development.

The antigen or binding partner may be a CD molecule including but not limited to, CD1a, CD1b, CD1c, CD1d, CD2, CD3γ, CD3δ, CD3ε, CD4, CD5, CD6, CD7, CD8α, CD8β, CD9, CD10, CD11a, CD11b, CD11c, CDw12, CD13, CD14, CD15, CD15s, CD16a, CD16b, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD45, CD45R, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD66a, CD66b, CD66c, CD66d, CD66e, CD66f, CD67, CD68, CD69, CDw70, CD71, CD72, CD73, CD74, CDw75, CDw76, CD77, CD79α, CD79β, CD80, CD81, CD82, CD83, CD84, CD85, CD86, CD87, CD88, CD89, CD90, CD91, CDw92, CD93, CD94, CD95, CD96, CD97, CD98, CD99, CD100, CD101, CD102, CD103, CD104, CD105, CD106, CD107a, CD107b, CDw108, CDw109, CD110-113, CD114, CD115, CD116, CD117, CD118, CD119, CD120a, CD120b, CD121a, CD121b, CD122, CD123, CDw124, CD125, CD126, CDw127, CDw128a, CDw128b, CD129, CDw130, CD131, CD132, CD133, CD134, CD135, CD136, CDw137, CD138, CD139, CD140a, CD140b, CD141, CD142, CD143, CD144, CDw145, CD146, CD147, CD148, CDw149, CD150, CD151, CD152, CD153, CD154, CD155, CD156, CD157, CD158a, CD158b, CD161, CD162, CD163, CD164, CD165, CD166, and TCRζ. The antigen or binding partner may be VEGF, VEGF receptor, EGFR, Her2, TNFa, TNFRI receptor, GPIIb/IIIa, IL-2R alpha chain, IL-2R beta chain, RSV F protein, alpha4 integrin, IgE, IgE receptor, digoxin, carpet viper venom, complement C5, OPGL, CA-125 tumor antigen, Staphylococci proteins, Staphylococcus epidermidis proteins, Staphylococcus aureus proteins, proteins involved Staphylococcal infection (including but not limited to, Staphylococcus aureus and Staphylococcus epidermidis), IL-6 receptor, CTLA-4, RSV, Tac subunit of IL-2 receptor, IL-5, and EpCam. The antigen or binding partner may be a fragment of a molecule.

Examples of bispecific ABPs include, but are not limited to, those with one ABP directed against a tumor cell antigen and the other ABP directed against a cytotoxic trigger molecule such as anti-FcγRI/anti-CD 15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; bispecific ABPs with one ABP which binds specifically to a tumor antigen and another ABP which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; bispecific ABPs for converting enzyme activated prodrugs such as anti-CD30/anti-alkaline phosphatase (which catalyzes conversion of mitomycin phosphate prodrug to mitomycin alcohol); bispecific ABPs which can be used as fibrinolytic agents such as anti-fibrin/anti-tissue plasminogen activator (tPA), anti-fibrin/anti-urokinase-type plasminogen activator (uPA); bispecific ABPs for targeting immune complexes to cell surface receptors such as anti-low density lipoprotein (LDL)/anti-Fc receptor (e.g. FcγRI, FcγRII or FcγRIII); bispecific ABPs for use in therapy of infectious diseases such as anti-CD3/anti-herpes simplex virus (HSV), anti-T-cell receptor:CD3 complex/anti-influenza, anti-FcγR/anti-HIV; bispecific ABPs for tumor detection in vitro or in vivo such as anti-CEA/anti-EOTUBE, anti-CEA/anti-DPTA, anti-p185$^{HER2}$/anti-hapten; bispecific ABPs as vaccine adjuvants (see Fanger, M W et al., Crit Rev Immunol. 1992;12(34):101-24, which is incorporated by reference herein); and bispecific ABPs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase (see Nolan, O et R. O'Kennedy, Biochim Biophys Acta. Aug. 1, 1990; 1040(1):1-11, which is incorporated by reference herein). Examples of trispecific ABPs include anti-CD3/anti-CD4/anti-CD37, anti-CD3/anti-CD5/anti-CD37 and anti-CD3/anti-CD8/anti-CD37.

Various references disclose modification of polypeptides by polymer conjugation or glycosylation. The term "ABP" or "antigen-binding polypeptide" includes, but is not limited to, polypeptides conjugated to a polymer such as PEG and may be comprised of one or more additional derivitizations of cysteine, lysine, N or C-terminal amino acids, or other residues. In addition, the ABP may comprise a linker, polymer or biologically active molecule, wherein the amino acid to which the linker, polymer, or biologically active molecule is conjugated may be a non-natural amino acid according to the present invention, or may be conjugated to a naturally encoded amino acid utilizing techniques known in the art such as coupling to lysine or cysteine. U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been substituted with a non-essential amino acid residue located in a specified region of the polypeptide. WO 00/26354 discloses a method of producing a glycosylated polypeptide variant with reduced allergenicity, which as compared to a corresponding parent polypeptide comprises at least one additional glycosylation site.

The term "antigen-binding polypeptide" also includes glycosylated ABP's, such as but not limited to, polypeptides glycosylated at any amino acid position, N-linked or O-linked glycosylated forms of the polypeptide. Variants containing single nucleotide changes are also considered as biologically active variants of ABP. In addition, splice variants are also included. The term "antigen-binding polypeptide" also includes ABP heterodimers, homodimers, heteromultimers, or homomultimers of any one or more ABP or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

In some embodiments, the antigen-binding polypeptides further comprise an addition, substitution or deletion that modulates biological activity of the ABP. For example, the additions, substitutions or deletions may modulate one or more properties or activities of the ABP, including but not limited to, modulating affinity for the antigen, modulate (including but not limited to, increases or decreases) antigen conformational or other secondary, tertiary or quaternary structural changes, stabilize antigen conformational or other secondary, tertiary or quaternary structural changes, induce or cause antigen conformational or other secondary, tertiary or quaternary structural changes, modulate circulating half-life, modulate therapeutic half-life, modulate stability of the polypeptide, modulate dose, modulate release or bio-availability, facilitate purification, or improve or alter a particular route of administration. Similarly, antigen-binding polypeptides may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term "antigen-binding polypeptide" also encompasses ABP homodimers, heterodimers, homomultimers, and heteromultimers that are linked, including but not limited to those linked directly via non-naturally encoded amino acid side chains, either to the same or different non-naturally encoded amino acid side chains, to naturally-encoded amino acid side chains, as fusions, or indirectly via a linker. Exemplary linkers include but are not limited to, small organic compounds, water soluble polymers of a variety of lengths such as poly(ethylene glycol) or polydextran, or polypeptides of various lengths.

Those of skill in the art will appreciate that amino acid positions corresponding to positions in a particular antigen-binding polypeptide sequence can be readily identified in a fragment of the antigen-binding polypeptide or related antigen-binding polypeptide, etc. For example, sequence alignment programs such as BLAST can be used to align and identify a particular position in a protein that corresponds with a position in a related sequence.

The term "antigen-binding polypeptide" encompasses antigen-binding polypeptides comprising one or more amino acid substitutions, additions or deletions. Antigen-binding polypeptides of the present invention may be comprised of modifications with one or more natural amino acids in conjunction with one or more non-natural amino acid modification. Exemplary substitutions in a wide variety of amino acid positions in naturally-occurring ABP polypeptides have been described, including but not limited to substitutions that modulate one or more of the biological activities of the antigen-binding polypeptide, such as but not limited to, increase agonist activity, increase solubility of the polypeptide, convert the polypeptide into an antagonist, etc. and are encompassed by the term "ABP."

A "non-naturally encoded amino acid" refers to an amino acid that is not one of the 20 common amino acids or pyrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, peptides or proteins such as serum albumin, or other moieties that increase serum half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide. Branched linkers may be used in antigen-binding polypeptides of the invention.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, hard drugs, soft drugs, dyes, lipids, nucleosides, oligonucleotides, toxins, cells, viruses, liposomes, microparticles and micelles. Classes of biologically active agents that are suitable for use with the invention include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

In certain embodiments, the ABP molecules of this invention can be used to direct biologically active molecules or detectable labels to a tumor site. This can facilitate tumor killing, detection and/or localization or other effect. Diagnostic probes or imaging probes may also be linked to ABP molecules of the invention. In certain particularly preferred embodiments, the biologically active molecule component of the ABP is a "radiopaque" label, e.g. a label that can be easily visualized using for example x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque multiurethanes (see U.S. Pat. No. 5,346,981), organobismuth composites (see, e.g., U.S. Pat. No. 5,256,334), radiopaque barium multimer complexes (see, e.g., U.S. Pat. No. 4,866,132), and the like.

The ABP's of this invention can be coupled directly to the radiopaque moiety or they can be attached to a "package" (e.g. a chelate, a liposome, a multimer microbead, etc.) carrying or containing the radiopaque material.

In addition to radioopaque labels, other labels are also suitable for use in this invention. Detectable labels suitable for use as the biologically active molecule component of the ABP's of this invention include any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g. multi-styrene, multipropylene, latex, etc.) beads.

Various preferred radiolabels include, but are not limited to $^{99}Tc$, $^{203}Pb$, $^{67}Ga$, $^{68}Ga$, $^{72}As$, $^{111}In$, $^{113}mIn$, $^{97}Ru$, $^{62}Cu$, $^{641}Cu$, $^{52}Fe$, $^{52}mMn$, $^{51}Cr$, $^{186}Re$, $^{188}Re$, $^{77}As$, $^{90}Y$, $^{67}Cu$, $^{169}Er$, $^{121}Sn$, $^{127}Te$, $^{142}Pr$, $^{143}Pr$, $^{198}Au$, $^{199}Au$, $^{161}Tb$, $^{109}Pd$, $^{165}Dy$, $^{149}Pm$, $^{151}Pm$, $^{153}Sm$, $^{157}Gd$, $^{159}Gd$, $^{166}Ho$, $^{172}Tm$, $^{169}Yb$, $^{175}Yb$, $^{175}Yb$, $^{177}Lu$, $^{105}Rh$, and $^{111}Ag$.

Means of detecting such labels are well known to those of skill in the art. Thus, for example, radiolabels may be detected using photographic film, scintillation detectors, and the like. Fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

In certain specific embodiments, this invention contemplates the use of immunoconjugates (chimeric moieties) for the detection of tumors and/or other cancer cells. Thus, for example, the bispecific antibodies of this invention can be conjugated to gamma-emitting radioisotopes (e.g., Na-22, Cr-51, Co-60, Tc-99, I-125, I-131, Cs-137, Ga-67, Mo-99) for detection with a gamma camera, to positron emitting isotopes (e.g. C-11, N-13, O-15, F-18, and the like) for detection on a Positron Emission Tomography (PET) instrument, and to metal contrast agents (e.g., Gd containing reagents, Eu containing reagents, and the like) for magnetic resonance imaging (MRI), In addition, the bispecific antibodies of this invention can be used in traditional immunohistochemistry (e.g. fluorescent labels, nanocrystal labels, enzymatic and colormetric labels etc.).

In another embodiment, the biologically active molecule can be a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

The biologically active molecule may also be a ligand, an epitope tag, a peptide, a protein, or another ABP. Ligand and antibodies may be those that bind to surface markers on immune cells. Chimeric molecules utilizing such antibodies as biologically active molecules act as bifunctional linkers establishing an association between the immune cells bearing binding partner for the ligand or ABP and the tumor cells expressing the EGFR family member(s).

Many of the pharmaceuticals and/or radiolabels described herein may be provided as a chelate, particularly where a pre-targeting strategy is utilized. The chelating molecule is typically coupled to a molecule (e.g. biotin, avidin, streptavidin, etc.) that specifically binds an epitope tag attached to the bispecific and/or multispecific ABP.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(-2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N'-,N'',N'''-tetra-acetic acid (DOTA), hydroxyethyldiamine triacetic acid (HEDTA), 1,4,8,11-tetra-azacyclotetradecane-N,N',N'',N'''-tetra-acetic acid (TETA), substituted DTPA, substituted EDTA, and the like.

Examples of certain preferred chelators include unsubstituted or, substituted 2-iminothiolanes and 2-iminothiacyclohexanes, in particular 2-imino-4-mercaptomethylthiolane, and SAPS (N-(4-[211At] astatophenethyl)succinimate).

One chelating agent, 1,4,7,10-tetraazacyclododecane-N,N,N'',N'''-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and ABP fragments. To make these conjugates, one carboxylic acid group of DOTA is converted to an active ester which can react with an amine or sulfhydryl group on the ABP or ABP fragment. Lewis et al. (1994) Bioconjugate Chem. 5: 565-576, describes a similar method wherein one carboxyl group of DOTA is converted to an active ester, and the activated DOTA is mixed with an ABP, linking the ABP to DOTA via the epsilon-amino group of a lysine residue of the ABP, thereby converting one carboxyl group of DOTA to an amide moiety.

Alternatively the chelating agent can be coupled, directly or through a linker, to an epitope tag or to a moiety that binds an epitope tag. Conjugates of DOTA and biotin have been described (see, e.g., Su (1995) J. Nucl. Med., 36 (5 Suppl): 154P, which discloses the linkage of DOTA to biotin via available amino side chain biotin derivatives such as DOTA-LC-biotin or DOTA-benzyl-4-(6-amino-caproamide)-biotin). Yau et al., WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) Nucl. Med. Biol., 19(2): 239-244 discloses a synthesis of macrocylic chelating agents for radiolabeling proteins with $^{111}$IN and $^{90}$Y. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

ABP's of this invention may be fused to other biologically active molecules, including, but are not limited to, cytotoxic drugs, toxins, peptides, proteins, enzymes and viruses (Chester, (2000) Dis. Markers 16:53-62; Rippmann et al. Biochem J. (2000) Biochem J. 349 (Pt. 3):805-812, Kreitman, R. J. (2001) Curr. Pharm. Biotechnol. 2:313-325; Rybak, S. M. (2001) Expert Opin. Biol. Ther. 1:995-1003; van Beusechem, V. W. et al. J. Virol. (2002) 76:2753-2762).

A potent cytotoxic agent, or payload, may be bound to ABP's that target and bind to antigens that are found predominantly on target cells (including but not limited to, cancer cells). The payload agent is linked to the ABP via a link that is stable in the bloodstream, or may be susceptible to cleavage under conditions present at, for example, the tumor site. Payload agents such as toxins are delivered to target cells and thus cell killing can be initiated via a mechanism dependent on the toxin.

Examples of such toxins include, but are not limited to, small molecules such as fungal derived calicheamicins (Hinman et al. (1993) Cancer Res. 53: 3336-3342) and maytansinoids (Liu et al. (1996) PNAS USA 93:8618-8623, Smith, S. (2001) Curr. Opin. Mol. Ther. 3(2):198-203), trichothene, and CC 1065, or proteins, e.g. ricin A chain (Messman, et al. (2000) Clin. Cancer Res. 6(4):1302-1313), Pseudomonas exotoxin (Tur et al. (2001) Intl. J. Mol. Med. 8(5):579-584), diphtheria toxin (LeMaistre et al. (1998) Blood 91(2):399-405), and ribosome-inactivating proteins (Tazzari, et al. (2001), J. Immunol. 167:4222-4229). In a specific embodiment, one or more calicheamicin molecules may be used. Members of the calicheamicin family of antibiotics are capable of producing double-stranded DNA breaks at subpicomolar concentrations. Structured analogues of calicheamicin are also known. See Hinman et al., Cancer Research 53: 3336-42 (1993); Lode et al. (1998) Cancer Research 58:2925-28. An example of an immunotoxin that has gained FDA approval is Mylotarg® (Wyeth Ayerst), a calichaemicin-conjugated anti-CD33 for acute myelogenous leukemia (Sievers et al. (1999) Blood 93(11):3678-3684; Bernstein (2000) Leukemia 14:474-475). In a similar fashion, ABP's of this invention may be fused to toxins. Alternatively, ABP's of the invention may be fused with botulinum A neurotoxin, a protein complex produced by the bacterium Clostridium botulinum.

In yet another embodiment, the ABP's of the invention may comprise one or more enzymatically active toxins and/or fragments thereof. Examples of such toxins include nonbinding active fragments of diphtheria toxin, diphtheria A chain, exotoxin A chain (from *Pseudomonas aeruginosa*), ricin A chain, abrin A chain, modeccin A chain, alpha-sarcin, dianthin proteins, *Phytolaca americana* proteins (PAPI, PAPAII, and PAP-S), momordica charantia inhibitor, curcin, crotin sapaonaria, officinalis inhibitor, gelonin, mitogellin, restrictoein, phenomycin, enomycin, and the tricothecenes. See e.g., WO 93/21232. Particularly preferred cytotoxins include Pseudomonas exotoxins (PE), Diphtheria toxins, ricin, and abrin. Pseudomonas exotoxin and Dipthteria toxin are well known. Like PE, diphtheria toxin (DT) kills cells by ADP-ribosylating elongation factor 2 thereby inhibiting protein synthesis. Additional citations regarding immunotoxins include Brinkmann, U. (2000) In Vivo 14:21-28, Niv et al. (2001) Curr. Pharm. Biotechnol. 2:19-46, Reiter et al. (2001) Adv. Cancer Res. 81:93-124, Kreitman, R. J. (1999) Curr. Opin. Immunol., 11:570-578; Hall (2001) Meth. Mol. Biol. 166:139-154; Kreitman (2001) Curr. Opin. Investig. Drugs 2(9):1282-1293. Methods of cloning genes encoding PE or DT fused to various ligands are well known to those of skill in the art (see, e.g., Siegall et al. (1989) FASEB J., 3: 2647-2652; and Chaudhary et al. (1987) Proc. Natl. Acad. Sci. USA, 84: 4538-4542). All citations are incorporated by reference herein.

Other suitable biologically active molecules include pharmacological agents or encapsulation systems containing various pharmacological agents. Thus, the targeting molecule of the chimeric molecule may be attached directly to a drug that is to be delivered directly to the tumor. Such drugs are well known to those of skill in the art and include, but are not limited to, doxirubicin, vinblastine, genistein, an antisense molecule, and the like.

Alternatively, the biologically active molecule may be an encapsulation system, such as a viral capsid, a liposome, or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735, Connor et al. (1985) Pharm. Ther., 28: 341-365. Due to their antigen specificity, ABP's of the invention may be used to direct drug-loaded liposomes to their target. See Park, J. W. et al. (2002) *Clin. Cancer Res.* 8, 1172-1181 and Shi, N. et al (2001) *Pharm. Res.* 18, 1091-1095.

ABP's of the invention may be conjugated to molecules such as PEG to improve in vivo delivery and pharmacokinetic profiles. Leong et al. describe site-specific PEGylation of a Fab' fragment of an anti-IL-8 antibody with a decreased clearance rate over the non-PEGylated form and little or no loss of antigen binding activity (Leong, S. R. et al. (2001) Cytokine 16:106-119).

The ABP's of the present invention may be linked to a prodrug. The term "prodrug" as used herein means a pharmacologically inactive, or reduced activity, derivative of an active drug. Prodrugs may be designed to modulate the amount of a drug or biologically active molecule that reaches a desired site of action through the manipulation of the properties of a drug, such as physicochemical, biopharmaceutical, or pharmacokinetic properties. Prodrugs are converted into active drug within the body through enzymatic or non-enzymatic reactions. Prodrugs may provide improved physicochemical properties such as better solubility, enhanced delivery characteristics, such as specifically targeting a particular cell, tissue, organ or ligand, and improved therapeutic value of the drug. ABP's of the invention may be fused to enzymes for prodrug activation (Kousparou, C. A., et al. (2002) *Int. J. Cancer* 99, 138-148). (2002) Recombinant molecules may comprise an ABP and an enzyme that acts upon a prodrug to release a cytotoxin such as cyanide.

The therapeutic agents may be administered as a prodrug and subsequently activated by a prodrug-activating enzyme that converts a prodrug like peptidyl chemotherapeutic agent to an active anti-cancer drug. See, e.g., WO 88/07378; WO 81/01145; U.S. Pat. No. 4,975,278. In general, the enzyme component includes any enzyme capable of acting on a prodrug in such a way as to convert it into its more active, cytotoxic form.

Enzymes that may be useful include, but are not limited to, alkaline phosphatase useful for converting phosphate-containing prodrugs into free drugs, arylsulfatase useful for converting sulfate containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amino nitrogens with phenoxyacetyl or phenylacetyl groups, respectively, into free drugs.

Alternatively, antibodies with enzymatic activity, also known in the art as "abzymes," may be used to convert the prodrugs of the invention into free active drugs. See e.g., Massey, (1987) 328:457-48.

One of skill will appreciate that the bispecific and/or multispecific ABP of this invention and the biologically active molecule moieties can typically be joined together in any order. Thus, for example, where the targeting molecule is a single chain protein the biologically active molecule may be joined to either the amino or carboxy termini of the targeting molecule. The biologically active molecule can also be joined to an internal region of the bispecific and/or multispecific ABP, or conversely. Similarly, the bispecific and/or multispecific ABP can be joined to an internal location or a terminus of the biologically active molecule. In any case, attachment points are selected that do not interfere with the respective activities of the bispecific and/or multispecific ABP or the biologically active molecule.

The bispecific and/or multispecific ABP and the biologically active molecule can be attached by any of a number of means well known to those of skill in the art. Typically the biologically active molecule is conjugated, either directly or through a linker (spacer), to the bispecific ABP. However, where both the biologically active molecule and the bispecific ABP are both polypeptides it may be desired to recombinantly express the chimeric molecule as a single-chain fusion protein.

In one embodiment, the bispecific and/or multispecific ABP is chemically conjugated to the biologically active molecule (e.g., a cytotoxin, a label, a ligand, a drug, an ABP, a liposome, etc.). Means of chemically conjugating molecules are well known to those of skill in the art.

The procedure for attaching an agent to an ABP or other polypeptide targeting molecule will vary according to the chemical structure of the agent. Polypeptides typically contain variety of functional groups; e.g., carboxylic acid (COOH) or free amine (—$NH_2$) groups, which are available for reaction with a suitable functional group on a biologically active molecule to bind the biologically active molecule thereto.

Alternatively, the bispecific ABP and/or biologically active molecule can be derivatized to expose or attach additional reactive functional groups. The derivatization can involve attachment of any of a number of linker molecules such as those available from Pierce Chemical Company, Rockford, Ill.

In some circumstances, it may be desirable to free the biologically active molecule from the bispecific and/or multispecific ABP, or activate a prodrug, when the chimeric moiety has reached its target site. Therefore, chimeric conjugates comprising linkages that are cleavable in the vicinity of the target site can be used when the biologically active molecule is to be released at the target site. Cleaving of the linkage to release the agent from the ABP may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225; and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. The length of the linker may be predetermined or selected depending upon a desired spatial relationship between the ABP and the molecule linked to it. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an ABP or other polypeptide.

In certain embodiments, the biologically active molecule comprises a chelate that is attached to an ABP or to an epitope tag. The bispecific and/or multispecific ABP bears a corresponding epitope tag or ABP so that simple contacting of the bispecific and/or multispecific ABP to the chelate results in attachment of the ABP to the biologically active molecule. The combining step can be performed after the moiety is used (pretargeting strategy) or the target tissue can be bound to the bispecific and/or multispecific ABP before the chelate is delivered. Methods of producing chelates suitable for coupling to various targeting moieties are well known to those of skill in the art (see, e.g., U.S. Pat. Nos. 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, and 6,001,329).

Where the bispecific and/or multispecific ABP and/or the biologically active molecule are both single chain proteins and relatively short (i.e., less than about 50 amino acids) they can be synthesized using standard chemical peptide synthesis techniques. Where both components are relatively short, the chimeric moiety can be synthesized as a single contiguous polypeptide. Alternatively, a bispecific and/or multispecific ABP and the biologically active molecule may be synthesized separately and then fused by condensation of the amino terminus of one molecule with the carboxyl terminus of the other molecule thereby forming a peptide bond. Alternatively, the bispecific and/or multispecific ABP and biologically active molecules may each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963), and Stewart et al., Solid Phase Peptide Synthesis, 2nd ed. Pierce Chem. Co., Rockford, Ill. (1984).

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S. Pat. Nos. 4,671,958, 4,659,839, 4,414,148, 4,699,784; 4,680,338; 4,569,789; and 4,589,071 which are incorporated by reference herein. A "multi-functional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired molecular length or molecular weight, and may be selected to provide a particular desired spacing or conformation between one of molecules linked to the ABP.

Where substituent groups are specified by their conventional chemical formulas, written from left to right, they equally encompass the chemically identical substituents that would result from writing the structure from right to left, for example, the structure —CH$_2$O— is equivalent to the structure —OCH$_2$—.

The term "substituents" includes but is not limited to "non-interfering substituents". "Non-interfering substituents" are those groups that yield stable compounds. Suitable non-interfering substituents or radicals include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{12}$ aralkyl, $C_1$-$C_{12}$ alkaryl, $C_3$-$C_{12}$ cycloalkyl, $C_3$-$C_{12}$ cycloalkenyl, phenyl, substituted phenyl, toluoyl, xylenyl, biphenyl, $C_2$-$C_{12}$ alkoxyalkyl, $C_2$-$C_{12}$ alkoxyaryl, $C_7$-$C_{12}$ aryloxyalkyl, $C_7$-$C_{12}$ oxyaryl, $C_1$-$C_6$ alkylsufinyl, $C_1$-$C_{10}$ alkylsulfonyl, —(CH$_2$)$_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NRC(O)—($C_1$-$C_{10}$ alkyl), —C(O)—($C_1$-$C_{10}$ alkyl), $C_2$-$C_{10}$ alkyl thioalkyl, —C(O)O—($C_1$-$C_{10}$ alkyl), —OH, —SO$_2$, =S, —COOH, —NR$_2$, carbonyl, —C(O)—($C_1$-$C_{10}$ alkyl)-CF3, —C(O)—CF3, —C(O)NR2, —($C_1$-$C_{10}$ aryl)-S—($C_6$-$C_{10}$ aryl), —C(O)—($C_1$-$C_{10}$ aryl), —(CH$_2$)$_m$—O—(—(CH$_2$)$_m$—

O—($C_1$-$C_{10}$ alkyl) wherein each m is from 1 to 8, —C(O)NR$_2$, —C(S)NR$_2$, —SO$_2$NR$_2$, —NRC(O)NR$_2$, —NRC(S)NR$_2$, salts thereof, and the like. Each R as used herein is H, alkyl or substituted alkyl, aryl or substituted aryl, aralkyl, or alkaryl.

The term "halogen" includes fluorine, chlorine, iodine, and bromine.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by the structures —CH$_2$CH$_2$— and —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated and unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses bicyclic and tricyclic ring structures. Similarly, the term "heterocycloalkylene" by itself or as part of another substituent means a divalent radical derived from heterocycloalkyl, and the term "cycloalkylene" by itself or as part of another substituent means a divalent radical derived from cycloalkyl.

As used herein, the term "water soluble polymer" refers to any polymer that is soluble in aqueous solvents. Linkage of water soluble polymers to ABP can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding and altered receptor dimerization or multimerization. The water soluble polymer may or may not have its own biological activity, and may be utilized as a linker for attaching an ABP to other substances, including but not limited to one or more ABP's, or one or more biologically active molecules. Suitable polymers include, but are not limited to, polyethylene glycol, polyethylene glycol propionaldehyde, mono $C_1$-$C_{10}$ alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include, but are not limited to, polyethylene glycol and serum albumin.

As used herein, the term "polyalkylene glycol" or "poly(alkene glycol)" refers to polyethylene glycol(poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (including but not limited to, aryloxy, arylthioxy, arylalkyl) includes both aryl and heteroaryl rings as defined above. Thus, the term "arylalkyl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by, for example, an oxygen atom (including but not limited to, phenoxymethyl, 2-pyridyloxymethyl, 3-(1-naphthyloxy)propyl, and the like).

Each of the above terms (including but not limited to, "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR"R"', —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such a radical. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, but are not limited to: halogen, —OR', =O, =NR', =N—OR', —NR'R", —SR', -halogen, —SiR'R"R"', —OC(O)R', —C(O)R', —CO$_2$R', —CONR'R", —OC(O)NR"R"', —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$) alkoxy, and fluoro(C$_1$-C$_4$)alkyl, in a number ranging from zero to the total number of open valences on the aromatic ring system; and where R', R", R'" and R"" are independently selected from hydrogen, alkyl, heteroalkyl, aryl and heteroaryl. When a compound of the invention includes more than one R group, for example, each of the R groups is independently selected as are each R', R", R'" and R"" groups when more than one of these groups is present.

As used herein, the term "modulated serum half-life" means the positive or negative change in circulating half-life of a modified ABP relative to its non-modified form. Serum half-life is measured by taking blood samples at various time points after administration of ABP, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of an ABP or ABP comprising a modified biologically active molecule, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, or an increase or decrease in another parameter or mechanism of action of the non-modified molecule.

The term "isolated," when applied to a nucleic acid or protein, denotes that the nucleic acid or protein is substantially free of other cellular components with which it is associated in the natural state. It can be in a homogeneous state. Isolated substances can be in either a dry or semi-dry state, or in solution, including but not limited to, an aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it means that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs incuding PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins: Structures and Molecular Properties* (W H Freeman & Co.; 2nd edition (December 1993)

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, optionally about 65%, about 70%, about 75%, about 80%, about 85%, about 90%, or about 95% identity over a specified region), when compared and aligned for maximum correspondence over a comparison window, or designated region as measured using one of the following sequence comparison algorithms or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence or a polynucleotide or polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, including but not limited to, by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.); or by manual alignment and visual inspection (see, e.g., Ausubel et al., *Current Protocols in Molecular Biology* (1995 supplement)).

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30° C. for short probes (including but not limited to, 10 to 50 nucleotides) and at least about 60° C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "non-eukaryote" refers to non-eukaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomnonas putida,* etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix,* etc.) phylogenetic domain.

The term "subject" as used herein, refers to an animal, preferably a mammal, most preferably a human, who is the object of treatment, observation or experiment.

The term "effective amount" as used herein refers to that amount of the (modified) non-natural amino acid polypeptide being administered which will relieve to some extent one or more of the symptoms of the disease, condition or disorder being treated. Compositions containing the (modified) non-natural amino acid polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "modified," as used herein refers to the presence of a post-translational modification on a polypeptide. The form "(modified)" term means that the polypeptides being discussed are optionally modified, that is, the polypeptides under discussion can be modified or unmodified.

The term "post-translationally modified" and "modified" refers to any modification of a natural or non-natural amino acid that occurs to such an amino acid after it has been incorporated into a polypeptide chain. The term encompasses, by way of example only, co-translational in vivo modifications, post-translational in vivo modifications, and post-translational in vitro modifications.

In prophylactic applications, compositions containing the (modified) non-natural amino acid polypeptide are administered to a patient susceptible to or otherwise at risk of a particular disease, disorder or condition. Such an amount is defined to be a "prophylactically effective amount." In this use, the precise amounts also depend on the patient's state of health, weight, and the like. It is considered well within the skill of the art for one to determine such prophylactically effective amounts by routine experimentation (e.g., a dose escalation clinical trial).

The term "protected" refers to the presence of a "protecting group" or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in or with the methods and compositions described herein.

By way of example only, blocking/protecting groups may be selected from:

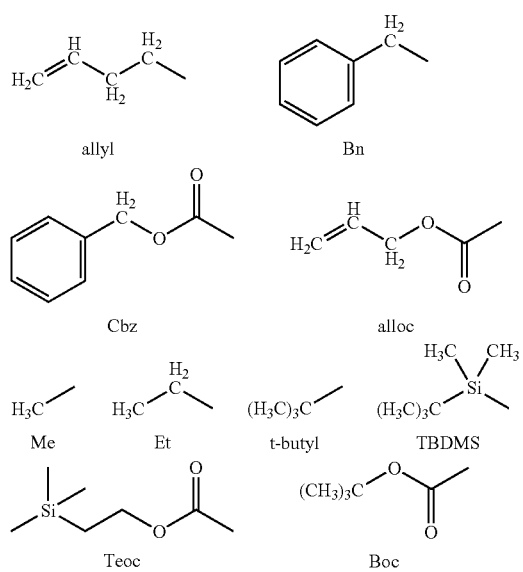

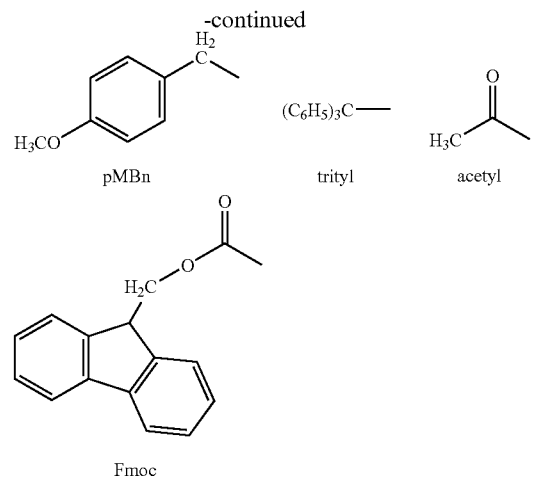

Other protecting groups are described in Greene and Wuts, Protective Groups in Organic Synthesis, 3rd Ed., John Wiley & Sons, New York, N.Y., 1999, which is incorporated herein by reference in its entirety.

In therapeutic applications, compositions containing the (modified) non-natural amino acid polypeptide are administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

The term "treating" is used to refer to either prophylactic and/or therapeutic treatments.

Unless otherwise indicated, conventional methods of mass spectroscopy, NMR, HPLC, protein chemistry, biochemistry, recombinant DNA techniques and pharmacology, within the skill of the art are employed.

DETAILED DESCRIPTION

I. Introduction

ABP molecules comprising at least one unnatural amino acid are provided in the invention. In certain embodiments of the invention, ABP with at least one unnatural amino acid includes at least one post-translational modification. In one embodiment, the at least one post-translational modification comprises attachment of a molecule including but not limited to, a label, a dye, a polymer, a water-soluble polymer, a derivative of polyethylene glycol, a photocrosslinker, a cytotoxic compound, a radionuclide, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination of the above or any other desirable compound or substance, comprising a second reactive group to at least one unnatural amino acid comprising a first reactive group utilizing chemistry methodology that is known to one of ordinary skill in the art to be suitable for the particular reactive groups. For example, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2] cycloaddition chemistry methodologies are utilized. In another example, the first reactive group is the azido moiety (including but not limited to, in the unnatural amino acid p-azido-L-phenylalanine) and the second reactive group is the alkynyl moiety. In certain embodiments of the modified ABP polypeptide of the present invention, at least one unnatural amino acid (including but not limited to, unnatural amino acid containing a keto functional group) comprising at least one post-translational modification, is used where the at least one post-translational modification comprises a saccharide moiety. In certain embodiments, the post-translational modification is made in vivo in a eukaryotic cell or in a non-eukaryotic cell.

In certain embodiments, the protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of post-translational modifications include, but are not limited to, acetylation, acylation, lipid-modification, palmitoylation, palmitate addition, phosphorylation, glycolipid-linkage modification, and the like. In one embodiment, the post-translational modification comprises attachment of an oligosaccharide to an asparagine by a GlcNAc-asparagine linkage (including but not limited to, where the oligosaccharide comprises (GlcNAc-Man)$_2$-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide of the invention can comprise a secretion or localization sequence, an epitope tag, a FLAG tag, a polyhistidine tag, a GST fusion, and/or the like. Examples of secretion signal sequences include, but are not limited to, a prokaryotic secretion signal sequence, an eukaryotic secretion signal sequence, an eukaryotic secretion signal sequence 5'-optimized for bacterial expression, a novel secretion signal sequence, pectate lyase secretion signal sequence, Omp A secretion signal sequence, and a phage secretion signal sequence. Examples of secretion signal sequences, include, but are not limited to, STII (prokaryotic), Fd GIII and M13 (phage), Bgl2 (yeast), and the signal sequence bla derived from a transposon.

An antigen-binding polypeptide comprising a non-natural amino acid may be used to modulate the therapeutic half-life, serum half-life, or circulation time of biologically active molecules, including but not limited to, small molecules, peptides, and oligonucleotides. Such small molecules, peptides, and oligonucleotides may have biological activities that include, but are not limited to, binding and/or recognition of a target molecule or cell type, anti-tumor, anti-angiogenic, anti-viral, and apoptotic activities. In addition, the antigen-binding polypeptide comprising a non-natural amino acid may provide a desired activity, including, but not limited to, effector function such as ADCC, phagocytosis, or complement-dependent cytotoxicity, activation of prodrugs, enzymatic activity, catalytic activity, blocking of protein-protein interactions, binding to a desired antigen, and targeting of the small molecule to a desired site. The blocking of protein-protein interactions of an ABP may modulate one or more activities of the attached biologically active molecule. Small molecules may be used as antagonists to interfere with the binding activities of other proteins or molecules.

The antigen-binding polypeptide and the small molecule may be joined by a linker, polymer or covalent bond. The linker, polymer, or small molecule itself may comprise a functional group that is unreactive toward the 20 common amino acids. The linker or polymer may be bifunctional. One or more bonds involved in joining the antigen-binding polypeptide via the linker, polymer, or covalent bond to the biologically active molecule may be irreversible, reversible or labile under desired conditions. One or more bonds involved in joining the antigen-binding polypeptide via the linker, polymer, or covalent bond to a molecule may allow modulated release of the antigen-binding polypeptide or other molecule. A diversity of small molecules may be generated by one skilled in the art by chemical means, isolation as natural products, or other means.

Rader et al. in Proc Natl Acad Sci U S A. 2003 Apr. 29; 100(9):5396-400, which is incorporated by reference herein, describe a method to provide effector function and extended serum half-life to small synthetic molecules via reacting them with a generic antibody molecule. The complex described was created by a reversible covalent bond between mAb 38C2, a catalytic antibody that mimics natural aldolase enzymes, and a diketone derivative of an integrin targeting Arg-Gly-Asp peptidomimetic via a reactive lysine residue on the antibody. In addition to an increase in half life of the peptidomimetic, the complex showed selective retargeting of the antibody to the surface of integrin $\alpha_v\beta_3$ and $\alpha_v\beta_5$ expressing cells.

The protein or polypeptide of interest can contain at least one, at least two, at least three, at least four, at least five, at least six, at least seven, at least eight, at least nine, or ten or more unnatural amino acids. The unnatural amino acids can be the same or different, for example, there can be 1, 2, 3, 4, 5, 6, 7, 8, 9, 10 or more different sites in the protein that comprise 1, 2, 3, 4, 5, 6, 7, 8, 9, 10 or more different unnatural amino acids. In certain embodiments, at least one, but fewer than all, of a particular amino acid present in a naturally occurring version of the protein is substituted with an unnatural amino acid.

The present invention provides methods and compositions based on antigen-binding polypeptides, or ABP, comprising at least one non-naturally encoded amino acid. Introduction of at least one non-naturally encoded amino acid into an ABP can allow for the application of conjugation chemistries that involve specific chemical reactions, including, but not limited to, with one or more non-naturally encoded amino acids while not reacting with the commonly occurring 20 amino acids. In some embodiments, the ABP comprising the non-naturally encoded amino acid is linked to a water soluble polymer, such as polyethylene glycol (PEG), via the side chain of the non-naturally encoded amino acid. This invention provides a highly efficient method for the selective modification of proteins with PEG derivatives, which involves the selective incorporation of non-genetically encoded amino acids, including but not limited to, those amino acids containing functional groups or substituents not found in the 20 naturally incorporated amino acids, including but not limited to a ketone, an azide or acetylene moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the naturally encoded amino acid. Known chemistry methodologies of a wide variety are suitable for use in the present invention to incorporate a water soluble polymer into the protein. Such methodologies include but are not limited to a Huisgen [3+2] cycloaddition reaction (see, e.g., Padwa, A. in *Comprehensive Organic Synthesis. Vol.* 4, (1991) Ed. Trost, B. M., Pergamon, Oxford, p. 1069-1109; and, Huisgen, R. in 1,3-*Dipolar Cycloaddition Chemistry,* (1984) Ed. Padwa, A., Wiley, New York, p. 1-176) with, including but not limited to, acetylene or azide derivatives, respectively.

Because the Huisgen [3+2] cycloaddition method involves a cycloaddition rather than a nucleophilic substitution reaction, proteins can be modified with extremely high selectivity. The reaction can be carried out at room temperature in aqueous conditions with excellent regioselectivity (1,4>1,5) by the addition of catalytic amounts of Cu(I) salts to the reaction mixture. See, e.g., Tornoe, et al., (2002) *Org. Chem.* 67:3057-3064; and, Rostovtsev, et al., (2002) *Angew. Chem. Int. Ed.* 41:2596-2599; and WO 03/101972. A molecule that can be added to a protein of the invention through a [3+2] cycloaddition includes virtually any molecule with a suitable functional group or substituent including but not limited to an azido or acetylene derivative. These molecules can be added to an unnatural amino acid with an acetylene group, including but not limited to, p-propargyloxyphenylalanine, or azido group, including but not limited to p-azido-phenylalanine, respectively.

The five-membered ring that results from the Huisgen [3+2] cycloaddition is not generally reversible in reducing environments and is stable against hydrolysis for extended periods in aqueous environments. Consequently, the physical and chemical characteristics of a wide variety of substances can be modified under demanding aqueous conditions with the active PEG derivatives of the present invention. Even more important, because the azide and acetylene moieties are specific for one another (and do not, for example, react with any of the 20 common, genetically-encoded amino acids), proteins can be modified in one or more specific sites with extremely high selectivity.

The invention also provides water soluble and hydrolytically stable derivatives of PEG derivatives and related hydrophilic polymers having one or more acetylene or azide moieties. The PEG polymer derivatives that contain acetylene moieties are highly selective for coupling with azide moieties that have been introduced selectively into proteins in response to a selector codon. Similarly, PEG polymer derivatives that contain azide moieties are highly selective for coupling with acetylene moieties that have been introduced selectively into proteins in response to a selector codon.

More specifically, the azide moieties comprise, but are not limited to, alkyl azides, aryl azides and derivatives of these azides. The derivatives of the alkyl and aryl azides can include other substituents so long as the acetylene-specific reactivity is maintained. The acetylene moieties comprise alkyl and aryl acetylenes and derivatives of each. The derivatives of the alkyl and aryl acetylenes can include other substituents so long as the azide-specific reactivity is maintained.

ABP comprising a non-naturally encoded amino acid may be used in assays that utilize the specificity of antibodies. For example, ABP molecules of the invention may be used to screen a population of potential antigens.

The present invention provides conjugates of substances having a wide variety of functional groups, substituents or moieties, with other substances including but not limited to a label; a dye; a polymer; a water-soluble polymer; a derivative of polyethylene glycol; a photocrosslinker; a cytotoxic compound; a radionuclide; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; or any combination of the above, or any other desirable compound or substance). The present invention also includes conjugates of substances having azide or acetylene moieties with PEG polymer derivatives having the corresponding acetylene or azide moieties. For example, a PEG polymer containing an azide moiety can be coupled to a biologically active molecule at a position in the protein that contains a non-genetically encoded amino acid bearing an acetylene functionality. The linkage by which the PEG and the biologically active molecule are coupled includes but is not limited to the Huisgen [3+2] cycloaddition product.

It is well established in the art that PEG can be used to modify the surfaces of biomaterials (see, e.g., U.S. Pat. No. 6,610,281; Mehvar, R., J. Pharmaceut. Sci., 3(1):125-136 (2000) which are incorporated by reference herein). The invention also includes biomaterials comprising a surface having one or more reactive azide or acetylene sites and one or more of the azide- or acetylene-containing polymers of the invention coupled to the surface via the Huisgen [3+2] cycloaddition linkage. Biomaterials and other substances can also be coupled to the azide- or acetylene-activated polymer derivatives through a linkage other than the azide or acetylene linkage, such as through a linkage comprising a carboxylic acid, amine, alcohol or thiol moiety, to leave the azide or acetylene moiety available for subsequent reactions.

The invention includes a method of synthesizing the azide- and acetylene-containing polymers of the invention. In the case of the azide-containing PEG derivative, the azide can be bonded directly to a carbon atom of the polymer. Alternatively, the azide-containing PEG derivative can be prepared by attaching a linking agent that has the azide moiety at one terminus to a conventional activated polymer so that the resulting polymer has the azide moiety at its terminus. In the case of the acetylene-containing PEG derivative, the acetylene can be bonded directly to a carbon atom of the polymer. Alternatively, the acetylene-containing PEG derivative can be prepared by attaching a linking agent that has the acetylene moiety at one terminus to a conventional activated polymer so that the resulting polymer has the acetylene moiety at its terminus.

More specifically, in the case of the azide-containing PEG derivative, a water soluble polymer having at least one active hydroxyl moiety undergoes a reaction to produce a substituted polymer having a more reactive moiety, such as a mesylate, tresylate, tosylate or halogen leaving group, thereon. The preparation and use of PEG derivatives containing sulfonyl acid halides, halogen atoms and other leaving groups are well known to the skilled artisan. The resulting substituted polymer then undergoes a reaction to substitute for the more reactive moiety an azide moiety at the terminus of the polymer. Alternatively, a water soluble polymer having at least one active nucleophilic or electrophilic moiety undergoes a reaction with a linking agent that has an azide at one terminus so that a covalent bond is formed between the PEG polymer and the linking agent and the azide moiety is positioned at the terminus of the polymer. Nucleophilic and electrophilic moieties, including amines, thiols, hydrazides, hydrazines, alcohols, carboxylates, aldehydes, ketones, thioesters and the like, are well known to the skilled artisan.

More specifically, in the case of the acetylene-containing PEG derivative, a water soluble polymer having at least one active hydroxyl moiety undergoes a reaction to displace a halogen or other activated leaving group from a precursor that contains an acetylene moiety. Alternatively, a water soluble polymer having at least one active nucleophilic or electrophilic moiety undergoes a reaction with a linking agent that has an acetylene at one terminus so that a covalent bond is formed between the PEG polymer and the linking agent and the acetylene moiety is positioned at the terminus of the polymer. The use of halogen moieties, activated leaving group, nucleophilic and electrophilic moieties in the context of organic synthesis and the preparation and use of PEG derivatives is well established to practitioners in the art.

The invention also provides a method for the selective modification of proteins to add other substances to the modified protein, including but not limited to water soluble polymers such as PEG and PEG derivatives containing an azide or acetylene moiety. The azide- and acetylene-containing PEG derivatives can be used to modify the properties of surfaces and molecules where biocompatibility, stability, solubility and lack of immunogenicity are important, while at the same time providing a more selective means of attaching the PEG derivatives to proteins than was previously known in the art.

II. Antigen-Binding Polypeptides

There is a wide variety of ABP's. ABPs are themselves specific for a very wide variety of antigens. There is also a large number of a very wide variety of ABP fragments that are antigen-specific. ABP therefore is intended to include any polypeptide that demonstrates an ability to specifically bind to a target molecule or antigen. Any known antibody or antibody fragment is an ABP.

ABP's of the invention may comprise an Fc region or Fc-like region. The Fc domain provides the link to effector functions such as complement or phagocytic cells. The Fc portion of an immunoglobulin has a long plasma half-life, whereas the Fab is short-lived (Capon, et al. (1989), Nature, 337:525-531). When constructed together with a therapeutic protein, an Fc domain can provide longer half-life or incorporate such functions as Fc receptor binding, protein A binding, complement fixation and perhaps even placental transfer. For example, the Fc region of an IgG1 antibody has been fused to the N-terminal end of CD30-L, a molecule which binds CD30 receptors expressed on Hodgkin's Disease tumor cells, anaplastic lymphoma cells, T-cell leukemia cells and other malignant cell types (U.S. Pat. No. 5,480,981). IL-10, an anti-inflammatory and antirejection agent has been fused to murine Fcγ2a in order to increase the cytokine's short circulating half-life. Zheng, X. et al. (1995), The Journal of Immunology, 154: 5590-5600. Studies have also evaluated the use of tumor necrosis factor receptor linked with the Fc protein of human IgG1 to treat patients with septic shock. Fisher, C. et al., N. Engl. J. Med., 334: 1697-1702 (1996); Van Zee, K. et al., The Journal of Immunology, 156: 2221-2230 (1996) and rheumatoid arthritis (Moreland, et al. (1997), N. Engl. J. Med., 337(3):141-147. Fc has also been fused with CD4 receptor to produce a therapeutic protein for treatment of AIDS (Capon et al. (1989), Nature, 337:525-531). In addition, the N-terminus of interleukin 2 has also been fused to the Fc portion of IgG1 or IgG3 to overcome the short half life of interleukin 2 and its systemic toxicity (Harvill et al. (1995), Immunotechnology, 1:95-105).

It is well known that Fc regions of antibodies are made up of monomeric polypeptide segments that may be linked into dimeric or multimeric forms by disulfide bonds or by non-covalent association. The number of intermolecular disulfide bonds between monomeric subunits of native Fc molecules ranges from 1 to 4 depending on the class (e.g., IgG, IgA, IgE) or subclass (e.g., IgG1, IgG2, IgG3, IgA1, IgGA2) of antibody involved. The term "Fc" as used herein is generic to the monomeric, dimeric, and multimeric forms of Fc molecules. It should be noted that Fc monomers will spontaneously dimerize when the appropriate Cys residues are present unless particular conditions are present that prevent dimerization through disulfide bond formation. Even if the Cys residues that normally form disulfide bonds in the Fc dimer are removed or replaced by other residues, the monomeric chains will generally dimerize through non-covalent interactions. The term "Fc" herein is used to mean any of these forms: the native monomer, the native dimer (disulfide bond linked), modified dimers (disulfide and/or non-covalently linked), and modified monomers (i.e., derivatives).

Variants, analogs or derivatives of the Fc portion may be constructed by, for example, making various substitutions of residues or sequences including non-naturally encoded amino acids. Variant (or analog) polypeptides include insertion variants, wherein one or more amino acid residues supplement an Fc amino acid sequence. Insertions may be located at either or both termini of the protein, or may be positioned within internal regions of the Fc amino acid sequence. Insertional variants with additional residues at either or both termini can include for example, fusion proteins and proteins including amino acid tags or labels. For example, the Fc molecule may optionally contain an N-terminal Met, especially when the molecule is expressed recombinantly in a bacterial cell such as E. coli. In Fc deletion variants, one or more amino acid residues in an Fc polypeptide are removed. Deletions can be effected at one or both termini of the Fc polypeptide, or with removal of one or more residues within the Fc amino acid sequence. Deletion variants, therefore, include all fragments of an Fc polypeptide sequence. In Fc substitution variants, one or more amino acid residues of an Fc polypeptide are removed and replaced with alternative residues. In one aspect, the substitutions are conservative in nature, however, the invention embraces substitutions that are also non-conservative. For example, cysteine residues can be deleted or replaced with other amino acids to prevent formation of some or all disulfide crosslinks of the Fc sequences. A protein may have one or more cysteine residues, and one may remove each of these cysteine residues or substitute one or more such cysteine residues with other amino acids, such as Ala or Ser, or a non-naturally encoded amino acid. As another example, modifications may also be made to introduce amino acid substitutions to (1) ablate the Fc receptor binding site; (2) ablate the complement (Clq) binding site; and/or to (3) ablate the antibody dependent cell-mediated cytotoxicity (ADCC) site. Such sites are known in the art, and any known substitutions are within the scope of Fc as used herein. For example, see Molecular Immunology, Vol. 29, No. 5, 633-639 (1992) with regards to ADCC sites in IgG1. Likewise, one or more tyrosine residues can be replaced by phenylalanine residues as well. In addition, other variant amino acid insertions, deletions (e.g., from 1-25 amino acids) and/or substitutions are also contemplated and are within the scope of the present invention. Conservative amino acid substitutions will generally be preferred. Furthermore, alterations may be in the form of altered amino acids, such as peptidomimetics or D-amino acids.

Fc sequences may also be derivatized, i.e., bearing modifications other than insertion, deletion, or substitution of amino acid residues. Preferably, the modifications are covalent in nature, and include for example, chemical bonding with polymers, lipids, other organic moieties, and inorganic moieties. Derivatives of the invention may be prepared to increase circulating half-life, or may be designed to improve targeting capacity for the polypeptide to desired cells, tissues, or organs. It is also possible to use the salvage receptor binding domain of the intact Fc molecule as the Fc part of the inventive compounds, such as described in WO 96/32478, entitled "Altered Polypeptides with Increased Half-Life". Additional members of the class of molecules designated as Fc herein are those that are described in WO 97/34631, entitled "Immunoglobulin-Like Domains with Increased Half-Lives". Both of the published PCT applications cited in this paragraph are hereby incorporated by reference.

Additional ABPs are likely to be discovered in the future. New ABPs can be identified through computer-aided secondary and tertiary structure analyses of the predicted protein sequences, and by selection techniques designed to identify molecules that bind to a particular target. Such later discovered ABPs also are included within this invention.

Thus, the description of ABPs is provided for illustrative purposes and by way of example only and not as a limit on the scope of the methods, compositions, strategies and techniques described herein. Further, reference to ABP's in this application is intended to use the generic term as an example of any ABP. Thus, it is understood that the modifications and chemistries described herein with reference to a specific antigen-binding polypeptide or protein can be equally applied to any antigen-binding polypeptide, including those specifically listed herein.

III. General Recombinant Nucleic Acid Methods for use with the Invention

In numerous embodiments of the present invention, nucleic acids encoding a ABP of interest will be isolated, cloned and often altered using recombinant methods. Such embodiments are used, including but not limited to, for protein expression or during the generation of variants, derivatives, expression cassettes, or other sequences derived from an antigen-binding polypeptide. In some embodiments, the sequences encoding the polypeptides of the invention are operably linked to a heterologous promoter.

A nucleotide sequence encoding an antigen-binding polypeptide comprising a non-naturally encoded amino acid may be synthesized on the basis of the amino acid sequence of the parent polypeptide and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction. See, e.g., Barany, et al., *Proc. Natl. Acad. Sci.* 88: 189-193 (1991); U.S. Pat. No. 6,521,427 which are incorporated by reference herein.

This invention utilizes routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

General texts which describe molecular biological techniques include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, New York, 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). These texts describe mutagenesis, the use of vectors, promoters and many other relevant topics related to, including but not limited to, the generation of genes that include selector codons for production of proteins that include unnatural amino acids, orthogonal tRNAs, orthogonal synthetases, and pairs thereof.

Various types of mutagenesis are used in the invention for a variety of purposes, including but not limited to, to produce libraries of tRNAs, to produce libraries of synthetases, to produce selector codons, to insert selector codons that encode unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, are also included in the present invention. In one embodiment, mutagenesis can be guided by known information of the naturally occurring molecule or altered or mutated naturally occurring molecule, including but not limited to, sequence, sequence comparisons, physical properties, secondary, tertiary, or quaternary structure, crystal structure or the like.

The texts and examples found herein describe these procedures. Additional information is found in the following publications and references cited within: Ling et al., *Approaches to DNA mutagenesis: an overview*, Anal Biochem. 254(2): 157-178 (1997); Dale et al., *Oligonucleotide-directed random mutagenesis using the phosphorothioate method*, Methods Mol. Biol. 57:369-374 (1996); Smith, *In vitro mutagenesis*, Ann. Rev. Genet. 19:423-462 (1985); Botstein & Shortle, *Strategies and applications of in vitro mutagenesis*, Science 229:1193-1201 (1985); Carter, *Site-directed mutagenesis*, Biochem. J. 237:1-7 (1986); Kunkel, *The efficiency of oligonucleotide directed mutagenesis*, in *Nucleic Acids & Molecular Biology* (Eckstein, F. and Lilley, D. M. J. eds., Springer Verlag, Berlin) (1987); Kunkel, *Rapid and efficient site-specific mutagenesis without phenotypic selection*, Proc. Natl. Acad. Sci. USA 82:488-492 (1985); Kunkel et al., *Rapid and efficient site-specific mutagenesis without phenotypic selection*, Methods in Enzymol. 154, 367-382 (1987); Bass et al., *Mutant Trp repressors with new DNA-binding specificities*, Science 242:240-245 (1988); *Methods in Enzymol.* 100: 468-500 (1983); *Methods in Enzymol.* 154: 329-350 (1987); Zoller & Smith, *Oligonucleotide-directed mutagenesis using M13-derived vectors: an efficient and general procedure for the production of point mutations in any DNA fragment*, Nucleic Acids Res. 10:6487-6500 (1982); Zoller & Smith, *Oligonucleotide-directed mutagenesis of DNA fragments cloned into M13 vectors*, Methods in Enzymol. 100:468-500 (1983); Zoller & Smith, *Oligonucleotide-directed mutagenesis: a simple method using two oligonucleotide primers and a single-stranded DNA template*, Methods in Enzymol. 154: 329-350 (1987); Taylor et al., *The use of phosphorothioate-modified DNA in restriction enzyme reactions to prepare nicked DNA*, Nucl. Acids Res. 13: 8749-8764 (1985); Taylor et al., *The rapid generation of oligonucleotide-directed mutations at high frequency using phosphorothioate-modified DNA*, Nucl. Acids Res. 13: 8765-8787 (1985); Nakamaye & Eckstein, *Inhibition of restriction endonuclease Nci I cleavage by phosphorothioate groups and its application to oligonucleotide-directed mutagenesis*, Nucl. Acids Res. 14: 9679-9698 (1986); Sayers et al., *5'-3' Exonucleases in phosphorothioate-based oligonucleotide-directed mutagenesis*, Nucl. Acids Res. 16:791-802 (1988); Sayers et al., *Strand specific cleavage of phosphorothioate-containing DNA by reaction with restriction endonucleases in the presence of ethidium bromide*, (1988) Nucl. Acids Res. 16: 803-814; Kramer et al., *The gapped duplex DNA approach to oligonucleotide-directed mutation construction*, Nucl. Acids Res. 12: 9441-9456 (1984); Kramer & Fritz *Oligonucleotide-directed construction of mutations via gapped duplex DNA*, Methods in Enzymol. 154:350-367 (1987); Kramer et al., *Improved enzymatic in vitro reactions in the gapped duplex DNA approach to oligonucleotide-directed construction of mutations*, Nucl. Acids Res. 16: 7207 (1988); Fritz et al., *Oligonucleotide-directed construction of mutations: a gapped duplex DNA procedure without enzymatic reactions in vitro*, Nucl. Acids Res. 16: 6987-6999 (1988); Kramer et al., *Different base/base mismatches are corrected with different efficiencies by the methyl-directed DNA mismatch-repair system of E. coli*, Cell 38:879-887 (1984); Carter et al., *Improved oligonucleotide site-directed mutagenesis using M13 vectors*, Nucl. Acids Res. 13: 4431-4443 (1985); Carter, *Improved oligonucleotide-directed mutagenesis using M13 vectors*, Methods in Enzymol. 154: 382403 (1987); Eghtedarzadeh & Henikoff, *Use of oligonucleotides to generate large deletions*, Nucl. Acids Res. 14: 5115 (1986); Wells et al., *Importance of hydrogen-bond formation in stabilizing the transition state of subtilisin*, Phil. Trans. R. Soc. Lond. A 317: 415-423 (1986); Nambiar et al., *Total synthesis and cloning of a gene coding for the ribonuclease S protein*, Science 223: 1299-1301 (1984); Sakmar and Khorana, *Total synthesis and expression of a gene for the alpha-subunit of bovine rod outer segment guanine nucleotide-binding protein (transducin)*, Nucl. Acids Res. 14: 6361-6372 (1988); Wells et al., *Cassette mutagenesis: an efficient method for generation of multiple mutations at defined sites*, Gene 34:315-323 (1985); Grundström et al., *Oligonucleotide-directed mutagenesis by microscale 'shotgun' gene synthesis*, Nucl. Acids Res. 13: 3305-3316 (1985); Mandecki, *Oligonucleotide-directed double-strand break repair in plasmids of Escherichia coli: a method for site-specific mutagenesis*, Proc. Natl. Acad. Sci. USA, 83:7177-7181 (1986); Arnold, *Protein engineering for unusual environments*, Current Opinion in Biotechnology 4:450-455 (1993); Sieber, et al., Nature Biotechnology, 19:456-460 (2001); W. P. C. Stemmer, Nature 370, 389-91 (1994); and, I. A. Lorimer, I. Pastan, Nucleic Acids Res. 23, 3067-8 (1995). Additional details on many of the above methods can be found in *Methods in Enzymology* Volume 154, which also describes useful controls for trouble-shooting problems with various mutagenesis methods.

The invention also relates to eukaryotic host cells, non-eukaryotic host cells, and organisms for the in vivo incorporation of an unnatural amino acid via orthogonal tRNA/RS pairs. Host cells are genetically engineered (including but not limited to, transformed, transduced or transfected) with the polynucleotides of the invention or constructs which include a polynucleotide of the invention, including but not limited to, a vector of the invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., Proc. Natl. Acad. Sci. USA 82, 5824 (1985), infection by viral vectors, high velocity ballistic penetration by small particles with the nucleic acid either within the matrix of small beads or particles, or on the surface (Klein et al., Nature 327, 70-73 (1987)).

The engineered host cells can be cultured in conventional nutrient media modified as appropriate for such activities as, for example, screening steps, activating promoters or selecting transformants. These cells can optionally be cultured into transgenic organisms. Other useful references, including but not limited to for cell isolation and culture (e.g., for subsequent nucleic acid isolation) include Freshney (1994) *Culture of Animal Cells a Manual of Basic Technique,* third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture; Fundamental Methods* Springer Lab Manual, Springer-Verlag (Berlin Heidelberg New York) and Atlas and Parks (eds.) *The Handbook of Microbiological Media* (1993) CRC Press, Boca Raton, Fla.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™ from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or preferably both. See, Giliman & Smith, *Gene* 8:81 (1979); Roberts, et al., *Nature,* 328:731 (1987); Schneider, B., et al., *Protein Expr. Purif.* 6435:10 (1995); Ausubel, Sambrook, Berger (all supra). A catalogue of bacteria and bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA Second Edition* Scientific American Books, N.Y. In addition, essentially any nucleic acid (and virtually any labeled nucleic acid, whether standard or non-standard) can be custom or standard ordered from any of a variety of commercial sources, such as the Midland Certified Reagent Company (Midland, Tex. available on the World Wide Web at mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

Selector Condons

Selector codons of the invention expand the genetic codon framework of protein biosynthetic machinery. For example, a selector codon includes, but is not limited to, a unique three base codon, a nonsense codon, such as a stop codon, including but not limited to, an amber codon (UAG), or an opal codon (UGA), an unnatural codon, a four or more base codon, a rare codon, or the like. It is readily apparent to those of ordinary skill in the art that there is a wide range in the number of selector codons that can be introduced into a desired gene, including but not limited to, one or more, two or more, more than three, 4, 5, 6, 7, 8, 9, 10 or more in a single polynucleotide encoding at least a portion of ABP.

In one embodiment, the methods involve the use of a selector codon that is a stop codon for the incorporation of unnatural amino acids in vivo in a eukaryotic cell. For example, an O-tRNA is produced that recognizes the stop codon, including but not limited to, UAG, and is aminoacylated by an O—RS with a desired unnatural amino acid. This O-tRNA is not recognized by the naturally occurring host's aminoacyl-tRNA synthetases. Conventional site-directed mutagenesis can be used to introduce the stop codon, including but not limited to, TAG, at the site of interest in a polypeptide of interest. See, e.g., Sayers, J. R., et al. (1988), 5,3'*Exonuclease in phosphorothioate-based oligonucleotide-directed mutagenesis. Nucleic Acids Res.* 791-802. When the O—RS, O-tRNA and the nucleic acid that encodes the polypeptide of interest are combined in vivo, the unnatural amino acid is incorporated in response to the UAG codon to give a polypeptide containing the unnatural amino acid at the specified position.

The incorporation of unnatural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Selector codons also comprise extended codons, including but not limited to, four or more base codons, such as, four, five, six or more base codons. Examples of four base codons include, including but not limited to, AGGA, CUAG, UAGA, CCCU and the like. Examples of five base codons include, but are not limited to, AGGAC, CCCCU, CCCUC, CUAGA, CUACU, UAGGC and the like. A feature of the invention includes using extended codons based on frameshift suppression. Four or more base codons can insert, including but not limited to, one or multiple unnatural amino acids into the same protein. For example, in the presence of mutated O-tRNAs, including but not limited to, a special frameshift suppressor tRNAs, with anticodon loops, for example, with at least 8-10 nt anticodon loops, the four or more base codon is read as single amino acid. In other embodiments, the anticodon loops can decode, including but not limited to, at least a four-base codon, at least a five-base codon, or at least a six-base codon or more. Since there are 256 possible four-base codons, multiple unnatural amino acids can be encoded in the same cell using a four or more base codon. See, Anderson et al., (2002) *Exploring the Limits of Codon and Anticodon Size, Chemistry and Biology,* 9:237-244; Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry,* 32:7939; and Hohsaka et al., (1999) *J. Am. Chem. Soc.,* 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.,* 121:12194. In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., (2000) *J. Mol. Biol.,* 298:195. In one embodiment, extended codons based on rare codons or nonsense codons can be used in the present invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology,* 20:177-182. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.,* 111:8322; and Piccirilli et al., (1990) *Nature,* 343:33; Kool, (2000) *Curr. Opin. Chem. Biol.,* 4:602. These bases in general mispair to some degree with natural bases and cannot be enzymatically replicated. Kool and co-workers demonstrated that hydrophobic packing interactions between bases can replace hydrogen bonding to drive the formation of base pair. See, Kool, (2000) *Curr. Opin. Chem. Biol.,* 4:602; and Guckian and Kool, (1998) *Angew. Chem. Int. Ed. Engl.,* 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.,* 121:11586; and Ogawa et al., (2000) *J. Am. Chem. Soc.,* 122:3274. A 3MN:3MN self-pair can be synthesized by KF with efficiency and selectivity sufficient for biological function. See, e.g., Ogawa et al., (2000) *J. Am. Chem. Soc.* 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.,* 123:7439. A novel metallobase pair, Dipic:Py, has also been developed, which forms a stable pair upon binding Cu(II). See, Meggers et al., (2000) *J. Am. Chem. Soc.* 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is incorporated into a gene but is not translated into protein. The sequence contains a structure that serves as a cue to induce the ribosome to hop over the sequence and resume translation downstream of the insertion.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein to include, for example, one or more selector codon for the incorporation of an unnatural amino acid. For example, a nucleic acid for a protein of interest is mutagenized to include one or more selector codon, providing for the incorporation of one or more unnatural amino acids. The invention includes any such variant, including but not limited to, mutant, versions of any protein, for example, including at least one unnatural amino acid. Similarly, the invention also includes corresponding nucleic acids, i.e., any nucleic acid with one or more selector codon that encodes one or more unnatural amino acid.

Nucleic acid molecules encoding a protein of interest such as ABP may be readily mutated to introduce a cysteine at any desired position of the polypeptide. Cysteine is widely used to introduce reactive molecules, water soluble polymers, proteins, or a wide variety of other molecules, onto a protein of interest. Methods suitable for the incorporation of cysteine into a desired position of the antigen-binding polypeptide are well known in the art, such as those described in U.S. Pat. No. 6,608,183, which is incorporated by reference herein, and standard mutagenesis techniques.

IV. Non-Naturally Encoded Amino Acids

A very wide variety of non-naturally encoded amino acids are suitable for use in the present invention. Any number of non-naturally encoded amino acids can be introduced into ABP. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, antigen-binding polypeptide that includes a non-naturally encoded amino acid containing an azido functional group can be reacted with a polymer (including but not limited to, poly (ethylene glycol) or, alternatively, a second polypeptide containing an alkyne moiety to form a stable conjugate resulting for the selective reaction of the azide and the alkyne functional groups to form a Huisgen [3+2] cycloaddition product.

The generic structure of an alpha-amino acid is illustrated as follows (Formula I):

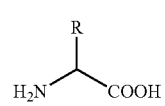

A non-naturally encoded amino acid is typically any structure having the above-listed formula wherein the R group is any substituent other than one used in the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occuring N— or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occuring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). See, also, U.S. Patent Application Publications 2003/0082575 and 2003/0108885, which is incorporated by reference herein. In addition to unnatural amino acids that contain novel side chains, unnatural amino acids that may be suitable for use in the present invention also optionally comprise modified backbone structures, including but not limited to, as illustrated by the structures of Formula II and III:

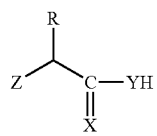

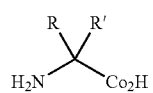

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenylalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) *Incorporation of azides into recombinant proteins for chemoselective modification by the Staudinger ligation, PNAS* 99:19-24, for additional methionine analogs.

In one embodiment, compositions of ABP that include an unnatural amino acid (such as p-(propargyloxy)-phenylalanine) are provided. Various compositions comprising p-(propargyloxy)-phenylalanine and, including but not limited to, proteins and/or cells, are also provided. In one aspect, a composition that includes the p-(propargyloxy)-phenylalanine unnatural amino acid, further includes an orthogonal tRNA. The unnatural amino acid can be bonded (including but not limited to, covalently) to the orthogonal tRNA, including but not limited to, covalently bonded to the orthogonal tRNA though an amino-acyl bond, covalently bonded to a 3'OH or a 2'OH of a terminal ribose sugar of the orthogonal tRNA, etc.

The chemical moieties via unnatural amino acids that can be incorporated into proteins offer a variety of advantages and manipulations of the protein. For example, the unique reactivity of a keto functional group allows selective modification of proteins with any of a number of hydrazine- or hydroxylamine-containing reagents in vitro and in vivo. A heavy atom unnatural amino acid, for example, can be useful for phasing X-ray structure data. The site-specific introduction of heavy atoms using unnatural amino acids also provides selectivity and flexibility in choosing positions for heavy atoms. Photoreactive unnatural amino acids (including but not limited to, amino acids with benzophenone and arylazides (including but not limited to, phenylazide) side chains), for example, allow for efficient in vivo and in vitro photocrosslinking of protein. Examples of photoreactive unnatural amino acids include, but are not limited to, p-azido-phenylalanine and p-benzoyl-phenylalanine. The protein with the photoreactive unnatural amino acids can then be crosslinked at will by excitation of the photoreactive group-providing temporal control. In one example, the methyl group of an unnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a [3+2] cycloaddition reaction.

A non-natural amino acid incorporated into a polypeptide at the amino terminus can be composed of an R group that is any substituent other than one used in the twenty natural amino acids and a $2^{nd}$ reactive group different from the $NH_2$ group normally present in α-amino acids (see Formula I). A similar non-natural amino acid can be incorporated at the carboxyl terminus with a $2^{nd}$ reactive group different from the COOH group normally present in α-amino acids (see Formula I).

Chemical Synthesis of Unnatural Amino Acids

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King, F. E. & Kidd, D. A. A. (1949) *A New Synthesis of Glutamine and of γ-Dipeptides of Glutamic Acid from Phthylated Intermediates. J. Chem. Soc.*, 3315-3319; Friedman, O. M. & Chatterrji, R. (1959) *Synthesis of Derivatives of Glutamine as Model Substrates for Anti-Tumor Agents. J. Am. Chem. Soc.* 81, 3750-3752; Craig, J. C. et al. (1988) *Absolute Configuration of the Enantiomers of 7-Chloro-4 [[4-(diethylamino)-1-methylbutyl]amino]quinoline* (Chloroquine). *J. Org. Chem.* 53, 1167-1170; Azoulay, M., Vilmont, M. & Frappier, F. (1991) *Glutamine analogues as Potential Antimalarials, Eur. J. Med. Chem.* 26, 201-5; Koskinen, A. M. P. & Rapoport, H. (1989) *Synthesis of 4-Substituted Prolines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Ion Cyclization. J. Org. Chem.* 1989:1859-1866; Barton et al., (1987) *Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives. Tetrahedron Lett.* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602-7. See also, patent applications entitled "Protein Arrays," filed Dec. 22, 2003, Ser. No. 10/744,899 and Ser. No. 60/435,821 filed on Dec. 22, 2002.

A. Carbonyl Reactive Groups

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

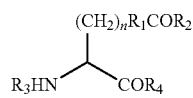

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

The synthesis of p-acetyl-(+/−)-phenylalanine and m-acetyl-(+/−)-phenylalanine is described in Zhang, Z., et al., Biochemistry 42: 6735-6746 (2003), which is incorporated by reference herein. Other carbonyl-containing amino acids can be similarly prepared by one skilled in the art.

In some embodiments, a polypeptide comprising a non-naturally encoded amino acid is chemically modified to generate a reactive carbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et al., *Bioconjug. Chem.* 3: 262-268 (1992); Geoghegan, K. & Stroh, J., *Bioconjug. Chem.* 3:138-146 (1992); Gaertner et al., *J. Biol. Chem.* 269:7224-7230 (1994). However, methods known in the art are restricted to the amino acid at the N-terminus of the peptide or protein.

In the present invention, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., *J. Am. Chem. Soc.* 81, 475-481 (1959); Shao, J. and Tam, J. P., *J. Am. Chem. Soc.* 117:3893-3899 (1995). Moreover, the unique reactivity of the carbonyl group allows for selective modification in the presence of the other amino acid side chains. See, e.g., Cornish, V. W., et al., *J. Am. Chem. Soc.* 118:8150-8151 (1996); Geoghegan, K. F. & Stroh, J. G., *Bioconjug. Chem.* 3:138-146 (1992); Mahal, L. K., et al., *Science* 276:1125-1128 (1997).

B. Hydrazine, Hydrazide or Semicarbazide Reactive Groups

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide -containing amino acids can be represented as follows:

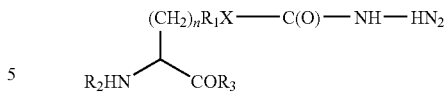

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R_1$ is not present, and X is not present. In some embodiments, n is 1, $R_1$ is phenyl, X is O, and the oxygen atom is positioned para to the alphatic group on the aryl ring.

Hydrazide-, hydrazine-, and semicarbazide-containing amino acids are available from commercial sources. For instance, L-glutamate-γ-hydrazide is available from Sigma Chemical (St. Louis, Mo.). Other amino acids not available commercially can be prepared by one skilled in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., *J. Am. Chem. Soc.* 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

C. Aminooxy-Containing Amino Acids

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, J., *J. Am. Chem. Soc.* 117:3893-3899 (1995); H. Hang and C. Bertozzi, *Acc. Chem. Res.* 34: 727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

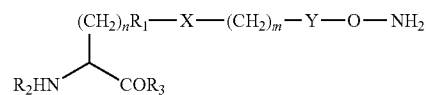

wherein n is 0-10; $R_1$ is an alkyl, aryl, substituted alkyl, or substituted aryl or not present; X is O, N, S or not present; m is 0-10; Y=C(O) or not present; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is O, m is 1, and Y is present. In some embodiments, n is 2, $R_1$ and X are not present, m is 0, and Y is not present.

Aminooxy-containing amino acids can be prepared from readily available amino acid precursors (homoserine, serine and threonine). See, e.g., M. Carrasco and R. Brown, *J. Org. Chem.* 68: 8853-8858 (2003). Certain aminooxy-containing amino acids, such as L-2-amino-4-(aminooxy)butyric acid, have been isolated from natural sources (Rosenthal, G. et al., Life Sci. 60: 1635-1641 (1997). Other aminooxy-containing amino acids can be prepared by one skilled in the art.

D. Azide and Alkyne Reactive Groups

The unique reactivity of azide and alkyne functional groups makes them extremely useful for the selective modification of polypeptides and other biological molecules. Organic azides, particularly alphatic azides, and alkynes are generally stable toward common reactive chemical conditions. In particular, both the azide and the alkyne functional groups are inert toward the side chains (i.e., R groups) of the 20 common amino acids found in naturally-occuring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., *Science* 301:964-7 (2003); Wang, Q., et al., *J. Am. Chem. Soc.* 125, 3192-3193 (2003); Chin, J. W., et al., *J. Am. Chem. Soc.* 124:9026-9027 (2002).

Because the Huisgen cycloaddition reaction involves a selective cycloaddition reaction (see, e.g., Padwa, A., in COMPREHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing ABP can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., *J. Am. Chem. Soc.* 125, 3192-3193 (2003); Tornoe, C. W., et al., *J. Org. Chem.* 67:3057-3064 (2002); Rostovtsev, et al., *Angew. Chem. Int. Ed.* 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the antigen-binding polypeptide comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, *Science* 287, 2007-2010 (2000). The azide-containing amino acid can be either an alkyl azide (including but not limited to, 2-amino-6-azido-1-hexanoic acid) or an aryl azide (p-azidophenylalanine).

Exemplary water soluble polymers containing an aryl ester and a phosphine moiety can be represented as follows:

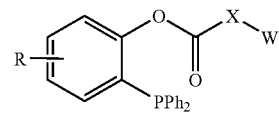

wherein X can be O, N, S or not present, Ph is phenyl, W is a water soluble polymer and R can be H, alkyl, aryl, substituted alkyl and substituted aryl groups. Exemplary R groups include but are not limited to —$CH_2$, —$C(CH_3)_3$, —OR', —NR'R", —SR', -halogen, —C(O)R', —CONR'R", —$S(O)_2$R', —$S(O)_2$NR'R", —CN and —$NO_2$. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —$C(O)CH_3$, —$C(O)CF_3$, —$C(O)CH_2OCH_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

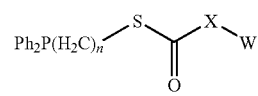

wherein n is 1-10; X can be O, N, S or not present, Ph is phenyl, and W is a water soluble polymer.

Exemplary alkyne-containing amino acids can be represented as follows:

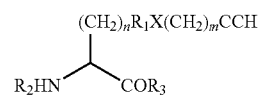

wherein n is 0-10; $R_1$ is an alkyl, aryl, substituted alkyl, or substituted aryl or not present; X is O, N, S or not present; m is 0-10, $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the acetylene moiety is positioned in the para position relative to the alkyl side chain. In some embodiments, n is 1, $R_1$ is phenyl, X is O, m is 1 and the propargyloxy group is positioned in the para position relative to the alkyl side chain (i.e., O-propargyl-tyrosine). In some embodiments, n is 1, $R_1$ and X are not present and m is 0 (i.e., proparylglycine).

Alkyne-containing amino acids are commercially available. For example, propargylglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., *J. Am. Chem. Soc.* 125: 11782-11783 (2003), and 4-alkynyl-L-phenylalanine can be synthesized as described in Kayser, B., et al., *Tetrahedron* 53(7): 2475-2484 (1997). Other alkyne-containing amino acids can be prepared by one skilled in the art.

Exemplary azide-containing amino acids can be represented as follows:

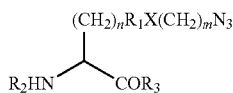

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the azide moiety is positioned para to the alkyl side chain. In some embodiments, n is 0-4 and $R_1$ and X are not present, and m=0. In some embodiments, n is 1, $R_1$ is phenyl, X is O, m is 2 and the P-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of skill in the art, including but not limited to, via displacement of a suitable leaving group (including but not limited to, halide, mesylate, tosylate) or via opening of a suitably protected lactone. See, e.g., *Advanced Organic Chemistry* by March (Third Edition, 1985, Wiley and Sons, New York).

E. Aminothiol Reactive Groups

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, *J. Am. Chem. Soc.* 1995, 117 (14) 3893-3899. In some embodiments, beta-substituted aminothiol amino acids can be incorporated into ABP polypeptides and then reacted with water soluble polymers comprising an aldehyde functionality. In some embodiments, a water soluble polymer, drug conjugate or other payload can be coupled to a ABP polypeptide comprising a beta-substituted aminothiol amino acid via formation of the thiazolidine.

Cellular Uptake of Unnatural Amino Acids

Unnatural amino acid uptake by a eukaryotic cell is one issue that is typically considered when designing and selecting unnatural amino acids, including but not limited to, for incorporation into a protein. For example, the high charge density of α-amino acids suggests that these compounds are unlikely to be cell permeable. Natural amino acids are taken up into the eukaryotic cell via a collection of protein-based transport systems. A rapid screen can be done which assesses which unnatural amino acids, if any, are taken up by cells. See, e.g., the toxicity assays in, e.g., the applications entitled "Protein Arrays," filed Dec. 22, 2003, Ser. No. 10/744,899 and Ser. No. 60/435,821 filed on Dec. 22, 2002; and Liu, D. R. & Schultz, P. G. (1999) Progress toward the evolution of an organism with an expanded genetic code. *PNAS United States* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, including but not limited to, in a eukaryotic cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, for example, in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, including but not limited to, as developed by Maxygen, Inc. (available on the World Wide Web at maxygen.com), is optionally used to develop novel enzymes and pathways. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.,* 91:10747-10751. Similarly Design-Path™, developed by Genencor (available on the World Wide Web at genencor.com) is optionally used for metabolic pathway engineering, including but not limited to, to engineer a pathway to create O-methyl-L-tyrosine in a cell. This technology reconstructs existing pathways in host organisms using a combination of new genes, including but not limited to, identified through functional genomics, and molecular evolution and design. Diversa Corporation (available on the World Wide Web at diversa.com) also provides technology for rapidly screening libraries of genes and gene pathways, including but not limited to, to create new pathways.

Typically, the unnatural amino acid produced with an engineered biosynthetic pathway of the invention is produced in a concentration sufficient for efficient protein biosynthesis, including but not limited to, a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and an unnatural amino acid is generated, in vivo selections are optionally used to further optimize the production of the unnatural amino acid for both ribosomal protein synthesis and cell growth.

Polypeptides with Unnatural Amino Acids

The incorporation of an unnatural amino acid can be done for a variety of purposes, including but not limited to, tailoring changes in protein structure and/or function, changing size, acidity, nucleophilicity, hydrogen bonding, hydrophobicity, accessibility of protease target sites, targeting to a moiety (including but not limited to, for a protein array), adding a biologically active molecule, attaching a polymer, attaching a radionuclide, modulating serum half-life, modulating tissue penetration (e.g. tumors), modulating active transport, modulating tissue, cell or organ specificity, modulating immunogenicity, modulating protease resistance, etc. Proteins that include an unnatural amino acid can have enhanced or even entirely new catalytic or biophysical properties. For example, the following properties are optionally modified by inclusion of an unnatural amino acid into a protein: toxicity, biodistribution, structural properties, spectroscopic properties, chemical and/or photochemical properties, catalytic ability, half-life (including but not limited to, serum half-life), ability to react with other molecules, including but not limited to, covalently or noncovalently, and the like. The compositions including proteins that include at least one unnatural amino acid are useful for, including but not limited to, novel therapeutics, diagnostics, catalytic enzymes, industrial enzymes, binding proteins (including but not limited to, antibodies), and including but not limited to, the study of protein structure and function. See, e.g., Dougherty, (2000) *Unnatural Amino Acids as Probes of protein Structure and Function, Current Opinion in Chemical Biology,* 4:645-652.

In one aspect of the invention, a composition includes at least one protein with at least one, including but not limited to, at least two, at least three, at least four, at least five, at least six, at least seven, at least eight, at least nine, or at least ten or more unnatural amino acids. The unnatural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the unnatural amino acid. For a given protein with more than one unnatural amino acids, the unnatural amino acids can be identical or different (including but not limited to, the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

ABP's of interest with at least one unnatural amino acid are a feature of the invention. The invention also includes polypeptides or proteins with at least one unnatural amino acid produced using the compositions and methods of the invention. An excipient (including but not limited to, a pharmaceutically acceptable excipient) can also be present with the protein.

By producing proteins or polypeptides of interest with at least one unnatural amino acid in eukaryotic cells, proteins or polypeptides will typically include eukaryotic post-translational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, including but not limited to, acetylation, acylation, lipid-modification, palmitoylation, palmitate addition, phosphorylation, glycolipid-linkage modification, glycosylation, and the like. In one aspect, the post-translational modification includes attachment of an oligosaccharide (including but not limited to, (GlcNAc-Man)$_2$-Man-GlcNAc-GlcNAc)) to an asparagine by a GlcNAc-asparagine linkage. See Table I which lists some examples of N-linked oligosaccharides of eukaryotic proteins (additional residues can also be present, which are not shown). In another aspect, the post-translational modification includes attachment of an oligosaccharide (including but not limited to, Gal-GalNAc, Gal-GlcNAc, etc.) to a serine or threonine by a GalNAc-serine or GalNAc-threonine linkage, or a GlcNAc-serine or a GlcNAc-threonine linkage.

TABLE 1

EXAMPLES OF OLIGOSACCHARIDES THROUGH GlcNAc-LINKAGE

| Type | Base Structure |
|---|---|
| High-mannose | Manα1-6↘<br>　　　　　Manα1-6↘<br>Manα1-3↗　　　　　Manβ1-4GlcNAcβ1-4GlcNAcβ1-Asn<br>　　　　　Manα1-3↗ |
| Hybrid | 　　　　　　　　Manα1-6↘<br>　　　　　　　　　　　Manβ1-4GlcNAcβ1-4GlcNAcβ1-Asn<br>GlcNAcβ1-2—Manα1-3↗ |
| Complex | GlcNAcβ1-2—Manα1-6↘<br>　　　　　　　　　　　Manβ1-4GlcNAcβ1-4GlcNAcβ1-Asn<br>GlcNAcβ1-2—Manα1-3↗ |

TABLE 1-continued

EXAMPLES OF OLIGOSACCHARIDES THROUGH GlcNAc-LINKAGE

| Type | Base Structure |
|---|---|
| Xylose | 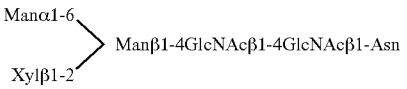 |

In yet another aspect, the post-translation modification includes proteolytic processing of precursors (including but not limited to, calcitonin precursor, calcitonin gene-related peptide precursor, preproparathyroid hormone, preproinsulin, proinsulin, prepro-opiomelanocortin, pro-opiomelanocortin and the like), assembly into a multisubunit protein or macromolecular assembly, translation to another site in the cell (including but not limited to, to organelles, such as the endoplasmic reticulum, the Golgi apparatus, the nucleus, lysosomes, peroxisomes, mitochondria, chloroplasts, vacuoles, etc., or through the secretory pathway). In certain embodiments, the protein comprises a secretion or localization sequence, an epitope tag, a FLAG tag, a polyhistidine tag, a GST fusion, or the like.

One advantage of an unnatural amino acid is that it presents additional chemical moieties that can be used to add additional molecules. These modifications can be made in vivo in a eukaryotic or non-eukaryotic cell, or in vitro. Thus, in certain embodiments, the post-translational modification is through the unnatural amino acid. For example, the post-translational modification can be through a nucleophilic-electrophilic reaction. Most reactions currently used for the selective modification of proteins involve covalent bond formation between nucleophilic and electrophilic reaction partners, including but not limited to the reaction of α-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish, et al., (1996) *Am. Chem. Soc.,* 118:8150-8151; Mahal, et al., (1997) *Science,* 276:1125-1128; Wang, et al., (2001) *Science* 292:498-500; Chin, et al., (2002) *Am. Chem. Soc.* 124:9026-9027; Chin, et al., (2002) *Proc. Natl. Acad. Sci.,* 99:11020-11024; Wang, et al., (2003) *Proc. Natl. Acad. Sci.,* 100:56-61; Zhang, et al., (2003) *Biochemistry,* 42:6735-6746; and, Chin, et al., (2003) *Science,* in press. This allows the selective labeling of virtually any protein with a host of reagents including fluorophores, crosslinking agents, saccharide derivatives and cytotoxic molecules. See also, U.S. patent application Ser. No. 10/686,944 entitled "Glycoprotein synthesis" filed Oct. 15, 2003 based on U.S. provisional patent application Ser. No. 60/419,265, filed Oct. 16, 2002, U.S. provisional patent application Ser. No. 60/420,990, filed Oct. 23, 2002, and U.S. provisional patent application Ser. No. 60/441,450, filed Jan. 16, 2003, which are incorporated by reference herein. Post-translational modifications, including but not limited to, through an azido amino acid, can also made through the Staudinger ligation (including but not limited to, with triarylphosphine reagents). See, e.g., Kiick et al., (2002) *Incorporation of azides into recombinant proteins for chemoselective modification by the Staudinger ligation,* PNAS 99:19-24.

This invention provides another highly efficient method for the selective modification of proteins, which involves the genetic incorporation of unnatural amino acids, including but not limited to, containing an azide or alkynyl moiety into proteins in response to a selector codon. These amino acid side chains can then be modified by, including but not limited to, a Huisgen [3+2] cycloaddition reaction (see, e.g., Padwa, A. in *Comprehensive Organic Synthesis,* Vol. 4, (1991) Ed. Trost, B. M., Pergamon, Oxford, p. 1069-1109; and, Huisgen, R. in 1,3-*Dipolar Cycloaddition Chemistry,* (1984) Ed. Padwa, A., Wiley, New York, p. 1-176) with, including but not limited to, alkynyl or azide derivatives, respectively. Because this method involves a cycloaddition rather than a nucleophilic substitution, proteins can be modified with extremely high selectivity. This reaction can be carried out at room temperature in aqueous conditions with excellent regioselectivity (1,4>1,5) by the addition of catalytic amounts of Cu(I) salts to the reaction mixture. See, e.g., Tornoe, et al., (2002) *Org. Chem.* 67:3057-3064; and, Rostovtsev, et al., (2002) *Angew. Chem. Int. Ed.* 41:2596-2599. Another method that can be used is the ligand exchange on a bisarsenic compound with a tetracysteine motif, see, e.g., Griffin, et al., (1998) *Science* 281:269-272.

A molecule that can be added to a protein of the invention through a [3+2] cycloaddition includes virtually any molecule with an azide or alkynyl derivative. Molecules include, but are not limited to, dyes, fluorophores, crosslinking agents, saccharide derivatives, polymers (including but not limited to, derivatives of polyethylene glycol), photocrosslinkers, cytotoxic compounds, affinity labels, derivatives of biotin, resins, beads, a second protein or polypeptide (or more), polynucleotide(s) (including but not limited to, DNA, RNA, etc.), metal chelators, cofactors, fatty acids, carbohydrates, and the like. These molecules can be added to an unnatural amino acid with an alkynyl group, including but not limited to, p-propargyloxyphenylalanine, or azido group, including but not limited to, p-azido-phenylalanine, respectively.

V. In Vivo Generation of ABP Comprising Non-Genetically-Encoded Amino Acids

The antigen-binding polypeptides of the invention can be generated in vivo using modified tRNA and tRNA synthetases to add to or substitute amino acids that are not encoded in naturally-occurring systems.

Methods for generating tRNAs and tRNA synthetases which use amino acids that are not encoded in naturally-occurring systems are described in, e.g., U.S. Patent Application Publications 2003/0082575 (Ser. No. 10/126,927) and 2003/0108885 (Ser. No. 10/126,931) which are incorporated by reference herein. These methods involve generating a translational machinery that functions independently of the synthetases and tRNAs endogenous to the translation system (and are therefore sometimes referred to as "orthogonal"). Typically, the translation system comprises an orthogonal tRNA (O-tRNA) and an orthogonal aminoacyl tRNA synthetase (O—RS). Typically, the O—RS preferentially aminoacylates the O-tRNA with at least one non-naturally occurring amino acid in the translation system and the O-tRNA recognizes at least one selector codon that is not recognized by other tRNAs in the system. The translation system thus inserts the non-naturally-encoded amino acid into a protein produced in the system, in response to an encoded selector codon, thereby "substituting" an amino acid into a position in the encoded polypeptide.

A wide variety of orthogonal tRNAs and aminoacyl tRNA synthetases have been described in the art for inserting particular synthetic amino acids into polypeptides, and are generally suitable for use in the present invention. For example, keto-specific O-tRNA/aminoacyl-tRNA synthetases are described in Wang, L., et al., *Proc. Natl. Acad. Sci. USA* 100:56-61 (2003) and Zhang, Z. et al., *Biochem.* 42(22): 6735-6746 (2003). Exemplary O—RS, or portions thereof, are encoded by polynucleotide sequences and include amino acid sequences disclosed in U.S. Patent Application Publications 2003/0082575 and 2003/0108885, each incorporated herein by reference. Corresponding O-tRNA molecules for use with the O—RSs are also described in U.S. Patent Application Publications 2003/0082575 (Ser. No. 10/126,927) and 2003/0108885 (Ser. No. 10/126,931) which are incorporated by reference herein.

An example of an azide-specific O-tRNA/aminoacyl-tRNA synthetase system is described in Chin, J. W., et al., *J. Am. Chem. Soc.* 124:9026-9027 (2002). Exemplary O—RS sequences for p-azido-L-Phe include, but are not limited to, nucleotide sequences SEQ ID NOs: 14-16 and 29-32 and amino acid sequences SEQ ID NOs: 46-48 and 61-64 as disclosed in U.S. Patent Application Publication 2003/0108885 (Ser. No. 10/126,931) which is incorporated by reference herein. Exemplary O-tRNA sequences suitable for use in the present invention include, but are not limited to, nucleotide sequences SEQ ID NOs: 1-3 as disclosed in U.S. Patent Application Publication 2003/0108885 (Ser. No. 10/126,931) which is incorporated by reference herein. Other examples of O-tRNA/aminoacyl-tRNA synthetase pairs specific to particular non-naturally encoded amino acids are described in U.S. Patent Application Publication 2003/0082575 (Serial No. 10/126,927) which is incorporated by reference herein. O—RS and O-tRNA that incorporate both keto- and azide-containing amino acids in *S. cerevisiae* are described in Chin, J. W., et al., *Science* 301:964-967 (2003).

Use of O-tRNA/aminoacyl-tRNA synthetases involves selection of a specific codon which encodes the non-naturally encoded amino acid. While any codon can be used, it is generally desirable to select a codon that is rarely or never used in the cell in which the O-tRNA/aminoacyl-tRNA synthetase is expressed. For example, exemplary codons include nonsense codon such as stop codons (amber, ochre, and opal), four or more base codons and other natural three-base codons that are rarely or unused.

Specific selector codon(s) can be introduced into appropriate positions in the ABP polynucleotide coding sequence using mutagenesis methods known in the art (including but not limited to, site-specific mutagenesis, cassette mutagenesis, restriction selection mutagenesis, etc.).

Methods for generating components of the protein biosynthetic machinery, such as O—RSs, O-tRNAs, and orthogonal O-tRNA/O—RS pairs that can be used to incorporate a non-naturally encoded amino acid are described in Wang, L., et al., *Science* 292: 498-500 (2001); Chin, J. W., et al., *J. Am. Chem. Soc.* 124:9026-9027 (2002); Zhang, Z. et al., *Biochemistry* 42: 6735-6746 (2003). Methods and compositions for the in vivo incorporation of non-naturally encoded amino acids are described in U.S. Patent Application Publication 2003/0082575 (Ser. No. 10/126,927) which is incorporated by reference herein. Methods for selecting an orthogonal tRNA-tRNA synthetase pair for use in in vivo translation system of an organism are also described in U.S. Patent Application Publications 2003/0082575 (Ser. No. 10/126,927) and 2003/0108885 (Ser. No. 10/126,931) which are incorporated by reference herein.

Methods for producing at least one recombinant orthogonal aminoacyl-tRNA synthetase (O—RS) comprise: (a) generating a library of (optionally mutant) RSs derived from at least one aminoacyl-tRNA synthetase (RS) from a first organism, including but not limited to, a prokaryotic organism, such as *Methanococcus jannaschii, Methanobacterium thermoautotrophicum, Halobacterium, Escherichia coli, A. fulgidus, P. furiosus, P. horikoshii, A. pernix, T. thermophilus,* or the like, or a eukaryotic organism; (b) selecting (and/or screening) the library of RSs (optionally mutant RSs) for members that aminoacylate an orthogonal tRNA (O-tRNA) in the presence of a non-naturally encoded amino acid and a natural amino acid, thereby providing a pool of active (optionally mutant) RSs; and/or, (c) selecting (optionally through negative selection) the pool for active RSs (including but not limited to, mutant RSs) that preferentially aminoacylate the O-tRNA in the absence of the non-naturally encoded amino acid, thereby providing the at least one recombinant O—RS; wherein the at least one recombinant O—RS preferentially aminoacylates the O-tRNA with the non-naturally encoded amino acid.

In one embodiment, the RS is an inactive RS. The inactive RS can be generated by mutating an active RS. For example, the inactive RS can be generated by mutating at least about 1, at least about 2, at least about 3, at least about 4, at least about 5, at least about 6, or at least about 10 or more amino acids to different amino acids, including but not limited to, alanine.

Libraries of mutant RSs can be generated using various techniques known in the art, including but not limited to rational design based on protein three dimensional RS structure, or mutagenesis of RS nucleotides in a random or rational design technique. For example, the mutant RSs can be generated by site-specific mutations, random mutations, diversity generating recombination mutations, chimeric constructs, rational design and by other methods described herein or known in the art.

In one embodiment, selecting (and/or screening) the library of RSs (optionally mutant RSs) for members that are active, including but not limited to, that aminoacylate an orthogonal tRNA (O-tRNA) in the presence of a non-naturally encoded amino acid and a natural amino acid, includes: introducing a positive selection or screening marker, including but not limited to, an antibiotic resistance gene, or the like, and the library of (optionally mutant) RSs into a plurality of cells, wherein the positive selection and/or screening marker comprises at least one selector codon, including but not limited to, an amber, ochre, or opal codon; growing the plurality of cells in the presence of a selection agent; identifying cells that survive (or show a specific response) in the presence of the selection and/or screening agent by suppressing the at least one selector codon in the positive selection or screening marker, thereby providing a subset of positively selected cells that contains the pool of active (optionally mutant) RSs. Optionally, the selection and/or screening agent concentration can be varied.

In one aspect, the positive selection marker is a chloramphenicol acetyltransferase (CAT) gene and the selector codon is an amber stop codon in the CAT gene. Optionally, the positive selection marker is a β-lactamase gene and the selector codon is an amber stop codon in the β-lactamase gene. In another aspect the positive screening marker comprises a fluorescent or luminescent screening marker or an affinity based screening marker (including but not limited to, a cell surface marker).

In one embodiment, negatively selecting or screening the pool for active RSs (optionally mutants) that preferentially aminoacylate the O-tRNA in the absence of the non-naturally encoded amino acid includes: introducing a negative selection or screening marker with the pool of active (optionally mutant) RSs from the positive selection or screening into a plurality of cells of a second organism, wherein the negative selection or screening marker comprises at least one selector codon (including but not limited to, an antibiotic resistance gene, including but not limited to, a chloramphenicol acetyltransferase (CAT) gene); and, identifying cells that survive or show a specific screening response in a first medium supplemented with the non-naturally encoded amino acid and a screening or selection agent, but fail to survive or to show the specific response in a second medium not supplemented with the non-naturally encoded amino acid and the selection or screening agent, thereby providing surviving cells or screened cells with the at least one recombinant O—RS. For example, a CAT identification protocol optionally acts as a positive selection and/or a negative screening in determination of appropriate O—RS recombinants. For instance, a pool of clones is optionally replicated on growth plates containing CAT (which comprises at least one selector codon) either with or without one or more non-naturally encoded amino acid. Colonies growing exclusively on the plates containing non-naturally encoded amino acids are thus regarded as containing recombinant O—RS. In one aspect, the concentration of the selection (and/or screening) agent is varied. In some aspects the first and second organisms are different. Thus, the first and/or second organism optionally comprises: a prokaryote, a eukaryote, a mammal, an *Escherichia coli,* a fungi, a yeast, an archaebacterium, a eubacterium, a plant, an insect, a protist, etc. In other embodiments, the screening marker comprises a fluorescent or luminescent screening marker or an affinity based screening marker.

In another embodiment, screening or selecting (including but not limited to, negatively selecting) the pool for active (optionally mutant) RSs includes: isolating the pool of active mutant RSs from the positive selection step (b); introducing a negative selection or screening marker, wherein the negative selection or screening marker comprises at least one selector codon (including but not limited to, a toxic marker gene, including but not limited to, a ribonuclease barnase gene, comprising at least one selector codon), and the pool of active (optionally mutant) RSs into a plurality of cells of a second organism; and identifying cells that survive or show a specific screening response in a first medium not supplemented with the non-naturally encoded amino acid, but fail to survive or show a specific screening response in a second medium supplemented with the non-naturally encoded amino acid, thereby providing surviving or screened cells with the at least one recombinant O—RS, wherein the at least one recombinant O—RS is specific for the non-naturally encoded amino acid. In one aspect, the at least one selector codon comprises about two or more selector codons. Such embodiments optionally can include wherein the at least one selector codon comprises two or more selector codons, and wherein the first and second organism are different (including but not limited to, each organism is optionally, including but not limited to, a prokaryote, a eukaryote, a mammal, an *Escherichia coli,* a fungi, yeast, an archaebacteria, a eubacteria, a plant, an insect, a protist, etc.). Also, some aspects include wherein the negative selection marker comprises a ribonuclease barnase gene (which comprises at least one selector codon). Other aspects include wherein the screening marker optionally comprises a fluorescent or luminescent screening marker or an affinity based screening marker. In the embodiments herein, the screenings and/or selections optionally include variation of the screening and/or selection stringency.

In one embodiment, the methods for producing at least one recombinant orthogonal aminoacyl-tRNA synthetase (O-RS) can further comprise: (d) isolating the at least one recombinant O—RS; (e) generating a second set of O—RS (optionally mutated) derived from the at least one recombinant O—RS; and, (f) repeating steps (b) and (c) until a mutated O—RS is obtained that comprises an ability to preferentially aminoacylate the O-tRNA. Optionally, steps (d)-(f) are repeated, including but not limited to, at least about two times. In one aspect, the second set of mutated O—RS derived from at least one recombinant O—RS can be generated by mutagenesis, including but not limited to, random mutagenesis, site-specific mutagenesis, recombination or a combination thereof.

The stringency of the selection/screening steps, including but not limited to, the positive selection/screening step (b), the negative selection/screening step (c) or both the positive and negative selection/screening steps (b) and (c), in the above-described methods, optionally includes varying the selection/screening stringency. In another embodiment, the positive selection/screening step (b), the negative selection/screening step (c) or both the positive and negative selection/screening steps (b) and (c) comprise using a reporter, wherein the reporter is detected by fluorescence-activated cell sorting (FACS) or wherein the reporter is detected by luminescence. Optionally, the reporter is displayed on a cell surface, on a phage display or the like and selected based upon affinity or catalytic activity involving the non-naturally encoded amino acid or an analogue. In one embodiment, the mutated synthetase is displayed on a cell surface, on a phage display or the like.

Methods for producing a recombinant orthogonal tRNA (O-tRNA) include: (a) generating a library of mutant tRNAs derived from at least one tRNA, including but not limited to, a suppressor tRNA, from a first organism; (b) selecting (including but not limited to, negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced orthogonal RS (O—RS), thereby providing at least one recombinant O-tRNA; wherein the at least one recombinant O-tRNA recognizes a selector codon and is not efficiency recognized by the RS from the second organism and is preferentially aminoacylated by the O—RS. In some embodiments the at least one tRNA is a suppressor tRNA and/or comprises a unique three base codon of natural and/or unnatural bases, or is a nonsense codon, a rare codon, an unnatural codon, a codon comprising at least 4 bases, an amber codon, an ochre codon, or an opal stop codon. In one embodiment, the recombinant O-tRNA possesses an improvement of orthogonality. It will be appreciated that in some embodiments, O-tRNA is optionally imported into a first organism from a second organism without the need for modification. In various embodiments, the first and second organisms are either the same or different and are optionally chosen from, including but not limited to, prokaryotes (including but not limited to, *Methanococcus jannaschii,*

*Methanobacterium thermoautotrophicum, Escherichia coli, Halobacterium,* etc.), eukaryotes, mammals, fungi, yeasts, archaebacteria, eubacteria, plants, insects, protists, etc. Additionally, the recombinant tRNA is optionally aminoacylated by a non-naturally encoded amino acid, wherein the non-naturally encoded amino acid is biosynthesized in vivo either naturally or through genetic manipulation. The non-naturally encoded amino acid is optionally added to a growth medium for at least the first or second organism.

In one aspect, selecting (including but not limited to, negatively selecting) or screening the library for (optionally mutant) tRNAs that are aminoacylated by an aminoacyl-tRNA synthetase (step (b)) includes: introducing a toxic marker gene, wherein the toxic marker gene comprises at least one of the selector codons (or a gene that leads to the production of a toxic or static agent or a gene essential to the organism wherein such marker gene comprises at least one selector codon) and the library of (optionally mutant) tRNAs into a plurality of cells from the second organism; and, selecting surviving cells, wherein the surviving cells contain the pool of (optionally mutant) tRNAs comprising at least one orthogonal tRNA or nonfunctional tRNA. For example, surviving cells can be selected by using a comparison ratio cell density assay.

In another aspect, the toxic marker gene can include two or more selector codons. In another embodiment of the methods, the toxic marker gene is a ribonuclease barnase gene, where the ribonuclease barnase gene comprises at least one amber codon. Optionally, the ribonuclease barnase gene can include two or more amber codons.

In one embodiment, selecting or screening the pool of (optionally mutant) tRNAs for members that are aminoacylated by an introduced orthogonal RS (O—RS) can include: introducing a positive selection or screening marker gene, wherein the positive marker gene comprises a drug resistance gene (including but not limited to, β-lactamase gene, comprising at least one of the selector codons, such as at least one amber stop codon) or a gene essential to the organism, or a gene that leads to detoxification of a toxic agent, along with the O—RS, and the pool of (optionally mutant) tRNAs into a plurality of cells from the second organism; and, identifying surviving or screened cells grown in the presence of a selection or screening agent, including but not limited to, an antibiotic, thereby providing a pool of cells possessing the at least one recombinant tRNA, where the at least one recombinant tRNA is aminoacylated by the O—RS and inserts an amino acid into a translation product encoded by the positive marker gene, in response to the at least one selector codons. In another embodiment, the concentration of the selection and/or screening agent is varied.

Methods for generating specific O-tRNA/O—RS pairs are provided. Methods include: (a) generating a library of mutant tRNAs derived from at least one tRNA from a first organism; (b) negatively selecting or screening the library for (optionally mutant) tRNAs that are aminoacylated by an aminoacyl-tRNA synthetase (RS) from a second organism in the absence of a RS from the first organism, thereby providing a pool of (optionally mutant) tRNAs; (c) selecting or screening the pool of (optionally mutant) tRNAs for members that are aminoacylated by an introduced orthogonal RS (O—RS), thereby providing at least one recombinant O-tRNA. The at least one recombinant O-tRNA recognizes a selector codon and is not efficiency recognized by the RS from the second organism and is preferentially aminoacylated by the O—RS. The method also includes (d) generating a library of (optionally mutant) RSs derived from at least one aminoacyl-tRNA synthetase (RS) from a third organism; (e) selecting or screening the library of mutant RSs for members that preferentially aminoacylate the at least one recombinant O-tRNA in the presence of a non-naturally encoded amino acid and a natural amino acid, thereby providing a pool of active (optionally mutant) RSs; and, (f) negatively selecting or screening the pool for active (optionally mutant) RSs that preferentially aminoacylate the at least one recombinant O-tRNA in the absence of the non-naturally encoded amino acid, thereby providing the at least one specific O-tRNA/O—RS pair, wherein the at least one specific O-tRNA/O—RS pair comprises at least one recombinant O—RS that is specific for the non-naturally encoded amino acid and the at least one recombinant O-tRNA. Specific O-tRNA/O—RS pairs produced by the methods are included. For example, the specific O-tRNA/O—RS pair can include, including but not limited to, a mutRNATyr-mutTyrRS pair, such as a mutRNATyr-SS12TyrRS pair, a mutRNALeu-mutLeuRS pair, a mutRNAThr-mutThrRS pair, a mutRNAGlu-mutGluRS pair, or the like. Additionally, such methods include wherein the first and third organism are the same (including but not limited to, *Methanococcus jannaschii*).

Methods for selecting an orthogonal tRNA-tRNA synthetase pair for use in an in vivo translation system of a second organism are also included in the present invention. The methods include: introducing a marker gene, a tRNA and an aminoacyl-tRNA synthetase (RS) isolated or derived from a first organism into a first set of cells from the second organism; introducing the marker gene and the tRNA into a duplicate cell set from a second organism; and, selecting for surviving cells in the first set that fail to survive in the duplicate cell set or screening for cells showing a specific screening response that fail to give such response in the duplicate cell set, wherein the first set and the duplicate cell set are grown in the presence of a selection or screening agent, wherein the surviving or screened cells comprise the orthogonal tRNA-tRNA synthetase pair for use in the in the in vivo translation system of the second organism. In one embodiment, comparing and selecting or screening includes an in vivo complementation assay. The concentration of the selection or screening agent can be varied.

The organisms of the present invention comprise a variety of organism and a variety of combinations. For example, the first and the second organisms of the methods of the present invention can be the same or different. In one embodiment, the organisms are optionally a prokaryotic organism, including but not limited to, *Methanococcus jannaschii, Methanobacterium thermoautotrophicum, Halobacterium, Escherichia coli, A. fulgidus, P. furiosus, P. horikoshii, A. pernix, T. thermophilus,* or the like. Alternatively, the organisms optionally comprise a eukaryotic organism, including but not limited to, plants (including but not limited to, complex plants such as monocots, or dicots), algae, protists, fungi (including but not limited to, yeast, etc), animals (including but not limited to, mammals, insects, arthropods, etc.), or the like. In another embodiment, the second organism is a prokaryotic organism, including but not limited to, *Methanococcus jannaschii, Methanobacterium thermoautotrophicum, Halobacterium, Escherichia coli, A. fulgidus, Halobacterium, P. furiosus, P. horikoshii, A. pernix, T. thermophilus,* or the like. Alternatively, the second organism can be a eukaryotic organism, including but not limited to, a yeast, a animal cell, a plant cell, a fungus, a mammalian cell, or the like. In various embodiments the first and second organisms are different.

VI. Location of Non-Naturally-Occurring Amino Acids in ABP

The present invention contemplates incorporation of one or more non-naturally-occurring amino acids into ABP. One or more non-naturally-occurring amino acids may be incorporated at a particular position which does not disrupt activity of the polypeptide. This can be achieved by making "conservative" substitutions, including but not limited to, substituting hydrophobic amino acids with hydrophobic amino acids, bulky amino acids for bulky amino acids, hydrophilic amino acids for hydrophilic amino acids) and/or inserting the non-naturally-occurring amino acid in a location that is not required for activity.

A variety of biochemical and structural approaches can be employed to select the desired sites for substitution with a non-naturally encoded amino acid within the antigen-binding polypeptide. It is readily apparent to those of ordinary skill in the art that any position of the polypeptide chain is suitable for selection to incorporate a non-naturally encoded amino acid, and selection may be based on rational design or by random selection for any or no particular desired purpose. Selection of desired sites may be for producing an ABP molecule having any desired property or activity, including but not limited to, agonists, super-agonists, inverse agonists, antagonists, receptor binding modulators, receptor activity modulators, dimer or multimer formation, no change to activity or property compared to the native molecule, or manipulating any physical or chemical property of the polypeptide such as solubility, aggregation, or stability. For example, locations in the polypeptide required for biological activity of ABP can be identified using alanine scanning or homolog scanning methods known in the art. Residues other than those identified as critical to biological activity by alanine or homolog scanning mutagenesis may be good candidates for substitution with a non-naturally encoded amino acid depending on the desired activity sought for the polypeptide. Alternatively, the sites identified as critical to biological activity may also be good candidates for substitution with a non-naturally encoded amino acid, again depending on the desired activity sought for the polypeptide. Another alternative would be to simply make serial substitutions in each position on the polypeptide chain with a non-naturally encoded amino acid and observe the effect on the activities of the polypeptide. It is readily apparent to those of ordinary skill in the art that any means, technique, or method for selecting a position for substitution with a non-natural amino acid into any polypeptide is suitable for use in the present invention.

Once residues that are likely to be intolerant to substitution with non-naturally encoded amino acids have been eliminated, the impact of proposed substitutions at each of the remaining positions can be examined from the secondary, tertiary or quaternary structure, or the three-dimensional crystal structure of the antigen-binding polypeptide and its binding partners. Thus, those of skill in the art can readily identify amino acid positions that can be substituted with non-naturally encoded amino acids.

Exemplary residues of incorporation of a non-naturally encoded amino acid include, but are not limited to, those that are excluded from potential antigen binding regions, may be fully or partially solvent exposed, have minimal or no hydrogen-bonding interactions with nearby residues, may be minimally exposed to nearby reactive residues, may be on one or more of the exposed faces of ABP, may be a site or sites of ABP that are juxtaposed to a second ABP, or other molecule or fragment thereof, may be in regions that are highly flexible, or structurally rigid, as predicted by the three-dimensional, secondary, tertiary, or quaternary structure of ABP, bound or unbound to its antigen, or coupled or not coupled to another ABP or other biologically active molecule, or may modulate the conformation of the ABP itself or a dimer or multimer comprising one or more ABP, by altering the flexibility or rigidity of the complete structure as desired. Residues for incorporation of non-natural amino acids may be a part of a cleavage sequence, linker sequence joining antibody fragments or ABPs, antibody-binding domain (including but not limited to, myc tag, FLAG or poly-His) or other affinity based sequence (including but not limited to, FLAG, poly-His, GST, etc.). Residues for incorporation of a non-natural amino acid may be N-terminal or C-terminal residues of an ABP or non-antigen binding residues of an ABP.

A wide variety of non-naturally encoded amino acids can be substituted for, or incorporated into, a given position in ABP. In general, a particular non-naturally encoded amino acid is selected for incorporation based on an examination of the three dimensional crystal structure of ABP with its antigen or the secondary, tertiary, or quarternary structure of ABP determined by any other means, a preference for conservative substitutions (i.e., aryl-based non-naturally encoded amino acids, such as p-acetylphenylalanine or O-propargyltyrosine substituting for Phe, Tyr or Trp), and the specific conjugation chemistry that one desires to introduce into the antigen-binding polypeptide (e.g., the introduction of 4-azidophenylalanine if one wants to effect a Huisgen [3+2] cycloaddition with a water soluble polymer bearing an alkyne moiety or a amide bond formation with a water soluble polymer that bears an aryl ester that, in turn, incorporates a phosphine moiety).

In one embodiment, the method further includes incorporating into the protein the unnatural amino acid, where the unnatural amino acid comprises a first reactive group; and contacting the protein with a molecule (including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination of the above, or any other desirable compound or substance) that comprises a second reactive group. The first reactive group reacts with the second reactive group to attach the molecule to the unnatural amino acid through a [3+2] cycloaddition. In one embodiment, the first reactive group is an alkynyl or azido moiety and the second reactive group is an azido or alkynyl moiety. For example, the first reactive group is the alkynyl moiety (including but not limited to, in unnatural amino acid p-propargyloxyphenylalanine) and the second reactive group is the azido moiety. In another example, the first reactive group is the azido moiety (including but not limited to, in the unnatural amino acid p-azido-L-phenylalanine) and the second reactive group is the alkynyl moiety.

In some cases, the non-naturally encoded amino acid substitution(s) will be combined with other additions, substitutions or deletions within the antigen-binding polypeptide to affect other biological traits of ABP. In some cases, the other additions, substitutions or deletions may increase the stability (including but not limited to, resistance to proteolytic degradation) of the ABP or increase affinity of the ABP for an ABP receptor or antigen. In some cases, the other additions, substitutions or deletions may increase the solubility (including but not limited to, when expressed in E. coli or other host cells) of the antigen-binding polypeptide. In some embodiments additions, substitutions or deletions may increase the polypeptide solubility following expression in E. coli or other recombinant host cells. In some embodiments sites are selected for substitution with a naturally encoded or non-natural amino acid in addition to another site for incorporation of a non-natural amino acid that results in increasing the polypeptide solubility following expression in E. coli or other recombinant host cells. In some embodiments, the antigen-binding polypeptides comprise another addition, substitution or deletion that modulates affinity for the ABP receptor, modulates (including but not limited to, increases or decreases) receptor dimerization, stabilizes receptor dimers, modulates circulating half-life, modulates release or bioavailability, facilitates purification, or improves or alters a particular route of administration. Similarly, antigen-binding polypeptides can comprise chemical or enzyme cleavage sequences, protease cleavage sequences, reactive groups, antibody-binding domains (including but not limited to, FLAG or poly-His) or other affinity based sequences (including, but not limited to, FLAG, poly-His, GST, etc.) or linked molecules (including, but not limited to, biotin) that improve detection (including, but not limited to, GFP), purification, transport through tissues or cell membranes, prodrug release or activation, ABP size reduction, or other traits of the polypeptide.

In some cases, 1, 2, 3, 4, 5, 6, 7, 8, 9, 10, or more amino acids are substituted with one or more non-naturally-encoded amino acids. In some cases, the ABP further includes 1, 2, 3, 4, 5, 6, 7, 8, 9, 10, or more substitutions of one or more non-naturally encoded amino acids for naturally-occurring amino acids. In some embodiments, at least two residues in the following regions of ABP are substituted with one or more non-naturally encoded amino acids. In some cases, the two or more non-naturally encoded residues are linked to one or more lower molecular weight linear or branched PEGs (approximately ~5-20 kDa in mass or less), thereby enhancing binding affinity and comparable serum half-life relative to the species attached to a single, higher molecular weight PEG.

In some embodiments, up to two of the residues of an antigen-binding polypeptide are substituted with one or more non-naturally-encoded amino acids.

VII. Expression in Non-Eukaryotes and Eukaryotes

To obtain high level expression of a cloned ABP polynucleotide, one typically subclones polynucleotides encoding an antigen-binding polypeptide of the invention into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al.

Bacterial expression systems for expressing ABP polypeptides of the invention are available in, including but not limited to, E. coli, Bacillus sp., Pseudomonas fluorescens, Pseudomonas aeruginosa, Pseudomonas putida, and Salmonella (Palva et al., Gene 22:229-235 (1983); Mosbach et al., Nature 302:543-545 (1983)). Kits for such expression systems are commercially available. Eukaryotic expression systems for mammalian cells, yeast, and insect cells are well known in the art and are also commercially available. In cases where orthogonal tRNAs and aminoacyl tRNA synthetases (described above) are used to express the antigen-binding polypeptides of the invention, host cells for expression are selected based on their ability to use the orthogonal components. Exemplary host cells include Gram-positive bacteria (including but not limited to B. brevis, B. subtilis, or Streptomyces) and Gram-negative bacteria (E. coli, Pseudomonas fluorescens, Pseudomonas aeruginosa, Pseudomonas putida), as well as yeast and other eukaryotic cells. Cells comprising O-tRNA/O—RS pairs can be used as described herein.

A eukaryotic host cell or non-eukaryotic host cell of the present invention provides the ability to synthesize proteins that comprise unnatural amino acids in large useful quantities. In one aspect, the composition optionally includes, including but not limited to, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the protein that comprises an unnatural amino acid, or an amount that can be achieved with in vivo protein production methods (details on recombinant protein production and purification are provided herein). In another aspect, the protein is optionally present in the composition at a concentration of, including but not limited to, at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, including but not limited to, a cell lysate, a buffer, a pharmaceutical buffer, or other liquid suspension (including but not limited to, in a volume of, including but not limited to, anywhere from about 1 nl to about 100 L). The production of large quantities (including but not limited to, greater that that typically possible with other methods, including but not limited to, in vitro translation) of a protein in a eukaryotic cell including at least one unnatural amino acid is a feature of the invention.

A eukaryotic host cell or non-eukaryotic host cell of the present invention provides the ability to biosynthesize proteins that comprise unnatural amino acids in large useful quantities. For example, proteins comprising an unnatural amino acid can be produced at a concentration of, including but not limited to, at least 10 µg/liter, at least 50 µg/liter, at least 75 µg/liter, at least 100 µg/liter, at least 200 µg/liter, at least 250 µg/liter, or at least 500 µg/liter, at least 1 mg/liter, at least 2 mg/liter, at least 3 mg/liter, at least 4 mg/liter, at least 5 mg/liter, at least 6 mg/liter, at least 7 mg/liter, at least 8 mg/liter, at least 9 mg/liter, at least 10 mg/liter, at least 20, 30, 40, 50, 60, 70, 80, 90, 100, 200, 300, 400, 500, 600, 700, 800, 900 mg/liter, 1 g/liter, 5 g/liter, 10 g/liter or more of protein in a cell extract, cell lysate, culture medium, a buffer, and/or the like.

I. Expression Systems, Culture and Isolation

ABP may be expressed in any number of suitable expression systems including, for example, yeast, insect cells, mammalian cells, and bacteria. A description of exemplary expression systems is provided below.

Yeast As used herein, the term "yeast" includes any of the various yeasts capable of expressing a gene encoding ABP. Such yeasts include, but are not limited to, ascosporogenous yeasts (*Endomycetales*), basidiosporogenous yeasts and yeasts belonging to the Fungi imperfecti (*Blastomycetes*) group. The ascosporogenous yeasts are divided into two families, Spermophthoraceae and Saccharomycetaceae. The latter is comprised of four subfamilies, Schizosaccharomycoideae (e.g., genus *Schizosaccharomyces*), Nadsonioideae, Lipomycoideae and Saccharomycoideae (e.g., genera *Pichia, Kluyveromyces* and *Saccharomyces*). The basidiosporogenous yeasts include the genera *Leucosporidium, Rhodosporidium, Sporidiobolus, Filobasidium,* and *Filobasidiella.* Yeasts belonging to the Fungi Imperfecti (*Blastomycetes*) group are divided into two families, Sporobolomycetaceae (e.g., genera *Sporobolomyces and Bullera*) and Cryptococcaceae (e.g., genus *Candida*).

Of particular interest for use with the present invention are species within the genera *Pichia, Kluyveromyces, Saccharomyces, Schizosaccharomyces, Hansenula, Torulopsis,* and *Candida,* including, but not limited to, *P. pastoris, P. guillerimondii, S. cerevisiae, S. carlsbergensis, S. diastaticus, S. douglasii, S. kluyveri, S, norbensis, S. oviformis, K lactis, K. fragilis, C. albicans, C. maltosa,* and *H. polymorpha.*

The selection of suitable yeast for expression of ABP is within the skill of one of ordinary skill in the art. In selecting yeast hosts for expression, suitable hosts may include those shown to have, for example, good secretion capacity, low proteolytic activity, good secretion capacity, good soluble protein production, and overall robustness. Yeast are generally available from a variety of sources including, but not limited to, the Yeast Genetic Stock Center, Department of Biophysics and Medical Physics, University of California (Berkeley, Calif.), and the American Type Culture Collection ("ATCC") (Manassas, Va.).

The term "yeast host" or "yeast host cell" includes yeast that can be, or has been, used as a recipient for recombinant vectors or other transfer DNA. The term includes the progeny of the original yeast host cell that has received the recombinant vectors or other transfer DNA. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding ABP, are included in the progeny intended by this definition.

Expression and transformation vectors, including extrachromosomal replicons or integrating vectors, have been developed for transformation into many yeast hosts. For example, expression vectors have been developed for *S. cerevisiae* (Sikorski et al., GENETICS (1998) 112:19; Ito et al., J. BACTERIOL. (1983) 153:163; Hinnen et al., PROC. NATL. ACAD. SCI. USA (1978) 75:1929); *C. albicans* (Kurtz et al., MOL. CELL. BIOL. (1986) 6:142); *C. maltosa* (Kunze et al., J. BASIC MICROBIOL. (1985) 25:141); *H. polymorpha* (Gleeson et al., J. GEN. MICROBIOL. (1986) 132:3459; Roggenkamp et al., MOL. GEN. GENET. (1986) 202:302); *K. fragilis* (Das et al., J. BACTERIOL. (1984) 158:1165); *K. lactis* (De Louvencourt et al., J. BACTERIOL. (1983) 154:737; Van den Berg et al., BIO/TECHNOLOGY (1990) 8:135); *P. guillerimondii* (Kunze et al., J. BASIC MICROBIOL. (1985) 25:141); *P. pastoris* (U.S. Pat. Nos. 5,324,639; 4,929,555; and 4,837,148; Cregg et al., MOL. CELL. BIOL. (1985) 5:3376); *Schizosaccharomyces pombe* (Beach and Nurse, NATURE (1981) 300:706); and *Y. lipolytica* (Davidow et al., CURR. GENET. (1985) 10:380 (1985); Gaillardin et al., CURR. GENET. (1985) 10:49); *A. nidulans* (Ballance et al., BIOCHEM. BIOPHYS. RES. COMMUN. (1983) 112:284-89; Tilburn et al., GENE (1983) 26:205-221; and Yelton et al., PROC. NATL. ACAD. SCI. USA (1984) 81:1470-74); *A. niger* (Kelly and Hynes, EMBO J. (1985) 4:475479); *T. reesia* (EP 0 244 234); and filamentous fungi such as, e.g., *Neurospora, Penicillium, Tolypocladium* (WO 91/00357), each incorporated by reference herein.

Control sequences for yeast vectors are well known to those of ordinary skill in the art and include, but are not limited to, promoter regions from genes such as alcohol dehydrogenase (ADH) (EP 0 284 044); enolase; glucokinase; glucose-6-phosphate isomerase; glyceraldehydes-3-phosphate-dehydrogenase (GAP or GAPDH); hexokinase; phosphofructokinase; 3-phosphoglycerate mutase; and pyruvate kinase (PyK) (EP 0 329 203). The yeast PHO5 gene, encoding acid phosphatase, also may provide useful promoter sequences (Myanohara et al., PROC. NATL. ACAD. SCI. USA (1983) 80:1). Other suitable promoter sequences for use with yeast hosts may include the promoters for 3-phosphoglycerate kinase (Hitzeman et al., J. BIOL. CHEM. (1980) 255:2073); and other glycolytic enzymes, such as pyruvate decarboxylase, triosephosphate isomerase, and phosphoglucose isomerase (Holland et al., BIOCHEMISTRY (1978) 17:4900; Hess et al., J. ADV. ENZYME REG. (1968) 7:149). Inducible yeast promoters having the additional advantage of transcription controlled by growth conditions may include the promoter regions for alcohol dehydrogenase 2; isocytochrome C; acid phosphatase; metallothionein; glyceraldehyde-3-phosphate dehydrogenase; degradative enzymes associated with nitrogen metabolism; and enzymes responsible for maltose and galactose utilization. Suitable vectors and promoters for use in yeast expression are further described in EP 0 073 657.

Yeast enhancers also may be used with yeast promoters. In addition, synthetic promoters may also function as yeast promoters. For example, the upstream activating sequences (UAS) of a yeast promoter may be joined with the transcription activation region of another yeast promoter, creating a synthetic hybrid promoter. Examples of such hybrid promoters include the ADH regulatory sequence linked to the GAP transcription activation region. See U.S. Pat. Nos. 4,880,734 and 4,876,197, which are incorporated by reference herein. Other examples of hybrid promoters include promoters that consist of the regulatory sequences of the ADH2, GAL4, GAL10, or PHO5 genes, combined with the transcriptional activation region of a glycolytic enzyme gene such as GAP or PyK. See EP 0 164 556. Furthermore, a yeast promoter may include naturally occurring promoters of non-yeast origin that have the ability to bind yeast RNA polymerase and initiate transcription.

Other control elements that may comprise part of the yeast expression vectors include terminators, for example, from GAPDH or the enolase genes (Holland et al., J. BIOL. CHEM. (1981) 256:1385). In addition, the origin of replication from the 2μ plasmid origin is suitable for yeast. A suitable selection gene for use in yeast is the trp1 gene present in the yeast plasmid. See Tschemper et al., GENE (1980) 10:157; Kingsman et al., GENE (1979) 7:141. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 gene.

Methods of introducing exogenous DNA into yeast hosts are well known to those of ordinary skill in the art, and typically include, but are not limited to, either the transformation of spheroplasts or of intact yeast host cells treated with alkali cations. For example, transformation of yeast can be carried out according to the method described in Hsiao et al., PROC. NATL. ACAD. SCI. USA (1979) 76:3829 and Van Solingen et al., J. BACT. (1977) 130:946. However, other methods for introducing DNA into cells such as by nuclear injection, electroporation, or protoplast fusion may also be used as described generally in SAMBROOK ET AL., MOLECULAR CLONING: A LAB. MANUAL (2001). Yeast host cells may then be cultured using standard techniques known to those of ordinary skill in the art.

Other methods for expressing heterologous proteins in yeast host cells are well known to those of ordinary skill in the art. See generally U.S. Patent Publication No. 20020055169, U.S. Pat. Nos. 6,361,969; 6,312,923; 6,183,985; 6,083,723; 6,017,731; 5,674,706; 5,629,203; 5,602,034; and 5,089,398; U.S. Reexamined Pat. Nos. RE37,343 and RE35,749; PCT Published Patent Applications WO 99/078621; WO 98/37208; and WO 98/26080; European Patent Applications EP 0 946 736; EP 0 732 403; EP 0 480 480; EP 0 460 071; EP 0 340 986; EP 0 329 203; EP 0 324 274; and EP 0 164 556. See also Gellissen et al., ANTONIE VAN LEEUWENHOEK (1992) 62(1-2):79-93; Romanos et al., YEAST (1992) 8(6):423-488; Goeddel, METHODS IN ENZYMOLOGY (1990) 185:3-7, each incorporated by reference herein.

The yeast host strains may be grown in fermentors during the amplification stage using standard feed batch fermentation methods well known to those of ordinary skill in the art. The fermentation methods may be adapted to account for differences in a particular yeast host's carbon utilization pathway or mode of expression control. For example, fermentation of a *Saccharomyces* yeast host may require a single glucose feed, complex nitrogen source (e.g., casein hydrolysates), and multiple vitamin supplementation. In contrast, the methylotrophic yeast *P. pastoris* may require glycerol, methanol, and trace mineral feeds, but only simple ammonium (nitrogen) salts for optimal growth and expression. See, e.g., U.S. Pat. No. 5,324,639; Elliott et al., J. PROTEIN CHEM. (1990) 9:95; and Fieschko et al., BIOTECH. BIOENG. (1987) 29:1113, incorporated by reference herein.

Such fermentation methods, however, may have certain common features independent of the yeast host strain employed. For example, a growth limiting nutrient, typically carbon, may be added to the fermentor during the amplification phase to allow maximal growth. In addition, fermentation methods generally employ a fermentation medium designed to contain adequate amounts of carbon, nitrogen, basal salts, phosphorus, and other minor nutrients (vitamins, trace minerals and salts, etc.). Examples of fermentation media suitable for use with *Pichia* are described in U.S. Pat. Nos. 5,324,639 and 5,231,178, which are incorporated by reference herein.

Baculovirus-Infected Insect Cells The term "insect host" or "insect host cell" refers to a insect that can be, or has been, used as a recipient for recombinant vectors or other transfer DNA. The term includes the progeny of the original insect host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding ABP, are included in the progeny intended by this definition.

The selection of suitable insect cells for expression of ABP is well known to those of ordinary skill in the art. Several insect species are well described in the art and are commercially available including *Aedes aegypti*, *Bombyx mori*, *Drosophila melanogaster*, *Spodoptera frugiperda*, and *Trichoplusia ni*. In selecting insect hosts for expression, suitable hosts may include those shown to have, inter alia, good secretion capacity, low proteolytic activity, and overall robustness. Insect are generally available from a variety of sources including, but not limited to, the Insect Genetic Stock Center, Department of Biophysics and Medical Physics, University of California (Berkeley, Calif.); and the American Type Culture Collection ("ATCC") (Manassas, Va.).

Generally, the components of a baculovirus-infected insect expression system include a transfer vector, usually a bacterial plasmid, which contains both a fragment of the baculovirus genome, and a convenient restriction site for insertion of the heterologous gene to be expressed; a wild type baculovirus with sequences homologous to the baculovirus-specific fragment in the transfer vector (this allows for the homologous recombination of the heterologous gene in to the baculovirus genome); and appropriate insect host cells and growth media. The materials, methods and techniques used in constructing vectors, transfecting cells, picking plaques, growing cells in culture, and the like are known in the art and manuals are available describing these techniques.

After inserting the heterologous gene into the transfer vector, the vector and the wild type viral genome are transfected into an insect host cell where the vector and viral genome recombine. The packaged recombinant virus is expressed and recombinant plaques are identified and purified. Materials and methods for baculovirus/insect cell expression systems are commercially available in kit form from, for example, Invitrogen Corp. (Carlsbad, Calif.). These techniques are generally known to those skilled in the art and fully described in SUMMERS AND SMITH, TEXAS AGRICULTURAL EXPERIMENT STATION BULLETIN No. 1555 (1987), herein incorporated by reference. See also, RICHARDSON, 39 METHODS IN MOLECULAR BIOLOGY: BACULOVIRUS EXPRESSION PROTOCOLS (1995); AUSUBEL ET AL., CURRENT PROTOCOLS IN MOLECULAR BIOLOGY 16.9-16.11 (1994); KING AND POSSEE, THE BACULOVIRUS SYSTEM: A LABORATORY GUIDE (1992); and O'REILLY ET AL., BACULOVIRUS EXPRESSION VECTORS: A LABORATORY MANUAL (1992).

Indeed, the production of various heterologous proteins using baculovirus/insect cell expression systems is well known in the art. See, e.g., U.S. Pat. Nos. 6,368,825; 6,342, 216; 6,338,846; 6,261,805; 6,245,528, 6,225,060; 6,183,987; 6,168,932; 6,126,944; 6,096,304; 6,013,433; 5,965,393; 5,939,285; 5,891,676; 5,871,986; 5,861,279; 5,858,368; 5,843,733; 5,762,939; 5,753,220; 5,605,827; 5,583,023; 5,571,709; 5,516,657; 5,290,686; WO 02/06305; WO 01/90390; WO 01/27301; WO 01/05956; WO 00/55345; WO 00/20032 WO 99/51721; WO 99/45130; WO 99/31257; WO 99/10515; WO 99/09193; WO 97/26332; WO 96/29400; WO 96/25496; WO 96/06161; WO 95/20672; WO 93/03173; WO 92/16619; WO 92/03628; WO 92/01801; WO 90/14428; WO 90/10078; WO 90/02566; WO 90/02186; WO 90/01556; WO 89/01038; WO 89/01037; WO 88/07082, which are incorporated by reference herein.

Vectors that are useful in baculovirus/insect cell expression systems are known in the art and include, for example, insect expression and transfer vectors derived from the baculovirus *Autographacalifornica* nuclear polyhedrosis virus (AcNPV), which is a helper-independent, viral expression vector. Viral expression vectors derived from this system usually use the strong viral polyhedrin gene promoter to drive expression of heterologous genes. See generally, Reilly ET AL., BACULOVIRUS EXPRESSION VECTORS: A LABORATORY MANUAL (1992).

Prior to inserting the foreign gene into the baculovirus genome, the above-described components, comprising a promoter, leader (if desired), coding sequence of interest, and transcription termination sequence, are typically assembled into an intermediate transplacement construct (transfer vector). Intermediate transplacement constructs are often maintained in a replicon, such as an extra chromosomal element (e.g., plasmids) capable of stable maintenance in a host, such as bacteria. The replicon will have a replication system, thus allowing it to be maintained in a suitable host for cloning and amplification. More specifically, the plasmid may contain the polyhedrin polyadenylation signal (Miller et al., ANN. REV. MICROBIOL. (1988) 42:177) and a prokaryotic ampicillin-resistance (amp) gene and origin of replication for selection and propagation in E. coli.

One commonly used transfer vector for introducing foreign genes into AcNPV is pAc373. Many other vectors, known to those of skill in the art, have also been designed including, for example, pVL985, which alters the polyhedrin start codon from ATG to ATT, and which introduces a BamHI cloning site 32 base pairs downstream from the ATT. See Luckow and Summers, 17 VIROLOGY 31 (1989). Other commercially available vectors include, for example, PBlue-Bac4.5/V5-His; pBlueBacHis2; pMelBac; pBlueBac4.5 (Invitrogen Corp., Carlsbad, Calif.).

After insertion of the heterologous gene, the transfer vector and wild type baculoviral genome are co-transfected into an insect cell host. Methods for introducing heterologous DNA into the desired site in the baculovirus virus are known in the art. See SUMMERS AND SMITH, TEXAS AGRICULTURAL EXPERIMENT STATION BULLETIN No. 1555 (1987); Smith et al., MOL. CELL. BIOL. (1983) 3:2156; Luckow and Summers, VIROLOGY (1989) 17:31. For example, the insertion can be into a gene such as the polyhedrin gene, by homologous double crossover recombination; insertion can also be into a restriction enzyme site engineered into the desired baculovirus gene. See Miller et al., BIOESSAYS (1989)4:91.

Transfection may be accomplished by electroporation. See TROTTER AND WOOD, 39 METHODS IN MOLECULAR BIOLOGY (1995); Mann and King, J. GEN. VIROL. (1989) 70:3501. Alternatively, liposomes may be used to transfect the insect cells with the recombinant expression vector and the baculovirus. See, e.g., Liebman et al., BIOTECHNIQUES (1999) 26(1):36; Graves et al., BIOCHEMISTRY (1998) 37:6050; Nomura et al., J. BIOL. CHEM. (1998) 273(22):13570; Schmidt et al., PROTEIN EXPRESSION AND PURIFICATION (1998) 12:323; Siffert et al., NATURE GENETICS (1998) 18:45; TILKINS ET AL., CELL BIOLOGY: A LABORATORY HANDBOOK 145-154 (1998); Cai et al., PROTEIN EXPRESSION AND PURIFICATION (1997) 10:263; Dolphin et al., NATURE GENETICS (1997) 17:491; Kost et al., GENE (1997) 190:139; Jakobsson et al., J. BIOL. CHEM. (1996) 271:22203; Rowles et al., J. BIOL. CHEM. (1996) 271(37):22376; Reversey et al., J. BIOL. CHEM. (1996) 271(39):23607-10; Stanley et al., J. BIOL. CHEM. (1995) 270:4121; Sisk et al., J. VIROL. (1994) 68(2):766; and Peng et al., BIOTECHNIQUES (1993) 14.2:274. Commercially available liposomes include, for example, Cellfectin® and Lipofectin® (Invitrogen, Corp., Carlsbad, Calif.). In addition, calcium phosphate transfection may be used. See TROTTER AND WOOD, 39 METHODS IN MOLECULAR BIOLOGY (1995); Kitts, NAR (1990) 18(19):5667; and Mann and King, J. GEN. VIROL. (1989) 70:3501.

Baculovirus expression vectors usually contain a baculovirus promoter. A baculovirus promoter is any DNA sequence capable of binding a baculovirus RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Moreover, expression may be either regulated or constitutive.

Structural genes, abundantly transcribed at late times in the infection cycle, provide particularly useful promoter sequences. Examples include sequences derived from the gene encoding the viral polyhedron protein (FRIESEN ET AL., The Regulation of Baculovirus Gene Expression in THE MOLECULAR BIOLOGY OF BACULOVIRUSES (1986); EP 0 127 839 and 0 155 476) and the gene encoding the p10 protein (Vlak et al., J. GEN. VIROL. (1988) 69:765).

The newly formed baculovirus expression vector is packaged into an infectious recombinant baculovirus and subsequently grown plaques may be purified by techniques known to those skilled in the art. See Miller et al., BIOESSAYS (1989) 4:91; SUMMERS AND SMITH, TEXAS AGRICULTURAL EXPERIMENT STATION BULLETIN No. 1555 (1987).

Recombinant baculovirus expression vectors have been developed for infection into several insect cells. For example, recombinant baculoviruses have been developed for, inter alia, *Aedes aegypti* (ATCC No. CCL-125), *Bombyx mori* (ATCC No. CRL-8910), *Drosophila melanogaster* (ATCC No. 1963), *Spodoptera frugiperda,* and *Trichoplusia ni.* See WO 89/046,699; Wright, NATURE (1986) 321:718; Carbonell et al., J. VIROL. (1985) 56:153; Smith et al., MOL. CELL. BIOL. (1983) 3:2156. See generally, Fraser et al., IN VITRO CELL. DEV. BIOL. (1989) 25:225. More specifically, the cell lines used for baculovirus expression vector systems commonly include, but are not limited to, Sf9 (*Spodoptera frugiperda*) (ATCC No. CRL-1711), Sf21 (*Spodoptera frugiperda*) (Invitrogen Corp., Cat. No. 11497-013 (Carlsbad, Calif.)), Tri-368 (*Trichopulsia ni*), and High-Five™ BTI-TN-5B 1-4 (*Trichopulsia ni*).

Cells and culture media are commercially available for both direct and fusion expression of heterologous polypeptides in a baculovirus/expression, and cell culture technology is generally known to those skilled in the art.

*E. Coli, Pseudomonas* species, and other Prokaryotes Bacterial expression techniques are well known in the art. A wide variety of vectors are available for use in bacterial hosts. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers is present, which provide for different characteristics.

A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al., ANNU. REV. GENET. (1984) 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., NATURE (1977) 198:1056], and maltose. Additional examples include promoter sequences derived from biosynthetic enzymes such as tryptophan (trp) [Goeddel et al., NUC. ACIDS RES. (1980) 8:4057; Yelverton et al., NUCL. ACIDS RES. (1981) 9:731; U.S. Pat. No. 4,738,921; EP Pub. Nos. 036 776 and 121 775, which are incorporated by reference herein]. The β-galactosidase (bla) promoter system [Weissmann (1981) "The cloning of interferon and other mistakes." In Interferon 3 (Ed. I. Gresser)], bacteriophage lambda PL [Shimatake et al., NATURE (1981) 292:128] and T5 [U.S. Pat. No. 4,689,406, which are incorporated by reference herein] promoter systems also provide useful promoter sequences. Preferred methods of the present invention utilize strong promoters, such as the T7 promoter to induce ABP at high levels. Examples of such vectors are well known in the art and include the pET29 series from Novagen, and the pPOP vectors described in WO99/05297, which is incorporated by reference herein. Such expression systems produce high levels of ABP in the host without compromising host cell viability or growth parameters. pET19 (Novagen) is another vector known in the art.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433, which is incorporated by reference herein]. For example, the tac promoter is a hybrid trp-lac promoter comprised of both trp promoter and lac operon sequences that is regulated by the lac repressor [Amann et al., GENE (1983) 25:167; de Boer et al., PROC. NATL. ACAD. SCI. (1983) 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al., J. MOL. BIOL. (1986) 189:113; Tabor et al., Proc Natl. Acad. Sci. (1985) 82:1074]. In addition, a hybrid promoter can also be comprised of a bacteriophage promoter and an *E. coli* operator region (EP Pub. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al., NATURE (1975) 254:34]. The SD sequence is thought to promote binding of mRNA to the ribosome by the pairing of bases between the SD sequence and the 3' and of *E. coli* 16S rRNA [Steitz et al. "Genetic signals and nucleotide sequences in messenger RNA", In Biological Regulation and Development: Gene Expression (Ed. R. F. Goldberger, 1979)]. To express eukaryotic genes and prokaryotic genes with weak ribosome-binding site [Sambrook et al. "Expression of cloned genes in *Escherichia coli*", Molecular Cloning: A Laboratory Manual, 1989].

The term "bacterial host" or "bacterial host cell" refers to a bacterial that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding ABP, are included in the progeny intended by this definition.

The selection of suitable host bacteria for expression of ABP is well known to those of ordinary skill in the art. In selecting bacterial hosts for expression, suitable hosts may include those shown to have, inter alia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, Calif.); and the American Type Culture Collection ("ATCC") (Manassas, Va.). Industrial/pharmaceutical fermentation generally use bacterial derived from K strains (e.g. W3110) or from bacteria derived from B strains (e.g. BL21). These strains are particularly useful because their growth parameters are extremely well known and robust. In addition, these strains are non-pathogenic, which is commercially important for safety and environmental reasons. In one embodiment of the methods of the present invention, the *E. coli* host is a strain of BL21. In another embodiment of the methods of the present invention, the *E. coli* host is a protease minus strain including, but not limited to, OMP— and LON—. In another embodiment of the methods of the present invention, the host cell strain is a species of *Pseudomonas*, including but not limited to, *Pseudomonas fluorescens, Pseudomonas aeruginosa*, and *Pseudomonas putida*. *Pseudomonas fluorescens* biovar 1, designated strain MB101, is known to be useful for recombinant production and is available for therapeutic protein production processes. An example of a *Pseudomonas* expression system includes the system available from The Dow Chemical Company as a host strain (Midland, Mich. available on the World Wide Web at dow.com). U.S. Pat. Nos. 4,755,465 and 4,859,600, which are incorporated by reference herein, describes the use of *Pseudomonas* strains as a host cell for human growth hormone production.

Once a recombinant host cell strain has been established (i.e., the expression construct has been introduced into the host cell and host cells with the proper expression construct are isolated), the recombinant host cell strain is cultured under conditions appropriate for production of ABP. As will be apparent to one of skill in the art, the method of culture of the recombinant host cell strain will be dependent on the nature of the expression construct utilized and the identity of the host cell. Recombinant host strains are normally cultured using methods that are well known to the art. Recombinant host cells are typically cultured in liquid medium containing assimilatable sources of carbon, nitrogen, and inorganic salts and, optionally, containing vitamins, amino acids, growth factors, and other proteinaceous culture supplements well known to the art. Liquid media for culture of host cells may optionally contain antibiotics or anti-fungals to prevent the growth of undesirable microorganisms and/or compounds including, but not limited to, antibiotics to select for host cells containing the expression vector.

Recombinant host cells may be cultured in batch or continuous formats, with either cell harvesting (in the case where the ABP accumulates intracellularly) or harvesting of culture supernatant in either batch or continuous formats. For production in prokaryotic host cells, batch culture and cell harvest are preferred.

The antigen-binding polypeptides of the present invention are normally purified after expression in recombinant systems. The ABP may be purified from host cells by a variety of methods known to the art. Normally, ABP produced in bacterial host cells is poorly soluble or insoluble (in the form of inclusion bodies). In one embodiment of the present invention, amino acid substitutions may readily be made in the antigen-binding polypeptide that are selected for the purpose of increasing the solubility of the recombinantly produced protein utilizing the methods disclosed herein as well as those known in the art. In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein. The precipitated protein may then be conveniently collected by centrifugation. Recombinant host cells may be disrupted or homogenized to release the inclusion bodies from within the cells using a variety of methods well known to those of ordinary skill in the art. Host cell disruption or homogenization may be performed using well known techniques including, but not limited to, enzymatic cell disruption, sonication, dounce homogenization, or high pressure release disruption. In one embodiment of the method of the present invention, the high pressure release technique is used to disrupt the E. coli host cells to release the inclusion bodies of ABP. When handling inclusion bodies of ABP, it is advantageous to minimize the homogenization time on repetitions in order to maximize the yield of inclusion bodies without loss due to factors such as solubilization, mechanical shearing or proteolysis.

Insoluble or precipitated ABP may then be solubilized using any of a number of suitable solubilization agents known to the art. Preferably, ABP is solubilized with urea or guanidine hydrochloride. The volume of the solubilized ABP should be minimized so that large batches may be produced using conveniently manageable batch sizes. This factor may be significant in a large-scale commercial setting where the recombinant host may be grown in batches that are thousands of liters in volume. In addition, when manufacturing ABP in a large-scale commercial setting, in particular for human pharmaceutical uses, the avoidance of harsh chemicals that can damage the machinery and container, or the protein product itself, should be avoided, if possible. It has been shown in the method of the present invention that the milder denaturing agent urea can be used to solubilize the ABP inclusion bodies in place of the harsher denaturing agent guanidine hydrochloride. The use of urea significantly reduces the risk of damage to stainless steel equipment utilized in the manufacturing and purification process of ABP while efficiently solubilizing the ABP inclusion bodies.

In the case of soluble ABP, ABP may be secreted into the periplasmic space or into the culture medium. In addition, soluble ABP may be present in the cytoplasm of the host cells. It may be desired to concentrate soluble ABP prior to performing purification steps. Standard techniques known to those skilled in the art may be used to concentrate soluble ABP from, for example, cell lysates or culture medium. In addition, standard techniques known to those skilled in the art may be used to disrupt host cells and release soluble ABP from the cytoplasm or periplasmic space of the host cells.

When ABP is produced as a fusion protein, the fusion sequence is preferably removed. Removal of a fusion sequence may be accomplished by enzymatic or chemical cleavage, preferably by enzymatic cleavage. Enzymatic removal of fusion sequences may be accomplished using methods well known to those in the art. The choice of enzyme for removal of the fusion sequence will be determined by the identity of the fusion, and the reaction conditions will be specified by the choice of enzyme as will be apparent to one skilled in the art. The cleaved ABP is preferably purified from the cleaved fusion sequence by well known methods. Such methods will be determined by the identity and properties of the fusion sequence and the ABP, as will be apparent to one skilled in the art. Methods for purification may include, but are not limited to, size-exclusion chromatography, hydrophobic interaction chromatography, ion-exchange chromatography or dialysis or any combination thereof.

The ABP is also preferably purified to remove DNA from the protein solution. DNA may be removed by any suitable method known to the art, such as precipitation or ion exchange chromatography, but is preferably removed by precipitation with a nucleic acid precipitating agent, such as, but not limited to, protamine sulfate. ABP may be separated from the precipitated DNA using standard well known methods including, but not limited to, centrifugation or filtration. Removal of host nucleic acid molecules is an important factor in a setting where the ABP is to be used to treat humans and the methods of the present invention reduce host cell DNA to pharmaceutically acceptable levels.

Methods for small-scale or large-scale fermentation can also be used in protein expression, including but not limited to, fermentors, shake flasks, fluidized bed bioreactors, hollow fiber bioreactors, roller bottle culture systems, and stirred tank bioreactor systems. Each of these methods can be performed in a batch, fed-batch, or continuous mode process.

Human ABP of the invention can generally be recovered using methods standard in the art. For example, culture medium or cell lysate can be centrifuged or filtered to remove cellular debris. The supernatant may be concentrated or diluted to a desired volume or diafiltered into a suitable buffer to condition the preparation for further purification. Further purification of the ABP of the present invention include separating deamidated and clipped forms of the ABP variant from the intact form.

Any of the following exemplary procedures can be employed for purification of antigen-binding polypeptides of the invention: affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), SDS-PAGE, or extraction.

Proteins of the present invention, including but not limited to, proteins comprising unnatural amino acids, antibodies to proteins comprising unnatural amino acids, binding partners for proteins comprising unnatural amino acids, etc., can be purified, either partially or substantially to homogeneity, according to standard procedures known to and used by those of skill in the art. Accordingly, polypeptides of the invention can be recovered and purified by any of a number of methods well known in the art, including but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against unnatural amino acids (or proteins comprising unnatural amino acids) are used as purification reagents, including but not limited to, for affinity-based purification of proteins comprising one or more unnatural amino acid(s). Once purified, partially or to homogeneity, as desired, the polypeptides are optionally used for a wide variety of utilities, including but not limited to, as assay components, therapeutics, prophylaxis, diagnostics, research reagents, and/or as immunogens for antibody production.

In addition to other references noted herein, a variety of purification/protein folding methods are well known in the art, including, but not limited to, those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana, (1997) *Bioseparation of Proteins*, Academic Press, Inc.; Bollag et al. (1996) *Protein Methods*, 2nd Edition Wiley-Liss, NY; Walker, (1996) *The Protein Protocols Handbook* Humana Press, NJ, Harris and Angal, (1990) *Protein Purification Applications: A Practical Approach* IRL Press at Oxford, Oxford, England; Harris and Angal, *Protein Purification Methods: A Practical Approach* IRL Press at Oxford, Oxford, England; Scopes, (1993) *Protein Purification: Principles and Practice* 3rd Edition Springer Verlag, NY; Janson and Ryden, (1998) *Protein Purification: Principles, High Resolution Methods and Applications, Second Edition* Wiley-VCH, NY; and Walker (1998), *Protein Protocols on CD-ROM* Humana Press, NJ; and the references cited therein.

One advantage of producing a protein or polypeptide of interest with an unnatural amino acid in a eukaryotic host cell or non-eukaryotic host cell is that typically the proteins or polypeptides will be folded in their native conformations. However, in certain embodiments of the invention, those of skill in the art will recognize that, after synthesis, expression and/or purification, proteins can possess a conformation different from the desired conformations of the relevant polypeptides. In one aspect of the invention, the expressed protein is optionally denatured and then renatured. This is accomplished utilizing methods known in the art, including but not limited to, by adding a chaperonin to the protein or polypeptide of interest, by solubilizing the proteins in a chaotropic agent such as guanidine HCl, utilizing protein disulfide isomerase, etc.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art (see, the references above, and Debinski, et al. (1993) *J. Biol. Chem.*, 268: 14065-14070; Kreitman and Pastan (1993) *Bioconjug. Chem.*, 4: 581-585; and Buchner, et al., (1992) *Anal. Biochem.*, 205: 263-270). Debinski, et al., for example, describe the denaturation and reduction of inclusion body proteins in guanidine-DTE. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of ABP, ABP thus produced may be misfolded and thus lacks or has reduced biological activity. The bioactivity of the protein may be restored by "refolding". In general, misfolded ABP is refolded by solubilizing (where the ABP is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. ABP may be refolded using standard methods known in the art, such as those described in U.S. Pat. Nos. 4,511,502, 4,511,503, and 4,512,922, which are incorporated by reference herein. The ABP may also be cofolded with other proteins to form heterodimers or heteromultimers. After refolding or cofolding, the ABP is preferably further purified.

General Purification Methods Any one of a variety of isolation steps may be performed on the cell lysate comprising ABP or on any ABP mixtures resulting from any isolation steps including, but not limited to, affinity chromatography, ion exchange chromatography, hydrophobic interaction chromatography, gel filtration chromatography, high performance liquid chromatography ("HPLC"), reversed phase-HPLC ("RP-HPLC"), expanded bed adsorption, or any combination and/or repetition thereof and in any appropriate order.

Equipment and other necessary materials used in performing the techniques described herein are commercially available. Pumps, fraction collectors, monitors, recorders, and entire systems are available from, for example, Applied Biosystems (Foster City, Calif.), Bio-Rad Laboratories, Inc. (Hercules, Calif.), and Amersham Biosciences, Inc. (Piscataway, N.J.). Chromatographic materials including, but not limited to, exchange matrix materials, media, and buffers are also available from such companies.

Equilibration, and other steps in the column chromatography processes described herein such as washing and elution, may be more rapidly accomplished using specialized equipment such as a pump. Commercially available pumps include, but are not limited to, HILOAD® Pump P-50, Peristaltic Pump P-1, Pump P-901, and Pump P-903 (Amersham Biosciences, Piscataway, N.J.).

Examples of fraction collectors include RediFrac Fraction Collector, FRAC-100 and FRAC-200 Fraction Collectors, and SUPERFRAC® Fraction Collector (Amersham Biosciences, Piscataway, N.J.). Mixers are also available to form pH and linear concentration gradients. Commercially available mixers include Gradient Mixer GM-1 and In-Line Mixers (Amersham Biosciences, Piscataway, N.J.).

The chromatographic process may be monitored using any commercially available monitor. Such monitors may be used to gather information like UV, pH, and conductivity. Examples of detectors include Monitor UV-1, UVICORD® S II, Monitor UV-M II, Monitor UV-900, Monitor UPC-900, Monitor pH/C-900, and Conductivity Monitor (Amersham Biosciences, Piscataway, N.J.). Indeed, entire systems are commercially available including the various AKTA® systems from Amersham Biosciences (Piscataway, N.J.).

In one embodiment of the present invention, for example, the ABP may be reduced and denatured by first denaturing the resultant purified ABP in urea, followed by dilution into TRIS buffer containing a reducing agent (such as DTT) at a suitable pH. In another embodiment, the ABP is denatured in urea in a concentration range of between about 2 M to about 9 M, followed by dilution in TRIS buffer at a pH in the range of about 5.0 to about 8.0. The refolding mixture of this embodiment may then be incubated. In one embodiment, the refolding mixture is incubated at room temperature for four to twenty-four hours. The reduced and denatured ABP mixture may then be further isolated or purified.

As stated herein, the pH of the first ABP mixture may be adjusted prior to performing any subsequent isolation steps. In addition, the first ABP mixture or any subsequent mixture thereof may be concentrated using techniques known in the art. Moreover, the elution buffer comprising the first ABP mixture or any subsequent mixture thereof may be exchanged for a buffer suitable for the next isolation step using techniques well known to those of ordinary skill in the art.

Ion Exchange Chromatogragphy In one embodiment, and as an optional, additional step, ion exchange chromatography may be performed on the first ABP mixture. See generally ION EXCHANGE CHROMATOGRAPHY: PRINCIPLES AND METHODS (Cat. No. 18-1114-21, Amersham Biosciences (Piscataway, N.J.)). Commercially available ion exchange columns include HITRAP®, HIPREP®, and HILOAD® Columns (Amersham Biosciences, Piscataway, N.J.). Such columns utilize strong anion exchangers such as Q SEPHAROSE® Fast Flow, Q SEPHAROSE® High Performance, and Q SEPHAROSE® XL; strong cation exchangers such as SP SEPHAROSE® High Performance, SP SEPHAROSE® Fast Flow, and SP SEPHAROSE® XL; weak anion exchangers such as DEAE SEPHAROSE® Fast Flow; and weak cation exchangers such as CM SEPHAROSE® Fast Flow (Amersham Biosciences, Piscataway, N.J.). Anion or cation exchange column chromatography may be performed on the ABP at any stage of the purification process to isolate substantially purified ABP. The cation exchange chromatography step may be performed using any suitable cation exchange matrix. Useful cation exchange matrices include, but are not limited to, fibrous, porous, non-porous, microgranular, beaded, or cross-linked cation exchange matrix materials. Such cation exchange matrix materials include, but are not limited to, cellulose, agarose, dextran, polyacrylate, polyvinyl, polystyrene, silica, polyether, or composites of any of the foregoing.

The cation exchange matrix may be any suitable cation exchanger including strong and weak cation exchangers. Strong cation exchangers may remain ionized over a wide pH range and thus, may be capable of binding ABP over a wide pH range. Weak cation exchangers, however, may lose ionization as a function of pH. For example, a weak cation exchanger may lose charge when the pH drops below about pH 4 or pH 5. Suitable strong cation exchangers include, but are not limited to, charged functional groups such as sulfopropyl (SP), methyl sulfonate (S), or sulfoethyl (SE). The cation exchange matrix may be a strong cation exchanger, preferably having an ABP binding pH range of about 2.5 to about 6.0. Alternatively, the strong cation exchanger may have an ABP binding pH range of about pH 2.5 to about pH 5.5. The cation exchange matrix may be a strong cation exchanger having an ABP binding pH of about 3.0. Alternatively, the cation exchange matrix may be a strong cation exchanger, preferably having an ABP binding pH range of about 6.0 to about 8.0. The cation exchange matrix may be a strong cation exchanger preferably having an ABP binding pH range of about 8.0 to about 12.5. Alternatively, the strong cation exchanger may have an ABP binding pH range of about pH 8.0 to about pH 12.0.

Prior to loading the ABP, the cation exchange matrix may be equilibrated, for example, using several column volumes of a dilute, weak acid, e.g., four column volumes of 20 mM acetic acid, pH 3. Following equilibration, the ABP may be added and the column may be washed one to several times, prior to elution of substantially purified ABP, also using a weak acid solution such as a weak acetic acid or phosphoric acid solution. For example, approximately 2-4 column volumes of 20 mM acetic acid, pH 3, may be used to wash the column. Additional washes using, e.g., 2-4 column volumes of 0.05 M sodium acetate, pH 5.5, or 0.05 M sodium acetate mixed with 0.1 M sodium chloride, pH 5.5, may also be used. Alternatively, using methods known in the art, the cation exchange matrix may be equilibrated using several column volumes of a dilute, weak base.

Alternatively, substantially purified ABP may be eluted by contacting the cation exchanger matrix with a buffer having a sufficiently low pH or ionic strength to displace the ABP from the matrix. The pH of the elution buffer may range from about pH 2.5 to about pH 6.0. More specifically, the pH of the elution buffer may range from about pH 2.5 to about pH 5.5, about pH 2.5 to about pH 5.0. The elution buffer may have a pH of about 3.0. In addition, the quantity of elution buffer may vary widely and will generally be in the range of about 2 to about 10 column volumes. Moreover, suitable buffers known to those of skill in the art may find use herein including, but not limited to, citrate, phosphate, formate, HEPES, and MES buffers ranging in concentration from at least about 5 mM to at least about 100 mM.

Following adsorption of the ABP polypeptide to the cation exchanger matrix, substantially purified ABP polypeptide may be eluted by contacting the matrix with a buffer having a sufficiently high pH or ionic strength to displace the ABP from the matrix. Suitable buffers for use in high pH elution of substantially purified ABP may include, but are not limited to, citrate, phosphate, formate, acetate, HEPES, and MES buffers ranging in concentration from at least about 5 mM to at least about 100 mM.

Reverse-Phase Chromatography RP-HPLC may be performed to purify proteins following suitable protocols that are known to those of ordinary skill in the art. See, e.g., Pearson et al., ANAL BIOCHEM. (1982) 124:217-230 (1982); Rivier et al., J. CHROM. (1983) 268:112-119; Kunitani et al., J. CHROM. (1986) 359:391-402. RP-HPLC may be performed on the ABP to isolate substantially purified ABP. In this regard, silica derivatized resins with alkyl functionalities with a wide variety of lengths, including, but not limited to, at least about $C_3$ to at least about $C_{30}$, at least about $C_3$ to at least about $C_{20}$, or at least about $C_3$ to at least about $C_{18}$, resins may be used. Alternatively, a polymeric resin may be used. For example, TosoHaas Amberchrome CG1000sd resin may be used, which is a styrene polymer resin. Cyano or polymeric resins with a wide variety of alkyl chain lengths may also be used. Furthermore, the RP-HPLC column may be washed with a solvent such as ethanol. The Source RP column is another example of a RP-HPLC column.

A suitable elution buffer containing an ion pairing agent and an organic modifier such as methanol, isopropanol, tetrahydrofuran, acetonitrile or ethanol, may be used to elute the ABP from the RP-HPLC column. The most commonly used ion pairing agents include, but are not limited to, acetic acid, formic acid, perchloric acid, phosphoric acid, trifluoroacetic acid, heptafluorobutyric acid, triethylamine, tetramethylammonium, tetrabutylammonium, and triethylammonium acetate. Elution may be performed using one or more gradients or isocratic conditions, with gradient conditions preferred to reduce the separation time and to decrease peak width. Another method involves the use of two gradients with different solvent concentration ranges. Examples of suitable elution buffers for use herein may include, but are not limited to, ammonium acetate and acetonitrile solutions.

Hydrophobic Interaction Chromatopraphy Purification Techniques Hydrophobic interaction chromatography (HIC) may be performed on the ABP. See generally HYDROPHOBIC INTERACTION CHROMATOGRAPHY HANDBOOK: PRINCIPLES AND METHODS (Cat. No. 18-1020-90, Amersham Biosciences (Piscataway, N.J.) which is incorporated by reference herein. Suitable HIC matrices may include, but are not limited to, alkyl- or aryl-substituted matrices, such as butyl-, hexyl-, octyl- or phenyl-substituted matrices including agarose, cross-linked agarose, sepharose, cellulose, silica, dextran, polystyrene, poly(methacrylate) matrices, and mixed mode resins, including but not limited to, a polyethyleneamine resin or a butyl- or phenyl-substituted poly(methacrylate) matrix. Commercially available sources for hydrophobic interaction column chromatography include, but are not limited to, HITRAP®, HIPREP®, and HILOAD® columns (Amersham Biosciences, Piscataway, N.J.).

Briefly, prior to loading, the HIC column may be equilibrated using standard buffers known to those of ordinary skill in the art, such as an acetic acid/sodium chloride solution or HEPES containing ammonium sulfate. Ammonium sulfate may be used as the buffer for loading the HIC column. After loading the ABP, the column may then washed using standard buffers and conditions to remove unwanted materials but retaining the ABP on the HIC column. ABP may be eluted with about 3 to about 10 column volumes of a standard buffer, such as a HEPES buffer containing EDTA and lower ammonium sulfate concentration than the equilibrating buffer, or an acetic acid/sodium chloride buffer, among others. A decreasing linear salt gradient using, for example, a gradient of potassium phosphate, may also be used to elute the ABP molecules. The eluant may then be concentrated, for example, by filtration such as diafiltration or ultrafiltration. Diafiltration may be utilized to remove the salt used to elute ABP.

Other Purification Techniques Yet another isolation step using, for example, gel filtration (GEL FILTRATION: PRINCIPLES AND METHODS (Cat. No. 18-1022-18, Amersham Biosciences, Piscataway, N.J.) which is incorporated by reference herein, hydroxyapatite chromatography (suitable matrices include, but are not limited to, HA-Ultrogel, High Resolution (Calbiochem), CHT Ceramic Hydroxyapatite (BioRad), Bio-Gel HTP Hydroxyapatite (BioRad)), HPLC, expanded bed adsorption, ultrafiltration, diafiltration, lyophilization, and the like, may be performed on the first ABP mixture or any subsequent mixture thereof, to remove any excess salts and to replace the buffer with a suitable buffer for the next isolation step or even formulation of the final drug product.

The non-naturally encoded amino acid present in the ABP may also be utilized to provide separation from other cellular proteins that do not contain the non-naturally encoded amino acid. Since the non-naturally encoded amino acid may comprise unique chemical functional groups, the coupling of the unique functional group to another molecule may provide a substantial purification step. For example, the non-naturally encoded amino acid may be coupled to another molecule that facilitates separation from other proteins. Such molecules for coupling to the non-natural amino acid include, but are not limited to, PEG and other polymers, beads, and other solid substances.

The yield of ABP, including substantially purified ABP, may be monitored at each step described herein using techniques known to those of ordinary skill in the art. Such techniques may also be used to assess the yield of substantially purified ABP following the last isolation step. For example, the yield of ABP may be monitored using any of several reverse phase high pressure liquid chromatography columns, having a variety of alkyl chain lengths such as cyano RP-HPLC, $C_{18}$RP-HPLC; as well as cation exchange HPLC and gel filtration HPLC.

In specific embodiments of the present invention, the yield of ABP after each purification step may be at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.9%, or at least about 99.99%, of the ABP in the starting material for each purification step.

Purity may be determined using standard techniques, such as SDS-PAGE, or by measuring ABP using Western blot and ELISA assays. For example, polyclonal antibodies may be generated against proteins isolated from negative control yeast fermentation and the cation exchange recovery. The antibodies may also be used to probe for the presence of contaminating host cell proteins.

RP-HPLC material Vydac C4 (Vydac) consists of silica gel particles, the surfaces of which carry C4-alkyl chains. The separation of ABP from the proteinaceous impurities is based on differences in the strength of hydrophobic interactions. Elution is performed with an acetonitrile gradient in diluted trifluoroacetic acid. Preparative HPLC is performed using a stainless steel column (filled with 2.8 to 3.2 liter of Vydac C4 silicagel). The Hydroxyapatite Ultrogel eluate is acidified by adding trifluoroacetic acid and loaded onto the Vydac C4 column. For washing and elution an acetonitrile gradient in diluted trifluoroacetic acid is used. Fractions are collected and immediately neutralized with phosphate buffer. The ABP fractions which are within the IPC limits are pooled.

DEAE Sepharose (Pharmacia) material consists of diethylaminoethyl (DEAE)-groups which are covalently bound to the surface of Sepharose beads. The binding of ABP to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and ABP is eluted with a buffer with increased ionic strength. The column is packed with DEAE Sepharose fast flow. The column volume is adjusted to assure a ABP load in the range of 3-10 mg ABP polypeptide/ml gel. The column is washed with water and equilibration buffer (sodium/potassium phosphate). The pooled fractions of the HPLC eluate are loaded and the column is washed with equilibration buffer. Then the column is washed with washing buffer (sodium acetate buffer) followed by washing with equilibration buffer. Subsequently, ABP is eluted from the column with elution buffer (sodium chloride, sodium/potassium phosphate) and collected in a single fraction in accordance with the master elution profile. The eluate of the DEAE Sepharose column is adjusted to the specified conductivity. The resulting drug substance is sterile filtered into Teflon bottles and stored at −70° C.

Additional methods that may be employed include, but are not limited to, steps to remove endotoxins. Endotoxins are lipopoly-saccharides (LPSs) which are located on the outer membrane of Gram-negative host cells, such as, for example, *Escherichia coli*. Methods for reducing endotoxin levels are known to one skilled in the art and include, but are not limited to, purification techniques using silica supports, glass powder or hydroxyapatite, reverse-phase, affinity, size-exclusion, anion-exchange chromatography, hydrophobic interaction chromatography, a combination of these methods, and the like. Modifications or additional methods may be required to remove contaminants such as co-migrating proteins from the polypeptide of interest A wide variety of methods and procedures can be used to assess the yield and purity of a ABP protein one or more non-naturally encoded amino acids, including but not limited to, the Bradford assay, SDS-PAGE, silver stained SDS-PAGE, coomassie stained SDS-PAGE, mass spectrometry (including but not limited to, MALDI-TOF) and other methods for characterizing proteins known to one skilled in the art.

VIII. Expression in Alternate Systems

Several strategies have been employed to introduce unnatural amino acids into proteins in non-recombinant host cells, mutagenized host cells, or in cell-free systems. These systems are also suitable for use in making the antigen-binding polypeptides of the present invention. Derivatization of amino acids with reactive side-chains such as Lys, Cys and Tyr resulted in the conversion of lysine to $N^2$-acetyl-lysine. Chemical synthesis also provides a straightforward method to incorporate unnatural amino acids. With the recent development of enzymatic ligation and native chemical ligation of peptide fragments, it is possible to make larger proteins. See, e.g., P. E. Dawson and S. B. H. Kent, *Annu. Rev. Biochem.*, 69:923 (2000). A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Cornish, D. Mendel and P. G. Schultz, *Angew. Chem. Int. Ed. Engl.*, 1995, 34:621 (1995); C. J. Noren, S. J. Anthony-Cahill, M. C. Griffith, P. G. Schultz, *A general method for site-specific incorporation of unnatural amino acids into proteins, Science* 244:182-188 (1989); and, J. D. Bain, C. G. Glabe, T. A. Dix, A. R. Chamberlin, E. S. Diala, *Biosynthetic site-specific incorporation of a non-natural amino acid into a polypeptide, J. Am. Chem. Soc.* 111:8013-8014 (1989). A broad range of functional groups has been introduced into proteins for studies of protein stability, protein folding, enzyme mechanism, and signal transduction.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, *FASEB J.*, 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem.*, 284:29 (2000); trifluoromethionine has been used to replace methionine in bacteriophage T4 lysozyme to study its interaction with chitooligosaccharide ligands by $^{19}F$ NMR, see, e.g., H. Duewel, E. Daub, V. Robinson and J. F. Honek, *Biochemistry,* 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, Angew. *Chem. Int. Ed. Engl.,* 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.*, 9:1665 (1990); J. O. Boles, K. Lewinski, M. Kunkle, J. D. Odom, B. Dunlap, L. Lebioda and M. Hatada, *Nat. Struct. Biol.*, 1:283 (1994); N. Budisa, B. Steipe, P. Demange, C. Eckerskorn, J. Kellermann and R. Huber, *Eur. J. Biochem.*, 230:788 (1995); and, N. Budisa, W. Karnbrock, S. Steinbacher, A. Humm, L. Prade, T. Neuefeind, L. Moroder and R. Huber, *J. Mol. Biol.*, 270:616 (1997). Methionine analogs with alkene or alkyne functionalities have also been incorporated efficiently, allowing for additional modification of proteins by chemical means. See, e.g., J. C. M. vanHest and D. A. Tirrell, *FEBS Lett.*, 428:68 (1998); J. C. M. van Hest, K. L. Kiick and D. A. Tirrell, *J. Am. Chem. Soc.*, 122:1282 (2000); and, K. L. Kiick and D. A. Tirrell, Tetrahedron, 56:9487 (2000); U.S. Pat. No. 6,586, 207; U.S. Patent Publication 2002/0042097, which are incorporated by reference herein.

The success of this method depends on the recognition of the unnatural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. For example, replacement of $Ala^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry,* 33:7107 (1994). An *Escherichia coli* strain harboring this mutant PheRS allows the incorporation of p-Cl-phenylalanine or p-Br-phenylalanine in place of phenylalanine. See, e.g., M. Tbba and H. Hennecke, *FEBS Lett.*, 364:272 (1995); and, N. Sharma, R. Furter, P. Kast and D. A. Tirrell, *FEBS Lett.*, 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S. Nishimura, *J. Biol. Chem.*, 275: 40324 (2000).

Another strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, *Science*, 292:501 (2001). ValRS can misaminoacylate tRNAVal with Cys, Thr, or aminobutyrate (Abu); these non-cognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNAVal with Cys. Because Abu sterically resembles Cys (—SH group of Cys is replaced with —CH3 in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing novel amino acids. For example, see the following publications and references cited within, which are as follows: Crick, F. J. C., Barrett, L. Brenner, S. Watts-Tobin, R. *General nature of the genetic code for proteins. Nature,* 192: 1227-1232 (1961); Hofmann, K., Bohn, H. *Studies on polypeptides. XXXVI. The effect of pyrazole-imidazole replacements on the S-protein activating potency of an S-peptide fragment, J. Am Chem,* 88(24):5914-5919 (1966); Kaiser, E. T. *Synthetic approaches to biologically active peptides and proteins including enyzmes, Acc Chem Res,* 47-54 (1989); Nakatsuka, T., Sasaki, T., Kaiser, E. T. *Peptide segment coupling catalyzed by the semisynthetic enzyme thiosubtilisin, J Am Chem Soc,* 3808-3810 (1987); Schnolzer, M., Kent, S B H. *Constructing proteins by dovetailing unprotected synthetic peptides: backbone-engineered HIV protease, Science,* 256(5054):221-225 (1992); Chaiken, I. M. *Semisynthetic peptides and proteins, CRC Crit Rev Biochem,* 11(3):255-301 (1981); Offord, R. E. *Protein engineering by chemical means? Protein Eng.,* 1(3):151-157 (1987); and, Jackson, D. Y., Burnier, J., Quan, C., Stanley, M., Tom, J., Wells, J. A. *A Designed Peptide Ligase for Total Synthesis of Ribonuclease A with Unnatural Catalytic Residues, Science,* 266(5183): 243 (1994).

Chemical modification has been used to introduce a variety of unnatural side chains, including cofactors, spin labels and oligonucleotides into proteins in vitro. See, e.g., Corey, D. R., Schultz, P. G. *Generation of a hybrid sequence-specific single-stranded deoxyribonuclease, Science,* 238(4832): 1401-1403 (1987); Kaiser, E. T., Lawrence D. S., Rokita, S. E. *The chemical modification of enzymatic specificity,* Annu Rev Biochem, 54:565-595 (1985); Kaiser, E. T., Lawrence, D. S. *Chemical mutation of enyzme active sites, Science,* 226 (4674):505-511 (1984); Neet, K. E., Nanci A, Koshland, D. E. *Properties of thiol-subtilisin, J Biol. Chem,* 243(24):6392-6401 (1968); Polgar, L. B., M. L. *A new enzyme containing a synthetically formed active site. Thiol-subtilisin. J. Am Chem Soc,* 3153-3154 (1966); and, Pollack, S. J., Nakayama, G. Schultz, P. G. *Introduction of nucleophiles and spectroscopic probes into antibody combining sites, Science,* 242(4881): 1038-1040 (1988).

Alternatively, biosynthetic methods that employ chemically modified aminoacyl-tRNAs have been used to incorporate several biophysical probes into proteins synthesized in vitro. See the following publications and references cited within: Brunner, J. *New Photolabeling and crosslinking methods, Annu. Rev Biochem,* 62:483-514 (1993); and, Krieg, U. C., Walter, P., Hohnson, A. E. *Photocrosslinking of the signal sequence of nascent preprolactin of the 54-kilodalton polypeptide of the signal recognition particle, Proc. Natl. Acad. Sci,* 83(22):8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. *A general method for site-specific incorporation of unnatural amino acids into proteins, Science,* 244: 182-188 (1989); M. W. Nowak, et al., *Science* 268:439-42 (1995); Bain, J. D., Glabe, C. G., Dix, T. A., Chamberlin, A. R., Diala, E. S. *Biosynthetic site-specific Incorporation of a non-natural amino acid into a polypeptide, J. Am Chem Soc,* 111:8013-8014 (1989); N. Budisa et al., *FASEB J.* 13:41-51 (1999); Ellman, J. A., Mendel, D., Anthony-Cahill, S., Noren, C. J., Schultz, P. G. *Biosynthetic method for introducing unnatural amino acids site-specifically into proteins, Methods in Enz.,* 301-336 (1992); and, Mendel, D., Cornish, V. W. & Schultz, P. G. *Site-Directed Mutagenesis with an Expanded Genetic Code, Annu Rev Biophys. Biomol Struct.* 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. 5', 3' *Exonuclease in phosphorothioate-based oligonucleotide-directed mutagensis, Nucleic Acids Res,* 16(3):791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10(6):425-432; and, Ellman, J. A., Mendel, D., Schultz, P. G. *Site-specific incorporation of novel backbone structures into proteins, Science,* 255(5041):197-200 (1992).

Microinjection techniques have also been use incorporate unnatural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, *Science,* 268:439 (1995); and, D. A. Dougherty, *Curr. Opin. Chem. Biol.,* 4:645 (2000). A Xenopus oocyte was coinjected with two RNA species made in vitro: an MRNA encoding the target protein with a UAG stop codon at the amino acid position of interest and an amber suppressor tRNA aminoacylated with the desired unnatural amino acid. The translational machinery of the oocyte then inserts the unnatural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, *J. Biol. Chem.,* 271:19991 (1996); the incorporation of biotinylated amino acids to identify surface-exposed residues in ion channels, see, e.g., J. P. Gallivan, H. A. Lester and D. A. Dougherty, *Chem. Biol.,* 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, *Cell,* 96:89 (1999); and, T. Lu, A. Y. Ting, J. Mainland, L. Y. Jan, P. G. Schultz and J. Yang, *Nat. Neurosci.,* 4:239 (2001).

The ability to incorporate unnatural amino acids directly into proteins in vivo offers the advantages of high yields of mutant proteins, technical ease, the potential to study the mutant proteins in cells or possibly in living organisms and the use of these mutant proteins in therapeutic treatments. The ability to include unnatural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties. However, the process is difficult, because the complex nature of tRNA-synthetase interactions that are required to achieve a high degree of fidelity in protein translation.

In one attempt to site-specifically incorporate para-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Furter, *Protein Sci.,* 7:419 (1998).

It may also be possible to obtain expression of an ABP polynucleotide of the present invention using a cell-free (in-vitro) translational system. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. See, e.g., Kim, D.-M. and J. R. Swartz, *Biotechnology and Bioengineering,* 74 :309-316 (2001); Kim, D.-M. and J. R. Swartz, *Biotechnology Letters,* 22, 1537-1542, (2000); Kim, D.-M., and J. R. Swartz, *Biotechnology Progress,* 16, 385-390, (2000); Kim, D.-M., and J. R. Swartz, *Biotechnology and Bioengineering,* 66, 180-188, (1999); and Patnaik, R. and J. R. Swartz, *Biotechniques* 24, 862-868, (1998); U.S. Pat. No. 6,337,191; U.S. Patent Publication No. 2002/0081660; WO 00/55353; WO 90/05785, which are incorporated by reference herein. Another approach that may be applied to the expression of antigen-binding polypeptides comprising a non-naturally encoded amino acid includes the mRNA-peptide fusion technique. See, e.g., R. Roberts and J. Szostak, *Proc. Natl Acad. Sci. (USA)* 94:12297-12302 (1997); A. Frankel, et al., *Chemistry & Biology* 10:1043-1050 (2003). In this approach, an mRNA template linked to puromycin is translated into peptide on the ribosome. If one or more tRNA molecules has been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the mRNA sequence. In this way, one may screen libraries of antigen-binding polypeptides comprising one or more non-naturally encoded amino acids to identify polypeptides having desired properties. More recently, in vitro ribosome translations with purified components have been reported that permit the synthesis of peptides substituted with non-naturally encoded amino acids. See, e.g., A. Forster et al., *Proc. Natl Acad. Sci. (USA)* 100:6353 (2003).

IX. Macromolecular Polymers Coupled to ABP

Various modifications to the non-natural amino acid polypeptides described herein can be effected using the compositions, methods, techniques and strategies described herein. These modifications include the incorporation of further functionality onto the non-natural amino acid component of the polypeptide, including but not limited to, a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; or any combination of the above, or any other desirable compound or substance. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of skill in the art could make with the disclosures herein) to adding other functionalities, including but not limited to those listed above.

A wide variety of macromolecular polymers and other molecules can be linked to antigen-binding polypeptides of the present invention to modulate biological properties of the ABP, and/or provide new biological properties to the ABP molecule. These macromolecular polymers can be linked to the ABP via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more.

The present invention provides substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous" PEGylated ABP preparations provided herein are those which are homogenous enough to display the advantages of a homogenous preparation, e.g., ease in clinical application in predictability of lot to lot pharmacokinetics.

One may also choose to prepare a mixture of polymer:protein conjugate molecules, and the advantage provided herein is that one may select the proportion of mono-polymer:protein conjugate to include in the mixture. Thus, if desired, one may prepare a mixture of various proteins with various numbers of polymer moieties attached (i.e., di-, tri-, tetra-, etc.) and combine said conjugates with the mono-polymer:protein conjugate prepared using the methods of the present invention, and have a mixture with a predetermined proportion of mono-polymer:protein conjugates.

The polymer selected may be water soluble so that the protein to which it is attached does not precipitate in an aqueous environment, such as a physiological environment. The polymer may be branched or unbranched. Preferably, for therapeutic use of the end-product preparation, the polymer will be pharmaceutically acceptable.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

As used herein, and when contemplating PEG:ABP conjugates, the term "therapeutically effective amount" refers to an amount which gives the desired benefit to a patient. The amount will vary from one individual to another and will depend upon a number of factors, including the overall physical condition of the patient and the underlying cause of the condition to be treated. The amount of ABP polypeptide used for therapy gives an acceptable rate of change and maintains desired response at a beneficial level. A therapeutically effective amount of the present compositions may be readily ascertained by one skilled in the art using publicly available materials and procedures.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments of this invention.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to the ABP by the formula:

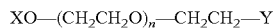

XO—(CH$_2$CH$_2$O)$_n$—CH$_2$CH$_2$—Y where n is 2 to 10,000 and X is H or a terminal modification, including but not limited to, a C$_{1-4}$ alkyl.

In some cases, a PEG used in the invention terminates on one end with hydroxy or methoxy, i.e., X is H or CH$_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to an antigen-binding polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the ABP to form a Huisgen [3+2] cycloaddition product. Alternatively, an alkyne group on the PEG can be reacted with an azide group present in a non-naturally encoded amino acid to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the ABP via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). Branched chain PEGs, including but not limited to, PEG molecules with each chain having a MW ranging from 1-100 kDa (including but not limited to, 1-50 kDa or 5-20 kDa) can also be used. A wide range of PEG molecules are described in, including but not limited to, the Shearwater Polymers, Inc. catalog, Nektar Therapeutics catalog, incorporated herein by reference.

Generally, at least one terminus of the PEG molecule is available for reaction with the non-naturally-encoded amino acid. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described above can be used, i.e., an azide moiety in the non-naturally encoded amino acid can be reacted with a PEG derivative containing an alkyne.

In some embodiments, the ABP variant with a PEG derivative contains a chemical functionality that is reactive with the chemical functionality present on the side chain of the non-naturally encoded amino acid.

The invention provides in some embodiments azide- and acetylene-containing polymer derivatives comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly(ethylene)glycol and other related polymers, including poly(dextran) and poly(propylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly(ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula —$CH_2CH_2O$—($CH_2CH_2O)_n$—$CH_2CH_2$—, where n is from about 3 to about 4000, typically from about 20 to about 2000, is suitable for use in the present invention. PEG having a molecular weight of from about 800 Da to about 100,000 Da are in some embodiments of the present invention particularly useful as the polymer backbone.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as R(-PEG-OH)$_m$ in which R is derived from a core moiety, such as glycerol, glycerol oligomers, or pentaerythritol, and m represents the number of arms. Multi-armed PEG molecules, such as those described in U.S. Pat. Nos. 5,932,462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(-YCHZ$_2$)$_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

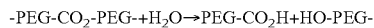

It is understood by those skilled in the art that the term poly(ethylene glycol) or PEG represents or includes all the forms known in the art including but not limited to those disclosed herein.

Many other polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da.

Those of ordinary skill in the art will recognize that the foregoing list for substantially water soluble backbones is by no means exhaustive and is merely illustrative, and that all polymeric materials having the qualities described above are contemplated as being suitable for use in the present invention.

In some embodiments of the present invention the polymer derivatives are "multi-functional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

In one embodiment, the polymer derivative has the structure:

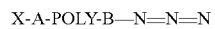

wherein:
N=N=N is an azide moiety;
B is a linking moiety, which may be present or absent;
POLY is a water-soluble non-antigenic polymer;
A is a linking moiety, which may be present or absent and which may be the same as B or different; and
X is a second functional group.

Examples of a linking moiety for A and B include, but are not limited to, a multiply-functionalized alkyl group containing up to 18, and more preferably between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and more preferably 5-6 carbon atoms. The aryl group may be substituted with one more carbon atoms, nitrogen, oxygen or sulfur atoms. Other examples of suitable linking groups include those linking groups described in U.S. Pat. Nos. 5,932,462; 5,643,575; and U.S. Pat. Appl. Publication 2003/0143596, each of which is incorporated by reference herein. Those of ordinary skill in the art will recognize that the foregoing list for linking moieties is by no means exhaustive and is merely illustrative, and that all linking moieties having the qualities described above are contemplated to be suitable for use in the present invention.

Examples of suitable functional groups for use as X include, but are not limited to, hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, alkene, ketone, and azide. As is understood by those skilled in the art, the selected X moiety should be compatible with the azide group so that reaction with the azide group does not occur. The azide-containing polymer derivatives may be homobifunctional, meaning that the second functional group (i.e., X) is also an azide moiety, or heterobifunctional, meaning that the second functional group is a different functional group.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the present invention.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182:1379 (1981), Zaplipsky et al. Eur. Polym. J. 19:1177 (1983)), hydrazide (See, e.g., Andresz et al. Makromol. Chem. 179: 301 (1978)), succinimidyl propionate and succinimidyl butanoate (see, e.g., Olson et al. in Poly(ethylene glycol) Chemistry & Biological Applications, pp 170-181, Harris & Zaplipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Macrolol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314(1993)), acrylol (see, e.g., Sawhney et al., Macromolecules, 26:581 (1993)), vinylsulfone (see, e.g., U.S. Pat. No. 5,900,461). All of the above references and patents are incorporated herein by reference.

In certain embodiments of the present invention, the polymer derivatives of the invention comprise a polymer backbone having the structure:

wherein:
X is a functional group as described above; and
n is about 20 to about 4000.

In another embodiment, the polymer derivatives of the invention comprise a polymer backbone having the structure:

wherein:
W is an aliphatic or aromatic linker moiety comprising between 1-10 carbon atoms;
n is about 20 to about 4000; and
X is a functional group as described above. m is between 1 and 10.

The azide-containing PEG derivatives of the invention can be prepared by a variety of methods known in the art and/or disclosed herein. In one method, shown below, a water soluble polymer backbone having an average molecular weight from about 800 Da to about 100,000 Da, the polymer backbone having a first terminus bonded to a first functional group and a second terminus bonded to a suitable leaving group, is reacted with an azide anion (which may be paired with any of a number of suitable counter-ions, including sodium, potassium, tert-butylammonium and so forth). The leaving group undergoes a nucleophilic displacement and is replaced by the azide moiety, affording the desired azide-containing PEG polymer.

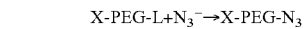

As shown, a suitable polymer backbone for use in the present invention has the formula X-PEG-L, wherein PEG is poly(ethylene glycol) and X is a functional group which does not react with azide groups and L is a suitable leaving group. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone. Examples of suitable leaving groups include, but are not limited to, chloride, bromide, iodide, mesylate, tresylate, and tosylate.

In another method for preparation of the azide-containing polymer derivatives of the present invention, a linking agent bearing an azide functionality is contacted with a water soluble polymer backbone having an average molecular weight from about 800 Da to about 100,000 Da, wherein the linking agent bears a chemical functionality that will react selectively with a chemical functionality on the PEG polymer, to form an azide-containing polymer derivative product wherein the azide is separated from the polymer backbone by a linking group.

An exemplary reaction scheme is shown below:

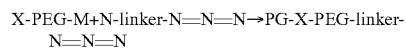

wherein:
PEG is poly(ethylene glycol) and X is a capping group such as alkoxy or a functional group as described above; and
M is a functional group that is not reactive with the azide functionality but that will react efficiently and selectively with the N functional group.

Examples of suitable functional groups include, but are not limited to, M being a carboxylic acid, carbonate or active ester if N is an amine; M being a ketone if N is a hydrazide or aminooxy moiety; M being a leaving group if N is a nucleophile.

Purification of the crude product may be accomplished by known methods including, but are not limited to, precipitation of the product followed by chromatography, if necessary.

A more specific example is shown below in the case of PEG diamine, in which one of the amines is protected by a protecting group moiety such as tert-butyl-Boc and the resulting mono-protected PEG diamine is reacted with a linking moiety that bears the azide functionality:

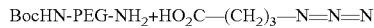

BocHN-PEG-NH$_2$+HO$_2$C—(CH$_2$)$_3$—N=N=N

In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine PEG derivative and the azide-bearing linker moiety. After successful formation of the amide bond, the resulting N-tert-butyl-Boc-protected azide-containing derivative can be used directly to modify bioactive molecules or it can be further elaborated to install other useful functional groups. For instance, the N-t-Boc group can be hydrolyzed by treatment with strong acid to generate an omega-amino-PEG-azide. The resulting amine can be used as a synthetic handle to install other useful functionality such as maleimide groups, activated disulfides, activated esters and so forth for the creation of valuable heterobifunctional reagents.

Heterobifunctional derivatives are particularly useful when it is desired to attach different molecules to each terminus of the polymer. For example, the omega-N-amino-N-azido PEG would allow the attachment of a molecule having an activated electrophilic group, such as an aldehyde, ketone, activated ester, activated carbonate and so forth, to one terminus of the PEG and a molecule having an acetylene group to the other terminus of the PEG.

In another embodiment of the invention, the polymer derivative has the structure:

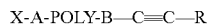

X-A-POLY-B—C≡C—R wherein:

R can be either H or an alkyl, alkene, alkyoxy, or aryl or substituted aryl group;

B is a linking moiety, which may be present or absent;

POLY is a water-soluble non-antigenic polymer;

A is a linking moiety, which may be present or absent and which may be the same as B or different; and X is a second functional group.

Examples of a linking moiety for A and B include, but are not limited to, a multiply-functionalized alkyl group containing up to 18, and more preferably between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and more preferably 5-6 carbon atoms. The aryl group may be substituted with one more carbon atoms, nitrogen, oxygen, or sulfur atoms. Other examples of suitable linking groups include those linking groups described in U.S. Pat. Nos. 5,932,462 and 5,643,575 and U.S. Pat. Appl. Publication 2003/0143596, each of which is incorporated by reference herein. Those of ordinary skill in the art will recognize that the foregoing list for linking moieties is by no means exhaustive and is intended to be merely illustrative, and that a wide variety of linking moieties having the qualities described above are contemplated to be useful in the present invention.

Examples of suitable functional groups for use as X include hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, ketone, and acetylene. As would be understood, the selected X moiety should be compatible with the acetylene group so that reaction with the acetylene group does not occur. The acetylene-containing polymer derivatives may be homobifunctional, meaning that the second functional group (i.e., X) is also an acetylene moiety, or heterobifunctional, meaning that the second functional group is a different functional group.

In another embodiment of the present invention, the polymer derivatives comprise a polymer backbone having the structure:

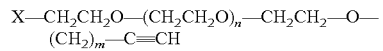

X—CH$_2$CH$_2$O—(CH$_2$CH$_2$O)$_n$—CH$_2$CH$_2$—O—(CH$_2$)$_m$—C≡CH wherein:

X is a functional group as described above;

n is about 20 to about 4000; and m is between 1 and 10.

Specific examples of each of the heterobifunctional PEG polymers are shown below.

The acetylene-containing PEG derivatives of the invention can be prepared using methods known to those skilled in the art and/or disclosed herein. In one method, a water soluble polymer backbone having an average molecular weight from about 800 Da to about 100,000 Da, the polymer backbone having a first terminus bonded to a first functional group and a second terminus bonded to a suitable nucleophilic group, is reacted with a compound that bears both an acetylene functionality and a leaving group that is suitable for reaction with the nucleophilic group on the PEG. When the PEG polymer bearing the nucleophilic moiety and the molecule bearing the leaving group are combined, the leaving group undergoes a nucleophilic displacement and is replaced by the nucleophilic moiety, affording the desired acetylene-containing polymer.

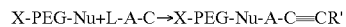

X-PEG-Nu+L-A-C→X-PEG-Nu-A-C≡CR'

As shown, a preferred polymer backbone for use in the reaction has the formula X-PEG-Nu, wherein PEG is poly (ethylene glycol), Nu is a nucleophilic moiety and X is a functional group that does not react with Nu, L or the acetylene functionality.

Examples of Nu include, but are not limited to, amine, alkoxy, aryloxy, sulfhydryl, imino, carboxylate, hydrazide, aminoxy groups that would react primarily via a SN2-type mechanism. Additional examples of Nu groups include those functional groups that would react primarily via an nucleophilic addition reaction. Examples of L groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

In another embodiment of the present invention, A is an aliphatic linker of between 1-10 carbon atoms or a substituted aryl ring of between 6-14 carbon atoms. X is a functional group which does not react with azide groups and L is a suitable leaving group In another method for preparation of the acetylene-containing polymer derivatives of the invention, a PEG polymer having an average molecular weight from about 800 Da to about 100,000 Da, bearing either a protected functional group or a capping agent at one terminus and a suitable leaving group at the other terminus is contacted by an acetylene anion.

An exemplary reaction scheme is shown below:

wherein:
PEG is poly(ethylene glycol) and X is a capping group such as alkoxy or a functional group as described above; and
R' is either H, an alkyl, alkoxy, aryl or aryloxy group or a substituted alkyl, alkoxyl, aryl or aryloxy group.

In the example above, the leaving group L should be sufficiently reactive to undergo SN2-type displacement when contacted with a sufficient concentration of the acetylene anion. The reaction conditions required to accomplish SN2 displacement of leaving groups by acetylene anions are well known in the art.

Purification of the crude product can usually be accomplished by methods known in the art including, but are not limited to, precipitation of the product followed by chromatography, if necessary.

Water soluble polymers can be linked to the antigen-binding polypeptides of the invention. The water soluble polymers may be linked via a non-naturally encoded amino acid incorporated in the antigen-binding polypeptide or any functional group or substituent of a non-naturally encoded or naturally encoded amino acid, or any functional group or substituent added to a non-naturally encoded or naturally encoded amino acid. Alternatively, the water soluble polymers are linked to an antigen-binding polypeptide incorporating a non-naturally encoded amino acid via a naturally-occurring amino acid (including but not limited to, cysteine, lysine or the amine group of the N-terminal residue). In some cases, the ABP of the invention comprise 1, 2, 3, 4, 5, 6, 7, 8, 9, 10 non-natural amino acids, wherein one or more non-naturally-encoded amino acid(s) are linked to water soluble polymer(s) (including but not limited to, PEG and/or oligosaccharides). In some cases, the ABP of the invention further comprise 1, 2, 3, 4, 5, 6, 7, 8, 9, 10, or more naturally-encoded amino acid(s) linked to water soluble polymers. In some cases, the ABP of the invention comprise one or more non-naturally encoded amino acid(s) linked to water soluble polymers and one or more naturally-occurring amino acids linked to water soluble polymers. In some embodiments, the water soluble polymers used in the present invention enhance the serum half-life of the ABP relative to the unconjugated form.

The number of water soluble polymers linked to an antigen-binding polypeptide (i.e., the extent of PEGylation or glycosylation) of the present invention can be adjusted to provide an altered (including but not limited to, increased or decreased) pharmacologic, pharmacokinetic or pharmacodynamic characteristic such as in vivo half-life. In some embodiments, the half-life of ABP is increased at least about 10, 20, 30, 40, 50, 60, 70, 80, 90 percent, 2-fold, 5-fold, 10-fold, 50-fold, or at least about 100-fold over an unmodified polypeptide.

PEG Derivatives Containing a Strong Nucleophilic Group (i.e., Hydrazide, Hydrazine, Hydroxylamine or Semicarbazide)

In one embodiment of the present invention, an antigen-binding polypeptide comprising a carbonyl-containing non-naturally encoded amino acid is modified with a PEG derivative that contains a terminal hydrazine, hydroxylamine, hydrazide or semicarbazide moiety that is linked directly to the PEG backbone.

In some embodiments, the hydroxylamine-terminal PEG derivative will have the structure:

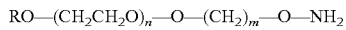

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivative will have the structure:

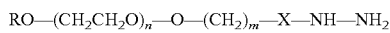

where R is a simple alkyl (methyl, ethyl, propyl, etc.), m is 2-10 and n is 100-1,000 and X is optionally a carbonyl group (C=O) that can be present or absent.

In some embodiments, the semicarbazide-containing PEG derivative will have the structure:

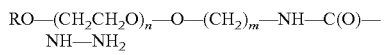

where R is a simple alkyl (methyl, ethyl, propyl, etc.), m is 2-10 and n is 100-1,000.

In another embodiment of the invention, an antigen-binding polypeptide comprising a carbonyl-containing amino acid is modified with a PEG derivative that contains a terminal hydroxylamine, hydrazide, hydrazine, or semicarbazide moiety that is linked to the PEG backbone by means of an amide linkage.

In some embodiments, the hydroxylamine-terminal PEG derivatives have the structure:

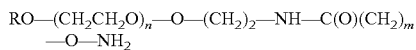

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivatives have the structure:

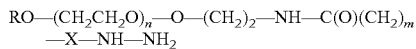

where R is a simple alkyl (methyl, ethyl, propyl, etc.), m is 2-10, n is 100-1,000 and X is optionally a carbonyl group (C=O) that can be present or absent.

In some embodiments, the semicarbazide-containing PEG derivatives have the structure:

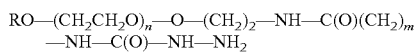

where R is a simple alkyl (methyl, ethyl, propyl, etc.), m is 2-10 and n is 100-1,000.

In another embodiment of the invention, an ABP comprising a carbonyl-containing amino acid is modified with a branched PEG derivative that contains a terminal hydrazine, hydroxylamine, hydrazide or semicarbazide moiety, with each chain of the branched PEG having a MW ranging from 10-40 kDa and, more preferably, from 5-20 kDa.

In another embodiment of the invention, an ABP comprising a non-naturally encoded amino acid is modified with a PEG derivative having a branched structure. For instance, in some embodiments, the hydrazine- or hydrazide-terminal PEG derivative will have the following structure:

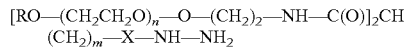

where R is a simple alkyl (methyl, ethyl, propyl, etc.), m is 2-10 and n is 100-1,000, and X is optionally a carbonyl group (C=O) that can be present or absent.

In some embodiments, the PEG derivatives containing a semicarbazide group will have the structure:

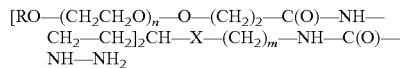

where R is a simple alkyl (methyl, ethyl, propyl, etc.), X is optionally NH, O, S, C(O) or not present, m is 2-10 and n is 100-1,000.

In some embodiments, the PEG derivatives containing a hydroxylamine group will have the structure:

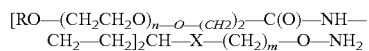

where R is a simple alkyl (methyl, ethyl, propyl, etc.), X is optionally NH, O, S, C(O) or not present, m is 2-10 and n is 100-1,000.

The degree and sites at which the water soluble polymer(s) are linked to the ABP can modulate the binding of the ABP to an antigen or receptor.

Methods and chemistry for activation of polymers as well as for conjugation of peptides are described in the literature and are known in the art. Commonly used methods for activation of polymers include, but are not limited to, activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTAL AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995).

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and WO 93/15189, and for conjugation between activated polymers and enzymes including but not limited to Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)). All references and patents cited are incorporated by reference herein.

PEGylation (i.e., addition of any water soluble polymer) of antigen-binding polypeptides containing a non-naturally encoded amino acid, such as p-azido-L-phenylalanine, is carried out by any convenient method. For example, ABP is PEGylated with an alkyne-terminated mPEG derivative. Briefly, an excess of solid mPEG(5000)-O—CH$_2$—C≡CH is added, with stirring, to an aqueous solution of p-azido-L-Phe-containing ABP at room temperature. Typically, the aqueous solution is buffered with a buffer having a pK$_a$ near the pH at which the reaction is to be carried out (generally about pH 4-10). Examples of suitable buffers for PEGylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PEGylated ABP variants from free mPEG(5000)-O—CH$_2$—C≡CH and any high-molecular weight complexes of the pegylated ABP which may form when unblocked PEG is activated at both ends of the molecule, thereby crosslinking ABP variant molecules. The conditions during hydrophobic interaction chromatography are such that free mPEG(5000)-O—CH$_2$—C≡CH flows through the column, while any crosslinked PEGylated ABP variant complexes elute after the desired forms, which contain one ABP variant molecule conjugated to one or more PEG groups. Suitable conditions vary depending on the relative sizes of the cross-linked complexes versus the desired conjugates and are readily determined by those skilled in the art. The eluent containing the desired conjugates is concentrated by ultrafiltration and desalted by diafiltration.

If necessary, the PEGylated ABP obtained from the hydrophobic chromatography can be purified further by one or more procedures known to those skilled in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (PROTEIN PURIFICATION METHODS, A PRACTICAL APPROACH (Harris & Angal, Eds.) IRL Press 1989, 293-306). The purity of the ABP-PEG conjugate can be assessed by proteolytic degradation (including but not limited to, trypsin cleavage) followed by mass spectrometry analysis. Pepinsky B., et al., *J. Pharmcol. & Exp. Ther.* 297 (3):1059-66 (2001).

A water soluble polymer linked to an amino acid of an ABP of the invention can be further derivatized or substituted without limitation.

Azide-Containing PEG Derivatives

In another embodiment of the invention, an antigen-binding polypeptide is modified with a PEG derivative that contains an azide moiety that will react with an alkyne moiety present on the side chain of the non-naturally encoded amino acid. In general, the PEG derivatives will have an average molecular weight ranging from 1-100 kDa and, in some embodiments, from 10-40 kDa.

In some embodiments, the azide-terminal PEG derivative will have the structure:

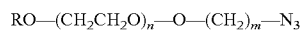

where R is a simple alkyl (methyl, ethyl, propyl, etc.), m is 2-10 and n is 100-1,000 (i.e., average molecular weight is between 5-40 kDa).

In another embodiment, the azide-terminal PEG derivative will have the structure:

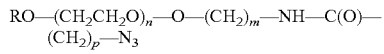
RO—(CH$_2$CH$_2$O)$_n$—O—(CH$_2$)$_m$—NH—C(O)—(CH$_2$)$_p$—N$_3$ where R is a simple alkyl (methyl, ethyl, propyl, etc.), m is 2-10, p is 2-10 and n is 100-1,000 (i.e., average molecular weight is between 5-40 kDa).

In another embodiment of the invention, an ABP comprising a alkyne-containing amino acid is modified with a branched PEG derivative that contains a terminal azide moiety, with each chain of the branched PEG having a MW ranging from 10-40 kDa and, more preferably, from 5-20 kDa. For instance, in some embodiments, the azide-terminal PEG derivative will have the following structure:

[RO—(CH$_2$CH$_2$O)$_n$—O—(CH$_2$)$_2$—NH—C(O)]$_2$CH(CH$_2$)$_m$—X—(CH$_2$)$_p$N$_3$ where R is a simple alkyl (methyl, ethyl, propyl, etc.), m is 2-10, p is 2-10, and n is 100-1,000, and X is optionally an O, N, S or carbonyl group (C=O), in each case that can be present or absent.

Alkyne-Containing PEG Derivatives

In another embodiment of the invention, an antigen-binding polypeptide is modified with a PEG derivative that contains an alkyne moiety that will react with an azide moiety present on the side chain of the non-naturally encoded amino acid.

In some embodiments, the alkyne-terminal PEG derivative will have the following structure:

RO—(CH$_2$CH$_2$O)$_n$—O—(CH$_2$)$_m$—C≡CH where R is a simple alkyl (methyl, ethyl, propyl, etc.), m is 2-10 and n is 100-1,000 (i.e., average molecular weight is between 5-40 kDa).

In another embodiment of the invention, an antigen-binding polypeptide comprising an alkyne-containing non-naturally encoded amino acid is modified with a PEG derivative that contains a terminal azide or terminal alkyne moiety that is linked to the PEG backbone by means of an amide linkage.

In some embodiments, the alkyne-terminal PEG derivative will have the following structure:

RO—(CH$_2$CH$_2$O)$_n$—O—(CH$_2$)$_m$—NH—C(O)—(CH$_2$)$_p$—C≡CH where R is a simple alkyl (methyl, ethyl, propyl, etc.), m is 2-10, p is 2-10 and n is 100-1,000.

In another embodiment of the invention, an antigen-binding polypeptide comprising an azide-containing amino acid is modified with a branched PEG derivative that contains a terminal alkyne moiety, with each chain of the branched PEG having a MW ranging from 10-40 kDa and, more preferably, from 5-20 kDa. For instance, in some embodiments, the alkyne-terminal PEG derivative will have the following structure:

[RO—(CH$_2$CH$_2$O)$_n$—O—(CH$_2$)$_2$—NH—C(O)]$_2$CH(CH$_2$)$_m$—X—(CH$_2$)$_p$C≡CH where R is a simple alkyl (methyl, ethyl, propyl, etc.), m is 2-10, p is 2-10, and n is 100-1,000, and X is optionally an O, N, S or carbonyl group (C=O), or not present.

Phosphine-Containing PEG Derivatives

In another embodiment of the invention, an antigen-binding polypeptide is modified with a PEG derivative that contains an activated functional group (including but not limited to, ester, carbonate) further comprising an aryl phosphine group that will react with an azide moiety present on the side chain of the non-naturally encoded amino acid. In general, the PEG derivatives will have an average molecular weight ranging from 1-100 kDa and, in some embodiments, from 10-40 kDa.

In some embodiments, the PEG derivative will have the structure:

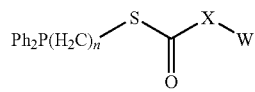

wherein n is 1-10; X can be O, N, S or not present, Ph is phenyl, and W is a water soluble polymer.

In some embodiments, the PEG derivative will have the structure:

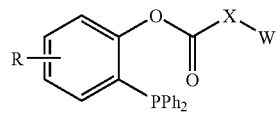

wherein X can be O, N, S or not present, Ph is phenyl, W is a water soluble polymer and R can be H, alkyl, aryl, substituted alkyl and substituted aryl groups. Exemplary R groups include but are not limited to —CH$_2$, —C(CH$_3$)$_3$, —OR', —NR'R", —SR', -halogen, —C(O)R', —CONR'R", —S(O)$_2$R', —S(O)$_2$NR'R", —CN and —NO$_2$. R', R", R'" and R""41 each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

Other PEG Derivatives and General PEGylation Techniques

Other exemplary PEG molecules that may be linked to antigen-binding polypeptides, as well as PEGylation methods include those described in, e.g., U.S. Patent Publication Nos. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949; 2002/0002250; 2001/0056171; 2001/0044526; 2001/0027217; 2001/

0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,612,460; 5,747,646; 5,834,594; 5,849,860; 5,980,948; 6,004,573; 6,129,912; WO 97/32607, EP 229,108, EP 402,378, WO 92/16555, WO 94/04193, WO 94/14758, WO 94/17039, WO 94/18247, WO 94/28024, WO 95/00162, WO 95/11924, W095/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, , WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multifunctional, or any combination thereof.

Enhancing Affinity for Serum Albumin

Various molecules can also be fused to the antigen-binding polypeptides of the invention to modulate the half-life of ABP in serum. In some embodiments, molecules are linked or fused to antigen-binding polypeptides of the invention to enhance affinity for endogenous serum albumin in an animal.

For example, in some cases, a recombinant fusion of an antigen-binding polypeptide and an albumin binding sequence is made. Exemplary albumin binding sequences include, but are not limited to, the albumin binding domain from streptococcal protein G (see. e.g., Makrides et al., *J. Pharmacol. Exp. Ther.* 277:534-542 (1996) and Sjolander et al., *J. Immunol. Methods* 201:115-123 (1997)), or albuminbinding peptides such as those described in, e.g., Dennis, et al., *J. Biol. Chem.* 277:35035-35043 (2002).

In other embodiments, the antigen-binding polypeptides of the present invention are acylated with fatty acids. In some cases, the fatty acids promote binding to serum albumin. See, e.g., Kurtzhals, et al., *Biochem. J.* 312:725-731 (1995).

In other embodiments, the antigen-binding polypeptides of the invention are fused directly with serum albumin (including but not limited to, human serum albumin). Those of skill in the art will recognize that a wide variety of other molecules can also be linked to ABP in the present invention to modulate binding to serum albumin or other serum components.

X. Glycosylation of ABP

The invention includes antigen-binding polypeptides incorporating one or more non-naturally encoded amino acids bearing saccharide residues. The saccharide residues may be either natural (including but not limited to, N-acetylglucosamine) or non-natural (including but not limited to, 3-fluorogalactose). The saccharides may be linked to the non-naturally encoded amino acids either by an N— or O-linked glycosidic linkage (including but not limited to, N-acetylgalactose-L-serine) or a non-natural linkage (including but not limited to, an oxime or the corresponding C— or S-linked glycoside).

The saccharide (including but not limited to, glycosyl) moieties can be added to antigen-binding polypeptides either in vivo or in vitro. In some embodiments of the invention, a nantigen-binding polypeptide comprising a carbonyl-containing non-naturally encoded amino acid is modified with a saccharide derivatized with an aminooxy group to generate the corresponding glycosylated polypeptide linked via an oxime linkage. Once attached to the non-naturally encoded amino acid, the saccharide may be further elaborated by treatment with glycosyltransferases and other enzymes to generate an oligosaccharide bound to the antigen-binding polypeptide. See, e.g., H. Liu, et al. *J. Am. Chem. Soc.* 125: 1702-1703 (2003).

In some embodiments of the invention, an antigen-binding polypeptide comprising a carbonyl-containing non-naturally encoded amino acid is modified directly with a glycan with defined structure prepared as an aminooxy derivative. One skilled in the art will recognize that other functionalities, including azide, alkyne, hydrazide, hydrazine, and semicarbazide, can be used to link the saccharide to the non-naturally encoded amino acid.

In some embodiments of the invention, an antigen-binding polypeptide comprising an azide or alkynyl-containing non-naturally encoded amino acid can then be modified by, including but not limited to, a Huisgen [3+2] cycloaddition reaction with, including but not limited to, alkynyl or azide derivatives, respectively. This method allows for proteins to be modified with extremely high selectivity.

XI. ABP Dimers and Multimers

The present invention also provides for ABP combinations including but not limited to ABP homodimers, heterodimers, homomultimers, or heteromultimers (i.e., trimers, tetramers, etc.) where an ABP polypeptide containing one or more non-naturally encoded amino acids is bound to another ABP or variant thereof or any other polypeptide that is non-ABP polypeptide or variant thereof, either directly to the polypeptide backbone or via a linker. Due to its increased molecular weight compared to monomers, the ABP dimer or multimer conjugates may exhibit new or desirable properties, including but not limited to different pharmacological, pharmacokinetic, pharmacodynamic, modulated therapeutic half-life, or modulated plasma half-life relative to the monomeric ABP. In some embodiments, the ABP dimers of the invention will modulate the dimerization of the ABP receptor. In other embodiments, the ABP dimers or multimers of the present invention will act as an ABP receptor antagonist, agonist, or modulator.

In some embodiments, one or more of ABP present in an ABP containing dimer or multimer comprises a non-naturally encoded amino acid linked to a water soluble polymer. In some embodiments, the ABPs are linked directly, including but not limited to, via an Asn-Lys amide linkage or Cys-Cys disulfide linkage. In some embodiments, the linked ABPs, and/or the linked non-ABP polypeptide, will comprise different non-naturally encoded amino acids to facilitate dimerization, including but not limited to, an alkyne in one non-naturally encoded amino acid of a first ABP and an azide in a second non-naturally encoded amino acid of a second ABP will be conjugated via a Huisgen [3+2] cycloaddition. Alternatively, a first ABP, and/or the linked non-ABP polypeptide comprising a ketone-containing non-naturally encoded amino acid can be conjugated to a second ABP polypeptide comprising a hydroxylamine-containing non-naturally encoded amino acid and the polypeptides are reacted via formation of the corresponding oxime.

Alternatively, the two ABPs, and/or the linked non-ABP polypeptide, are linked via a linker. Any hetero- or homo-bifunctional linker can be used to link the two ABPs, and/or the linked non-ABP polypeptides, which can have the same or different primary sequence. In some cases, the linker used to tether the ABP, and/or the linked non-ABP polypeptides together can be a bifunctional PEG reagent. The linker may have a wide range of molecular weight or molecular length.

Larger or smaller molecular weight linkers may be used to provide a desired spatial relationship or conformation between the ABP and the linked entity. Linkers having longer or shorter molecular length may also be used to provide a desired space or flexibility between the ABP and the linked entity. Similarly, a linker having a particular shape or conformation may be utilized to impart a particular shape or conformation to the ABP or the linked entity, either before or after the ABP reaches its target. The functional groups present on each end of the linker may be selected to modulate the release of an ABP or a non-ABP polypeptide under desired conditions. This optimization of the spatial relationship between the ABP and the linked entity may provide new, modulated, or desired properties to the molecule.

In some embodiments, the invention provides water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. The invention provides, in some embodiments, water-soluble compounds that comprise at least one arm of a branched molecular structure. For example, the branched molecular structure can be dendritic.

In some embodiments, the invention provides multimers comprising one or more ABP formed by reactions with water soluble activated polymers that have the structure:

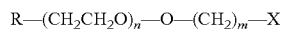

$R-(CH_2CH_2O)_n-O-(CH_2)_m-X$ wherein n is from about 5 to 3,000, m is 2-10, X can be an azide, an alkyne, a hydrazine, a hydrazide, an aminooxy group, a hydroxylamine, a acetyl, or carbonyl-containing moiety, and R is a capping group, a functional group, or a leaving group that can be the same or different as X. R can be, for example, a functional group selected from the group consisting of hydroxyl, protected hydroxyl, alkoxyl, N-hydroxysuccinimidyl ester, 1-benzotriazolyl ester, N-hydroxysuccinimidyl carbonate, 1-benzotriazolyl carbonate, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, and ketone.

XII. Measurement of ABP Activity and Affinity of ABP for the ABP Antigen or Binding Partner ABP activity can be determined using standard in vitro or in vivo assays. For example, cells or cell lines that bind ABP (including but not limited to, cells containing native ABP antigen or binding partner or recombinant ABP antigen or binding partner producing cells) can be used to monitor ABP binding. For a non-PEGylated or PEGylated antigen-binding polypeptide comprising a non-natural amino acid, the affinity of the ABP for its antigen or binding partner can be measured by using techniques known in the art such as a BIAcore™ biosensor (Pharmacia).

Regardless of which methods are used to create the ABP's, the ABP's are subject to assays for biological activity. Tritiated thymidine assays may be conducted to ascertain the degree of cell division, if appropriate. Other biological assays, however, may be used to ascertain the desired activity. Biological assays such as measuring the ability to inhibit an antigen's biological activity, such as an enzymatic, proliferative, or metabolic activity also provides an indication of ABP activity. Other in vitro assays may be used to ascertain biological activity. In general, the test for biological activity should provide analysis for the desired result, such as increase or decrease in biological activity (as compared to non-altered ABP), different biological activity (as compared to non-altered ABP), receptor affinity analysis, conformational or structural changes, or serum half-life analysis, as appropriate for the antigen's biological activity.

The above compilation of references for assay methodologies is not exhaustive, and those skilled in the art will recognize other assays useful for testing for the desired end result.

XIII. Measurement of Potency, Functional In Vivo Half-Life, and Pharmacokinetic Parameters An important aspect of the invention is the prolonged biological half-life that is obtained by construction of ABP with or without conjugation of the ABP to a water soluble polymer moiety. The rapid decrease of ABP serum concentrations has made it important to evaluate biological responses to treatment with conjugated and non-conjugated ABP and variants thereof. Preferably, the conjugated and non-conjugated ABP and variants thereof of the present invention have prolonged serum half-lives also after i.v. administration, making it possible to measure by, e.g. ELISA method or by a primary screening assay. Measurement of in vivo biological half-life is carried out as described herein.

Pharmacokinetic parameters for an antigen-binding polypeptide comprising a non-naturally encoded amino acid can be evaluated in normal Sprague-Dawley male rats (N=5 animals per treatment group). Animals will receive either a single dose of 25 ug/rat iv or 50 ug/rat sc, and approximately 5-7 blood samples will be taken according to a pre-defined time course, generally covering about 6 hours for a n antigen-binding polypeptide comprising a non-naturally encoded amino acid not conjugated to a water soluble polymer and about 4 days for an antigen-binding polypeptide comprising a non-naturally encoded amino acid and conjugated to a water soluble polymer. Pharmacokinetic data for ABP is well-studied in several species and can be compared directly to the data obtained for ABP comprising a non-naturally encoded amino acid.

The specific activity of ABP in accordance with this invention can be determined by various assays known in the art. The biological activity of the ABP muteins, or fragments thereof, obtained and purified in accordance with this invention can be tested by methods described or referenced herein or known to those skilled in the art.

XIV. Administration and Pharmaceutical Compositions

The polypeptides or proteins of the invention (including but not limited to, ABP, synthetases, proteins comprising one or more unnatural amino acid, etc.) are optionally employed for therapeutic uses, including but not limited to, in combination with a suitable pharmaceutical carrier. Such compositions, for example, comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are well known in the art and can be applied to administration of the polypeptides of the invention.

Therapeutic compositions comprising one or more polypeptide of the invention are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of unnatural herein to natural amino acid homologues (including but not limited to, comparison of an ABP modified to include one or more unnatural amino acids to a natural amino acid ABP), i.e., in a relevant assay.

Administration is by any of the routes normally used for introducing a molecule into ultimate contact with blood or tissue cells. The unnatural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Polypeptide compositions can be administered by a number of routes including, but not limited to oral, intravenous, intraperitoneal, intramuscular, transdermal, subcutaneous, topical, sublingual, or rectal means. Compositions comprising non-natural amino acid polypeptides, modified or unmodified, can also be administered via liposomes. Such administration routes and appropriate formulations are generally known to those of skill in the art.

The ABP comprising a non-natural amino acid, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged ABP can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, GH, ABP, G-CSF, GM-CSF, IFNs, interleukins, antibodies, and/or any other pharmaceutically delivered protein), along with formulations in current use, provide preferred routes of administration and formulation for the polypeptides of the invention.

The dose administered to a patient, in the context of the present invention, is sufficient to have a beneficial therapeutic response in the patient over time, or, including but not limited to, to inhibit infection by a pathogen, or other appropriate activity, depending on the application. The dose is determined by the efficacy of the particular vector, or formulation, and the activity, stability or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (including but not limited to, cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, for example, to a 70 kilogram patient, is typically in the range equivalent to dosages of currently-used therapeutic proteins, adjusted for the altered activity or serum half-life of the relevant composition. The vectors of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 or ED-50 of the relevant formulation, and/or observation of any side-effects of the unnatural amino acids at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Human antigen-binding polypeptides of the invention can be administered directly to a mammalian subject. Administration is by any of the routes normally used for introducing ABP to a subject. The ABP compositions according to embodiments of the present invention include those suitable for oral, rectal, topical, inhalation (including but not limited to, via an aerosol), buccal (including but not limited to, sublingual), vaginal, parenteral (including but not limited to, subcutaneous, intramuscular, intradermal, intraarticular, intrapleural, intraperitoneal, inracerebral, intraarterial, or intravenous), topical (i.e., both skin and mucosal surfaces, including airway surfaces) and transdermal administration, although the most suitable route in any given case will depend on the nature and severity of the condition being treated. Administration can be either local or systemic. The formulations of compounds can be presented in unit-dose or multi-dose sealed containers, such as ampules and vials. ABP of the invention can be prepared in a mixture in a unit dosage injectable form (including but not limited to, solution, suspension, or emulsion) with a pharmaceutically acceptable carrier. ABP of the invention can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) of the present invention (see, e.g., *Remington's Pharmaceutical Sciences*, 17$^{th}$ ed. 1985)).

Suitable carriers include buffers containing phosphate, borate, HEPES, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates, including glucose, mannose, or dextrins; chelating agents such as EDTA; divalent metal ions such as zinc, cobalt, or copper; sugar alcohols such as mannitol or sorbitol; salt-forming counter ions such as sodium; and/or nonionic surfactants such as Tween™, Pluronics™, or PEG.

ABP's of the invention, including those linked to water soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J. Biomed. Mater. Res.*, 15: 167-277 (1981); Langer, *Chem. Tech.*, 12: 98-105 (1982), ethylene vinyl acetate (Langer et al., supra) or poly-D-(-)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (U. Sidman et al., *Biopolymers*, 22, 547-556 (1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; Epstein et al., *Proc. Natl. Acad. Sci. U.S.A.*, 82: 3688-3692 (1985); Hwang et al., *Proc. Natl. Acad. Sci. U.S.A.*, 77: 4030-4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. All references and patents cited are incorporated by reference herein.

Liposomally entrapped ABP can be prepared by methods described in, e.g., DE 3,218,121; Epstein et al., *Proc. Natl. Acad. Sci. U.S.A.*, 82: 3688-3692 (1985); Hwang et al., *Proc. Natl. Acad. Sci. U.S.A.*, 77: 4030-4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Composition and size of liposomes are well known or able to be readily determined empirically by one skilled in the art. Some examples of liposomes as described in, e.g., Park J W, et al., *Proc. Natl. Acad. Sci. USA* 92:1327-1331 (1995); Lasic D and Papahadjopoulos D (eds): MEDICAL APPLICATIONS OF LIPOSOMES (1998); Drummond D C, et al., Liposomal drug delivery systems for cancer therapy, in Teicher B (ed): CANCER DRUG DISCOVERY AND DEVELOPMENT (2002); Park J W, et al., *Clin. Cancer Res.* 8:1172-1181 (2002); Nielsen U B, et al., *Biochem. Biophys. Acta* 1591(1-3):109-118 (2002); Mamot C, et al., *Cancer Res.* 63: 3154-3161 (2003). All references and patents cited are incorporated by reference herein.

The dose administered to a patient in the context of the present invention should be sufficient to cause a beneficial response in the subject over time. Generally, the total pharmaceutically effective amount of the ABP of the present invention administered parenterally per dose is in the range of about 0.01 μg/kg/day to about 100 μg/kg, or about 0.05 mg/kg to about 1 mg/kg, of patient body weight, although this is subject to therapeutic discretion. The frequency of dosing is also subject to therapeutic discretion, and may be more frequent or less frequent than the commercially available ABP products approved for use in humans. Generally, a PEGylated antigen-binding polypeptide of the invention can be administered by any of the routes of administration described above.

XV. Therapeutic Uses of Antigen-Binding Polypeptides of the Invention

The ABP polypeptides of the invention are useful for treating a wide range of disorders. The pharmaceutical compositions containing the ABP may be formulated at a strength effective for administration by various means to a human patient experiencing disorders that may be affected by ABP agonists or antagonists, such as but not limited to, anti-proliferatives, anti-inflammatory, or anti-virals are used, either alone or as part of a condition or disease. Average quantities of ABP may vary and in particular should be based upon the recommendations and prescription of a qualified physician. The exact amount of ABP is a matter of preference subject to such factors as the exact type of condition being treated, the condition of the patient being treated, as well as the other ingredients in the composition. The invention also provides for administration of a therapeutically effective amount of another active agent such as an anti-cancer chemotherapeutic agent. The amount to be given may be readily determined by one skilled in the art based upon therapy with ABP.

EXAMPLES

The following examples are offered to illustrate, but not to limit the claimed invention.

Example 1

This example describes one of the many potential sets of criteria for the selection of preferred sites of incorporation of non-naturally encoded amino acids into ABP.

This example demonstrates how preferred sites within the antigen-binding polypeptide were selected for introduction of a non-naturally encoded amino acid. The three dimensional structure composed of two molecules of ABP, or the secondary, tertiary, or quaternary structure of ABP was used to determine preferred positions into which one or more non-naturally encoded amino acids could be introduced.

The following criteria were used to evaluate each position of ABP for the introduction of a non-naturally encoded amino acid: the residue (a) should not interfere with binding of either ABP based on structural analysis of three dimensional structures, or the secondary, tertiary, or quaternary structure of ABP, b) should not be affected by alanine or homolog scanning mutagenesis (c) should be surface exposed and exhibit minimal van der Waals or hydrogen bonding interactions with surrounding residues, (d) may be on one or more of the exposed faces of AIBP, (e) may be a site or sites of ABP that are juxtaposed to a second ABP, or other molecule or fragment thereof, (f) should be either deleted or variable in ABP variants, (g) would result in conservative changes upon substitution with a non-naturally encoded amino acid, (h) may modulate the conformation of the ABP itself or a dimer or multimer comprising one or more ABP, by altering the flexibility or rigidity of the complete structure as desired, (i) could be found in either highly flexible regions or structurally rigid regions and (j) are found in complementarity determining regions (CDR) or not. In addition, further calculations were performed on the ABP molecule, utilizing the Cx program (Pintar et al. *Bioinformatics,* 18, pp 980) to evaluate the extent of protrusion for each protein atom. As a result, in some embodiments, the non-naturally encoded encoded amino acid is substituted at, but not limited to, one or more positions of ABP.

Example 2

This example details cloning and expression of ABP including a non-naturally encoded amino acid in *E. coli*.

An introduced translation system that comprises an orthogonal tRNA (O-tRNA) and an orthogonal aminoacyl tRNA synthetase (O-RS) is used to express ABP containing a non-naturally encoded amino acid. The O-RS preferentially aminoacylates the O-tRNA with a non-naturally encoded amino acid. In turn the translation system inserts the non-naturally encoded amino acid into ABP, in response to an encoded selector codon.

The transformation of *E. coli* with plasmids containing the modified ABP gene and the orthogonal aminoacyl tRNA synthetase/tRNA pair (specific for the desired non-naturally encoded amino acid) allows the site-specific incorporation of non-naturally encoded amino acid into the ABP. The transformed *E. coli*, grown at 37° C. in media containing between 0.01-100 mM of the particular non-naturally encoded amino acid, expresses modified ABP with high fidelity and efficiency. The His-tagged ABP containing a non-naturally encoded amino acid is produced by the *E. coli* host cells as inclusion bodies or aggregates. The aggregates are solubilized and affinity purified under denaturing conditions in 6M guanidine HCl. Refolding is performed by dialysis at 4° C. overnight in 50 mM TRIS-HCl. pH8.0, 40 μM $CUSO_4$, and 2% (w/v) Sarkosyl. The material is then dialyzed against 20 mM TRIS-HCl, pH 8.0, 100 mM NaCl, 2 mM $CaCl_2$, followed by removal of the His-tag. See Boissel et al., (1993) 268:15983-93. Methods for purification of ABP are well known in the art and are confirmed by SDS-PAGE, Western Blot analyses, or electrospray-ionization ion trap mass spectrometry and the like.

Expression Constructs

Periplasmic scFv-108: The variable regions (VL and VH) of the EGFR-specific monoclonal antibody mAb108 (U.S. Pat. No. 6,217,866 which is incorporated by reference herein) were cloned as a scFv fragment with $(GGGGS)_4$ linker sequence (SEQ ID NO: 32)downstream of a yeast BGL2 (C7) periplasmic leader sequence (Humphreys, DP et al. Protein Expr Purif. November 2000;20(2):252-64). An epitope sequence recognized by the c-myc antibody as well as a 6×-His tag were cloned downstream of the VL domain. The wild type scFv-108 construct, as well as variants containing the amber stop codon (TAG) in the VL domain (see FIG. 2, Panel A) were cloned into an *E. coli* expression vector under the control of an inducible promoter. This plasmid also constitutively expressed an amber suppressor tyrosyl $tRNA^{Tyr}_{CUA}$ from *Methanococcus jannaschii* (Mj $tRNA^{Tyr/CUA}$). Locations of the amber stop codons are indicated. The construct made is shown as SEQ ID NO: 18 (nucleotide sequence) and SEQ ID NO: 19 (translated protein sequence). The construct is described in Tables 3 and 4.

TABLE 2

O-RS and O-tRNA sequences.

| | | |
|---|---|---|
| SEQ ID NO: 1 | *M. jannaschii* $mtRNA_{CUA}^{Tyr}$ | tRNA |
| SEQ ID NO: 2 | HLAD03; an optimized amber supressor tRNA | tRNA |
| SEQ ID NO: 3 | HL325A; an optimized AGGA frameshift supressor tRNA | tRNA |
| SEQ ID NO: 4 | Aminoacyl tRNA synthetase for the incorporation of p-azido-L-phenylalanine p-Az-PheRS(6) | RS |
| SEQ ID NO: 5 | Aminoacyl tRNA synthetase for the incorporation of p-benzoyl-L-phenylalanine p-BpaRS(1) | RS |
| SEQ ID NO: 6 | Aminoacyl tRNA synthetase for the incorporation of propargyl-phenylalanine Propargyl-PheRS | RS |
| SEQ ID NO: 7 | Aminoacyl tRNA synthetase for the incorporation of propargyl-phenylalanine Propargyl-PheRS | RS |
| SEQ ID NO: 8 | Aminoacyl tRNA synthetase for the incorporation of propargyl-phenylalanine Propargyl-PheRS | RS |
| SEQ ID NO: 9 | Aminoacyl tRNA synthetase for the incorporation of p-azido-phenylalanine p-Az-PheRS(1) | RS |
| SEQ ID NO: 10 | Aminoacyl tRNA synthetase for the incorporation of p-azido-phenylalanine p-Az-PheRS(3) | RS |
| SEQ ID NO: 11 | Aminoacyl tRNA synthetase for the incorporation of p-azido-phenylalanine p-Az-PheRS(4) | RS |
| SEQ ID NO: 12 | Aminoacyl tRNA synthetase for the incorporation of p-azido-phenylalanine p-Az-PheRS(2) | RS |
| SEQ ID NO: 13 | Aminoacyl tRNA synthetase for the incorporation of p-acetyl-phenylalanine (LW1) | RS |
| SEQ ID NO: 14 | Aminoacyl tRNA synthetase for the incorporation of p-acetyl-phenylalanine (LW5) | RS |
| SEQ ID NO: 15 | Aminoacyl tRNA synthetase for the incorporation of p-acetyl-phenylalanine (LW6) | RS |
| SEQ ID NO: 16 | Aminoacyl tRNA synthetase for the incorporation of p-azido-phenylalanine (AzPheRS-5) | RS |
| SEQ ID NO: 17 | Aminoacyl tRNA synthetase for the incorporation of p-azido-phenylalanine (AzPheRS-6) | RS |

TABLE 3

| Sequence | Position (SEQ ID NO: 18) |
|---|---|
| C7 leader | 15-83 |
| VH | 84-446 |
| GlySer linker | 447-506 |
| VL | 507-827 |
| Myc | 843-887 |
| His | 888-905 |
| TAA | 906-908 |

TABLE 4

| Sequence | Position (SEQ ID NO: 19) |
|---|---|
| C7 leader | 1-23 |
| VH | 24-144 |
| GlySer linker | 145-164 |
| VL | 165-276 |
| Myc | 277-291 |
| His | 292-297 |

Cytoplasmic scFv-108: VH-linker-VL (VH-GlySer-VL) sequences containing an N-terminal MetGly-sequence and a 6x-His sequence were cloned into an expression vector under control of the T7 promoter (see FIG. 2, Panel B). Location of the amber stop codons and PEGylated residues are indicated. The construct made is shown as SEQ ID NO: 20 (nucleotide sequence) and SEQ ID NO: 21 (translated protein sequence). The construct is described in Table 5.

TABLE 5

| Sequence | Position (SEQ ID NO: 20) |
|---|---|
| His | 3-26 |
| VH | 27-389 |
| GlySer linker | 390-449 |
| VL | 450-767 |

Fab-108: The VL and VH sequences of mAb108 were cloned into pFT3, a plasmid encoding the g3 (VL) and STII (VH) periplasmic leader sequences, as well as the human κ constant and CH1 domains. The C-terminus of the CH1 domain contained a 6-His tag to facilitate purification. Amber mutations were introduced into the CH1 domain, and the entire bicistronic cassette was cloned into the expression plasmid that constitutively expressed an amber suppressor tyrosyl tRNA$^{Tyr/CUA}$ from *Methanococcus jannaschii* (Mj tRNA$^{Tyr/CUA}$) (see FIG. 2, Panel C). The two Shine Delgamo sequences (SD) driving translation of the VL and VH domains of the Fab fragment are shown. The construct made is shown as SEQ ID NO: 22 (nucleotide sequence) and SEQ ID NO: 23 and 24 (translated protein sequence of VL Kappa chain of Fab 108; VH-CH1 chain of Fab108). The construct is described in Table 6.

TABLE 6

| Sequence | Position (SEQ ID NO: 22) |
|---|---|
| g3 leader | 15-68 |
| VL | 81-416 |
| K chain | 432-755 |
| STII leader | 788-856 |
| VH | 875-1237 |
| CH1 domain | 1247-1543 |
| His | 1544-1561 |

Figure 2:
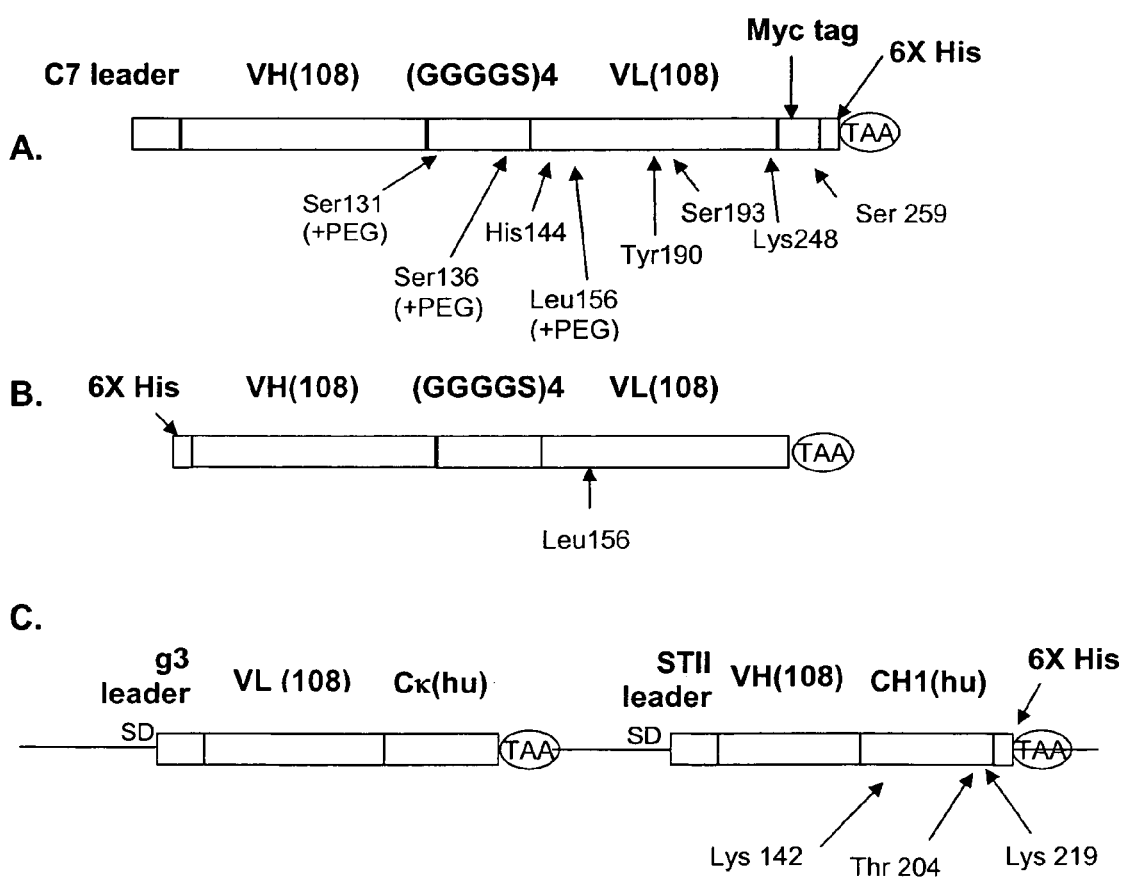
FIG. 2—Constructs used for periplasmic (FIG. 2, Panel A) and cytoplasmic (FIG. 2, Panel B) expression/suppression of scFv-108 are shown. Locations of the amber stop codons are indicated. Bicistronic cassette used for expression/suppression of the Fab-108 fragment (FIG. 2, Panel C) is shown. Constructs used for periplasmic expression/suppression of scFv-4D5 fragments are shown (FIG. 2, Panel D and Panel E). A cistron for expression/suppression of Fab-4D5 fragment is shown (FIG. 2, Panel F).
Figure 2:
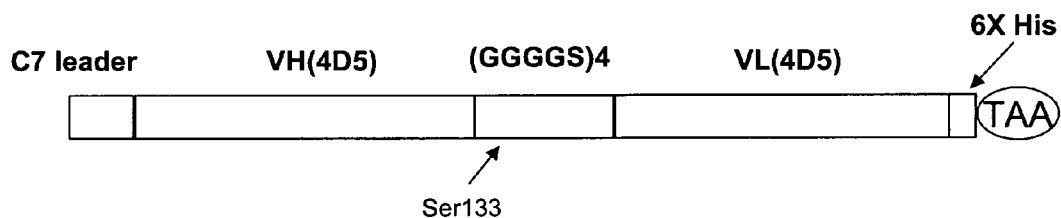
Figure 2:
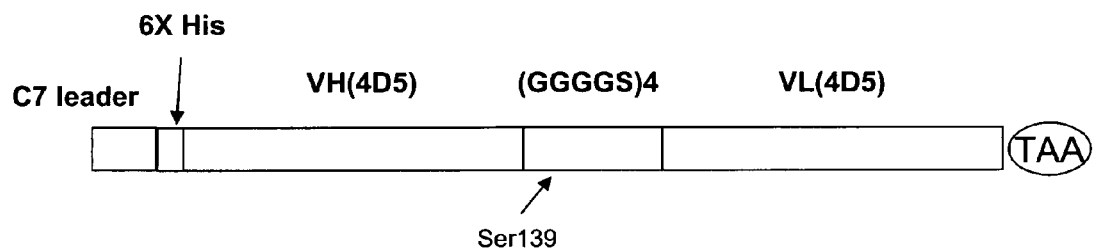
Figure 2:
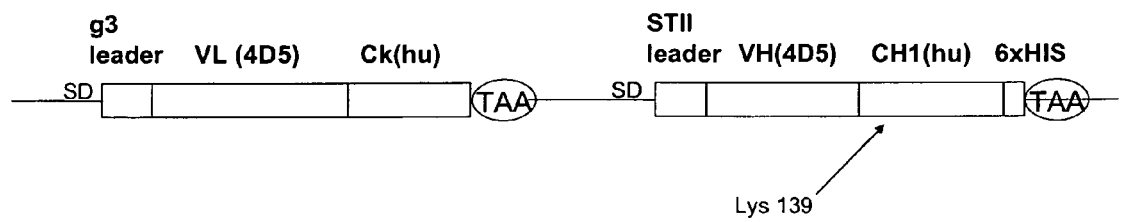

Periplasmic scFv-4D5: The variable regions (VL and VH) of the HER2-specific monoclonal antibody mAb-4D5 (Carter, P., et. al., Biotechnology (NY). February 1992;10(2): 163-7) were cloned as scFv fragments downstream of a yeast BGL2 (C7) periplasmic leader sequence. A 6x-His tag was cloned either at the C-terminus of the VL sequence (scFv-4D5-His; FIG. 2, Panel D), or at the N-terminus of the VH domain (His-scFv-4D5; FIG. 2, Panel E). The wild type scFv-4D5 constructs, as well as a variant containing the amber stop codon (TAG) in the GlySer linker domain were cloned into the *E. coli* expression vector that constitutively expressed an amber suppressor tyrosyl tRNA$^{Tyr/CUA}$ from *Methanococcus jannaschii* (Mj tRNA$^{Tyr/CUA}$). The 6x-His C terminal construct made is shown as SEQ ID NO: 25 (nucleotide sequence) and SEQ ID NO: 26 (translated protein sequence). The 6x-His N terminal construct made is shown as SEQ ID NO: 27 (nucleotide sequence) and SEQ ID NO: 28 (translated protein sequence). The 6x-His C terminal construct is described in Table 7, and the 6x-His N terminal construct is described in Table 8.

TABLE 7

| Sequence | Position (SEQ ID NO: 25) |
|---|---|
| C7 leader | 15-83 |
| VH | 84-443 |
| GlySer linker | 444-503 |
| VL | 504-824 |
| His | 825-848 |

TABLE 8

| Sequence | Position (SEQ ID NO: 27) |
|---|---|
| C7 leader | 15-83 |
| His | 84-107 |
| VH | 108-470 |
| GlySer linker | 471-530 |
| VL | 531-854 |

Fab-4D5: The VL and VH sequences of mAb 4D5 were subcloned into pFT3, a plasmid encoding the g3 and STII periplasmic leader sequences, as well as the human κ constant and CH1 domains, and then were cloned into the expression plasmid that constitutively expressed an amber suppressor tyrosyl tRNA$^{Tyr/CUA}$ from *Methanococcus jannaschii* (Mj tRNA$^{Tyr/CUA}$). FIG. 2, Panel F shows the cistron used for expression of Fab-4D5. An amber mutation was introduced into the CH1 domain of Fab 4D5 at lysine 139. This lysine corresponds to K142 in Fab 108. A Fab-4D5 construct containing an extra cysteine residue (THT<u>C</u>AA) at the C-terminus of the CH1 domain was made by overlapping PCR (Fab-4D5-cys). The construct made is shown as SEQ ID NO: 29 (nucleotide sequence) and SEQ ID NO: 30 and 31 (translated protein sequence of VL Kappa chain of Fab 4D5; VH-CH1 chain of Fab 4D5). The construct is described in Table 9.

TABLE 9

| Sequence | Position |
|---|---|
| g3 leader | 1-54 |
| VL | 67-386 |
| K chain | 403-726 |
| STII leader | 759-827 |
| VH | 846-1205 |
| CH1 domain | 1215-1511 |
| His | 1512-1529 |

Expression/Suppression

Suppression with para-acetyl-phenylalanine (pAcF): Suppression of the amber mutations in E. coli was achieved using standard protocols known in the art. Briefly, for the periplasmic suppression of antibody fragments in E. coli (scFv and Fab), the expression vector construct was transformed into E. coli host cells with a plasmid encoding the orthogonal tyrosyl-tRNA-synthetase from M. jannaschii (MjTyrRS). Overnight bacterial cultures were diluted 1:100 into shake flasks containing either LB media (Luria-Bertani) or Superbroth, and grown at 37° C. to an OD of approximately 0.8. Fab and scFv expression was induced while suppression of the amber codon was achieved by the addition of para-acetyl-phenylalanine (pAcF) to a final concentration of 4 mM. Cultures were incubated at 25° C. overnight. Expression of wild type (lacking amber codon) scFv and Fab fragments (including Fab-4D5-cys) was performed under identical conditions. Expression/suppression of cytoplasmic scFv fragments (FIG. 2, Panel B) was achieved in a similar manner.

Suppression with aa9.2: Suppression of amber mutations with a derivative of pAcF (aa 9.2) was achieved in a similar manner as pAcF, except that the orthogonal tyrosyl-tRNA-synthetase from M. jannaschii (MjTyrRS) used was specific for this amino acid. Suppression was achieved by the addition of aa9.2 (4 mM) at the time of induction.

Protein Extraction and Purification

Cells were harvested by centrifugation and resuspended in periplasmic release buffer (50 mM NaPO$_4$, 20% sucrose, 1 mM EDTA, pH 8.0) supplemented with 100 ug/ml of lysozyme and incubated on ice for 30 minutes. After centrifugation, antibody fragments in the supernatant were immobilized on ProBind beads (Invitrogen; Carlsbad, Calif.) by virtue of their His tag, the beads washed extensively with binding buffer and then the bound fragments eluted from the beads with 0.5 M imidazole. Purified fragments were dialyzed in storage buffer (50 mM HEPES, 150 mM NaCl, 10% glycerol, 5% sucrose, pH 7.8). For small scale analysis of scFv fragments expressed in the cytoplasm, E. coli from 15 ml of culture were collected by centrifugation and re-suspended in 1 ml of lysis buffer (B-PER, Pierce Biotechnology; Rockford, Ill.) supplemented with 10 ug/ml of DNase. The mixture was incubated at 37° C. for 30 minutes, diluted to 1× in Protein Loading buffer (Invitrogen; Carlsbad, Calif.) and analyzed by SDS-PAGE.

Figure 3:
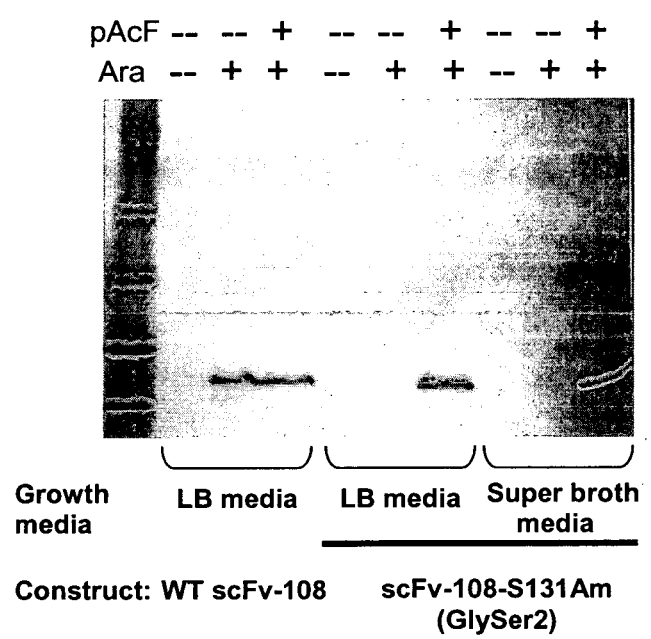
FIG. 3—Suppression (FIG. 3, Panel A) of amber mutations in the second serine of the GlySer linker (S131Am) and analysis of IMAC purification of the corresponding pAcF-containing scFv (FIG. 3, Panel B) are shown.
Figure 3:
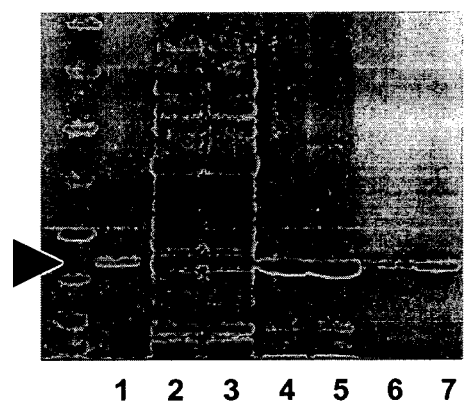

FIG. 3, Panel A shows the suppression of amber mutations in the second serine of the GlySer linker (S131 Am), and purification of the corresponding pAcF-containing scFv is shown (FIG. 3, Panel B). The Western blot analysis shown as FIG. 3, Panel A demonstrates that pAcF is required to suppress the amber stop mutation when the cells are grown either in LB or Superbroth media. The presence of pAcF does not affect expression of a scFv lacking the TAG stop codon (WT scFv-108). FIG. 3, Panel B shows the purification of pAcF-scFv 108-(S131) by immobilized metal affinity chromatography (IMAC). Estimated yield of the pAcF-containing scFv was 1.5 mg/L. Position of the scFv fragment is indicated by the arrowhead. The Coomassie gel was loaded as follows: lane 1—scFv control (1.7 ug); lane 2—IMAC pre-bind (20 ul/70 ml); lane 3—IMAC void (20 ul/70 ml); lane 4—IMAC elution (5 ul/1.3 ml); lane 5—NAP10 buffer exchange (10 ul/1.5 ml); lane 6—IMAC beads post-elution; lane 7—scFv control (3.4 ug).

Figure 4:
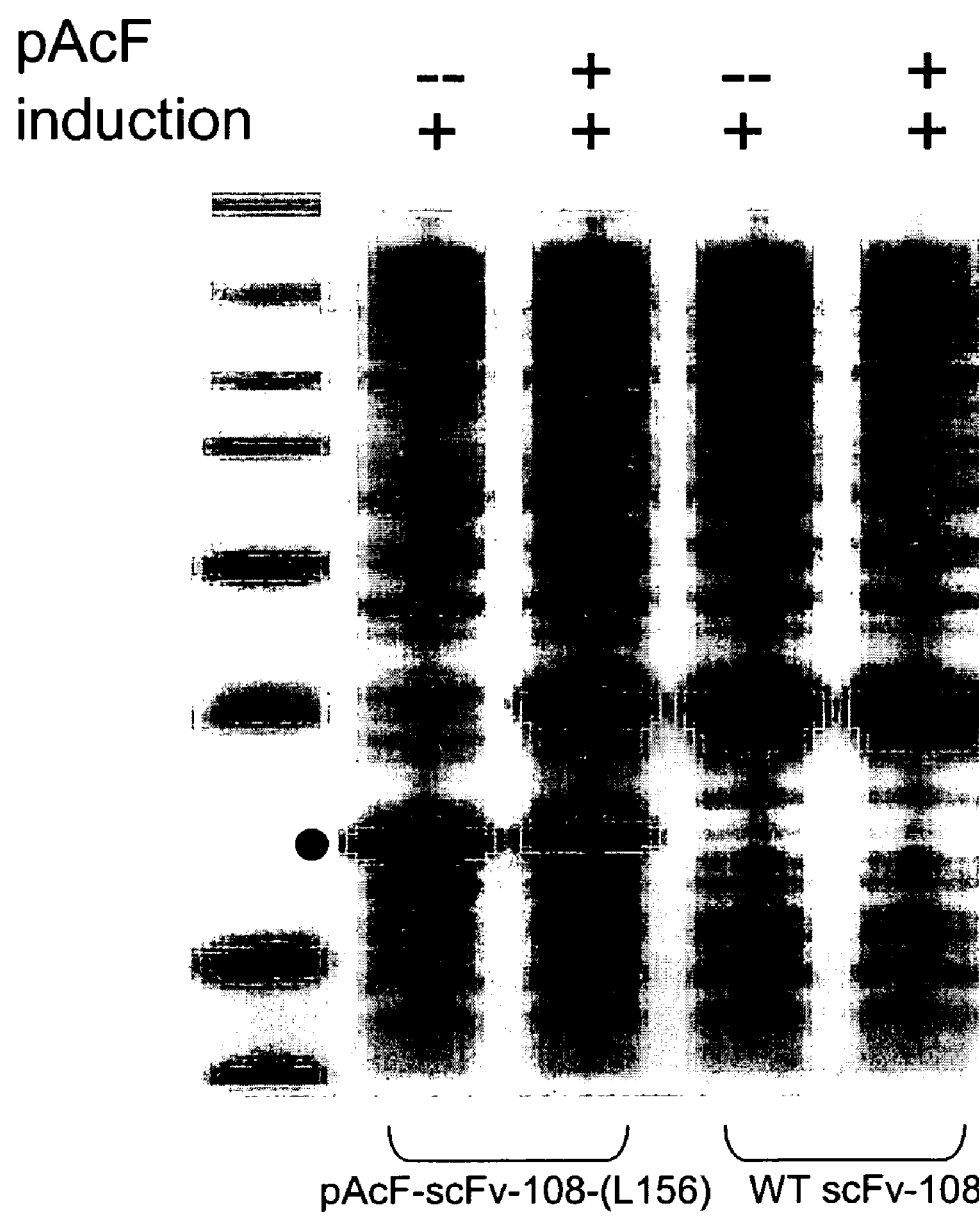
FIG. 4—Suppression of an amber mutation in the VL chain (L156) during cytoplasmic expression of a scFv is shown.

Suppression of an amber mutation in the VL chain (L156) during cytoplasmic expression of a scFv is shown in FIG. 4. Yields were >100 mg/L of E. coli culture, and suppression of the stop codon was absolutely dependent on the presence of pAcF. Full length scFv is indicated by the arrowhead. Products truncated at the amber codon are indicated by a filled circle.

PEGylation/Dimerization of Antibody Fragments (1)

PEGylation: Approximately 1 mg of pAcF-scFv-108 protein was concentrated in reaction buffer (100 mM NaOAc, 150 mM NaCl, 1 mM EDTA, pH 4.0) to a final volume of 50 ul. The reaction mixture was incubated at 28° C. for 32 hours with a 100-fold molar excess of mono-functional (hydroxylamine) 5K PEG (equilibrated in reaction buffer) in a final volume of 100 ul. PEGylated material was evaluated following gel electrophoresis and used directly in cell binding assays.

Dimerization: A similar procedure was used to dimerize pAcF-containing scFv-108 fragments. Briefly, the starting pAcF containing scFv fragments were concentrated to a concentration of >5 ug/ul in reaction buffer and then incubated with a bi-functional hydroxylamine-conjugated PEG linker (364 Da). Unreactive PEG was removed by dialysis, and a fresh aliquot of pAcF-scFv fragment (1 molar protein:protein equivalence) was added to the mixture. The mixture was then incubated at 28° C. for another 32 hours. The dimer was loaded onto a cation ion exchange column (SP-5PW) equilibrated with 20 mM sodium acetate (pH 4.0) and eluted over a NaCl gradient (0-0.4M).

Figure 5:
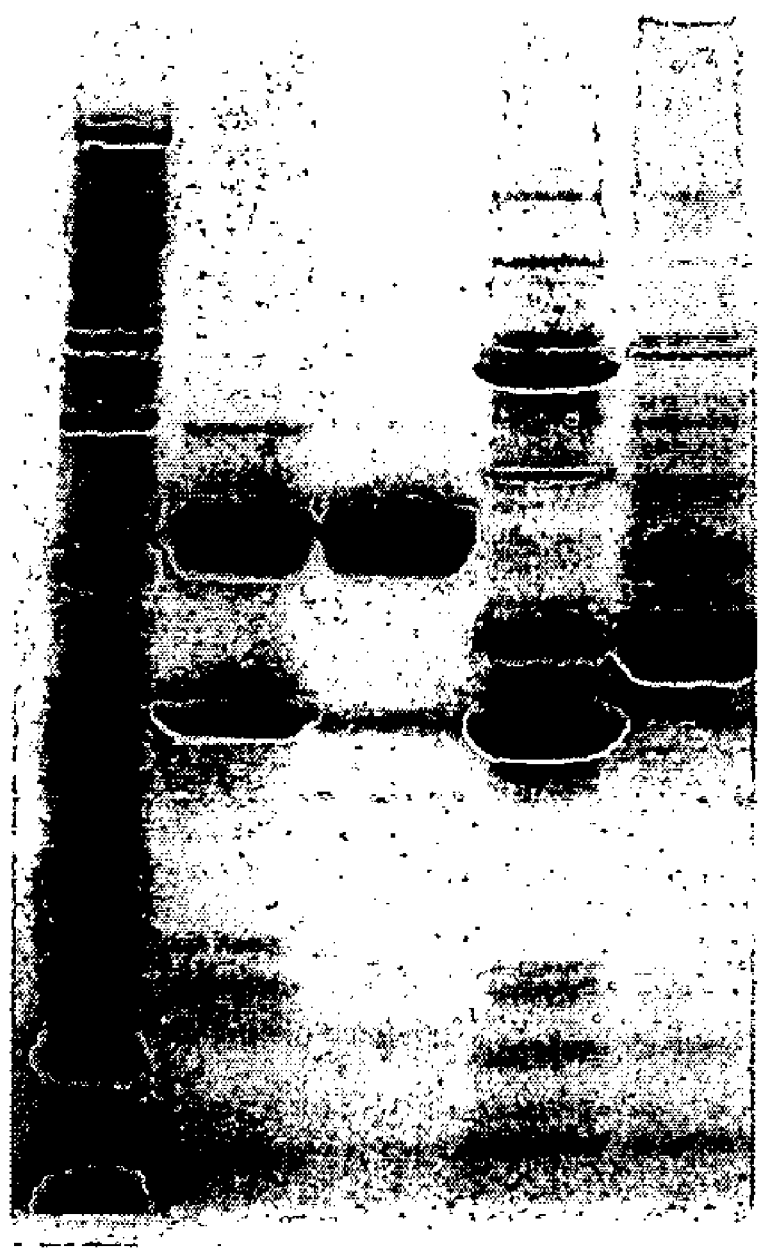
FIG. 5—PEGylation and dimerization of pAcF-scFv-108 fragments is shown in FIG. 5, Panel A. Position of the mono-PEGylated scFv and the dimer are indicated by the single and double arrowheads respectively.
Figure 5:
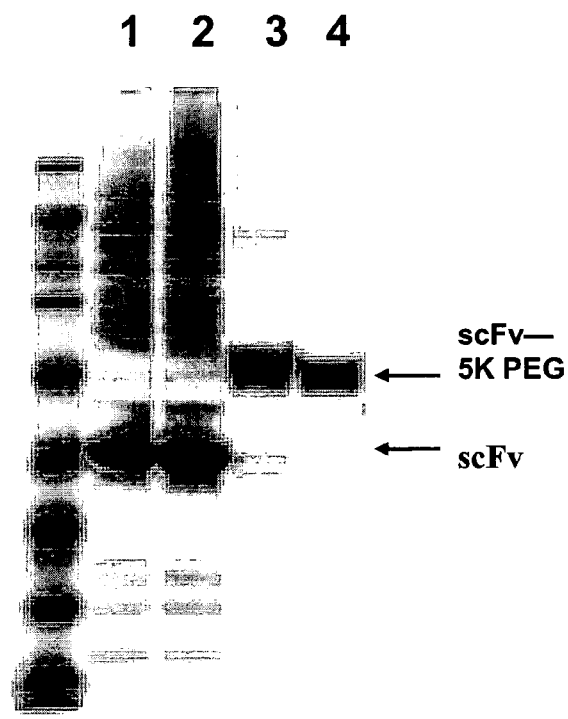
Figure 5:
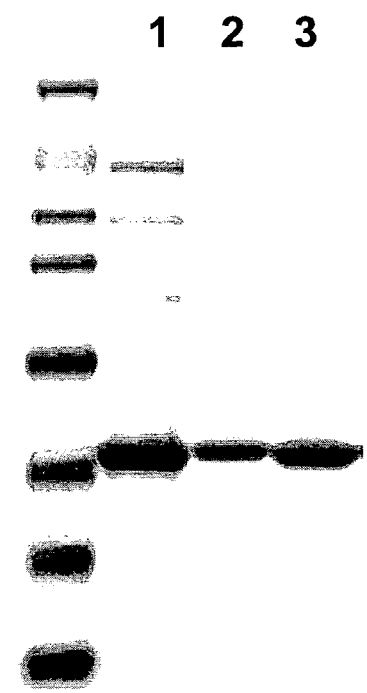

PEGylation and dimerization of pAcF-scFv-108 fragments is shown in FIG. 5. FIG. 5, Panel A shows PEGylation (5K) of pAcF-scFv-108-(L156) and pAcF-scFv-108-(S136) and dimerization of pAcF-scFv-108-(S136). The gel was loaded as follows: lane 1—pAcF-scFv-108-(L156) (5K PEG); lane 2—pAcF-scFv-108-(S136) (5K PEG); lane 3—dimerization of pAcF-scFv-108-(S136) (364 da PEG) linker; lane 4—dimerization of pAcF-scFv-108-(S136); linker was not removed following the first PEGylation reaction. Position of the mono-PEGylated scFv fragments and the scFv-108-(S136) dimer are indicated by the single and double arrowheads, respectively. The absence of dimerization in lane 4 demonstrates that scFv were not coupled through intermolecular disulfide bond formation. FIG. 5, Panel C shows that the conjugation of PEG to scFv fragments is absolutely dependent on the presence of pAcF. No PEGylation of WT scFv fragments was observed. The gel was loaded as follows: lane 1—WT scFv 108 control; lane 2—scFv WT, in reaction buffer, no PEG, 16 hours; lane 3—scFv WT+5K PEG, in reaction buffer, 16 hours.

Figure 6:
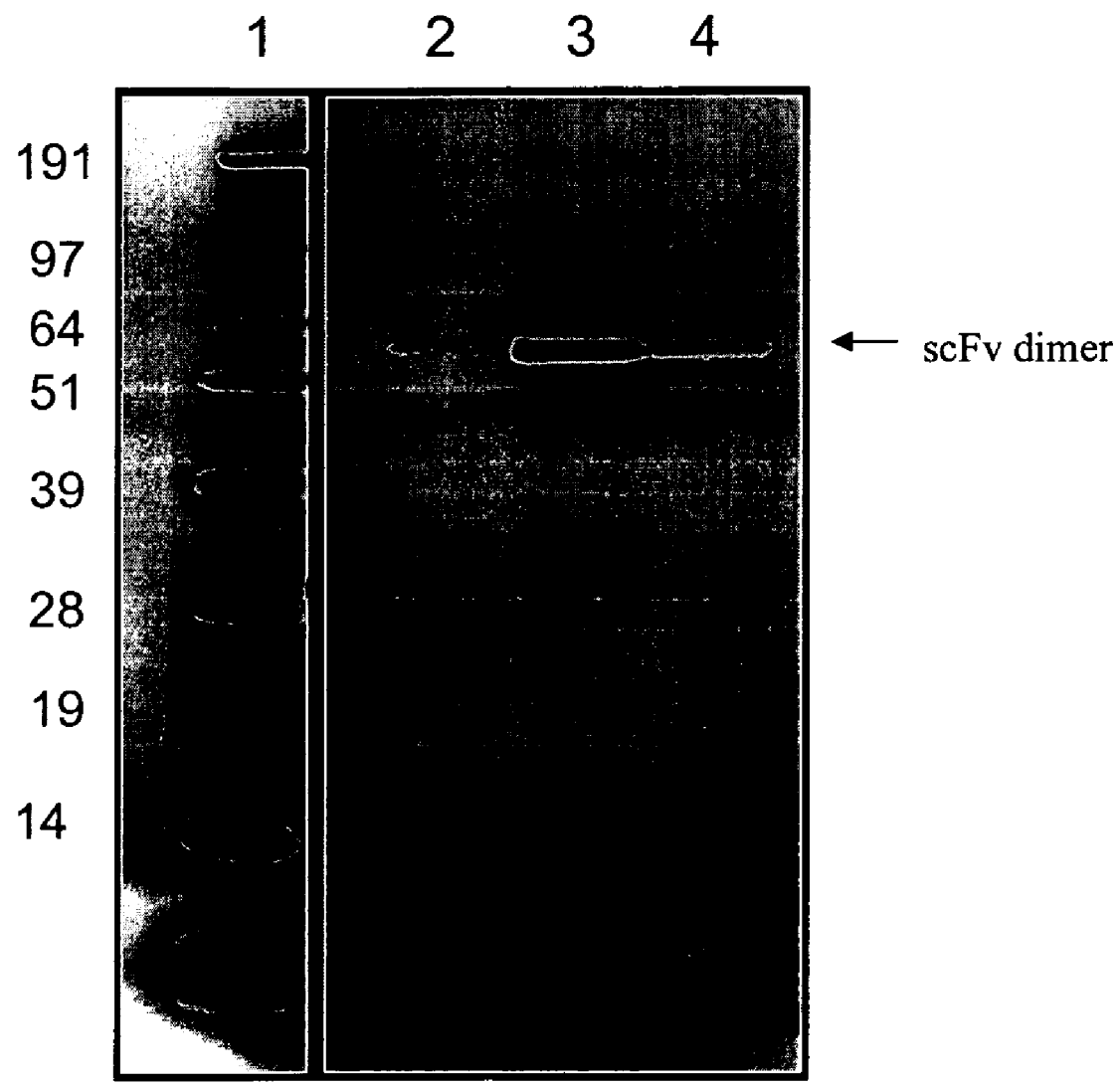
FIG. 6—A gel showing fractions taken during purification of scFv-108 homodimers is shown.

FIG. 6 shows SDS PAGE analysis of fractions taken during cation exchange chromatography of scFv homodimers. pAcF-scFv108-(S131) fragments were homodimerized using a bifunctional hydroxylamine 364 dalton PEG linker. Fractions were taken at different points in the NaCl gradient (0-0.4 M) during cation exchange chromatography. The gel was loaded as follows: lane 1—marker, lane 2—pAcF-scFv108 (S131)-X-pAcF-scFv108(S131) Fraction #1, lane 3—pAcF-scFv108(S131)-X-pAcF-scFv108(S131) Fraction #2, lane 4—pAcF-scFv108(S131)-X-pAcF-scFv108(S131) Fraction #3.

Figure 8:
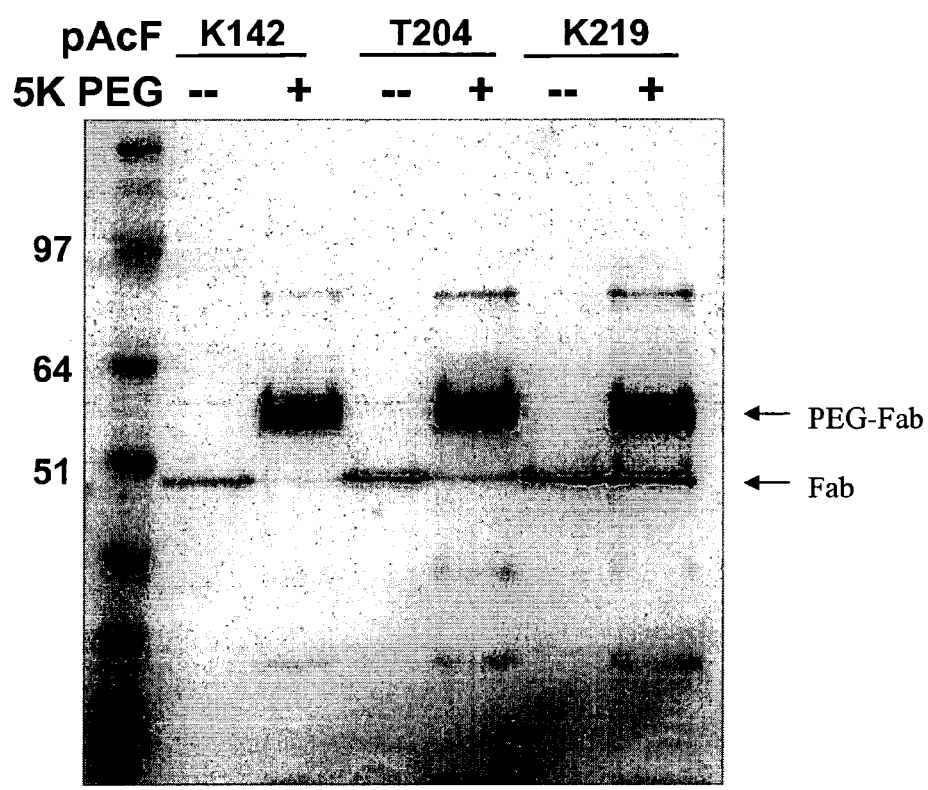
FIG. 8—A gel showing pAcF and pAcF-PEG-containing Fab fragments of mAb 108 is shown as FIG. 8, Panel A. Binding of Fab fragments of mAb 108 to A431 cells expressing EGF receptors are shown in FIG. 8, Panels B-D.
Figure 8:
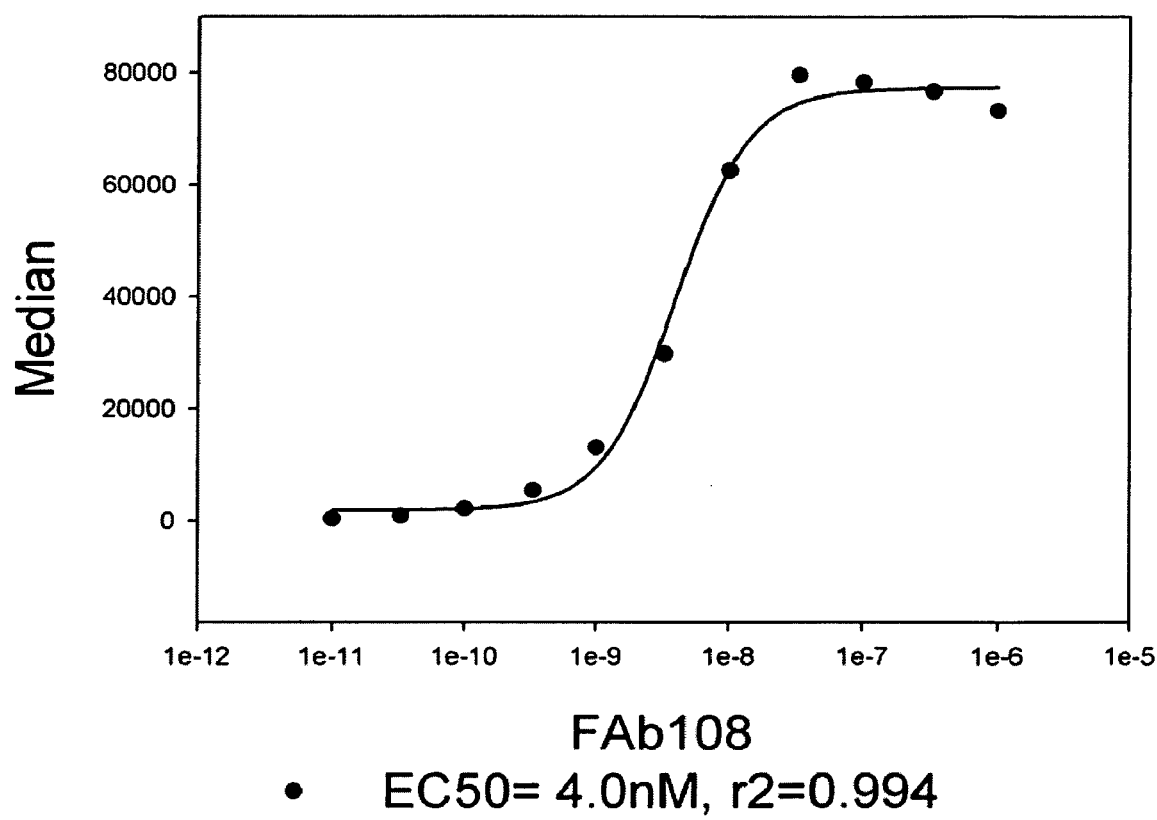
Figure 8:
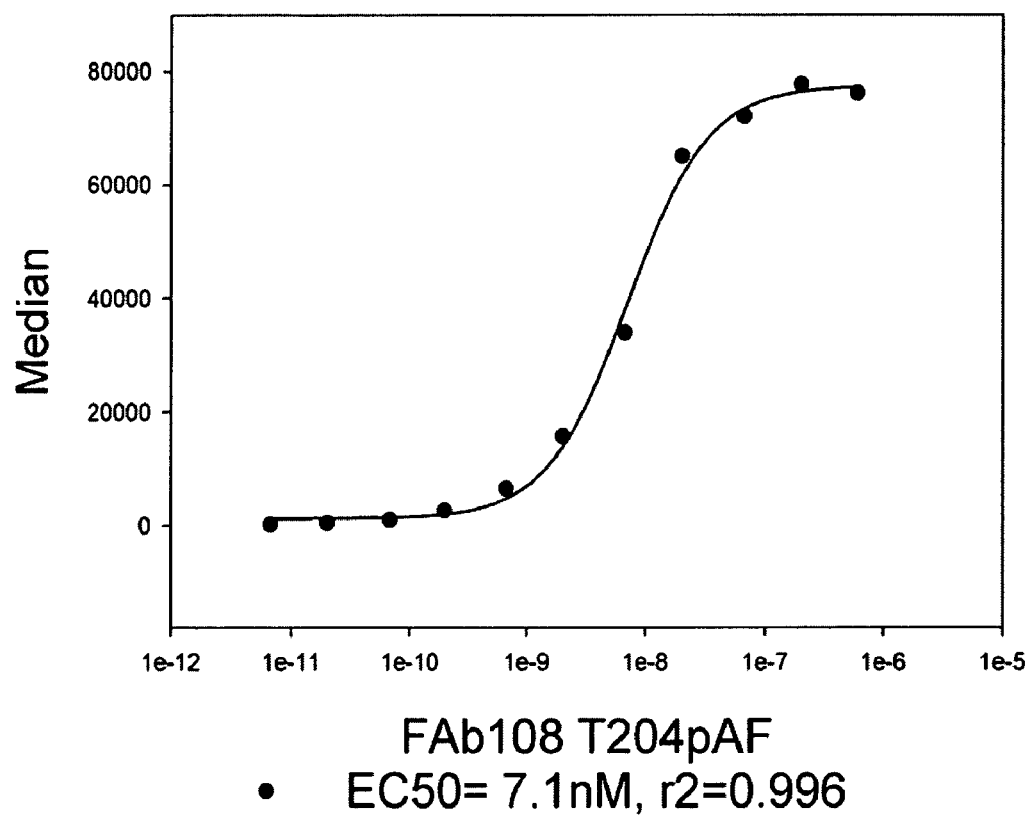
Figure 8:
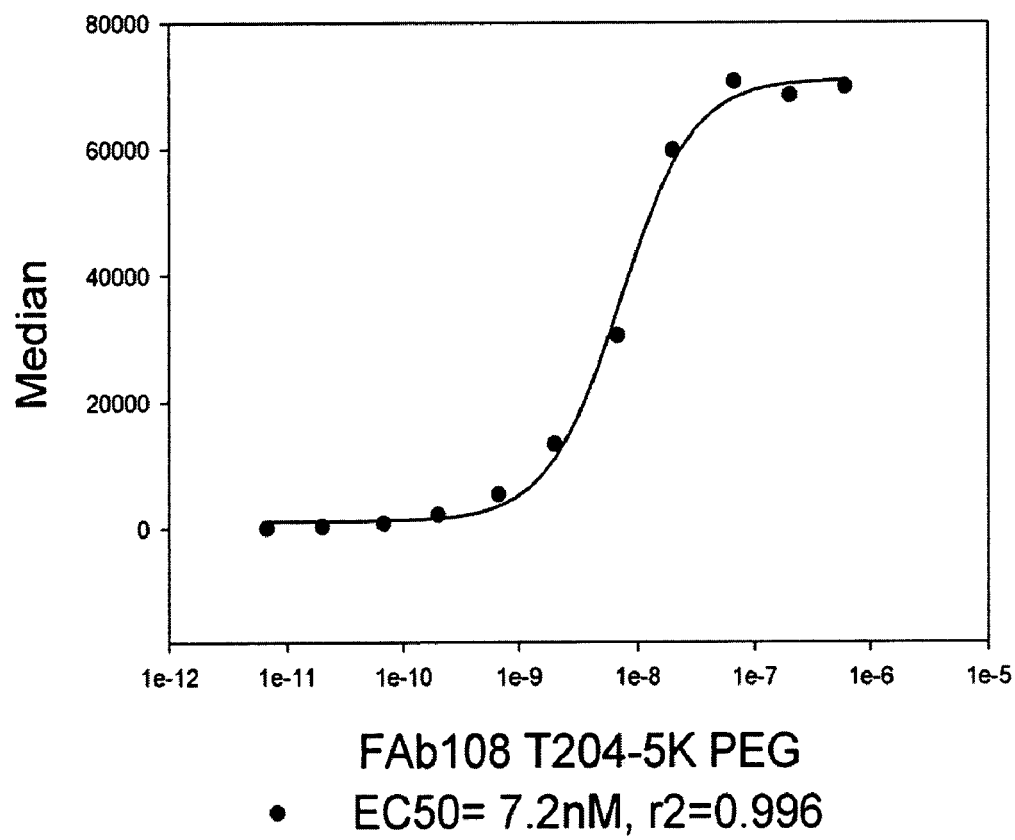

FIG. 8, Panel A shows SDS PAGE analysis of pAcF and pAcF-PEGylated Fab fragments. Fab-108 fragments modified at K142, T204, and K219 are shown, and the efficiency of PEGylation is site specific. PEGylation of pAcF-containing Fab fragments was performed using hydroxylamine conjugated 5K PEG.

Figure 10:
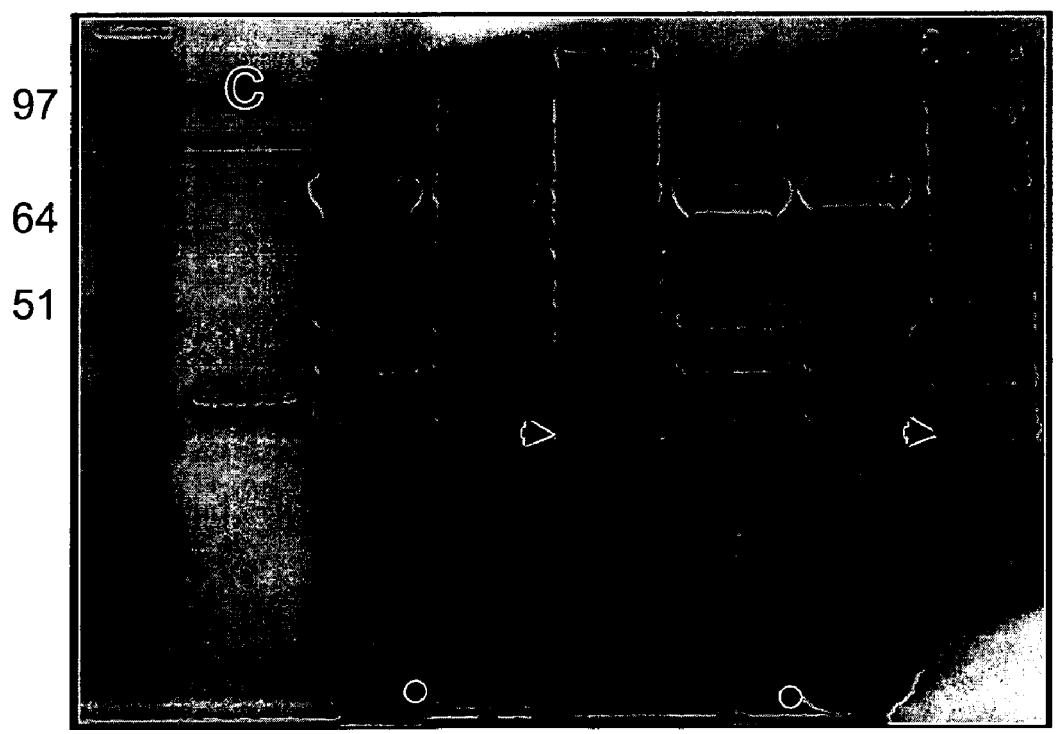
FIG. 10—Gels showing the suppression of an amber mutation in the second serine of the GlySer linker of the C-terminal (FIG. 10, Panel A) or N-terminal scFv-4D5 (FIG. 10, Panel B) fragments are shown.
Figure 10:
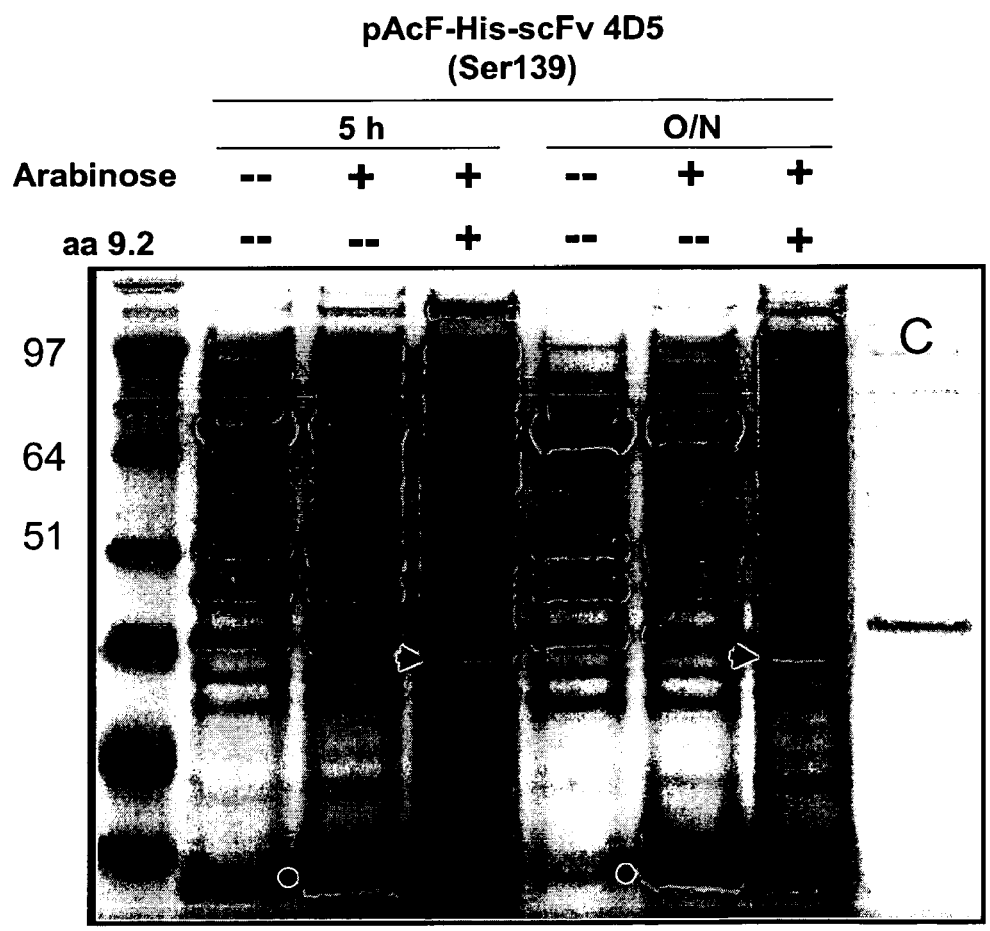

FIG. 10, Panel A and B show suppression of an amber mutation in the second serine of the GlySer linker of the C-terminal (pAcF-scFv-4D5-His (S133); FIG. 10, Panel A) or N-terminal (pAcF-His-scFv-4D5(S139); FIG. 10, Panel B)

scFv-4D5 fragments. Expression of the scFv proteins was induced by the addition of 0.02% arabinose for either 5 hours or overnight (16 hours). Suppression of the amber mutation was achieved by the concomitant addition of aa9.2 (4 mM). The suppressed product is indicated by the arrowhead, and the truncated protein by the filled-in circle. Suppression yields of greater than 50% were achieved (1.5 mg/L). The control lane loaded with scFv 108, which runs slightly higher than scFv-4D5, is indicated (C).

Figure 11:
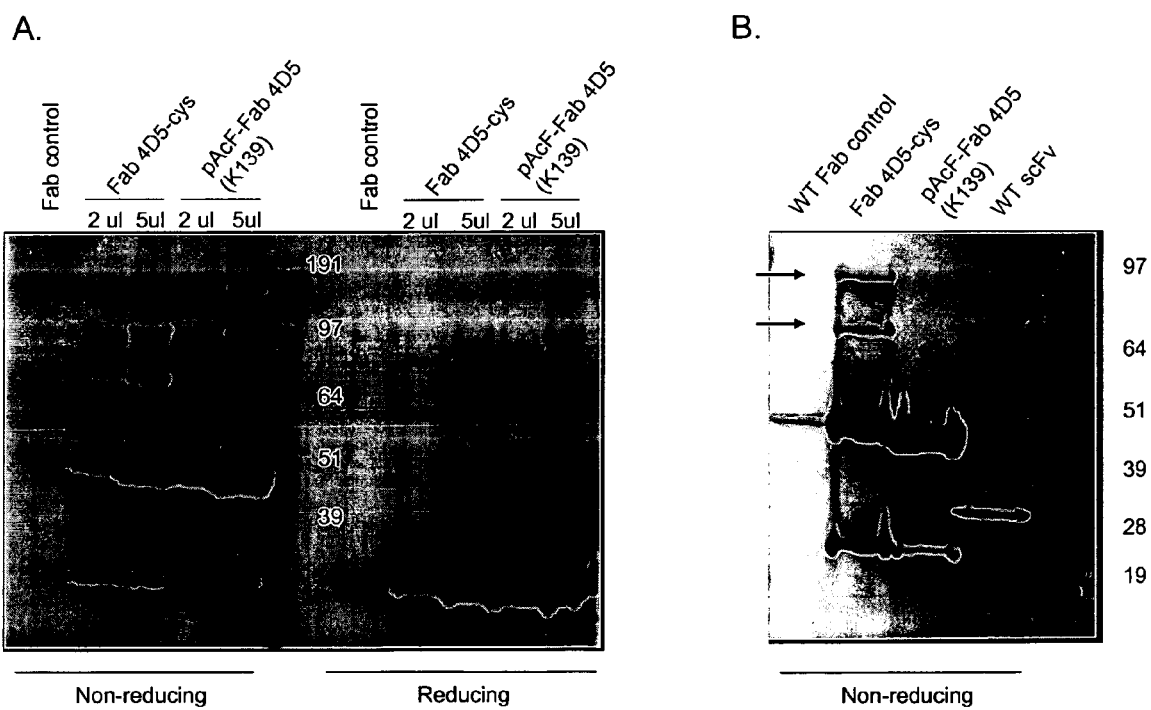
FIG. 11—SDS-PAGE analysis is shown of pAcF-Fab-4D5-(K139) and Fab -4D5-cys under both reducing and non-reducing conditions (FIG. 11, Panel A).
Figure 12:
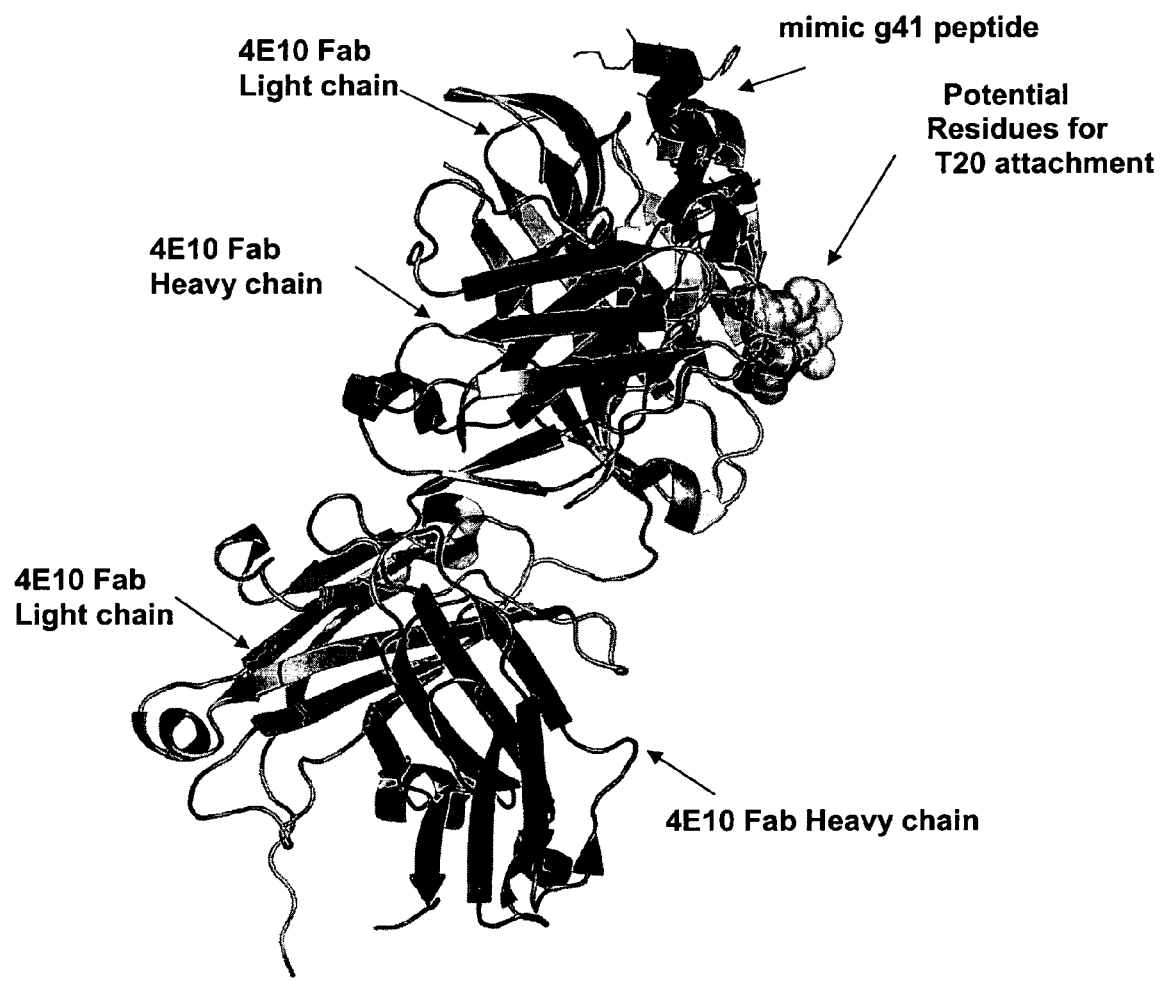
FIG. 12—HIV-1 neutralizing human Fab 4E10 linked to peptide T20 is shown.

Fab fragments pAcF-Fab-4D5-(K139) and Fab-4D5-cys were expressed and purified in the same manner. FIG. 11, Panel A shows samples resolved by SDS-PAGE under both reducing and non-reducing conditions. Fab fragment yields were as follows: pAcF-Fab-4D5-(K139), 0.37 mg/L/OD (final $OD_{600}$=3.14) and Fab-4D5-cys 0.23 mg/L/OD (final $OD_{600}$=3.26). FIG. 11, Panel B shows a Western blot of samples (5 ul) shown in FIG. 11, Panel A using an anti-His antibody. The samples were run under non-reducing conditions. Multimeric VH-CH1 complexes from the Fab-4D5-cys construct are indicated with arrows. No multimeric complexes were seen with pAcF-Fab-4D5-(K139).

PEGylation/Dimerization of Antibody Fragments (2)

PEGylation: Approximately 1 mg of pAcF-scFv-108 protein was concentrated in native reaction buffer (20 mM NaOAc, 150 mM NaCl, 1 mM EDTA, pH 4.0) and denaturing reaction buffer (20 mM NaOAc, 150 mM NaCl, 1 mM EDTA, 8 M Urea, pH 4.0) to a final volume of 50 ul. The reaction mixture was incubated at 28° C. for 32 hours with a 100-fold molar excess of mono-functional (hydroxylamine) 5K PEG (equilibrated in corresponding reaction buffers) in a final volume of 100 ul. After 16 hours, the reaction mixture was evaluated by SDS-PAGE and used directly in cell binding assays.

Conjugation of a polypeptide with a linker, polymer, biologically active molecule, or other molecule under denaturing conditions may have one or more advantages. Such advantages include, but are not limited to, easier conjugation due to the improved accessibility of the reactive group, easier refolding of the conjugated polypeptide compared to non-conjugated polypeptide, and the ability to use polypeptide at a higher concentration for conjugation than the polypeptide concentration usable under non-denaturing conditions. Denaturing conditions may be desired, for example, if the polypeptide is unstable and cannot be highly concentrated for the conjugation reaction. However, conjugation of polypeptides under denaturing conditions may result in undesirable and/or unintended sites of conjugation in polypeptides with one or more cysteines, lysines, or other amino acids upon reaction with standard cysteine-based conjugation chemistries such as maleimide chemistries, or lysine-based chemistries such as maleimide chemistries. Such undesirable and/or unintended sites of conjugation may have an impact on the activity of the conjugated polypeptide. On the other hand, polypeptides such as ABP comprising one or more non-naturally encoded amino acids may be conjugated in a site-specific manner under denaturing conditions since the reactive groups involved in the conjugation reaction are part of a non-naturally encoded amino acid. Thus, any advantages obtained from conjugation under denaturing conditions may be exploited with the use of polypeptides comprising one or more non-naturally encoded amino acids.

FIG. 5B shows SDS-PAGE analysis of PEGylated pAcF-scFv-(S136) and control samples. The gel was loaded as follows: lane 1—pAcF-scFv-(S136); lane 2—pAcF-scFv-(s136), incubated at 28° C. for 16 hours; lane 3—pAcF-scFv-(S136), 5 K PEG, incubated at 28° C. for 16 hours, native condition; lane 4—pAcF-scFv-(S136), 5 K PEG, incubated at 28° C. for 16 hours, denaturing condition. Arrows indicate scFv and PEGylated scFv. FIG. 5C shows that the conjugation of PEG to scFv fragments is absolutely dependent on the presence of pAcF. No PEGylation of WT scFv fragments was observed. The gel was loaded as follows: lane 1—WT scFv 108 control; lane 2—scFv WT, in reaction buffer, no PEG, 16 hours; lane 3—scFv WT+5K PEG, in reaction buffer, 16 hours.

Figure 13:
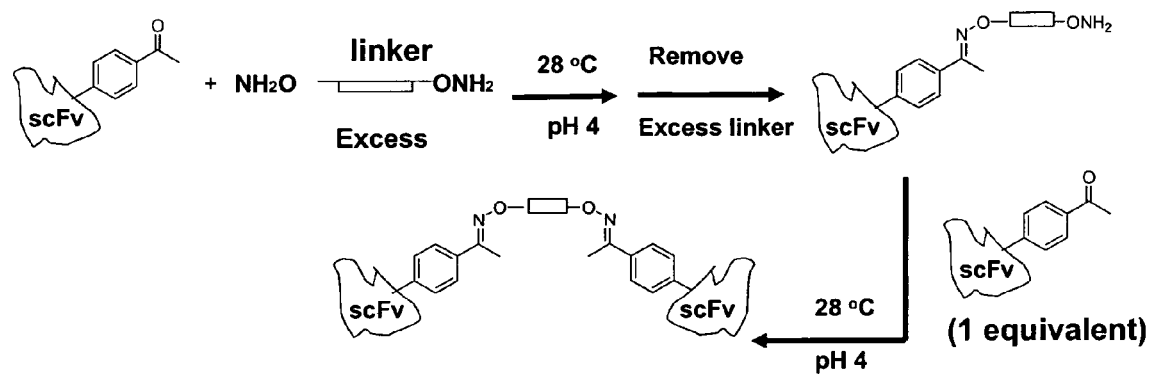
FIG. 13—A diagram of a dimerization procedure is shown.

Sequential dimerization: Briefly, the starting pAcF containing scFv fragments were concentrated to a concentration of 10 mg/ml in reaction buffer and then incubated with 100 fold excess of a bi-functional hydroxylamine-conjugated PEG linker (364 Da). The reaction mixture was incubated for 16 hours at 28° C. Unreactive PEG was removed by dialysis, and a fresh aliquot of pAcF-scFv fragment (1 molar protein: protein equivalence) was added to the mixture. The mixture was then incubated at 28° C. for another 32 hours. See FIG. 13. The dimer was loaded onto a cation ion exchange column (SP-5PW, 20 micron) equilibrated with 20 mM sodium acetate (pH 4.0) and eluted over a NaCl gradient (0-0.4M).

Figure 14:
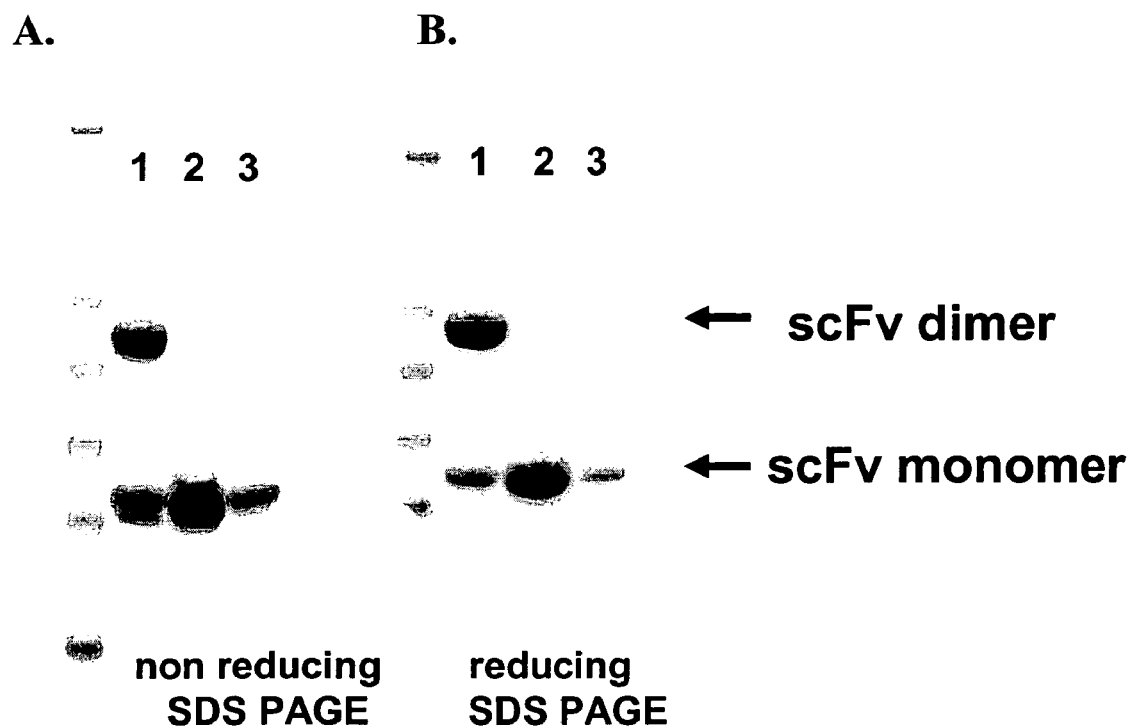
FIG. 14—Non-reducing (FIG. 14, Panel A) and reducing (FIG. 14, Panel B) SDS-PAGE analysis of scFv dimer formation is shown.

FIG. 14, Panel A and B show non-reducing and reducing SDS PAGE analysis of dimerization samples. The gels were loaded as follows: lane 1—final scFv dimerization reaction mixture with 364 Da PEG bifunctional linker; lane 2—final scFv dimerization reaction control without 364 Da PEG bifunctional linker; lane3—scFv. Arrows indicate scFv dimers and scFv monomers. scFv dimers were synthesized only in the presence of the bifunctional linker. The absence of dimerization in lane 2 demonstrates that the scFv were not coupled through inter-molecular disulfide bond formation. Since no difference was observed between samples analyzed on reducing and non-reducing SDS PAGE gels, the presence of the bifunctional linker did not facilitate inter-molecular disulfide bond formation.

Figure 15:
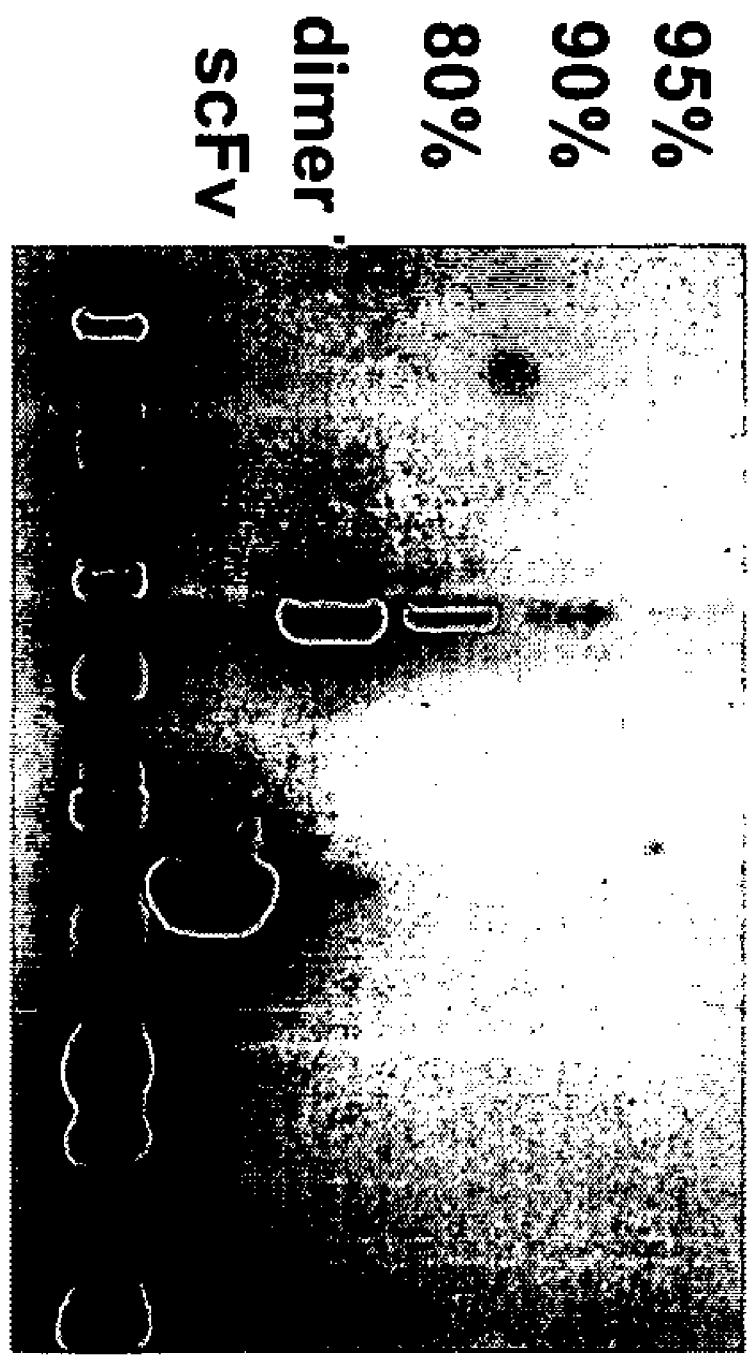
FIG. 15—SDS-PAGE analysis of purified scFv dimer is shown.

Dimer purification: The dimerization reaction mixture was purified using strong cation exchange column (SP-5PW, 20 micron). Buffer A: 20 mM NaOAc, pH 4.0; buffer B: 20 mM NaOAc, 1 M NaCl, pH 4.0. scFv dimer eluted at 40% B. SDS PAGE analysis (FIG. 15) of the purified dimer showed that, after one column purification, the purity of the dimer was approximately 90%.

Figure 9:
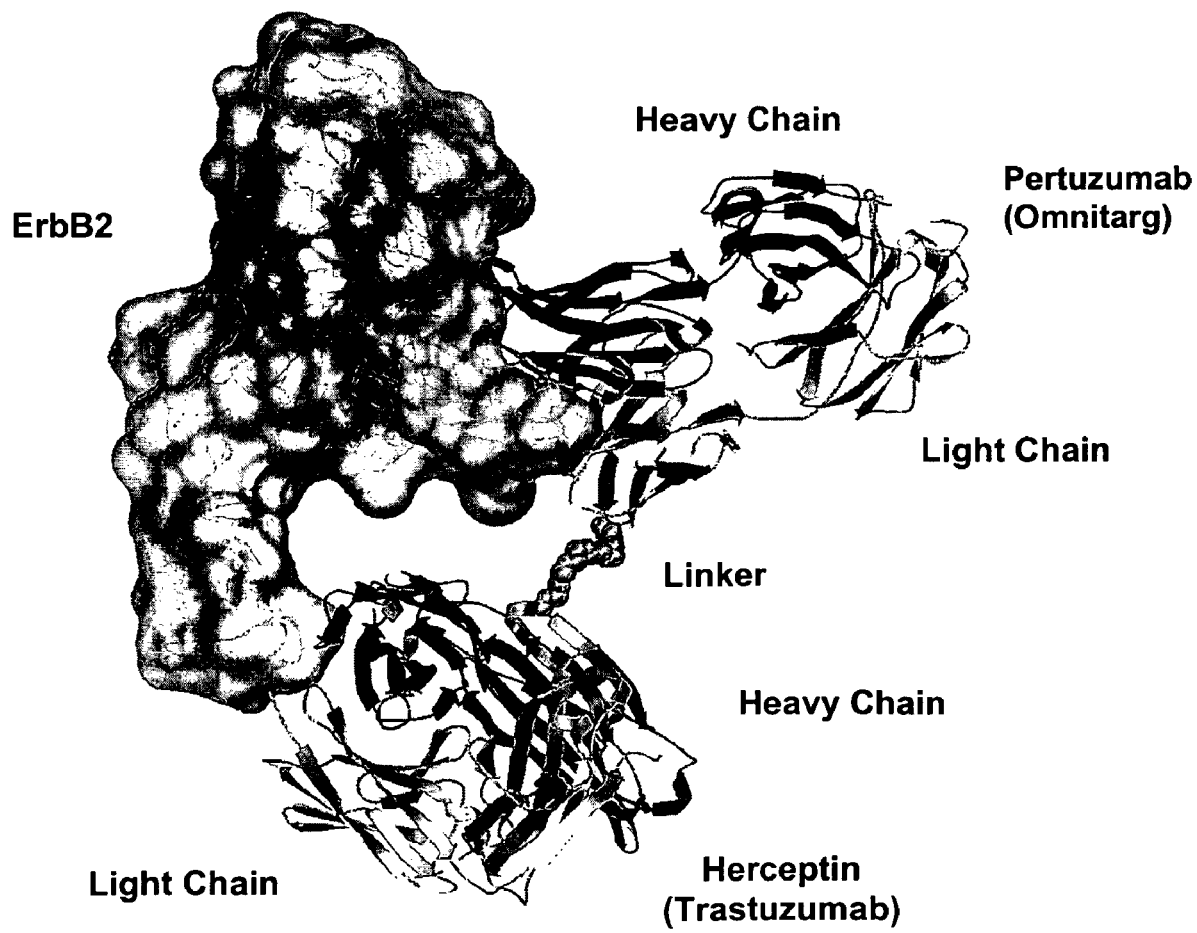
FIG. 9—An example of a hetero-bifunctional ABP of the present invention is shown.

An example of a hetero-bifunctional ABP of the present invention is shown in FIG. 9. Based on the known crystal structure determined for two different antibody molecules (for example Herceptin and Omnitarg) that bind to different epitopes of the same antigen (for example ErbB2), specific amino acid positions are identified such that they fit within a certain desired selection criteria. Desired selection criteria for amino acid position in this example include the relative proximity of one or more specific amino acid positions on each molecule. Such amino acid positions may be desired to form the hetero-bifunctional molecule shown in FIG. 9 using a linker molecule. Specific amino acid positions on each molecule that fit the criteria are shown in Table 10 below, as is a linker molecule that may be used to form a hetero-bifunctional ABP. Those of ordinary skill in the art will recognize that the list is by no means exhaustive and is merely illustrative, and that all amino acid positions that fit a certain desired selection criteria are contemplated to be suitable for use in the present invention. A non-natural amino acid of the present invention may be substituted at one or more of these positions in each molecule to provide the chemical functional groups utilized for linker attachment. A wide variety of other selection criteria may also be utilized to identify amino acid positions to fit the desired criteria, including but not limited to, proximity between the same or different molecules, conformation change modulation, distance modulation between ABP's or molecules linked to an ABP, linker length or shape, surface exposure, modulation of ligand binding characteristics, modulation of receptor dimerization, etc.

TABLE 10

| Potential Linkage Sites (Heavy chain of Herceptin-Light chain of Pertuzumab) | distances (Å) |
|---|---|
| Asn211-Asp28 | 15.4 Å |
| Asn211-Gly68 | 15.8 Å |
| Asn211-Ser30 | 15.8 Å |
| Asn211-Ser67 | 17.8 Å |
| Lys213-Asp28 | 18.0 Å |
| Asn211-Thr69 | 18.1 Å |
| Lys213-Gly68 | 18.2 Å |
| Lys208-Ser30 | 19.2 Å |
| Lys213-Thr69 | 20.1 Å |
| Lys208-Ser67 | 20.6 Å |
| Lys213-Asp70 | 21.8 Å |
| Thr123-Tyr92 | 24.9 Å |
| Ser122-Tyr92 | 26.2 Å |
| Gln13-Tyr92 | 27.9 Å |

Based on the interaction of HIV-1 neutralizing human Fab 4E10 with HIV gp41 env protein, specific amino acid positions are identified such that they fit within a certain desired selection criteria. Desired selection criteria for amino acid position in this example include residues that would be used for conjugation of T-20 peptide to the Fab such that the binding of T-20 to gp41 occurs without a negative effect to the binding and recognition of the complementarity determining regions (CDR) of 4E10 to gp41. T-20, also known as DP-178, inhibits entry of HIV into cells by acting as a viral fusion inhibitor. FIG. 12 shows HIV neutralizing human Fab 4E10 with a mimic g41 peptide. Potential residues for attachment of T-20 peptide are shown. Potential residues for incorporation of non-naturally encoded amino acids include, but are not limited to, Gln64—heavy chain of the Fab; Glu1—light chain of the Fab, and Gln27—light chain of the Fab. Those of ordinary skill in the art will recognize that the list is by no means exhaustive and is merely illustrative, and that all amino acid positions that fit a certain desired selection criteria are contemplated to be suitable for use in the present invention. A wide variety of other selection criteria may also be utilized to identify amino acid positions to fit the desired criteria, including but not limited to, proximity between the same or different molecules, conformation change modulation, distance modulation between ABP's or molecules linked to an ABP, inclusion of a linker, linker length or shape, surface exposure, modulation of ligand binding characteristics, modulation of receptor dimerization, etc.

Example 3

This example details introduction of a carbonyl-containing amino acid and subsequent reaction with an aminooxy-containing PEG.

This Example demonstrates a method for the generation of an antigen-binding polypeptide that incorporates a ketone-containing non-naturally encoded amino acid that is subsequently reacted with an aminooxy-containing PEG of approximately 5,000 MW. Each of the residues identified according to the criteria of Example 1 is separately substituted with a non-naturally encoded amino acid having the following structure:

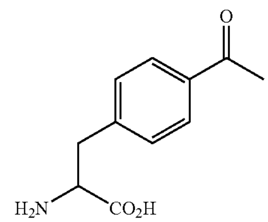

The sequences utilized for site-specific incorporation of p-acetyl-phenylalanine into ABP are SEQ ID NO: 1 (mut-tRNA, *M. jannaschii* mtRNA$_{CUA Tyr}$), and 13, 14 or 15 (TyrRS LW1, 5, or 6) described in Example 2 above.

Once modified, the ABP variant comprising the carbonyl-containing amino acid is reacted with an aminooxy-containing PEG derivative of the form:

$$R\text{-PEG(N)—O—(CH}_2)_n\text{—O—NH}_2$$

where R is methyl, n is 3 and N is approximately 5,000 MW. The purified ABP containing p-acetylphenylalanine dissolved at 10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and then stirred for 10-16 hours at room temperature (Jencks, W. *J. Am. Chem. Soc.* 1959, 81, pp 475). The PEG-ABP is then diluted into appropriate buffer for immediate purification and analysis.

Example 4

Conjugation with a PEG consisting of a hydroxylamine group linked to the PEG via an amide linkage.

A PEG reagent having the following structure is coupled to a ketone-containing non-naturally encoded amino acid using the procedure described in Example 3:

$$R\text{-PEG(N)—O—(CH}_2)_2\text{—NH—C(O)(CH}_2)_n\text{—O—NH}_2$$

where R=methyl, n=4 and N is approximately 20,000 MW. The reaction, purification, and analysis conditions are as described in Example 3.

Example 5

This example details the introduction of two distinct non-naturally encoded amino acids into ABP.

This example demonstrates a method for the generation of an antigen-binding polypeptide that incorporates non-naturally encoded amino acid comprising a ketone functionality at two positions identified according to Example 1, wherein X* represents a non-naturally encoded amino acid. The antigen-binding polypeptide is prepared as described in Examples 1 and 2, except that the suppressor codon is introduced at two distinct sites within the nucleic acid.

Example 6

This example details conjugation of antigen-binding polypeptide to a hydrazide-containing PEG and subsequent in situ reduction.

An antigen-binding polypeptide incorporating a carbonyl-containing amino acid is prepared according to the procedure described in Examples 2 and 3. Once modified, a hydrazide-containing PEG having the following structure is conjugated to the ABP:

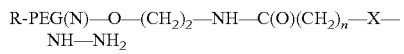

where R=methyl, n=2 and N=10,000 MW and X is a carbonyl (C=O) group. The purified ABP containing p-acetylphenylalanine is dissolved at between 0.1-10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 1 to 100-fold excess of hydrazide-containing PEG, and the corresponding hydrazone is reduced in situ by addition of stock 1 M NaCNBH$_3$ (Sigma Chemical, St. Louis, Mo.), dissolved in H$_2$O, to a final concentration of 10-50 mM. Reactions are carried out in the dark at 4° C. to RT for 18-24 hours. Reactions are stopped by addition of 1 M Tris (Sigma Chemical, St. Louis, Mo.) at about pH 7.6 to a final Tris concentration of 50 mM or diluted into appropriate buffer for immediate purification.

Example 7

This example details introduction of an alkyne-containing amino acid into an ABP and derivatization with mPEG-azide.

Any of the residues identified according to Example 1 are substituted with the following non-naturally encoded amino acid:

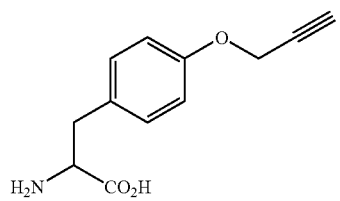

The sequences utilized for site-specific incorporation of p-propargyl-tyrosine are SEQ ID NO: 1 (muttRNA, *M. jannaschii* mtRNA$_{CUA}^{Tyr}$), and 6, 7 or 8 described in Example 2 above. The antigen-binding polypeptide containing the propargyl tyrosine is expressed in *E. coli* and purified using the conditions described in Example 3.

The purified ABP containing propargyl-tyrosine dissolved at between 0.1-10 mg/mL in PB buffer (100 mM sodium phosphate, 0.15 M NaCl, pH=8) and a 10 to 1000-fold excess of an azide-containing PEG is added to the reaction mixture. A catalytic amount of CuSO$_4$ and Cu wire are then added to the reaction mixture. After the mixture is incubated (including but not limited to, about 4 hours at room temperature or 37° C., or overnight at 4° C.), H$_2$O is added and the mixture is filtered through a dialysis membrane. The sample can be analyzed for the addition, including but not limited to, by similar procedures described in Example 3.

In this Example, the PEG will have the following structure:

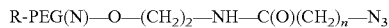

where R is methyl, n is 4 and N is 10,000 MW.

Example 8

This example details substitution of a large, hydrophobic amino acid in ABP with propargyl tyrosine.

A Phe, Trp or Tyr residue present within the sequence of ABP is substituted with the following non-naturally encoded amino acid as described in Example 7:

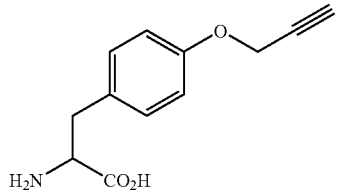

Once modified, a PEG is attached to the ABP variant comprising the alkyne-containing amino acid. The PEG will have the following structure:

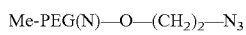

and coupling procedures would follow those in Example 7. This will generate a ABP variant comprising a non-naturally encoded amino acid that is approximately isosteric with one of the naturally-occurring, large hydrophobic amino acids and which is modified with a PEG derivative at a distinct site within the polypeptide.

Example 9

This example details generation of an ABP homodimer, heterodimer, homomultimer, or heteromultimer separated by one or more PEG linkers.

The alkyne-containing ABP variant produced in Example 7 is reacted with a bifunctional PEG derivative of the form:

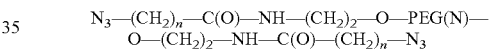

where n is 4 and the PEG has an average MW of approximately 5,000, to generate the corresponding ABP homodimer where the two ABP molecules are physically separated by PEG. In an analogous manner an antigen-binding polypeptide may be coupled to one or more other polypeptides to form heterodimers, homomultimers, or heteromultimers. Coupling, purification, and analyses will be performed as in Examples 7 and 3.

Example 10

This example details coupling of a saccharide moiety to ABP.

One or more amino acid residues of the ABP is substituted with the non-naturally encoded amino acid below, as described in Example 3.

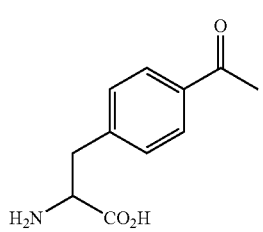

Once modified, the ABP variant comprising the carbonyl-containing amino acid is reacted with a β-linked aminooxy analogue of N-acetylglucosamine (GlcNAc). The ABP variant (10 mg/mL) and the aminooxy saccharide (21 mM) are mixed in aqueous 100 mM sodium acetate buffer (pH 5.5) and incubated at 37° C. for 7 to 26 hours. A second saccharide is coupled to the first enzymatically by incubating the saccharide-conjugated ABP (5 mg/mL) with UDP-galactose (16 mM) and β-1,4-galacytosyltransferase (0.4 units/mL) in 150 mM HEPES buffer (pH 7.4) for 48 hours at ambient temperature (Schanbacher et al. *J. Biol. Chem.* 1970, 245, 5057-5061).

Example 11

This example details generation of a PEGylated ABP antagonist.

One or more of the ABP amino acid residues is substituted with the following non-naturally encoded amino acid as described in Example 3.

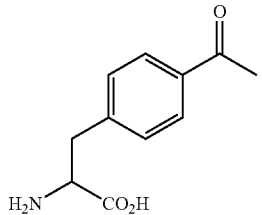

Once modified, the ABP variant comprising the carbonyl-containing amino acid will be reacted with an aminooxy-containing PEG derivative of the form:

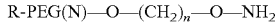

where R is methyl, n is 4 and N is 20,000 MW to generate a ABP antagonist comprising a non-naturally encoded amino acid that is modified with a PEG derivative at a single site within the polypeptide. Coupling, purification, and analyses are performed as in Example 3.

Example 12

Generation of an ABP Homodimer, Heterodimer, Homomultimer, or Heteromultimer in Which the ABP Molecules are Linked Directly An ABP variant comprising the alkyne-containing amino acid can be directly coupled to another ABP variant comprising the azido-containing amino acid, each of which comprise non-naturally encoded amino acid substitutions at the sites described in, but not limited to, Example 10. This will generate the corresponding ABP homodimer where the two ABP variants are physically joined. In an analogous manner an antigen-binding polypeptide may be coupled to one or more other polypeptides to form heterodimers, homomultimers, or heteromultimers. Coupling, purification, and analyses are performed as in Examples 3, 6, and 7.

Example 13

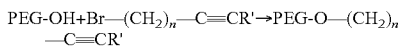

The polyalkylene$^A$ glycol (P—OH)$^B$ is reacted with the alkyl halide (A) to form the ether (B). In these compounds, n is an integer from one to nine and R' can be a straight- or branched-chain, saturated or unsaturated C1, to C20 alkyl or heteroalkyl group. R' can also be a C3 to C7 saturated or unsaturated cyclic alkyl or cyclic heteroalkyl, a substituted or unsubstituted aryl or heteroaryl group, or a substituted or unsubstituted alkaryl (the alkyl is a C1 to C20 saturated or unsaturated alkyl) or heteroalkaryl group. Typically, PEG-OH is polyethylene glycol (PEG) or monomethoxy polyethylene glycol (mPEG) having a molecular weight of 800 to 40,000 Daltons (Da).

Example 14

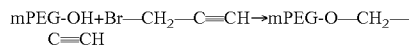

mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). A solution of propargyl bromide, dissolved as an 80% weight solution in xylene (0.56 mL, 5 mmol, 50 equiv., Aldrich), and a catalytic amount of KI were then added to the solution and the resulting mixture was heated to reflux for 2 hours. Water (1 mL) was then added and the solvent was removed under vacuum. To the residue was added CH$_2$Cl$_2$ (25 mL) and the organic layer was separated, dried over anhydrous Na$_2$SO$_4$, and the volume was reduced to approximately 2 mL. This CH$_2$Cl$_2$ solution was added to diethyl ether (150 mL) drop-wise. The resulting precipitate was collected, washed with several portions of cold diethyl ether, and dried to afford propargyl-O-PEG.

Example 15

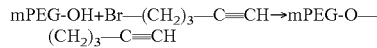

The mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). Fifty equivalents of 5-bromo-1-pentyne (0.53 mL, 5 mmol, Aldrich) and a catalytic amount of KI were then added to the mixture. The resulting mixture was heated to reflux for 16 hours. Water (1 mL) was then added and the solvent was removed under vacuum. To the residue was added CH$_2$Cl$_2$ (25 mL) and the organic layer was separated, dried over anhydrous Na$_2$SO$_4$, and the volume was reduced to approximately 2 mL. This CH$_2$Cl$_2$ solution was added to diethyl ether (150 mL) drop-wise. The resulting precipitate was collected, washed with several portions of cold diethyl ether, and dried to afford the corresponding alkyne. 5-chloro-1-pentyne may be used in a similar reaction.

Example 16

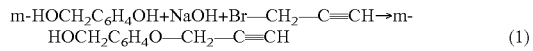

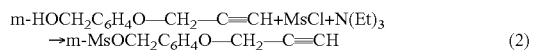

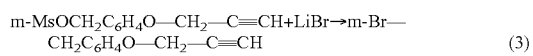

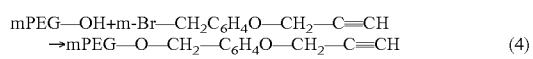

To a solution of 3-hydroxybenzylalcohol (2.4 g, 20 mmol) in THF (50 mL) and water (2.5 mL) was first added powdered sodium hydroxide (1.5 g, 37.5 mmol) and then a solution of propargyl bromide, dissolved as an 80% weight solution in xylene (3.36 mL, 30 mmol). The reaction mixture was heated at reflux for 6 hours. To the mixture was added 10% citric acid (2.5 mL) and the solvent was removed under vacuum. The residue was extracted with ethyl acetate (3×15 mL) and the combined organic layers were washed with saturated NaCl solution (10 mL), dried over MgSO$_4$ and concentrated to give the 3-propargyloxybenzyl alcohol.

Methanesulfonyl chloride (2.5 g, 15.7 mmol) and triethylamine (2.8 mL, 20 mmol) were added to a solution of compound 3 (2.0 g, 11.0 mmol) in CH$_2$Cl$_2$ at 0° C. and the reaction was placed in the refrigerator for 16 hours. A usual work-up afforded the mesylate as a pale yellow oil. This oil (2.4 g, 9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous Na$_2$SO$_4$, and concentrated to give the desired bromide.

mPEG-OH 20 kDa (1.0 g, 0.05 mmol, Sunbio) was dissolved in THF (20 mL) and the solution was cooled in an ice bath. NaH (6 mg, 0.25 mmol) was added with vigorous stirring over a period of several minutes followed by addition of the bromide obtained from above (2.55 g, 11.4 mmol) and a catalytic amount of KI. The cooling bath was removed and the resulting mixture was heated to reflux for 12 hours. Water (1.0 mL) was added to the mixture and the solvent was removed under vacuum. To the residue was added CH$_2$Cl$_2$ (25 mL) and the organic layer was separated, dried over anhydrous Na$_2$SO$_4$, and the volume was reduced to approximately 2 mL. Dropwise addition to an ether solution (150 mL) resulted in a white precipitate, which was collected to yield the PEG derivative.

Example 17

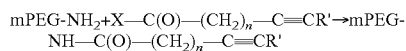

mPEG-NH$_2$+X—C(O)—(CH$_2$)$_n$—C≡CR'→mPEG-NH—C(O)—(CH$_2$)$_n$—C≡CR'

The terminal alkyne-containing poly(ethylene glycol) polymers can also be obtained by coupling a poly(ethylene glycol) polymer containing a terminal functional group to a reactive molecule containing the alkyne functionality as shown above. n is between 1 and 10. R' can be H or a small alkyl group from C1 to C4.

Example 18

HO$_2$C—(CH$_2$)$_2$—C≡CH+NHS+DCC→NHSO—C(O)—(CH$_2$)$_2$—C≡CH (1)

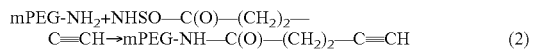

mPEG-NH$_2$+NHSO—C(O)—(CH$_2$)$_2$—C≡CH→mPEG-NH—C(O)—(CH$_2$)$_2$—C≡CH (2)

4-pentynoic acid (2.943 g, 3.0 mmol) was dissolved in CH$_2$Cl$_2$ (25 mL). N-hydroxysuccinimide (3.80 g, 3.3 mmol) and DCC (4.66 g, 3.0 mmol) were added and the solution was stirred overnight at room temperature. The resulting crude NHS ester 7 was used in the following reaction without further purification.

mPEG-NH$_2$ with a molecular weight of 5,000 Da (mPEG-NH$_2$, 1 g, Sunbio) was dissolved in THF (50 mL) and the mixture was cooled to 4° C. NHS ester 7 (400 mg, 0.4 mmol) was added portion-wise with vigorous stirring. The mixture was allowed to stir for 3 hours while warming to room temperature. Water (2 mL) was then added and the solvent was removed under vacuum. To the residue was added CH$_2$Cl$_2$ (50 mL) and the organic layer was separated, dried over anhydrous Na$_2$SO$_4$, and the volume was reduced to approximately 2 mL. This CH$_2$Cl$_2$ solution was added to ether (150 mL) drop-wise. The resulting precipitate was collected and dried in vacuo.

Example 19

This Example represents the preparation of the methane sulfonyl ester of poly(ethylene glycol), which can also be referred to as the methanesulfonate or mesylate of poly(ethylene glycol). The corresponding tosylate and the halides can be prepared by similar procedures.

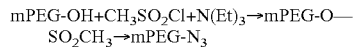

mPEG-OH+CH$_3$SO$_2$Cl+N(Et)$_3$→mPEG-O—SO$_2$CH$_3$→mPEG-N$_3$

The mPEG-OH (MW=3,400, 25 g, 10 mmol) in 150 mL of toluene was azeotropically distilled for 2 hours under nitrogen and the solution was cooled to room temperature. 40 mL of dry CH$_2$Cl$_2$ and 2.1 mL of dry triethylamine (15 mmol) were added to the solution. The solution was cooled in an ice bath and 1.2 mL of distilled methanesulfonyl chloride (15 mmol) was added dropwise. The solution was stirred at room temperature under nitrogen overnight, and the reaction was quenched by adding 2 mL of absolute ethanol. The mixture was evaporated under vacuum to remove solvents, primarily those other than toluene, filtered, concentrated again under vacuum, and then precipitated into 100 mL of diethyl ether. The filtrate was washed with several portions of cold diethyl ether and dried in vacuo to afford the mesylate.

The mesylate (20 g, 8 mmol) was dissolved in 75 ml of THF and the solution was cooled to 4° C. To the cooled solution was added sodium azide (1.56 g, 24 mmol). The reaction was heated to reflux under nitrogen for 2 hours. The solvents were then evaporated and the residue diluted with CH$_2$Cl$_2$ (50 mL). The organic fraction was washed with NaCl solution and dried over anhydrous MgSO$_4$. The volume was reduced to 20 ml and the product was precipitated by addition to 150 ml of cold dry ether.

Example 20

N$_3$—C$_6$H$_4$—CO$_2$H→N$_3$—C$_6$H$_4$CH$_2$OH (1)

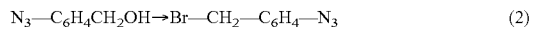

N$_3$—C$_6$H$_4$CH$_2$OH→Br—CH$_2$—C$_6$H$_4$—N$_3$ (2)

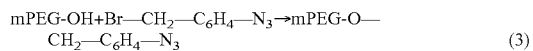

mPEG-OH+Br—CH$_2$—C$_6$H$_4$—N$_3$→mPEG-O—CH$_2$—C$_6$H$_4$—N$_3$ (3)

4-azidobenzyl alcohol can be produced using the method described in U.S. Pat. No. 5,998,595, which is incorporated by reference herein. Methanesulfonyl chloride (2.5 g, 15.7 mmol) and triethylamine (2.8 mL, 20 mmol) were added to a solution of 4-azidobenzyl alcohol (1.75 g, 11.0 mmol) in CH$_2$Cl$_2$ at 0° C. and the reaction was placed in the refrigerator for 16 hours. A usual work-up afforded the mesylate as a pale yellow oil. This oil (9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous Na$_2$SO$_4$, and concentrated to give the desired bromide.

mPEG-OH 20 kDa (2.0 g, 0.1 mmol, Sunbio) was treated with NaH (12 mg, 0.5 mmol) in THF (35 mL) and the bromide (3.32 g, 15 mmol) was added to the mixture along with a catalytic amount of KI. The resulting mixture was heated to reflux for 12 hours. Water (1.0 mL) was added to the mixture and the solvent was removed under vacuum. To the residue was added $CH_2Cl_2$ (25 mL) and the organic layer was separated, dried over anhydrous $Na_2SO_4$, and the volume was reduced to approximately 2 mL. Dropwise addition to an ether solution (150 mL) resulted in a precipitate, which was collected to yield mPEG-O—$CH_2$—$C_6H_4$—$N_3$.

Example 21

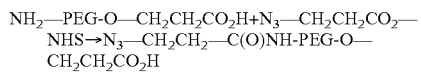

$NH_2$—PEG-O—$CH_2CH_2CO_2H$ (MW 3,400 Da, 2.0 g) was dissolved in a saturated aqueous solution of $NaHCO_3$ (10 mL) and the solution was cooled to 0° C. 3-azido-1-N-hydroxysuccinimido propionate (5 equiv.) was added with vigorous stirring. After 3 hours, 20 mL of $H_2O$ was added and the mixture was stirred for an additional 45 minutes at room temperature. The pH was adjusted to 3 with 0.5 N $H_2SO_4$ and NaCl was added to a concentration of approximately 15 wt %. The reaction mixture was extracted with $CH_2Cl_2$ (100 mL×3), dried over $Na_2SO_4$ and concentrated. After precipitation with cold diethyl ether, the product was collected by filtration and dried under vacuum to yield the omega-carboxy-azide PEG derivative.

Example 22

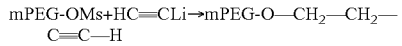

To a solution of lithium acetylide (4 equiv.), prepared as known in the art and cooled to −78° C. in THF, is added dropwise a solution of mPEG-OMs dissolved in THF with vigorous stirring. After 3 hours, the reaction is permitted to warm to room temperature and quenched with the addition of 1 mL of butanol. 20 mL of $H_2O$ is then added and the mixture was stirred for an additional 45 minutes at room temperature. The pH was adjusted to 3 with 0.5 N $H_2SO_4$ and NaCl was added to a concentration of approximately 15 wt %. The reaction mixture was extracted with $CH_2Cl_2$ (100 mL×3), dried over $Na_2SO_4$ and concentrated. After precipitation with cold diethyl ether, the product was collected by filtration and dried under vacuum to yield the 1-(but-3-ynyloxy)-methoxy-polyethylene glycol (mPEG).

Example 23

The azide- and acetylene-containing amino acids were incorporated site-selectively into proteins using the methods described in L. Wang, et al., (2001), Science 292:498-500, J. W. Chin et al., Science 301:964-7 (2003)), J. W. Chin et al., (2002), Journal of the American Chemical Society 124:9026-9027; J. W. Chin, & P. G. Schultz, (2002), Chem Bio Chem 11:1135-1137; J. W. Chin, et al., (2002), PNAS United States of America 99:11020-11024: and, L. Wang, & P. G. Schultz, (2002), Chem. Comm., 1-10. Once the amino acids were incorporated, the cycloaddition reaction was carried out with 0.01 mM protein in phosphate buffer (PB), pH 8, in the presence of 2 mM PEG derivative, 1 mM $CuSO_4$, and ~1 mg Cu-wire for 4 hours at 37° C.

Example 24

This example describes methods to measure in vitro and in vivo activity of ABP comprising a non-naturally encoded amino acid and PEGylated ABP.

Cell Binding Assays

Cells ($3\times10^6$) are incubated in duplicate in PBS/1% BSA (100 µl) in the absence or presence of various concentrations (volume: 10 µl) of unlabeled ABP, ABP or a negative control and in the presence of $^{125}$I-ABP (approx. 100,000 cpm or 1 ng) at 0° C. for 90 minutes (total volume: 120 µl). Cells are then resuspended and layered over 200 µl ice cold FCS in a 350 µl plastic centrifuge tube and centrifuged (1000 g; 1 minute). The pellet is collected by cutting off the end of the tube and pellet and supernatant counted separately in a gamma counter (Packard).

Specific binding (cpm) is determined as total binding in the absence of a competitor (mean of duplicates) minus binding (cpm) in the presence of 100-fold excess of unlabeled ABP (non-specific binding). The non-specific binding is measured for each of the cell types used. Experiments are run on separate days using the same preparation of $^{125}$I-ABP and should display internal consistency. The binding is inhibited in a dose dependent manner by unlabeled natural ABP or ABP, but not by the negative control. The ability of ABP to compete for the binding of natural $^{125}$I-ABP suggests that the receptors recognize both forms equally well.

For binding assays with scFv-108, A431 cells were collected following treatment with trypsin, re-suspended in FACS buffer (PBS, 2% FBS, 0.01% $NaN_3$), and then seeded into 96-well round bottom microtiter plates ($3\times10^5$ cell/well). Cells were incubated with different concentrations of wild type or pAcF-containing scFv-108 fragments for 30 minutes on ice. Unbound scFv proteins were removed by washing following centrifugation (repeated 2-3 times). Cells were then incubated with the mAb-108 (ATCC # HB 9764) at a concentration of 7.5 nM ($EC_{80}$) for 30 minutes. After two washes, the cells were incubated with an APC-labeled (allophycocyanin) anti-mouse antibody (10 ug/ml) for 30 minutes on ice. After washing the cells two times to remove the secondary antibody, the cells were re-suspended in FACS buffer supplemented with propidium iodine (0.5 ug/ml), and analyzed by flow cytometry. For binding assays with Fab-108, cells were incubated with increasing amounts of Fab-108 under the same conditions as used for the scFv-108 assays. Fab binding was detected using an anti-His antibody followed by an APC-labeled anti-mouse secondary antibody.

Figure 7:
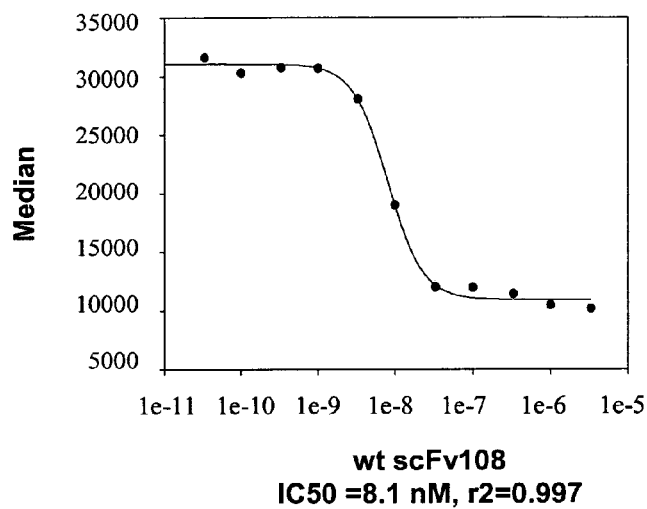
FIG. 7—Binding of pAcF or pAcF-PEG-containing scFv proteins to A431 cells expressing EGF receptors are shown in FIG. 7, Panels A-C.
Figure 7:
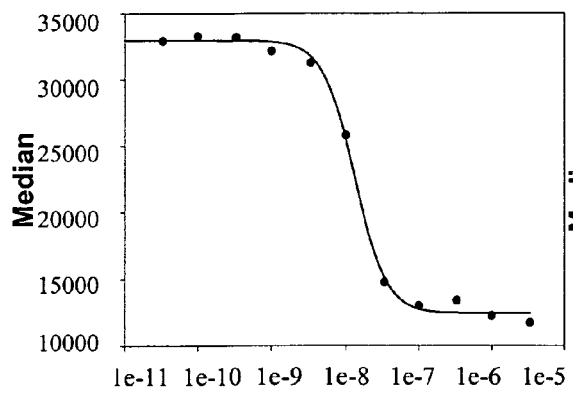
Figure 7:
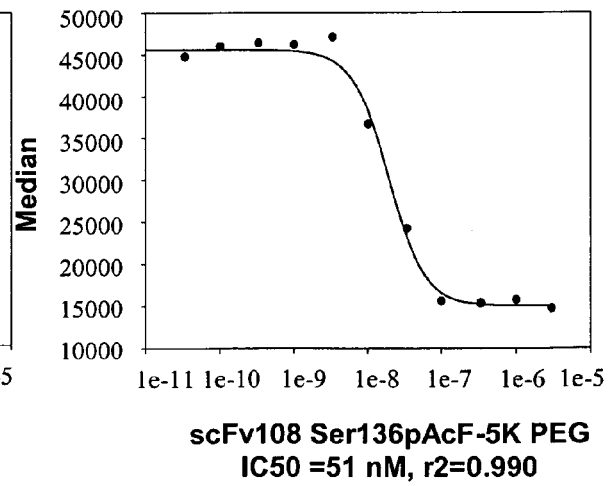

FIG. 7, Panels A-C shows competition binding curves of the scFv proteins containing p-acetyl-phenylalanine (pAcF) or pAcF with PEG and WT scFv to A431 cells expressing EGF receptors. Cells were incubated with the scFv proteins at various concentrations after washing to remove unbound scFv's, and the cells were treated with the mAb108 as described above. All proteins were expressed in the periplasm. Table 11 summarizes the binding of the modified scFv's (pAcF and pAcF with PEG) relative to the wild type scFv:

TABLE 11

| scFv 108 | IC50 |
|---|---|
| WT | 1x (8.1 nm) |
| Ser131pAcF | 1.3x |
| Ser131pAcF-5K PEG | 5.0x |
| Ser136pAcF | 1.6x |
| Ser136pAcF-5K PEG | 6.3x |
| His144pAcF | 2.6x |
| Leu156pAcF | 1.8x |
| Leu156pAcF-5K PEG | 2.9x |
| Tyr190pAcF | 2.1x |
| Ser193pAcF | 1.8x |
| Lys248pAcF | 2.1x |
| Ser259pAcF | 0.5x |

FIG. 8, Panels B-D show binding of pAcF or pAcF-PEG-containing Fab-108 fragments and WT Fab to A431 cells expressing EGF receptors. PEGylation of the Fab fragments results in a minimal decrease in the affinity of the Fab fragments to the EGF receptors. Binding of modified Fab fragments relative to that of the wild type Fab is shown in Table 12. Binding conditions were as described previously.

TABLE 12

| Fab108 | EC50 |
|---|---|
| WT | 1x (4.0 nM) |
| Lys142pAcF | 1.7x |
| Lys142pAcF-5K PEG | 2.8x |
| Thr204pAcF | 1.7x |
| Thr204pAcF-5K PEG | 1.8x |
| Lys219pAcF | 2.0x |

In Vivo Studies of PEGylated ABP

PEG-ABP, unmodified ABP and buffer solution are administered to mice or rats. The results will show superior activity and prolonged half life of the PEGylated ABP of the present invention compared to unmodified ABP.

Measurement of the In Vivo Half-Life of Conjuzated and Non-Conjugated ABP and Variants Thereof.

Male Sprague Dawley rats (about 7 weeks old) are used. On the day of administration, the weight of each animal is measured. 100 μg per kg body weight of the non-conjugated and conjugated ABP samples are each injected intravenously into the tail vein of three rats. At 1 minute, 30 minutes, 1, 2, 4, 6, and 24 hours after the injection, 500 μl of blood is withdrawn from each rat while under $CO_2$-anesthesia. The blood samples are stored at room temperature for 1.5 hours followed by isolation of serum by centrifugation (4° C., 18000×g for 5 minutes). The serum samples are stored at −80° C. until the day of analysis. The amount of active ABP in the serum samples is quantified by the ABP in vitro activity assay after thawing the samples on ice.

Example 31

Human Clinical Trial of the Safety and/or Efficacy of PEGylated ABP Comprising a Non-Naturally Encoded Amino Acid.

Objective To compare the safety and pharmacokinetics of subcutaneously administered PEGylated recombinant human ABP comprising a non-naturally encoded amino acid with a commercially available product specific for the same target antigen (e.g. Herceptin®, Bexxar®, Campath®, CEA-Scan®, Enbrel®, Erbitux®, Humira®, Myoscint®, Prostascint®, Raptiva®, Remicade®, ReoPro®, Rituxan®, Simulect®, Synagis®, Verluma®, Xolair®, Zenapax®, Zevalin®, or Avastin®.

Patients Eighteen healthy volunteers ranging between 20-40 years of age and weighing between 60-90 kg are enrolled in the study. The subjects will have no clinically significant abnormal laboratory values for hematology or serum chemistry, and a negative urine toxicology screen, HIV screen, and hepatitis B surface antigen. They should not have any evidence of the following: hypertension; a history of any primary hematologic disease; history of significant hepatic, renal, cardiovascular, gastrointestinal, genitourinary, metabolic, neurologic disease; a history of anemia or seizure disorder; a known sensitivity to bacterial or mammalian-derived products, PEG, or human serum albumin; habitual and heavy consumer to beverages containing caffeine; participation in any other clinical trial or had blood transfused or donated within 30 days of study entry; had exposure to ABP within three months of study entry; had an illness within seven days of study entry; and have significant abnormalities on the pre-study physical examination or the clinical laboratory evaluations within 14 days of study entry. All subjects are evaluable for safety and all blood collections for pharmacokinetic analysis are collected as scheduled. All studies are performed with institutional ethics committee approval and patient consent.

Study Design This will be a Phase 1, single-center, open-label, randomized, two-period crossover study in healthy male volunteers. Eighteen subjects are randomly assigned to one of two treatment sequence groups (nine subjects/group). ABP is administered over two separate dosing periods as a bolus s.c. injection in the upper thigh using equivalent doses of the PEGylated ABP comprising a non-naturally encoded amino acid and the commercially available product chosen. The dose and frequency of administration of the commercially available product is as instructed in the package label. Additional dosing, dosing frequency, or other parameter as desired, using the commercially available products may be added to the study by including additional groups of subjects. Each dosing period is separated by a 14-day washout period. Subjects are confined to the study center at least 12 hours prior to and 72 hours following dosing for each of the two dosing periods, but not between dosing periods. Additional groups of subjects may be added if there are to be additional dosing, frequency, or other parameter, to be tested for the PEGylated ABP as well. The experimental formulation of ABP is the PEGylated ABP comprising a non-naturally encoded amino acid.

Blood Sampling Serial blood is drawn by direct vein puncture before and after administration of ABP. Venous blood samples (5 mL) for determination of serum ABP concentrations are obtained at about 30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Each serum sample is divided into two aliquots. All serum samples are stored at −20° C. Serum samples are shipped on dry ice. Fasting clinical laboratory tests (hematology, serum chemistry, and urinalysis) are performed immediately prior to the initial dose on day 1, the morning of day 4, immediately prior to dosing on day 16, and the morning of day 19.

Bioanalytical Methods A radioimmunoassay (RA) or ELISA kit procedure is used for the determination of serum ABP concentrations.

Safety Determinations Vital signs are recorded immediately prior to each dosing (Days 1 and 16), and at 6, 24, 48, and 72 hours after each dosing. Safety determinations are based on the incidence and type of adverse events and the changes in clinical laboratory tests from baseline. In addition, changes from pre-study in vital sign measurements, including blood pressure, and physical examination results are evaluated.

Data Analysis Post-dose serum concentration values are corrected for pre-dose baseline ABP concentrations by subtracting from each of the post-dose values the mean baseline ABP concentration determined from averaging the ABP levels from the three samples collected at 30, 20, and 10 minutes before dosing. Pre-dose serum ABP concentrations are not included in the calculation of the mean value if they are below the quantification level of the assay. Pharmacokinetic parameters are determined from serum concentration data corrected for baseline ABP concentrations. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Safety Results The incidence of adverse events is equally distributed across the treatment groups. There are no clinically significant changes from baseline or pre-study clinical laboratory tests or blood pressures, and no notable changes from pre-study in physical examination results and vital sign measurements. The safety profiles for the two treatment groups should appear similar.

Pharmacokinetic Results Mean serum ABP concentration-time profiles (uncorrected for baseline ABP levels) in all 18 subjects after receiving a single dose of one or more of commercially available products specific for the same target antigen are compared to the PEGylated ABP comprising a non-naturally encoded amino acid at each time point measured. All subjects should have pre-dose baseline ABP concentrations within the normal physiologic range. Pharmacokinetic parameters are determined from serum data corrected for pre-dose mean baseline ABP concentrations and the $C_{max}$ and $t_{max}$ are determined. The mean $t_{max}$ for the clinical comparator(s) chosen is significantly shorter than the $t_{max}$ for the PEGylated ABP comprising the non-naturally encoded amino acid. Terminal half-life values are significantly shorter for the commercially available ABP products tested compared with the terminal half-life for the PEGylated ABP comprising a non-naturally encoded amino acid.

Although the present study is conducted in healthy male subjects, similar absorption characteristics and safety profiles would be anticipated in other patient populations; such as male or female patients with cancer or chronic renal failure, pediatric renal failure patients, patients in autologous predeposit programs, or patients scheduled for elective surgery.

In conclusion, subcutaneously administered single doses of PEGylated ABP comprising non-naturally encoded amino acid will be safe and well tolerated by healthy male subjects. Based on a comparative incidence of adverse events, clinical laboratory values, vital signs, and physical examination results, the safety profiles of the commercially available forms of ABP and PEGylated ABP comprising non-naturally encoded amino acid will be equivalent. The PEGylated ABP comprising non-naturally encoded amino acid potentially provides large clinical utility to patients and health care providers.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference herein in their entirety for all purposes.

ADDITIONAL AND ALTERNATE EMBODIMENTS OF THE INVENTION

1. An antigen-binding polypeptide comprising one or more non-naturally encoded amino acids.
2. The antigen-binding polypeptide of claim 1, wherein the antigen-binding polypeptide comprises one or more post-translational modifications.
3. The antigen-binding polypeptide of claim 1, wherein the antigen-binding polypeptide is linked to a linker, polymer, or biologically active molecule.
4. The antigen-binding polypeptide of claim 3, wherein the polypeptide is linked to a water soluble polymer.
5. The antigen-binding polypeptide of claim 1, wherein the polypeptide is linked to a bifunctional polymer, bifunctional linker, or at least one additional antigen-binding polypeptide.
6. The antigen-binding polypeptide of claim 5, wherein the bifunctional linker or polymer is linked to a second polypeptide.
7. The antigen-binding polypeptide of claim 6, wherein the second polypeptide is an antigen-binding polypeptide.
8. The antigen-binding polypeptide of claim 6, wherein the second polypeptide is a non-antigen-binding polypeptide.
9. The antigen-binding polypeptide of claim 4, wherein the water soluble polymer comprises a poly(ethylene glycol) moiety.
10. The antigen-binding polypeptide of claim 5, wherein the bifunctional polymer is a poly(ethylene glycol) moiety.
11. The antigen-binding polypeptide of claim 4, wherein said water soluble polymer is linked to a non-naturally encoded amino acid present in said antigen-binding polypeptide.
12. The antigen-binding polypeptide of claim 1, comprising at least two amino acids linked to a water soluble polymer comprising a poly(ethylene glycol) moiety.
13. The antigen-binding polypeptide of claim 12, wherein at least one amino acid linked to said water soluble polymer is a non-naturally encoded amino acid.
14. The antigen-binding polypeptide of claim 1, wherein the antigen-binding polypeptide comprises one or more amino acid substitution, addition or deletion that modulates affinity of the antigen-binding polypeptide for an ABP receptor or antigen.
15. The antigen-binding polypeptide of claim 1, wherein the antigen-binding polypeptide comprises one or more amino acid substitution, addition or deletion that modulates the stability, expression level in a recombinant host cell or synthesized in vitro, immunogenicity, protease resistance, tissue or organ specificity, or solubility of the antigen-binding polypeptide.
16. The antigen-binding polypeptide of claim 1, wherein the non-naturally encoded amino acid is reactive toward a linker, polymer, or biologically active molecule that is otherwise unreactive toward any of the 20 common amino acids in the polypeptide.
17. The antigen-binding polypeptide of claim 1, wherein the non-naturally encoded amino acid comprises a carbonyl group, an aminooxy group, a hydrazine group, a hydrazide group, a semicarbazide group, an azide group, or an alkyne group.
18. The antigen-binding polypeptide of claim 17, wherein the non-naturally encoded amino acid comprises a carbonyl group.

19. The antigen-binding polypeptide of claim 18, wherein the non-naturally encoded amino acid has the structure:

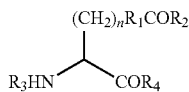

wherein n is 0-10; R1 is an alkyl, aryl, substituted alkyl, or substituted aryl; R2 is H, an alkyl, aryl, substituted alkyl, and substituted aryl; and R3 is H, an amino acid, a polypeptide, or an amino terminus modification group, and R4 is H, an amino acid, a polypeptide, or a carboxy terminus modification group.

20. The antigen-binding polypeptide of claim 17, wherein the non-naturally encoded amino acid comprises an aminooxy group.

21. The antigen-binding polypeptide of claim 17, wherein the non-naturally encoded amino acid comprises a hydrazide group.

22. The antigen-binding polypeptide of claim 17, wherein the non-naturally encoded amino acid comprises a hydrazine group.

23. The antigen-binding polypeptide of claim 17, wherein the non-naturally encoded amino acid comprises a semicarbazide group.

24. The antigen-binding polypeptide of claim 17, wherein the non-naturally encoded amino acid comprises an azide group.

25. The antigen-binding polypeptide of claim 24, wherein the non-naturally encoded amino acid has the structure:

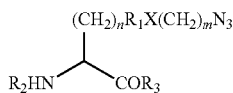

wherein n is 0-10; R1 is an alkyl, aryl, substituted alkyl, substituted aryl or not present; X is O, N, S or not present; m is 0-10; R2 is H, an amino acid, a polypeptide, or an amino terminus modification group, and R3 is H, an amino acid, a polypeptide, or a carboxy terminus modification group.

26. The antigen-binding polypeptide of claim 17, wherein the non-naturally encoded amino acid comprises an alkyne group.

27. The antigen-binding polypeptide of claim 26, wherein the non-naturally encoded amino acid has the structure:

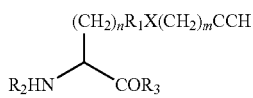

wherein n is 0-10; R1 is an alkyl, aryl, substituted alkyl, or substituted aryl; X is O, N, S or not present; m is 0-10, R2 is H, an amino acid, a polypeptide, or an amino terminus modification group, and R3 is H, an amino acid, a polypeptide, or a carboxy terminus modification group.

28. The antigen-binding polypeptide of claim 4, wherein the water soluble polymer has a molecular weight of between about 0.1 kDa and about 100 kDa.

29. The antigen-binding polypeptide of claim 28, wherein the water soluble polymer has a molecular weight of between about 0.1 kDa and about 50 kDa.

30. The antigen-binding polypeptide of claim 4, which is made by reacting an antigen-binding polypeptide comprising a carbonyl-containing amino acid with a water soluble polymer comprising an aminooxy, a hydrazine, hydrazide or semicarbazide group.

31. The antigen-binding polypeptide of claim 30, wherein the aminooxy, hydrazine, hydrazide or semicarbazide group is linked to the water soluble polymer through an amide linkage.

32. The antigen-binding polypeptide of claim 4, which is made by reacting a water soluble polymer comprising a carbonyl group with a polypeptide comprising a non-naturally encoded amino acid that comprises an aminooxy, a hydrazine, a hydrazide or a semicarbazide group.

33. The antigen-binding polypeptide of claim 4, which is made by reacting an antigen-binding polypeptide comprising an alkyne-containing amino acid with a water soluble polymer comprising an azide moiety.

34. The antigen-binding polypeptide of claim 4, which is made by reacting an antigen-binding polypeptide comprising an azide-containing amino acid with a water soluble polymer comprising an alkyne moiety.

35. The antigen-binding polypeptide of claim 17, wherein the azide or alkyne group is linked to a water soluble polymer through an amide linkage.

36. The antigen-binding polypeptide of claim 4, wherein the water soluble polymer is a branched or multiarmed polymer.

37. The antigen-binding polypeptide of claim 36, wherein each branch of the water soluble polymer has a molecular weight of between about 1 kDa and 100 kDa.

38. The antigen-binding polypeptide of claim 1, wherein the polypeptide is an antigen-binding polypeptide antagonist.

39. The antigen-binding polypeptide of claim 38, wherein the polypeptide comprises one or more post-translational modification, linker, polymer, or biologically active molecule.

40. The antigen-binding polypeptide of claim 39, wherein the polymer comprises a moiety selected from a group consisting of a water soluble polymer and poly(ethylene glycol).

41. The antigen-binding polypeptide of claim 1, wherein the non-naturally encoded amino acid comprises a saccharide moiety.

42. The antigen-binding polypeptide of claim 3, wherein the linker, polymer, or biologically active molecule is linked to the polypeptide via a saccharide moiety.

43. An isolated nucleic acid comprising a polynucleotide that hybridizes under stringent conditions to an antigen-binding polypeptide-encoding polynucleotide, wherein the polynucleotide comprises at least one selector codon.

44. The isolated nucleic acid of claim 43, wherein the selector codon is selected from the group consisting of an amber codon, ochre codon, opal codon, a unique codon, a rare codon, and a four-base codon.

45. A method of making the antigen-binding polypeptide of claim 3, the method comprising contacting an isolated antigen-binding polypeptide comprising a non-naturally encoded amino acid with a linker, polymer, or biologically active molecule comprising a moiety that reacts with the non-naturally encoded amino acid.

46. The method of claim 45, wherein the polymer comprises a moiety selected from a group consisting of a water soluble polymer and poly(ethylene glycol).

47. The method of claim 45, wherein the non-naturally encoded amino acid comprises a carbonyl group, an aminooxy group, a hydrazide group, a hydrazine group, a semicarbazide group, an azide group, or an alkyne group.

48. The method of claim 45, wherein the non-naturally encoded amino acid comprises a carbonyl moiety and the linker, polymer, or biologically active molecule comprises an aminooxy, a hydrazine, a hydrazide, or a semicarbazide moiety.

49. The method of claim 48, wherein the aminooxy, hydrazine, hydrazide, or semicarbazide moiety is linked to the linker, polymer, or biologically active molecule through an amide linkage.

50. The method of claim 45, wherein the non-naturally encoded amino acid comprises an alkyne moiety and the linker, polymer, or biologically active molecule comprises an azide moiety.

51. The method of claim 45, wherein the non-naturally encoded amino acid comprises an azide moiety and the linker, polymer, or biologically active molecule comprises an alkyne moiety.

52. The method of claim 47, wherein the azide or alkyne moiety is linked to a linker, polymer, or biologically active molecule through an amide linkage.

53. The method of claim 46, wherein the poly(ethylene glycol) moiety has an average molecular weight of between about 0.1 kDa and about 100 kDa.

54. The method of claim 46, wherein the poly(ethylene glycol) moiety is a branched or multiarmed polymer.

55. A composition comprising the antigen-binding polypeptide of claim 1 and a pharmaceutically acceptable carrier.

56. The composition of claim 55, wherein the non-naturally encoded amino acid is linked to a water soluble polymer.

57. A method of treating a patient having a disorder modulated by ABP comprising administering to the patient a therapeutically-effective amount of the composition of claim 55.

58. A cell comprising the nucleic acid of claim 43.

59. The cell of claim 58, wherein the cell comprises an orthogonal tRNA synthetase or an orthogonal tRNA.

60. A method of making an antigen-binding polypeptide comprising a non-naturally encoded amino acid, the method comprising, culturing cells comprising a polynucleotide or polynucleotides encoding an antigen-binding polypeptide comprising a selector codon, an orthogonal RNA synthetase and an orthogonal tRNA under conditions to permit expression of the antigen-binding polypeptide comprising a non-naturally encoded amino acid; and purifying the antigen-binding polypeptide.

61. A method of modulating serum half-life or circulation time of an antigen-binding polypeptide, the method comprising substituting one or more non-naturally encoded amino acids for any one or more naturally occurring amino acids in the antigen-binding polypeptide.

62. An antigen-binding polypeptide encoded by a polynucleotide wherein said polynucleotide comprises a selector codon, and wherein said polypeptide comprises at least one non-naturally encoded amino acid.

63. The antigen-binding polypeptide of claim 62, wherein the non-naturally encoded amino acid is linked to a linker, polymer, water soluble polymer, or biologically active molecule.

64. The antigen-binding polypeptide of claim 63, wherein the water soluble polymer comprises a poly(ethylene glycol) moiety.

65. The antigen-binding polypeptide of claim 62, wherein the non-naturally encoded amino acid comprises a carbonyl group, an aminooxy group, a hydrazide group, a hydrazine group, a semicarbazide group, an azide group, or an alkyne group.

66. The antigen-binding polypeptide of claim 64, wherein the poly(ethylene glycol) moiety has a molecular weight of between about 0.1 kDa and about 100 kDa.

67. The antigen-binding polypeptide of claim 64, wherein the poly(ethylene glycol) moiety is a branched or multiarmed polymer.

68. The antigen-binding polypeptide of claim 67, wherein the poly(ethylene glycol) moiety has a molecular weight of between about 1 kDa and about 100 kDa.

69. A composition comprising the antigen-binding polypeptide of claim 62 and a pharmaceutically acceptable carrier.

70. A bispecific ABP comprising a first ABP and a second ABP joined to each other wherein said first ABP and said second ABP bind specifically to different epitopes wherein said first ABP has binding specificity for at least one epitope on a first antigen, and the second ABP has binding specificity for a second epitope on the first antigen or a second antigen which is different from said first epitope, and wherein said bispecific ABP comprises at least one non-naturally encoded amino acid.

71. The bispecific ABP of claim 70, wherein said first ABP and said second ABP are joined by a linker.

72. The bispecific ABP of claim 71, wherein said linker is a peptide linker.

73. The bispecific ABP of claim 72, wherein said linker is a peptide linker that lacks a proteolytic cleavage site.

74. The bispecific ABP of claim 70, wherein said first ABP is a single chain ABP and said second ABP is a single chain ABP and said first ABP is coupled to said second ABP by a peptide linker.

75. A composition comprising a bispecific ABP of claim 70 and a pharmaceutically acceptable carrier.

76. A method for treating a disease or condition, said method comprising administering to a patient in need thereof a therapeutically effective amount of the composition of claim 75.

77. An ABP comprising the bispecific ABP of claim 70, coupled to a biologically active molecule.

78. The ABP of claim 77, wherein said biologically active molecule is selected from the group consisting of a cytotoxin, a label, a radionuclide, a drug, a liposome, a ligand, and an ABP.

79. The ABP of claim 77, wherein said ABP is a fusion protein.

80. A method of detecting a cell or tissue expressing one or more antigens, said method comprising: contacting a cell or tissue with an ABP of claim 70 attached to a detectable label; and detecting said label wherein detection of said label in association with a cell or tissue indicates the presence of a cell or tissue expressing one or more antigens bound by the ABP.

81. The method of claim 80, wherein said detectable label is selected from the group consisting of a gamma emitter, a positron emitter, an MRI label, and a fluorescent label.

82. The method of claim 80, wherein said detectable label is a gamma emitter and said detecting comprises imaging with a gamma camera.

83. The method of claim 80, wherein said detectable label is a positron emitter and said detecting comprises imaging with positron emission tomography (PET).

84. The method of claim 80, wherein said detectable label is an MRI label and said detecting comprises detecting with magnetic resonance imaging.

85. An antigen-binding polypeptide comprising a water soluble polymer linked by a covalent bond to the antigen-binding polypeptide at a single amino acid.

86. The antigen-binding polypeptide of claim 85, wherein the water soluble polymer comprises a poly(ethylene glycol) moiety.

87. The antigen-binding polypeptide of claim 85, wherein the amino acid covalently linked to the water soluble polymer is a non-naturally encoded amino acid.

88. An antigen-binding polypeptide comprising at least one linker, polymer, or biologically active molecule, wherein said linker, polymer, or biologically active molecule is attached to the polypeptide through a functional group of a non-naturally encoded amino acid ribosomally incorporated into the polypeptide.

89. The antigen-binding polypeptide of claim 88, wherein said antigen-binding polypeptide is monoPEGylated.

90. An antigen-binding polypeptide comprising a linker, polymer, or biologically active molecule that is attached to one or more non-naturally encoded amino acids wherein said non-naturally encoded amino acid is ribosomally incorporated into the polypeptide at pre-selected sites.

91. The antigen-binding polypeptide of claim 90, wherein the antigen-binding polypeptide comprises one said linker, polymer, or biologically active molecule.

92. The antigen-binding polypeptide of claim 1, wherein the antigen-binding polypeptide comprises one or more amino acid substitution, addition, or deletion that modulates serum half-life or circulation time of the antigen-binding polypeptide.

93. A method of modulating immunogenicity of an antigen-binding polypeptide, the method comprising substituting one or more non-naturally encoded amino acids for any one or more naturally occurring amino acids in the antigen-binding polypeptide.

94. The isolated nucleic acid of claim 43, wherein the sequence of the isolated nucleic acid is selected from the group consisting of SEQ ID NO: 18, 20, 22, 25, 27, and 29 or fragment thereof.

95. An antigen-binding polypeptide wherein the polypeptide is selected from the group consisting of SEQ ID NO: 19, 21, 23, 24, 26, 28, 30, 31 or fragment thereof.

96. The antigen-binding polypeptide of claim 3, wherein the antigen-binding polypeptide is linked to the linker, polymer, or biologically active molecule under denaturing conditions.

---

What is claimed is:

1. A single chain Fv (scFv) comprising the amino acid sequence of SEQ ID NO:19, wherein the scFv specifically binds EGFR.

2. A single chain Fv (scFv) comprising the amino acid sequence of SEQ ID NO:21, wherein the scFv specifically binds EGFR.

3. A Fab antibody fragment comprising a light chain comprising the amino acid sequence of SEQ ID NO:23 and a variable heavy-CH1 chain domain comprising the amino acid sequence of SEQ ID NO:24, wherein the Fab antibody fragment specifically binds EGFR.

4. A single chain Fv (scFv) comprising the amino acid sequence of SEQ ID NO:26, wherein the scFv specifically binds HER2.

5. A single chain Fv (scFv) comprising the amino acid sequence of SEQ ID NO:28, wherein the scFv specifically binds HER2.

6. A Fab antibody fragment comprising a light chain comprising the amino acid sequence of SEQ ID NO:30 and a variable heavy-CH1 chain domain comprising the amino acid sequence of SEQ ID NO:31, wherein the Fab antibody fragment specifically binds HER2.

7. A composition comprising the scFv of any one of claims 1, 2, 4 or 5.

8. A composition comprising the Fab antibody fragment of any one of claims 3 or 6.

* * * * *

UNITED STATES PATENT AND TRADEMARK OFFICE
CERTIFICATE OF CORRECTION

PATENT NO. : 7,632,924 B2
APPLICATION NO. : 11/155909
DATED : December 15, 2009
INVENTOR(S) : Cho et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 644 days.

Signed and Sealed this

Twenty-first Day of December, 2010

David J. Kappos
*Director of the United States Patent and Trademark Office*

SEQUENCE LISTING

```
<160> NUMBER OF SEQ ID NOS: 31

<210> SEQ ID NO 1
<211> LENGTH: 77
<212> TYPE: DNA
<213> ORGANISM: Methanococcus jannaschii

<400> SEQUENCE: 1
ccggcggtag ttcagcaggg cagaacggcg gactctaaat ccgcatggcg ctggttcaaa      60
tccggcccgc cggacca                                                    77

<210> SEQ ID NO 2
<211> LENGTH: 88
<212> TYPE: DNA
<213> ORGANISM: Halobacterium sp. NRC-1

<400> SEQUENCE: 2
cccagggtag ccaagctcgg ccaacggcga cggactctaa atccgttctc gtaggagttc      60
gagggttcga atcccttccc tgggacca                                        88

<210> SEQ ID NO 3
<211> LENGTH: 89
<212> TYPE: DNA
<213> ORGANISM: Halobacterium sp. NRC-1

<400> SEQUENCE: 3
gcgagggtag ccaagctcgg ccaacggcga cggacttcct aatccgttct cgtaggagtt      60
cgagggttcg aatccctccc ctcgcacca                                       89

<210> SEQ ID NO 4
<211> LENGTH: 306
<212> TYPE: PRT
<213> ORGANISM: Methanococcus jannaschii

<400> SEQUENCE: 4
```

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
            130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
            290                 295                 300

Arg Leu
305

<210> SEQ ID NO 5
<211> LENGTH: 306
<212> TYPE: PRT
<213> ORGANISM: Methanococcus jannaschii

<400> SEQUENCE: 5

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60
```

```
Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 6
<211> LENGTH: 305
<212> TYPE: PRT
<213> ORGANISM: Methanococcus jannaschii

<400> SEQUENCE: 6

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
```

```
                115                 120                 125
Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Cys Ile His Asn
            180                 185                 190

Pro Val Leu Thr Gly Leu Asp Gly Glu Gly Lys Met Ser Ser Ser Lys
                195                 200                 205

Gly Asn Phe Ile Ala Val Asp Asp Ser Pro Glu Glu Ile Arg Ala Lys
    210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
    290                 295                 300

Leu
305

<210> SEQ ID NO 7
<211> LENGTH: 305
<212> TYPE: PRT
<213> ORGANISM: Methanococcus jannaschii

<400> SEQUENCE: 7

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ile Pro Tyr
145                 150                 155                 160

Leu Pro Val Asp Val Ala Val Gly Gly Met Glu Gln Arg Lys Ile His
                165                 170                 175
```

```
Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
    210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
    290                 295                 300

Leu
305

<210> SEQ ID NO 8
<211> LENGTH: 305
<212> TYPE: PRT
<213> ORGANISM: Methanococcus jannaschii

<400> SEQUENCE: 8

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Lys Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
    210                 215                 220

Ile Lys Lys Ala Tyr Cys Pro Ala Gly Val Val Glu Gly Asn Pro Ile
225                 230                 235                 240
```

```
Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
    290                 295                 300

Leu
305

<210> SEQ ID NO 9
<211> LENGTH: 306
<212> TYPE: PRT
<213> ORGANISM: Methanococcus jannaschii

<400> SEQUENCE: 9

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Asn Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
```

```
                  290                 295                 300

Arg Leu
305

<210> SEQ ID NO 10
<211> LENGTH: 306
<212> TYPE: PRT
<213> ORGANISM: Methanococcus jannaschii

<400> SEQUENCE: 10

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 11
<211> LENGTH: 306
<212> TYPE: PRT
<213> ORGANISM: Methanococcus jannaschii
```

```
<400> SEQUENCE: 11

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Val His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 12
<211> LENGTH: 306
<212> TYPE: PRT
<213> ORGANISM: Methanococcus jannaschii

<400> SEQUENCE: 12

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45
```

-continued

```
Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Ser Phe Gln Leu Asp Lys
                100                 105                 110

Asp Tyr Thr Leu Asn Val Tyr Arg Leu Ala Leu Lys Thr Thr Leu Lys
                115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Ser His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190

Asn Pro Val Leu Thr Gly Leu Asp Gly Glu Gly Lys Met Ser Ser Ser
                195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
                275                 280                 285

Asn Ala Val Ala Glu Glu Leu Ile Lys Ile Leu Glu Pro Ile Arg Lys
290                 295                 300

Arg Leu
305

<210> SEQ ID NO 13
<211> LENGTH: 306
<212> TYPE: PRT
<213> ORGANISM: Methanococcus jannaschii

<400> SEQUENCE: 13

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
                35                  40                  45

Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Glu Phe Gln Leu Asp Lys
                100                 105                 110
```

-continued

```
Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 14
<211> LENGTH: 306
<212> TYPE: PRT
<213> ORGANISM: Methanococcus jannaschii

<400> SEQUENCE: 14

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Gly Thr His
145                 150                 155                 160

Tyr Arg Gly Val Asp Val Ala Val Gly Gly Met Glu Gln Arg Lys Ile
```

```
                165                 170                 175
His Met Leu Ala Arg Glu Leu Leu Pro Lys Lys Val Cys Ile His
        180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
        260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
    290                 295                 300

Arg Leu
305

<210> SEQ ID NO 15
<211> LENGTH: 306
<212> TYPE: PRT
<213> ORGANISM: Methanococcus jannaschii

<400> SEQUENCE: 15

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Gly His
145                 150                 155                 160

Tyr Leu Gly Val Asp Val Ile Val Gly Gly Met Glu Gln Arg Lys Ile
                165                 170                 175

His Met Leu Ala Arg Glu Leu Leu Pro Lys Lys Val Cys Ile His
        180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220
```

```
Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Leu Ile Lys Ile Leu Glu Pro Ile Arg Lys
290                 295                 300

Arg Leu
305

<210> SEQ ID NO 16
<211> LENGTH: 306
<212> TYPE: PRT
<213> ORGANISM: Methanococcus jannaschii

<400> SEQUENCE: 16

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Arg Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Val Ile His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285
```

```
Asn Ala Val Ala Glu Glu Leu Ile Lys Ile Leu Glu Pro Ile Arg Lys
    290                 295                 300

Arg Leu
305

<210> SEQ ID NO 17
<211> LENGTH: 306
<212> TYPE: PRT
<213> ORGANISM: Methanococcus jannaschii

<400> SEQUENCE: 17

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 18
<211> LENGTH: 920
<212> TYPE: DNA
```

```
<213> ORGANISM: Artificial
<220> FEATURE:
<223> OTHER INFORMATION: Synthetic construct

<400> SEQUENCE: 18
accacaggtc tcccatgcga ttcagtacga cgctggcaac ggccgctacg gcactcttct      60
ttactgcaag tcaggtaagc gcgcaggttc agctgcagca gtctggagct gagctgatga     120
agcctggggc ctcagtgaag atatcctgca aggctactgg ctacacattc agtagttact     180
ggatagagtg ggtaaagcag aggcctggac atggccttga gtggattgga gagattttac     240
cgggaagtaa aaaactaac tacaatgaga agttcaaggg aaaggccaca ttcactgcag      300
atacatcctc caacacagcc tacatgcaat ttagcagcct gacatctgag gactctgccg     360
tctattactg tgcaagatat tactatagga acgacgacta tggtatggac tactggggtc     420
aaggaacctc agtcaccgtc tcctcaggcg gcggcggctc cggtggtggt ggatctggtg     480
ggggcggcag cggcggtggc ggcagtgaaa tccacatgac acagactaca tcctccctgt     540
ctgcctctct gggagacaga gtcaccatca gttgcagtgc aagtcaggac atcaggaatt     600
atttaaactg gtatcagcag aaacctgatg gaactgttaa actcctgatc tattacacat     660
caactttaca ttcaggagtc ccatcaaggt tcagtggcag cgggtctggg acagattatt     720
ctctcaccat cagcaacctg gaacctgaag atattgccac ttattattgt cagcagtata     780
gtaagattcc gtacacgttc acaggggga ccaagctgga aataaaacgg gctgatgctg      840
cagaacaaaa actcatctca gaagaggatc tgaatagcgc cgtcgaccat catcatcacc     900
atcattaagg taccaaccaa                                                 920

<210> SEQ ID NO 19
<211> LENGTH: 297
<212> TYPE: PRT
<213> ORGANISM: Artificial
<220> FEATURE:
<223> OTHER INFORMATION: Synthetic construct

<400> SEQUENCE: 19

Met Arg Phe Ser Thr Thr Leu Ala Thr Ala Ala Thr Ala Leu Phe Phe
1               5                   10                  15

Thr Ala Ser Gln Val Ser Ala Gln Val Gln Leu Gln Gln Ser Gly Ala
            20                  25                  30

Glu Leu Met Lys Pro Gly Ala Ser Val Lys Ile Ser Cys Lys Ala Thr
        35                  40                  45

Gly Tyr Thr Phe Ser Ser Tyr Trp Ile Glu Trp Val Lys Gln Arg Pro
    50                  55                  60

Gly His Gly Leu Glu Trp Ile Gly Glu Ile Leu Pro Gly Ser Lys Lys
65                  70                  75                  80

Thr Asn Tyr Asn Glu Lys Phe Lys Gly Lys Ala Thr Phe Thr Ala Asp
                85                  90                  95

Thr Ser Ser Asn Thr Ala Tyr Met Gln Phe Ser Ser Leu Thr Ser Glu
            100                 105                 110

Asp Ser Ala Val Tyr Tyr Cys Ala Arg Tyr Tyr Arg Asn Asp Asp
        115                 120                 125

Tyr Gly Met Asp Tyr Trp Gly Gln Gly Thr Ser Val Thr Val Ser Ser
    130                 135                 140

Gly Gly Gly Gly Ser Gly Gly Gly Gly Ser Gly Gly Gly Gly Ser Gly
145                 150                 155                 160

Gly Gly Gly Ser Glu Ile His Met Thr Gln Thr Thr Ser Ser Leu Ser
```

```
                    165                 170                 175
Ala Ser Leu Gly Asp Arg Val Thr Ile Ser Cys Ser Ala Ser Gln Asp
            180                 185                 190

Ile Arg Asn Tyr Leu Asn Trp Tyr Gln Gln Lys Pro Asp Gly Thr Val
        195                 200                 205

Lys Leu Leu Ile Tyr Tyr Thr Ser Thr Leu His Ser Gly Val Pro Ser
    210                 215                 220

Arg Phe Ser Gly Ser Gly Ser Gly Thr Asp Tyr Ser Leu Thr Ile Ser
225                 230                 235                 240

Asn Leu Glu Pro Glu Asp Ile Ala Thr Tyr Tyr Cys Gln Gln Tyr Ser
                245                 250                 255

Lys Ile Pro Tyr Thr Phe Thr Gly Gly Thr Lys Leu Glu Ile Lys Arg
            260                 265                 270

Ala Asp Ala Ala Glu Gln Lys Leu Ile Ser Glu Glu Asp Leu Asn Ser
        275                 280                 285

Ala Val Asp His His His His His His
    290                 295

<210> SEQ ID NO 20
<211> LENGTH: 779
<212> TYPE: DNA
<213> ORGANISM: Artificial
<220> FEATURE:
<223> OTHER INFORMATION: Synthetic construct

<400> SEQUENCE: 20
ccatgggcca ccaccaccac caccaccagg ttcagctgca gcagtctgga gctgagctga      60
tgaagcctgg ggcctcagtg aagatatcct gcaaggctac tggctacaca ttcagtagtt     120
actggataga gtgggtaaag cagaggcctg acatggcct gagtggatt ggagagattt       180 taccgggaag taaaaaaact aactacaatg agaagttcaa gggaaaggcc acattcactg     240
cagatacatc ctccaacaca gcctacatgc aatttagcag cctgacatct gaggactctg     300
ccgtctatta ctgtgcaaga tattactata ggaacgacga ctatggtatg gactactggg     360
gtcaaggaac ctcagtcacc gtctcctcag gcggcggcgg ctccggtggt ggtggatctg     420 gtggggcgg cagcggcggt ggcggcagtg aaatccacat gacacagact acatcctccc     480
tgtctgcctc tctgggagac agagtcacca tcagttgcag tgcaagtcag gacatcagga     540
attatttaaa ctggtatcag cagaaacctg atggaactgt taaactcctg atctattaca     600
catcaacttt acattcagga gtcccatcaa ggttcagtgg cagcgggtct gggacagatt     660
attctctcac catcagcaac ctggaacctg aagatattgc cacttattat tgtcagcagt     720
atagtaagat tccgtacacg ttcacagggg ggaccaagct ggaaatataa aggtaccaa     779

<210> SEQ ID NO 21
<211> LENGTH: 255
<212> TYPE: PRT
<213> ORGANISM: Artificial
<220> FEATURE:
<223> OTHER INFORMATION: Synthetic construct

<400> SEQUENCE: 21

Met Gly His His His His His His Gln Val Gln Leu Gln Gln Ser Gly
1               5                   10                  15

Ala Glu Leu Met Lys Pro Gly Ala Ser Val Lys Ile Ser Cys Lys Ala
            20                  25                  30

Thr Gly Tyr Thr Phe Ser Ser Tyr Trp Ile Glu Trp Val Lys Gln Arg
```

|  | 35 |  |  | 40 |  |  | 45 |  |  |  |  |
|---|---|---|---|---|---|---|---|---|---|---|---|

Pro Gly His Gly Leu Glu Trp Ile Gly Glu Ile Leu Pro Gly Ser Lys
 50                              55                      60

Lys Thr Asn Tyr Asn Glu Lys Phe Lys Gly Lys Ala Thr Phe Thr Ala
 65                  70                      75                      80

Asp Thr Ser Ser Asn Thr Ala Tyr Met Gln Phe Ser Ser Leu Thr Ser
                 85                      90                      95

Glu Asp Ser Ala Val Tyr Tyr Cys Ala Arg Tyr Tyr Arg Asn Asp
                100                     105                     110

Asp Tyr Gly Met Asp Tyr Trp Gly Gln Gly Thr Ser Val Thr Val Ser
            115                     120                     125

Ser Gly Gly Gly Ser Gly Gly Gly Ser Gly Gly Gly Ser
 130                     135                     140

Gly Gly Gly Gly Ser Glu Ile His Met Thr Gln Thr Thr Ser Ser Leu
 145                     150                     155                     160

Ser Ala Ser Leu Gly Asp Arg Val Thr Ile Ser Cys Ser Ala Ser Gln
                165                     170                     175

Asp Ile Arg Asn Tyr Leu Asn Trp Tyr Gln Gln Lys Pro Asp Gly Thr
            180                     185                     190

Val Lys Leu Leu Ile Tyr Tyr Thr Ser Thr Leu His Ser Gly Val Pro
        195                     200                     205

Ser Arg Phe Ser Gly Ser Gly Ser Gly Thr Asp Tyr Ser Leu Thr Ile
 210                     215                     220

Ser Asn Leu Glu Pro Glu Asp Ile Ala Thr Tyr Tyr Cys Gln Gln Tyr
 225                     230                     235                     240

Ser Lys Ile Pro Tyr Thr Phe Thr Gly Gly Thr Lys Leu Glu Ile
                245                     250                     255

<210> SEQ ID NO 22
<211> LENGTH: 1578
<212> TYPE: DNA
<213> ORGANISM: Artificial
<220> FEATURE:
<223> OTHER INFORMATION: Synthetic construct

<400> SEQUENCE: 22
accaccggtc tcccatgaaa aaactgctgt tcgcgattcc gctggtggtg ccgttctata     60
gccatagcac catggagctc gaaatccaca tgacacagac tacatcctcc ctgtctgcct    120
ctctgggaga cagagtcacc atcagttgca gtgcaagtca ggacatcagg aattatttaa    180
actggtatca gcagaaacct gatggaactg ttaaactcct gatctattac acatcaactt    240
tacattcagg agtcccatca aggttcagtg gcagcgggtc tgggacagat tattctctca    300
ccatcagcaa cctggaacct gaagatattg ccacttatta ttgtcagcag tatagtaaga    360
ttccgtacac gttcacaggg gggaccaagc tggaaataaa acgggctgat gctgcaaagc    420
ttgagatcaa acgaactgtg gctgcaccat ctgtcttcat cttcccgcca tctgatgagc    480
agttgaaatc tggaactgcc tctgttgtgt gcctgctgaa taacttctat cccagagagg    540
ccaaagtaca gtggaaggtg gataacgccc tccaatcggg taactcccag gagagtgtca    600
cagagcagga cagcaaggac agcacctaca gcctcagcag caccctgacg ctgagcaaag    660
cagactacga gaaacacaaa gtctacgcct gcgaagtcac ccatcagggc ctgtcctcgc    720
ccgtcacaaa gagcttcaac aggggagagt gttaagctgg ggatcctcta gaggttgagg    780
tgattttatg aaaaagaata tcgcatttct tcttgcatct atgttcgttt tttctattgc    840

```
tacaaacgcg tacgctcagg ttcagctgct cgagcaggtt cagctgcagc agtctggagc    900
tgagctgatg aagcctgggg cctcagtgaa gatatcctgc aaggctactg gctacacatt    960
cagtagttac tggatagagt gggtaaagca gaggcctgga catggccttg agtggattgg   1020
agagatttta ccgggaagta aaaaaactaa ctacaatgag aagttcaagg gaaaggccac   1080
attcactgca gatacatcct ccaacacagc ctacatgcaa tttagcagcc tgacatctga   1140
ggactctgcc gtctattact gtgcaagata ttactatagg aacgacgact atggtatgga   1200
ctactggggt caaggaacct cagtcaccgt ctcctcagcg ggcccatcgg tcttcccccT   1260
ggcaccctcc tccaagagca cctctggggg cacagcggcc ctgggctgcc tggtcaagga   1320
ctacttcccc gaaccggtga cggtgtcgtg gaactcaggc gccctgacca gcggcgtgca   1380
caccttcccg gctgtcctac agtcctcagg actctactcc ctcagcagcg tggtgactgt   1440
gccctctagc agcttgggca cccagaccta catctgcaac gtgaatcaca agcccagcaa   1500
caccaaggtg gacaagaaag ttgagcccaa atcttgtgac aaacatcatc atcatcatca   1560
ttagggtacc accataac                                                  1578
```

<210> SEQ ID NO 23
<211> LENGTH: 246
<212> TYPE: PRT
<213> ORGANISM: Artificial
<220> FEATURE:
<223> OTHER INFORMATION: Synthetic construct

<400> SEQUENCE: 23

```
Met Lys Lys Leu Leu Phe Ala Ile Pro Leu Val Val Pro Phe Tyr Ser
1               5                   10                  15

His Ser Thr Met Glu Leu Glu Ile His Met Thr Gln Thr Thr Ser Ser
            20                  25                  30

Leu Ser Ala Ser Leu Gly Asp Arg Val Thr Ile Ser Cys Ser Ala Ser
        35                  40                  45

Gln Asp Ile Arg Asn Tyr Leu Asn Trp Tyr Gln Gln Lys Pro Asp Gly
    50                  55                  60

Thr Val Lys Leu Leu Ile Tyr Tyr Thr Ser Thr Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Pro Glu Asp Ile Ala Thr Tyr Tyr Cys Gln Gln
            100                 105                 110

Tyr Ser Lys Ile Pro Tyr Thr Phe Thr Gly Gly Thr Lys Leu Glu Ile
        115                 120                 125

Lys Arg Ala Asp Ala Ala Lys Leu Glu Ile Lys Arg Thr Val Ala Ala
    130                 135                 140

Pro Ser Val Phe Ile Phe Pro Pro Ser Asp Glu Gln Leu Lys Ser Gly
145                 150                 155                 160

Thr Ala Ser Val Val Cys Leu Leu Asn Asn Phe Tyr Pro Arg Glu Ala
                165                 170                 175

Lys Val Gln Trp Lys Val Asp Asn Ala Leu Gln Ser Gly Asn Ser Gln
            180                 185                 190

Glu Ser Val Thr Glu Gln Asp Ser Lys Asp Ser Thr Tyr Ser Leu Ser
        195                 200                 205

Ser Thr Leu Thr Leu Ser Lys Ala Asp Tyr Glu Lys His Lys Val Tyr
    210                 215                 220

Ala Cys Glu Val Thr His Gln Gly Leu Ser Ser Pro Val Thr Lys Ser
```

Phe Asn Arg Gly Glu Cys
                245

<210> SEQ ID NO 24
<211> LENGTH: 235
<212> TYPE: PRT
<213> ORGANISM: Artificial
<220> FEATURE:
<223> OTHER INFORMATION: Synthetic construct

<400> SEQUENCE: 24

Gln Val Gln Leu Leu Glu Gln Val Gln Leu Gln Gln Ser Gly Ala Glu
1               5                   10                  15

Leu Met Lys Pro Gly Ala Ser Val Lys Ile Ser Cys Lys Ala Thr Gly
            20                  25                  30

Tyr Thr Phe Ser Ser Tyr Trp Ile Glu Trp Val Lys Gln Arg Pro Gly
        35                  40                  45

His Gly Leu Glu Trp Ile Gly Glu Ile Leu Pro Gly Ser Lys Lys Thr
    50                  55                  60

Asn Tyr Asn Glu Lys Phe Lys Gly Lys Ala Thr Phe Thr Ala Asp Thr
65                  70                  75                  80

Ser Ser Asn Thr Ala Tyr Met Gln Phe Ser Ser Leu Thr Ser Glu Asp
                85                  90                  95

Ser Ala Val Tyr Tyr Cys Ala Arg Tyr Tyr Arg Asn Asp Asp Tyr
            100                 105                 110

Gly Met Asp Tyr Trp Gly Gln Gly Thr Ser Val Thr Val Ser Ser Ala
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys His His His His His
225                 230                 235

<210> SEQ ID NO 25
<211> LENGTH: 863
<212> TYPE: DNA
<213> ORGANISM: Artificial
<220> FEATURE:
<223> OTHER INFORMATION: Synthetic construct

<400> SEQUENCE: 25
accacaggtc tcccatgcga ttcagtacga cgctggcaac ggccgctacg gcactcttct      60
ttactgcaag tcaggtaagc gcggaagttc aactggttga atctggtggc ggtctggtgc     120
aaccaggtgg ttctctgcgt ctgtcttgcg ccgcgtccgg tttcaacatt aaagacacct     180
acattcactg ggtgcgccag gctccgggta agggtctgga atgggtggcc cgcatttatc     240
caacgaatgg ctacacccgc tacgcggatt ccgtgaaagg ccgtttcacg attagcgctg     300

-continued

| | |
|---|---|
| ataccagcaa gaacaccgct tatctgcaaa tgaacagcct gcgtgccgaa gacaccgccg | 360 |
| tgtactattg tagccgttgg ggcggtgatg gcttttacgc gatggactac tggggccagg | 420 |
| gtacgctggt cacggtttct tctggcggcg gcggctccgg tggtggtgga tctggtgggg | 480 |
| gcggcagcgg cggtggcggc agtgatattc aaatgactca atctccttcc tctctgtctg | 540 |
| caagcgttgg tgatcgtgtg accatcacct gtcgcgcatc ccaggatgta aataccgcag | 600 |
| tagcgtggta tcagcagaag ccgggtaaag caccaaaact gctgatttat tccgcgagct | 660 |
| ttctgtatag cggcgtacca agccgtttta gcggttctcg tagcggtact gattttaccc | 720 |
| tgaccatctc ctctctgcag cctgaggatt ttgcgaccta ttattgccag cagcattata | 780 |
| cgacgccgcc tacgtttggc cagggtacta aggtggaaat taaaagcggc catcatcatc | 840 |
| accatcatta aggtacccaa cca | 863 |

<210> SEQ ID NO 26
<211> LENGTH: 278
<212> TYPE: PRT
<213> ORGANISM: Artificial
<220> FEATURE:
<223> OTHER INFORMATION: Synthetic construct

<400> SEQUENCE: 26

Met Arg Phe Ser Thr Thr Leu Ala Thr Ala Ala Thr Ala Leu Phe Phe
1               5                   10                  15

Thr Ala Ser Gln Val Ser Ala Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Asn Ile Lys Asp Thr Tyr Ile His Trp Val Arg Gln Ala Pro
    50                  55                  60

Gly Lys Gly Leu Glu Trp Val Ala Arg Ile Tyr Pro Thr Asn Gly Tyr
65                  70                  75                  80

Thr Arg Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ser Arg Trp Gly Gly Asp Gly Phe Tyr
        115                 120                 125

Ala Met Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Gln Met Thr Gln Ser Pro Ser Ser Leu Ser Ala
                165                 170                 175

Ser Val Gly Asp Arg Val Thr Ile Thr Cys Arg Ala Ser Gln Asp Val
            180                 185                 190

Asn Thr Ala Val Ala Trp Tyr Gln Gln Lys Pro Gly Lys Ala Pro Lys
        195                 200                 205

Leu Leu Ile Tyr Ser Ala Ser Phe Leu Tyr Ser Gly Val Pro Ser Arg
    210                 215                 220

Phe Ser Gly Ser Arg Ser Gly Thr Asp Phe Thr Leu Thr Ile Ser Ser
225                 230                 235                 240

Leu Gln Pro Glu Asp Phe Ala Thr Tyr Tyr Cys Gln Gln His Tyr Thr
                245                 250                 255

```
Thr Pro Pro Thr Phe Gly Gln Gly Thr Lys Val Glu Ile Lys Ser Gly
        260                 265                 270

His His His His His His
        275

<210> SEQ ID NO 27
<211> LENGTH: 869
<212> TYPE: DNA
<213> ORGANISM: Artificial
<220> FEATURE:
<223> OTHER INFORMATION: Synthetic construct

<400> SEQUENCE: 27
accacaggtc tcccatgcga ttcagtacga cgctggcaac ggccgctacg gcactcttct      60
ttactgcaag tcaggtaagc gcgggccacc accaccacca ccactctggt gaagttcaac    120
tggttgaatc tggtggcggt ctggtgcaac aggtggttc tctgcgtctg tcttgcgccg    180
cgtccggttt caacattaaa gacacctaca ttcactgggt gcgccaggct ccgggtaagg    240
gtctggaatg ggtggcccgc atttatccaa cgaatggcta caccgctac gcggattccg    300
tgaaaggccg tttcacgatt agcgctgata ccagcaagaa caccgcttat ctgcaaatga    360
acagcctgcg tgccgaagac accgccgtgt actattgtag ccgttggggc ggtgatggct    420
tttacgcgat ggactactgg ggccagggta cgctggtcac ggtttcttct ggcggcggcg    480
gctccggtgg tggtggatct ggtggggggcg gcagcggcgg tggcggcagt gatattcaaa    540
tgactcaatc tccttcctct ctgtctgcaa gcgttggtga tcgtgtgacc atcacctgtc    600
gcgcatccca ggatgtaaat accgcagtag cgtggtatca gcagaagccg ggtaaagcac    660
caaaactgct gatttattcc gcgagctttc tgtatagcgg cgtaccaagc cgttttagcg    720
gttctcgtag cggtactgat tttaccctga ccatctcctc tctgcagcct gaggattttg    780
cgacctatta ttgccagcag cattatacga cgccgcctac gtttggccag ggtactaagg    840
tggaaattaa aagctaaggt acccaacca                                       869

<210> SEQ ID NO 28
<211> LENGTH: 280
<212> TYPE: PRT
<213> ORGANISM: Artificial
<220> FEATURE:
<223> OTHER INFORMATION: Synthetic construct

<400> SEQUENCE: 28

Met Arg Phe Ser Thr Thr Leu Ala Thr Ala Ala Thr Ala Leu Phe Phe
1               5                   10                  15

Thr Ala Ser Gln Val Ser Ala Gly His His His His His His Ser Gly
            20                  25                  30

Glu Val Gln Leu Val Glu Ser Gly Gly Gly Leu Val Gln Pro Gly Gly
        35                  40                  45

Ser Leu Arg Leu Ser Cys Ala Ala Ser Gly Phe Asn Ile Lys Asp Thr
    50                  55                  60

Tyr Ile His Trp Val Arg Gln Ala Pro Gly Lys Gly Leu Glu Trp Val
65                  70                  75                  80

Ala Arg Ile Tyr Pro Thr Asn Gly Tyr Thr Arg Tyr Ala Asp Ser Val
                85                  90                  95

Lys Gly Arg Phe Thr Ile Ser Ala Asp Thr Ser Lys Asn Thr Ala Tyr
            100                 105                 110

Leu Gln Met Asn Ser Leu Arg Ala Glu Asp Thr Ala Val Tyr Tyr Cys
        115                 120                 125
```

```
Ser Arg Trp Gly Gly Asp Gly Phe Tyr Ala Met Asp Tyr Trp Gly Gln
    130                 135                 140
Gly Thr Leu Val Thr Val Ser Ser Gly Gly Gly Ser Gly Gly Gly Gly
145                 150                 155                 160
Gly Ser Gly Gly Gly Gly Ser Gly Gly Gly Gly Ser Asp Ile Gln Met
                165                 170                 175
Thr Gln Ser Pro Ser Ser Leu Ser Ala Ser Val Gly Asp Arg Val Thr
            180                 185                 190
Ile Thr Cys Arg Ala Ser Gln Asp Val Asn Thr Ala Val Ala Trp Tyr
        195                 200                 205
Gln Gln Lys Pro Gly Lys Ala Pro Lys Leu Leu Ile Tyr Ser Ala Ser
    210                 215                 220
Phe Leu Tyr Ser Gly Val Pro Ser Arg Phe Ser Gly Ser Arg Ser Gly
225                 230                 235                 240
Thr Asp Phe Thr Leu Thr Ile Ser Ser Leu Gln Pro Glu Asp Phe Ala
                245                 250                 255
Thr Tyr Tyr Cys Gln Gln His Tyr Thr Thr Pro Pro Thr Phe Gly Gln
            260                 265                 270
Gly Thr Lys Val Glu Ile Lys Ser
        275                 280

<210> SEQ ID NO 29
<211> LENGTH: 1538
<212> TYPE: DNA
<213> ORGANISM: Artificial
<220> FEATURE:
<223> OTHER INFORMATION: Synthetic construct

<400> SEQUENCE: 29
atgaaaaaac tgctgttcgc gattccgctg gtggtgccgt tctatagcca tagcaccatg     60
gagctcgata ttcaaatgac tcaatctcct tcctctctgt ctgcaagcgt tggtgatcgt    120
gtgaccatca cctgtcgcgc atcccaggat gtaaataccg cagtagcgtg gtatcagcag    180
aagccgggta agcaccaaa actgctgatt tattccgcga gctttctgta tagcggcgta    240
ccaagccgtt ttagcggttc tcgtagcggt actgatttta ccctgaccat ctcctctctg    300
cagcctgagg attttgcgac ctattattgc cagcagcatt atacgacgcc gcctacgttt    360
ggccagggta ctaaggtgga aattaaaaag cttgagatca acgaactgt ggctgcacca    420
tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660
tgcgaagtca cccatcaggg cctgtcctcg cccgtcacaa agagcttcaa caggggagag    720
tgttaagctg gggatcctct agaggttgag gtgattttat gaaaagaat atcgcatttc    780
ttcttgcatc tatgttcgtt ttttctattg ctacaaacgc gtacgctcag gttcagctgc    840
tcgaggaagt tcaactggtt gaatctggtg gcggtctggt gcaaccaggt ggttctctgc    900
gtctgtcttg cgccgcgtcc ggtttcaaca ttaaagacac ctacattcac tgggtgcgcc    960
aggctccggg taagggtctg gaatgggtgg cccgcattta tccaacgaat ggctacaccc   1020
gctacgcgga ttccgtgaaa ggccgtttca cgattagcgc tgataccagc aagaacaccg   1080
cttatctgca aatgaacagc ctgcgtgccg aagacaccgc cgtgtactat tgtagccgtt   1140
```

```
ggggcggtga tggcttttac gcgatggact actggggcca gggtacgctg gtcacggttt    1200 cttctgggc  ccaatcggtc ttccccctgg caccctcctc aagagcacc  tctgggggca    1260 cagcggccct gggctgcctg gtcaaggact acttccccga accggtgacg gtgtcgtgga    1320
actcaggcgc cctgaccagc ggcgtgcaca ccttcccggc tgtcctacag tcctcaggac    1380
tctactccct cagcagcgtg gtgactgtgc cctctagcag cttgggcacc cagacctaca    1440
tctgcaacgt gaatcacaag cccagcaaca ccaaggtgga caagaaagtt gagcccaaat    1500
cttgtgacaa acatcatcat catcatcatt aaggtacc                             1538
```

<210> SEQ ID NO 30
<211> LENGTH: 219
<212> TYPE: PRT
<213> ORGANISM: Artificial
<220> FEATURE:
<223> OTHER INFORMATION: Synthetic construct

<400> SEQUENCE: 30

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 31
<211> LENGTH: 234
<212> TYPE: PRT
<213> ORGANISM: Artificial
<220> FEATURE:
<223> OTHER INFORMATION: Synthetic construct

<400> SEQUENCE: 31

```
Gln Val Gln Leu Leu Glu Glu Val Gln Leu Val Glu Ser Gly Gly Gly
 1               5                  10                  15
```

-continued

```
Leu Val Gln Pro Gly Gly Ser Leu Arg Leu Ser Cys Ala Ala Ser Gly
            20                  25                  30

Phe Asn Ile Lys Asp Thr Tyr Ile His Trp Val Arg Gln Ala Pro Gly
            35                  40                  45

Lys Gly Leu Glu Trp Val Ala Arg Ile Tyr Pro Thr Asn Gly Tyr Thr
    50                  55                  60

Arg Tyr Ala Asp Ser Val Lys Gly Arg Phe Thr Ile Ser Ala Asp Thr
65                  70                  75                  80

Ser Lys Asn Thr Ala Tyr Leu Gln Met Asn Ser Leu Arg Ala Glu Asp
                85                  90                  95

Thr Ala Val Tyr Tyr Cys Ser Arg Trp Gly Gly Asp Gly Phe Tyr Ala
            100                 105                 110

Met Asp Tyr Trp Gly Gln Gly Thr Leu Val Thr Val Ser Ser Gly Ala
            115                 120                 125

Gln Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys His His His His His His
225                 230
```